US010745447B2

(12) United States Patent
Asokan et al.

(10) Patent No.: US 10,745,447 B2
(45) Date of Patent: Aug. 18, 2020

(54) METHODS AND COMPOSITIONS FOR ANTIBODY-EVADING VIRUS VECTORS

(71) Applicants: The University of North Carolina at Chapel Hill, Chapel Hill, NC (US); University of Florida Research Foundation, Inc., Gainesville, FL (US)

(72) Inventors: Aravind Asokan, Chapel Hill, NC (US); Mavis Agbandje-McKenna, Gainesville, FL (US); Long Ping Victor Tse, Carrboro, NC (US); Brittney Gurda, Collegeville, PA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/763,706

(22) PCT Filed: Sep. 28, 2016

(86) PCT No.: PCT/US2016/054143
§ 371 (c)(1),
(2) Date: Mar. 27, 2018

(87) PCT Pub. No.: WO2017/058892
PCT Pub. Date: Apr. 6, 2017

(65) Prior Publication Data
US 2019/0048041 A1 Feb. 14, 2019

Related U.S. Application Data

(60) Provisional application No. 62/234,016, filed on Sep. 28, 2015.

(51) Int. Cl.
*C07K 14/005* (2006.01)
*C07K 16/08* (2006.01)
*C12N 15/86* (2006.01)
*A61K 39/00* (2006.01)

(52) U.S. Cl.
CPC .......... *C07K 14/005* (2013.01); *C07K 16/081* (2013.01); *C12N 15/86* (2013.01); *A61K 2039/505* (2013.01); *A61K 2039/507* (2013.01); *C07K 2317/33* (2013.01); *C07K 2317/34* (2013.01); *C07K 2317/76* (2013.01); *C12N 2750/14122* (2013.01); *C12N 2750/14143* (2013.01); *C12N 2810/6027* (2013.01)

(58) Field of Classification Search
CPC ................ C07K 14/005; C07K 16/081; C07K 2317/34; C07K 2317/33; C07K 2317/76; C07K 14/015; C12N 15/86; C12N 2810/6027; C12N 2750/14143; C12N 2750/14122; C12N 7/00; C12N 2750/14171; C12N 2750/14121; C12N 15/8645; C12N 2750/14141; C12N 15/864; C12N 2750/14011; C12N 2750/14021; C12N 2750/14111; C12N 2799/025; A61K 2039/507; A61K 2039/505; A61K 48/00; A61K 39/23; A61K 2039/6075; A61K 39/12; A61K 39/42
See application file for complete search history.

(56) References Cited

U.S. PATENT DOCUMENTS

| | | | |
|---|---|---|---|
| 5,399,346 | A | 3/1995 | Anderson et al. |
| 5,478,745 | A | 12/1995 | Samulski et al. |
| 5,863,541 | A | 1/1999 | Samulski et al. |
| 5,869,248 | A | 2/1999 | Yuan et al. |
| 5,877,022 | A | 3/1999 | Stinchcomb et al. |
| 5,882,652 | A | 3/1999 | Valdes et al. |
| 5,905,040 | A | 5/1999 | Mazzara et al. |
| 5,916,563 | A | 6/1999 | Young et al. |
| 6,013,487 | A | 1/2000 | Mitchell |
| 6,040,183 | A | 3/2000 | Ferrari et al. |
| 6,083,702 | A | 7/2000 | Mitchell et al. |
| 6,093,570 | A | 7/2000 | Ferrari et al. |
| 6,156,303 | A | 12/2000 | Russell et al. |
| 6,468,524 | B1 | 10/2002 | Chiorini et al. |
| 6,562,958 | B1 | 5/2003 | Breton et al. |
| 6,733,757 | B2 | 5/2004 | Patel et al. |
| 6,822,071 | B1 | 11/2004 | Stephens et al. |
| 6,962,815 | B2 | 11/2005 | Bartlett |
| 6,984,517 | B1 | 1/2006 | Chiorini et al. |
| 7,071,172 | B2 | 7/2006 | Mccown et al. |

(Continued)

FOREIGN PATENT DOCUMENTS

| | | | |
|---|---|---|---|
| EP | 1033405 | A2 | 9/2000 |
| EP | 1777296 | A2 | 4/2007 |

(Continued)

OTHER PUBLICATIONS

Li C, Wu S, Albright B, Hirsch M, Li W, Tseng YS, Agbandje-McKenna M, McPhee S, Asokan A, Samulski RJ. Development of Patient-specific AAV Vectors After Neutralizing Antibody Selection for Enhanced Muscle Gene Transfer. Mol Ther. Feb. 2016;24(1):53-65. doi: 10.1038/mt.2015.134. Epub Jul. 29, 2015.*

(Continued)

*Primary Examiner* — Rachel B Gill
(74) *Attorney, Agent, or Firm* — Myers Bigel, P.A.

(57) ABSTRACT

The present invention provides AAV capsid proteins comprising a modification in the amino acid sequence and virus vectors comprising the modified AAV capsid protein. The invention also provides methods of administering the virus vectors and virus capsids of the invention to a cell or to a subject in vivo.

33 Claims, 24 Drawing Sheets

Specification includes a Sequence Listing.

(56) References Cited

U.S. PATENT DOCUMENTS 7,105,345 B2 9/2006 Wilson et al.
7,198,951 B2 4/2007 Gao et al.
7,201,898 B2 4/2007 Monahan et al.
7,214,786 B2 5/2007 Kovalic et al.
7,252,997 B1 8/2007 Hallek et al.
7,259,151 B2 8/2007 Arbetman et al.
7,282,199 B2 10/2007 Gao et al.
7,588,772 B2 9/2009 Kay et al.
7,712,893 B2 5/2010 Dobashi
7,718,424 B2 5/2010 Chiorini et al.
7,749,492 B2 7/2010 Bartlett et al.
7,777,097 B2 8/2010 Glazebrook et al.
7,790,449 B2 9/2010 Gao et al.
7,867,484 B2 * 1/2011 Samulski ........... A61K 48/0091 424/93.2
7,892,809 B2 * 2/2011 Bowles .................. C12N 15/86 435/235.1
7,906,111 B2 3/2011 Wilson et al.
8,067,014 B2 11/2011 Kay et al.
8,299,321 B2 10/2012 Cao
8,318,480 B2 11/2012 Gao et al.
8,343,764 B2 1/2013 Abad et al.
8,628,966 B2 1/2014 Chatterjee et al.
8,664,475 B2 3/2014 Puzio et al.
8,679,837 B2 3/2014 Zolotukhin et al.
8,734,809 B2 5/2014 Gao et al.
8,802,440 B2 * 8/2014 Zhong ................ A61K 48/0091 435/456
8,906,387 B2 12/2014 Kay et al.
8,906,675 B2 12/2014 Gao et al.
8,927,514 B2 1/2015 Chatterjee et al.
8,952,217 B2 2/2015 Puzio et al.
8,962,332 B2 2/2015 Gao et al.
9,012,224 B2 * 4/2015 Bowles .................. C12N 15/86 435/235.1
9,157,098 B2 * 10/2015 Zhong ................ A61K 48/0091
9,409,953 B2 * 8/2016 Asokan ................ C07K 14/005
9,441,244 B2 9/2016 Schaffer et al.
9,475,845 B2 * 10/2016 Asokan ................ C07K 14/005
9,567,376 B2 2/2017 Cronin et al.
9,585,971 B2 3/2017 Deverman et al.
9,587,250 B2 3/2017 Gao et al.
9,611,302 B2 * 4/2017 Srivastava ........... C07K 14/005
9,623,120 B2 4/2017 Chatterjee et al.
9,677,088 B2 6/2017 Nakai et al.
9,677,089 B2 6/2017 Gao et al.
9,695,220 B2 7/2017 Vandenberghe et al.
9,719,070 B2 8/2017 Vandenberghe et al.
9,725,485 B2 * 8/2017 Srivastava ........... C07K 14/005
9,737,619 B2 8/2017 Ansell et al.
9,775,918 B2 * 10/2017 Zhong ................ A61K 48/0091
9,777,291 B2 10/2017 Chatterjee et al.
9,783,825 B2 10/2017 Chatterjee et al.
9,790,472 B2 10/2017 Gao et al.
9,803,218 B2 10/2017 Chatterjee et al.
9,834,789 B2 12/2017 Chatterjee et al.
9,839,696 B2 12/2017 Chatterjee et al.
9,879,275 B2 1/2018 Nadzan et al.
9,890,396 B2 2/2018 Chatterjee et al.
9,909,142 B2 3/2018 Yazicioglu et al.
9,920,097 B2 * 3/2018 Zhong ................ A61K 48/0091
9,944,908 B2 4/2018 Vateen et al.
9,976,157 B2 5/2018 Poraty-Gavra et al.
10,011,640 B2 * 7/2018 Srivastava ........... C07K 14/005
10,072,251 B2 9/2018 Gao et al.
10,077,291 B2 * 9/2018 Asokan ................ C07K 14/005
10,081,659 B2 * 9/2018 Chiorini ............... C07K 14/005
10,119,125 B2 11/2018 Vandenberghe et al.
10,214,566 B2 2/2019 Schaffer et al.
10,369,193 B2 8/2019 Passini et al.
10,385,320 B2 8/2019 Kay et al.
10,392,632 B2 8/2019 Wright et al.
10,406,244 B2 9/2019 Kay et al.
10,414,803 B2 9/2019 Nathwani et al.
10,426,844 B2 10/2019 Agbandje-McKenna et al.
2003/0017131 A1 1/2003 Park et al.
2003/0053990 A1 3/2003 Rabinowitz et al.
2003/0063990 A1 3/2003 Rabinowitz et al.
2004/0013645 A1 1/2004 Monahan et al.
2004/0031072 A1 2/2004 La Rosa et al.
2004/0214272 A1 10/2004 La Rosa et al.
2005/0287122 A1 12/2005 Bartlett et al.
2006/0107345 A1 5/2006 Alexandrov et al.
2006/0123505 A1 6/2006 Kikuchi et al.
2006/0236419 A1 10/2006 La Rosa et al.
2007/0124833 A1 5/2007 Abad et al.
2007/0196338 A1 * 8/2007 Samulski ........... A61K 48/0091 424/93.2
2007/0243526 A1 10/2007 Kay et al.
2008/0229439 A1 9/2008 La Rosa et al.
2009/0215879 A1 8/2009 Diprimio et al.
2009/0275107 A1 11/2009 Lock et al.
2010/0037352 A1 2/2010 Alexandrov et al.
2010/0047174 A1 2/2010 Kay et al.
2011/0061124 A1 3/2011 Nadzan et al.
2011/0067143 A2 3/2011 La Rosa et al.
2011/0131679 A2 6/2011 La Rosa et al.
2011/0209246 A1 8/2011 Kovalic et al.
2011/0214206 A1 9/2011 La Rosa et al.
2011/0236353 A1 9/2011 Wilson et al.
2011/0294218 A1 12/2011 Chatterjee et al.
2012/0009268 A1 * 1/2012 Asokan ................ C07K 14/005 424/499
2012/0137379 A1 5/2012 Gao et al.
2012/0216318 A1 8/2012 La Rosa et al.
2012/0255046 A1 10/2012 Kay et al.
2013/0096182 A1 4/2013 Chatterjee
2013/0152224 A1 6/2013 Abad et al.
2013/0185831 A1 7/2013 Kovalic et al.
2013/0195801 A1 8/2013 Gao et al.
2013/0203841 A1 * 8/2013 Zhong ................ A61K 48/0091 514/44 R
2013/0216501 A1 * 8/2013 Zhong ................ A61K 48/0091 424/93.2
2013/0224836 A1 8/2013 Muramatsu
2013/0326723 A1 12/2013 La Rosa et al.
2014/0037585 A1 2/2014 Wright et al.
2014/0050701 A1 2/2014 Zhong et al.
2014/0056854 A1 * 2/2014 Asokan ................ C07K 14/005 424/93.6
2014/0130203 A1 5/2014 La Rosa et al.
2014/0162319 A2 6/2014 Hareendran et al.
2014/0199313 A1 7/2014 Plesch et al.
2014/0223605 A1 8/2014 Puzio et al.
2014/0259218 A1 9/2014 Kovalic et al.
2014/0296486 A1 10/2014 Gao et al.
2014/0335054 A1 11/2014 Gao et al.
2014/0341852 A1 * 11/2014 Srivastava ........... C07K 14/005 424/93.2
2015/0079038 A1 3/2015 Deverman et al.
2015/0082481 A1 3/2015 La Rosa et al.
2015/0126588 A1 5/2015 Nakai et al.
2015/0133530 A1 * 5/2015 Srivastava ........... C07K 14/005 514/44 R
2015/0184189 A1 7/2015 Abad et al.
2015/0191739 A1 7/2015 La Rosa et al.
2015/0197763 A1 7/2015 La Rosa et al.
2015/0344911 A1 12/2015 Chatterjee et al.
2016/0017295 A1 1/2016 Schaffer et al.
2016/0106865 A1 * 4/2016 Zhong ................ A61K 48/0091 424/93.2
2016/0215024 A1 7/2016 Vandenberghe et al.
2016/0222067 A1 8/2016 Gao et al.
2016/0264984 A1 9/2016 La Rosa et al.
2016/0289275 A1 10/2016 Chiorini et al.
2016/0319294 A1 11/2016 Kovalic et al.
2016/0333372 A1 11/2016 Srivastava et al.
2016/0361439 A1 12/2016 Agbandje-Mckenna et al.
2016/0369299 A1 12/2016 Boye et al.
2017/0007720 A1 1/2017 Boye et al.
2017/0028082 A1 2/2017 Wilson et al.
2017/0049910 A1 2/2017 Cronin et al.
2017/0067908 A1 3/2017 Nakai et al.

(56) References Cited

U.S. PATENT DOCUMENTS

2017/0088852 A1 3/2017 Dangoor et al.
2017/0088858 A1 3/2017 Gao et al.
2017/0096683 A1 4/2017 Scaria et al.
2017/0130245 A1 5/2017 Kotin et al.
2017/0159027 A1 6/2017 Wilson et al.
2017/0204144 A1 7/2017 Deverman et al.
2017/0211092 A1 7/2017 Chatterjee et al.
2017/0211093 A1 7/2017 Chatterjee et al.
2017/0211094 A1 7/2017 Chatterjee et al.
2017/0211095 A1 7/2017 Chatterjee et al.
2017/0240885 A1 8/2017 Deverman et al.
2017/0275337 A1* 9/2017 Srivastava ........... C07K 14/005
2017/0298323 A1 10/2017 Vandenberghe et al.
2017/0349911 A1 12/2017 Gao et al.
2018/0002722 A1 1/2018 Asokan et al.
2018/0030096 A1* 2/2018 Aslanidi .............. C07K 14/005
2018/0030479 A1 2/2018 Gao et al.
2018/0036428 A1* 2/2018 Zhong ................ A61K 48/0091
2018/0066022 A1 3/2018 Chalberg et al.
2018/0066285 A1 3/2018 Ojala et al.
2018/0105559 A1* 4/2018 Srivastava ........... C07K 14/005
2018/0112229 A1 4/2018 Nadzan et al.
2018/0119167 A1 5/2018 Abad et al.
2018/0135074 A1* 5/2018 Srivastava ........... C07K 14/805
2018/0135076 A1 5/2018 Linden
2018/0163227 A1 6/2018 Chatterjee et al.
2018/0214576 A1 8/2018 Fitzgerald et al.
2018/0244727 A1* 8/2018 Zhong ................ A61K 48/0091
2018/0265863 A1 9/2018 Esteves et al.
2018/0355376 A1 12/2018 Chiorini et al.
2018/0362592 A1 12/2018 Gao et al.
2018/0371024 A1 12/2018 Asokan et al.
2019/0055524 A1 2/2019 Vandenberghe et al.
2019/0085301 A1 3/2019 Gao et al.
2019/0100560 A1 4/2019 Vandenberghe et al.
2019/0249195 A1 8/2019 Marsic et al.
2019/0255192 A1 8/2019 Kirn et al.
2019/0262373 A1 8/2019 Woodard et al.
2019/0284576 A1 9/2019 Qu et al.
2019/0292561 A1 9/2019 Qu et al.
2019/0367562 A1 12/2019 Asokan et al.

FOREIGN PATENT DOCUMENTS

EP 1887081 A2 2/2008
EP 2194140 A2 6/2010
EP 2359869 A2 8/2011
EP 2492347 A1 8/2012
EP 2660325 A2 11/2013
EP 2847337 A1 3/2015
EP 2315833 B1 4/2015
EP 1453547 B1 9/2016
EP 2007795 B1 11/2016
EP 2206728 B9 3/2018
EP 2675484 B1 5/2018
EP 2263692 B1 9/2018
EP 3244931 B1 10/2018
EP 1633767 B1 11/2018
EP 3060575 B1 12/2018
EP 3250239 B1 12/2018
EP 3459965 A1 3/2019
EP 3511021 A1 7/2019
EP 3108000 B1 8/2019
RU 2 457 252 C2 7/2012
WO WO 90/05142 A1 5/1990
WO WO 98/11244 A2 3/1998
WO WO 99/61601 A2 12/1999
WO WO 00/02806 A1 1/2000
WO WO 00/17377 A2 3/2000
WO WO-2000/023477 A2 4/2000
WO 00/28004 5/2000
WO WO-2001/11034 A2 2/2001
WO WO-2001/081581 A2 11/2001
WO 01/92551 12/2001
WO WO-2002010210 A2 2/2002
WO WO-2003/000906 A2 1/2003
WO WO-2003/008540 A2 1/2003
WO WO-2003/033515 A1 4/2003
WO WO-2003/042361 A2 5/2003
WO WO-2003/052051 A2 6/2003
WO WO 03/095647 A2 11/2003
WO WO 2013/190059 A1 12/2003
WO WO 2004/027019 A2 4/2004
WO WO 2006/021724 A2 3/2006
WO WO 2006/029319 A2 3/2006
WO WO 2006/066066 A2 6/2006
WO WO 2006/073052 A1 7/2006
WO WO 2006/119137 A1 11/2006
WO WO-2007/084773 A2 7/2007
WO WO-2007/089632 A2 8/2007
WO WO 2007/100465 A2 9/2007
WO WO-2007/120542 A2 10/2007
WO WO-2007/127264 A2 11/2007
WO WO-2009/037279 A1 3/2009
WO WO-2009/105612 A2 8/2009
WO WO 2009/108274 A2 9/2009
WO WO-2010/129021 A1 11/2010
WO WO-2010/138263 A2 12/2010
WO WO-2011/020710 A2 2/2011
WO WO-2011/122950 A1 10/2011
WO WO-2012/112578 A2 8/2012
WO WO-2013/027223 A2 2/2013
WO WO-2013/158879 A1 10/2013
WO WO-2013/170078 A1 11/2013
WO WO-2013/173512 A2 11/2013
WO WO-2014/124282 A1 8/2014
WO WO-2014/193716 A2 12/2014
WO WO 2014/194132 A1 12/2014
WO WO-2015/013313 A2 1/2015
WO 2015121501 8/2015
WO WO-2015/164757 A1 10/2015
WO WO-2015/168666 A2 11/2015
WO WO 2015/181823 A1 12/2015
WO WO 2015/191508 A1 12/2015
WO WO 2016/054557 A1 4/2016
WO WO-2016/065001 A1 4/2016
WO WO-2016/081811 A1 5/2016
WO WO 2016/081811 A1 5/2016
WO WO 2016/115382 A1 7/2016
WO WO 2016/134338 A1 8/2016
WO WO 2016/164642 A1 10/2016
WO WO-2016/172008 A1 10/2016
WO WO 2016/179644 A1 11/2016
WO WO 2017/015102 A1 1/2017
WO WO 2017/066764 A2 4/2017
WO WO-2017/070516 A1 4/2017
WO WO 2017/096164 A1 6/2017
WO WO-2017/106236 A1 6/2017
WO WO 2017/143100 A1 8/2017
WO WO-2017/147123 A1 8/2017
WO WO-2017139643 A1 8/2017
WO WO 2017/180854 A1 10/2017
WO WO 2017/192750 A1 11/2017
WO WO 2017/201248 A1 11/2017
WO WO 2018/022608 A2 2/2018
WO WO-2018/035213 A1 2/2018
WO WO 2018/035213 A1 2/2018
WO WO-2018/064624 A1 4/2018
WO WO 2018/064624 A1 4/2018
WO WO-2018/075798 A1 4/2018
WO WO 2018/119330 A2 6/2018
WO WO 2018/152333 8/2018
WO WO 2018/160582 A1 9/2018
WO WO 2018/170310 A1 9/2018
WO WO 2018/209154 A1 11/2018
WO WO 2018/237066 12/2018
WO WO 2019/006418 A2 1/2019
WO WO 2019/141765 A1 7/2019
WO WO 2019/168961 A1 9/2019
WO WO 2019/169004 A1 9/2019
WO WO 2019/169132 9/2019
WO WO 2019/173434 A1 9/2019
WO WO 2019/173538 A1 9/2019
WO WO 2019/178412 A1 9/2019

(56) References Cited

FOREIGN PATENT DOCUMENTS

| | | | |
|---|---|---|---|
| WO | WO 2019/195423 | A1 | 10/2019 |
| WO | WO 2019/195444 | A1 | 10/2019 |
| WO | WO 2019/195449 | A1 | 10/2019 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14.*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.*

Gurda BL, Raupp C, Popa-Wagner R, Naumer M, Olson NH, Ng R, McKenna R, Baker TS, Kleinschmidt JA, Agbandje-McKenna M. Mapping a neutralizing epitope onto the capsid of adeno-associated virus serotype 8. J Virol. Aug. 2012;86(15):7739-51. doi: 10.1128/JVI.00218-12. Epub May 16, 2012.*

International Search Report and the Written Opinion of the International Searching Authority corresponding to International Patent Application No. PCT/US2016/054143 (34 pages) (dated Mar. 23, 2017).

Askoan et al. "Adeno-Associated Virus Type 2 Contains an Integrin a5β1 Binding Domain Essential for Viral Cell Entry" Journal of Virology, 80(18):8961-8969 (2006).

Chao et al. "Several Log Increase in Therapeutic Transgene Delivery by Distinct Adeno-Associated Viral Serotype Vectors" Molecular Therapy, 2(6):619-623 (2000).

Diprimio et al. "Surface Loop Dynamics in Adeno-Associated Virus Capsid Assembly" Journal of Virology, 82(11):5178-5189 (2008).

Gurda et al. "Capsid Antibodies to Different Adeno-Associated Virus Serotypes Bind Common Regions" Journal of Virology, 87(16):9111-9124 (2013).

Huang et al. "Characterization of the Adeno-Associated Virus 1 and 6 Sialic Acid Binding Site" Journal of Virology, 90(11):5219-5230 (2016).

International Preliminary Report on Patentability corresponding to International Patent Application No. PCT/US2016/054143 (21 pages) (dated Apr. 3, 2018).

Li et al. "Engineering and Selection of Shuffled AAV Genomes: A New Strategy for Producing Targeted Biological Nanoparticles" Molecular Therapy, 16(7):1252-1260 (2008).

Li et al. "Single Amino Acid Modification of Adeno-Associated Virus Capsid Changes Transduction and Humoral Immune Profiles" Journal of Virology, 86(15):7752-7759 (2012).

Li et al. "Development of Patient-specific AAV Vectors After Neutralizing Antibody Selection for Enhanced Muscle Gene Transfer" Molecular Therapy, 24(1):53-65 (2016).

Pulicherla et al. "Engineering Liver-detargeted AAV9 Vectors for Cardiac and Musculoskeletal Gene Transfer" Molecular Therapy, 19(6):1070-1078 (2011).

Shen et al. "Engraftment of a Galactose Receptor Footprint onto Adeno-associated Viral Capsids Improves Transduction Efficiency" The Journal of Biological Chemistry, 288(40):28814-28823 (2013).

Tellez et al. "Characterization of Naturally-Occurring Humoral Immunity to AAV in Sheep" PLoS ONE, 8(9):e75142 (2013).

Tse et al. "Structure-guided evolution of antigenically distinct adeno-associated virus variants for immune invasion" Proceedings of the National Academy of Sciences, 114(24):E4812-E4821 (2017).

Tseng et al. "Mapping the AAV capsid host antibody response toward the development of second generation gene delivery vectors" Frontiers in Immunology, 5(9):1-11 (2014).

Tseng et al. "Adeno-Associated Virus Serotype 1 (AAV1)- and AAV5-Antibody Complex Structures Reveal Evolutionary Commonalities in Parvovirus Antigenic Reactivity" Journal of Virology, 89(3):1794-1808 (2015).

Tseng et al. "Generation and characterization of anti-Adeno-associated virus serotype 8 (AAV8) and anti-AAV9 monoclonal antibodies" Journal of Virological Methods, 236:105-110 (2016).

Smith et al. "Characterizing the Antigenic Structure of Neutropic Adeno-associated Virus 9" American Society for Virology, 34th Annual Meeting, Jul. 11-15, 2015, Abstract # W31-7.

Huang et al. "Characterizing of the AAV1 and AAV6 sialic acid binding site" American Society for Virology, 34th Annual Meeting, Jul. 11-15, 2015, Abstract # W54-2.

Huang et al. "Determine essential receptor binding residues and antigenic epitope for AAV1" Poster presented at the 15th Biennial International Parvovirus Workshop, University of Bordeaux, France, Jun. 22-26, 2014, Abstract P-6.

Tseng et al. "Adeno-associated virus serotype 1 and 5 capsid—antibody structures reveal evolutionary commonalities in parvovirus antigenic reactivity" Poster presented at the 15th Biennial International Parvovirus Workshop, Jun. 22-26, 2014, University of Bordeaux, France, Abstract P-24.

Wu et al. "alpha2,3 and alpha2,6 N-Linked Sialic Acids Facilitate Efficient Binding and Transduction by Adeno-Associated Virus Types 1 and 6" Journal of Virology, 80(18):9093-9103 (2006).

Bell et al. "Identification of the Galactose Binding Domain of the Adeno-Associated Virus Serotype 9 Capsid" Journal of Virology, 86(13):7326-7333 (2012).

Xiao et al. "Interpretation of Electron Density with Stereographic Roadmap Projections" Journal of Structural Biology, 158(2):182-187 (2007).

Huang et al. "Characterizing of the AAV1 and AAV6 sialic acid binding site" Oral presentation, American Society for Virology, 34th Annual Meeting, Ontario, Canada, Jul. 14, 2015 (13 pages).

Smith et al. "Characterizing the Antigenic Structure of Neutropic Adeno-associated Virus 9" Oral presentation, American Society for Virology, 34th Annual Meeting, Ontario, Canada, Jul. 11-15, 2015 (16 pages).

Summerford et al. "Membrane-Associated Heparan Sulfate Proteoglycan is a Receptor for Adeno-Associated Virus Type 2 Virions" Journal of Virology, 72(2):1438-1445 (1998).

Ng et al. "Structural Characterization of the Dual Glycan Binding Adeno-Associated Virus Serotype 6" Journal of Virology, 84(24):12945-12957 (2010).

Wu et al. "Single Amino Acid Changes Can Influence Titer, Heparin Binding, and Tissue Tropism in Different Adeno-Associated Virus Serotypes" Journal of Virology, 80(22):11393-11397 (2006).

Dimattia et al. "Structural Insight into the Unique Properties of Adeno-Associated Virus Serotype 9" Journal of Virology, 86(12):6947-6958 (2012).

Foust et al. "Intravascular AAV9 preferentially targets neonatal neurons and adult astrocytes" Nature Biotechnology, 27(1):59-65 (2009).

Asuri et al. "Directed Evolution of Adeno-associated Virus for Enhanced Gene Delivery and Gene Targeting in Human Pluripotent Stem Cells" Molecular Therapy, 20(2):329-338 (2012).

Adachi et al. "Drawing a high-resolution functional map of adeno-associated virus capsid by massively parallel sequencing" Nature Communications, 5(3075):1-14 (2014).

Partial supplementary European search report corresponding to European patent application No. 16852471.8 (17 pages) (dated Apr. 24, 2019).

Extended European Search Report issued by the European Patent Office for Application No. 16852471.8, dated Jul. 29, 2019, 13 pages.

Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12).1072-1082 (2013).

Smith et al., "Structural Mapping of AAV9 Antigenic Sites and the Engineering of Immune Escape Variants," Molecular Therapy; 20th Annual Meeting of the American Society of Gene and Cell Therapy (ASGCT).; Washington, DC, USA; May 10-13, 2017, Nature Publishing Group, GB vol. 25, No. 5, Suppl 1 (2017).

Mingozzi et al., "Overcoming the Host Immune Response to Adeno-Associated Virus Gene Delivery Vectors: The Race Between

(56) References Cited

OTHER PUBLICATIONS

Clearance, Tolerance, Neutralization, and Escape," Annual Review of Virology 1(1).:511-534 (2017) (Abstract only).
Chirmule et al., "Humoral immunity to adeno-associated virus type 2 vectors following administration to murine and nonhuman primate muscle," Journal of Virology, The American Society for Microbiology, US, 74(5):2420-2425 (2000).
Lisowski et al., "Selection and evaluation of clinically relevant AAV variants in a xenograft liver model," Nature 506(7488).:A73382-386 (2014).
Grimm et al., "In vitro and in vivo gene therapy vector evolution via multispecies interbreeding and retargeting of adeno-associated viruses," Journal of Virology, The American Society for Microbiology, US 82(12).:5887-5911 (2008).
Exam Report No. 1 issued by the Australian Patent Office for Application No. 2016206624, dated Jul. 24, 2019, 2 pages.
International Search Report and Written Opinion issued by the International Searching Authority for Application No. PCT/US2016/013460, dated May 12, 2016, 11 pages.
International Search Report and the Written Opinion of the International Searching Authority corresponding to International Patent Application No. PCT/US2018/018381 (14 pages) (dated Jul. 5, 2018).
Shen et al., Multiple Roles for Sialylated Glycans in Determining the Cardiopulmonary Tropism of Adeno-Associated Virus 4, Journal of Virology 87(24).:13206-13213 (2013).
Extended European Search Report corresponding to European Patent Application No. 16737901.5 (6 pages). (dated May 15, 2018).
Huang et al. "Parvovirus qlycan interactions" Current Opinion in Virology 7:108-118 (2014).
Murlidharan et al. "265. Polysialic Acid as a Novel Regulator of AAV Tropism in the Developing Brain" Molecular Therapy 23(Supplement 1).:S106 (2015), 1 page.
Murlidharan et al. "Unique Glycan Signatures Regulate Adeno-Associated Virus Tropism in the Developing Brain" Journal of Virology 89(7).:3976-3987 (2015).
Agbandje et al. "The Structure of Human Parvovirus B19 at 8 A; Resolution." Virology 203(1).:106-115 (1994).
Altschul et al. "Basic Local Alignment Search Tool" Journal of Molecular Biology 215:403-410 (1990).
Altschul et al. "Local Alignment Statistics" Methods in Enzymology 266:460-480 (1996).
Altschul et al.,"Gapped BLAST and PSI-BLAST: a new generation of protein database search programs" Nucleic Acids Research 25(17).:3389-3402 (1997).
Andino et al. "AAV-mediated knockdown of phospholamban leads to improved contractility and calcium handling in cardiomyocytes" The Journal of Gene Medicine 10:132-142 (2008).
Bantel-Schaal et al. "Human Adeno-Associated Virus Type 5 is Only Distantly Related to Other Known Primate Helper-Dependent Parvoviruses" Journal of Virology 73(2).:939-947 (1999).
Brichard et al. "The Tyrosinase Gene Codes for an Antigen Recognized by Autologous Cytolytic T Lymphocytes on HLA-AZ Melanomas" Journal of Experimental Medicine178:489-495 (1993).
Brown et al. "Erythrocyte P Antigen: Cellular Receptor for B19 Parvovirus" Science 262(5130).:114-117 (1993).
Brown et al. "Chimeric Parvovirus β19 Capsids for the Presentation of Foreign Epitopes" Virology 198(2).:477-488 (1994).
Chapman et al. "Structure, Sequence, and Function Correlations among Parvoviruses" Virology 194(2).:491-508 (1993).
Chiorini et al. "Cloning of Adeno-Associated Virus Type 4 (AAV4) and Generation of Recombinant AAV4 Particles" Journal of Virology 71(9).:6823-6833 (1997).
Chiorini et al. "Cloning and Characterization of Adeno-Associated Virus Type 5" Journal of Virology 73(2).:1309-1319 (1999).
Chipman et al. "Cryo-electron microscopy studies of empty capsids of human parvovirus 819 complexed with its cellular receptor" Proceedings of the National Academy of Sciences 93:7502-7506 (1996).
Cleves, Ann E. "Protein transport: The nonclassical ins and outs" Current Biology 7:R318-R320 (1997).
Conway et al. "High-titer recombinant adeno-associated virus production utilizing a recombinant herpes simplex virus type 1 vector expressing AAV-2 Rep and Cap" Gene Therapy6:986-993 (1999).
Devereux et al. "A comprehensive set of sequence analysis programs for the VAX" Nucleic Acids Research 12(1).:387-395 (1984).
Fang et al. "Stable antibody expression at therapeutic levels using the 2A peptide" Nature Biotechnology 23:584-590(2005).
Ferrari et al. "New developments in the generation of Ad-free high-titer rAAV gene therapy vectors" Nature Medicine 3(11).:1295-1297 (1997).
Gao et al. "Novel adeno-associated viruses from rhesus monkeys as vectors for human gene therapy" Proceedings of the National Academy of Sciences 99(18):11854-11859 (2002).
Gao et al. "Clades of Adeno-Associated Viruses are Widely Disseminated in Human Tissues" Journal of Virology 78(12).:6381-6388 (2004).
GenBank Accession No. AF028704 "Adeno-associated virus 6, complete genome" NCBI (2 paqes). (Jan. 12, 1998).
GenBank Accession No. AF028705 "Adeno-associated virus 3B, complete genome" NCBI (2 pages). (Jan. 12, 1998).
GenBank Accession No. AF063497 "Adeno-associated virus 1, complete genome" NCBI (2 pages). (Apr. 27, 1999).
GenBank Accession No. AF288061 "Hamster parvovirus 5' terminal hairpin gene sequence" NCBI (1 page). (Apr. 13, 2001), replaced by AH009962.
GenBank Accession No. AF513851 "Adeno-associated virus 7 nonstructural protein and capsid protein genes, complete eds." NCBI (2 pages). (Sep. 5, 2002).
GenBank Accession No. AF513852 "Adeno-associated virus 8 nonstructural protein and capsid protein genes, complete eds" NCBI (2 pages). (Sep. 5, 2002).
GenBank Accession No. AF043303 "Adeno-Associated virus 2, complete genome" NCBJ (4 pages). (May 20, 2010).
GenBank Accession No. AH009962 "Hamster parvovirus" NCBI (1 page). (Aug. 25, 2016), replaced AF288061.
GenBank Accession No. AY028223 "B19 virus isolate patient_A.1.1 genomic sequence" NCBI (1 page). (Apr. 16, 2001).
GenBank Accession No. AY028226 "819 virus isolate patient_A.2.1 genomic sequence" NCB/ (1 page). (Apr. 16, 2001).
GenBank Accession No. AY530579 "Adeno-associated virus 9 isolate hu.14 capsid protein VP1 (cap). gene, complete eds" NCBI (2 pages). (Jun. 24, 2004).
GenBank Accession No. J00306 "Human somatostatin I gene and flanks" NCBJ (2 pages). (Jan. 13, 1995).
GenBank Accession No. J01901 "Adeno-associated virus 2, complete genome" NCBJ (3 paqes). (Apr. 27, 1993).
GenBank Accession No. J02275 "Minute virus of mice, complete genome" NCBJ (4 pages). (May 22, 1995).
GenBank Accession No. NC_001862 "Adeno-associated virus 6, complete genome" NCBJ (3 pages). (Jan. 12, 2004).
GenBank Accession No. NC_001863 "Adeno-associated virus 38, complete genome" NCB/ (3 pages). (Jan. 12, 2014).
GenBank Accession No. NC_006152 "Adeno-associated virus 5, complete genome" NCBI (3 pages). (Dec. 8, 2008).
GenBankAccession No. NC_001540 "Bovine parvovirus, complete genome" NCBI (4 paqes). (Nov. 30, 2009).
GenBank Accession No. NC_001701 "Goose parvovirus, complete genome" NCBI (4 pages). (Jan. 28, 2010).
GenBank Accession No. NC_001829 "Adeno-associated virus-4, complete genome" NCBI (3 pages). (Jan. 28, 2010).
GenBank Accession No. NC_002077 "Adeno-associated virus-1, complete genome" NCBI (3 pages). (Mar. 11, 2010).
GenBank Accession No. NC_006261 "Adeno-associated virus-8, complete genome" NCBI (3 pages). (Mar. 11, 2010).
GenBank Accession No. NC_001729 "Adeno-associated virus-3, complete genome" NCBI (3 pages). (Jun. 28, 2010).
GenBank Accession No. NC_001401 "Adeno-associated virus-2, complete genome" NCBI (5 pages). (Dec. 2, 2014).
GenBank Accession No. NC_000883 "Human parvovirus 819, complete genome" NCBI (4 pages). (Feb. 10, 2015).

(56) References Cited

OTHER PUBLICATIONS

GenBank Accession No. NC_001358 "Parvovirus H1, complete genome" NCBI (3 pages). (Feb. 10, 2015).
GenBank Accession No. NC_001510 "Minute virus of mice, complete genome" NCBI (5 pages). (Mar. 28, 2016).
GenBank Accession No. NP_044927 "capsid [Adeno-associated virus-4]" NCBI (2 pages). (Jan. 28, 2010).
GenBank Accession No. P01166 "Somatostatin precursor [Contains:Somatostatin 28; Somatostatin-14]" NCBI (2 pages). (Sep. 15, 2003).
GenBank Accession No. P61278 "Somatostatin precursor [Contains:Somatostatin 28; Somatostatin-14]" NCBI (4 pages). (Nov. 13, 2019).
GenBank Accession No. U89790 "Adeno-associated virus 4, complete genome" NCBI (3 pages). (Aug. 21, 1997).
GenBank Accession No. X01457 "Parvovirus h-1, complete genome" NCBI (3 pages). (Apr. 18, 2005).
Gorman et al. "Stable alteration of pre-mRNA splicing patterns by modified U7 small nuclear RNAs" Proceedings of the National Academy of Sciences 95:4929:4934 (1998).
Gregorevic et al. "Systemic Microdystrophin Gene Delivery Improves Skeletal Muscle Structure and Function in Old Dystrophic mdx Mice" Molecular Therapy 16(4).:657-664 (2008).
Grifman et al. "Incorporation of Tumor-Targeting Peptides into Recombinant Adeno-Associated Virus Capsids" Molecular Therapy 3(6).:964-975 (2001).
Hauck et al. "Characterization of Tissue Tropism Determinants of Adeno-Associated Virus Type 1" Journal of Virology 77(4).:2768-2774 (2003).
Hoshijima et al. "Chronic suppression of heart-failure progression by a pseudophosphorylated mutant of phospholamban via in vivo cardiac rAAV gene delivery" Nature Medicine 8:864-871 (2002).
International Preliminary Report on Patentability corresponding to International Patent Application No. PCT/US2016/013460 (8 pages) (dated Jul. 27, 2017).
Karlin et al. "Applications and statistics for multiple high-scoring segments in molecular sequences" Proceedings of National Academy of Sciences 90:5873-5877 (1993).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).
Kawakami et al. "Cloning of the gene coding for a shared human melanoma antigen recognized by autologous T cells infiltrating into tumor" Proceedings of the National Academy of Sciences 91:3515-3519 (1994).
Levine et al. "The Tumor Suppressor Genes" Annual Review of Biochemistry 62:623-651 (1993).
Li et al. "Construction of phospholamban antisense RNA recombinant adeno-associated virus vector and its effects in rat cardiomyocytes" Acta Pharmalogica Sinica 26(1).51-55 (2005).
Margolskee, R. F. "Epstein-Barr Virus Based Expression Vectors" Current Topics in Microbiology and Immunology 158:67-95 (1992).
Miyamura et al. "Parvovirus particles at platforms for protein presentation" Proceedings of National Academy of Sciences 91:8507-8511 (1995).
Mori et al. "Two novel adeno-associated viruses from cynomolgus monkey:pseudotyping characterization of capsid protein" Virology 330:375-383 (2004).
Muramatsu et al. "Nucleotide Sequencing and Generation of an Infectious Clone of Adeno-Associated Virus 3" Virology 22(0367).:208-217 (1996).
Muzyczka, N. "Use of Adeno-Associated Virus as a General Transduction Vector for Mammalian Cells" Current Topics in Microbiology and Immunology 158:97-129 (1992).
Needleman et al. "A General Method Applicable to the Search for Similarities in the Amino Acid Sequence of Two Proteins" Journal of Molecular Biology 48(3).:443-453 (1970).
Padron et al. "Structure of Adeno-Associated Virus Type 4" Journal of Virology 79(8).:5047-5058 (2005).
Palombo et al. "Site-Specific Integration in Mammalian Cells Mediated by a New Hybrid Baculovirus-Adeno-Associated Virus Vector" Journal ofvirology72(6).:5025-5034 (1998).
Pearson et al. "Improved tools for biological sequence comparison" Proceedings of National Academy Sciences 85:2444-2448 (1988).
Puttaraju et al. "Spliceosome-mediated RNA trans-splicing as a tool for gene therapy" Nature Biotechnology 17:246-252 (1999).
Robbins et al. "Recognition of Tyrosinase by Tumor-infiltrating Lymphocytes from a Patient Responding to Immunotherapy" Cancer Research 54:3124-3126 (1994).
Rosenberg "The Immunotherapy of Solid Cancers Based on Cloning the Genes Encoding Tumor-Rejection Antigens" Annual Review of Medicine 47:481-491 (1996).
Rosenberg et al. "A New Era for Cancer Immunotherapy Based on the Genes that Encode Cancer Antigens" Immunity 10:281-287 (1999).
Shade et al. "Nucleotide Sequence and Genome Organization of Human Parvovirus B19 Isolated from the Serum of a Child during Aplastic Crisis" Journal of Virology 28(3):921-936 (1986).
Sharp et al. "RNA Interference" Science 287(5462):2431-2433 (2000).
Shi et al. "Insertional Mutagenesis at Positions 520 and 584 of Adeno-Associated Virus Type 2 (AAV2). Capsid Gene and Generation of AAV2 Vectors with Eliminated Heparin-Binding Ability and Introduced Novel Tropism" Human Gene Therapy 17:353-361 (2006).
Smith et al. "Comparison of Biosequences" Advances in Applied Mathematics 2:482-489 (1981).
Srivastava et al. "Nucleotide Sequence and Organization of the Adeno-Associated Virus 2 Genome" Journal of Virology 45(2):555-564 (1983).
Tinsley et al. "Amelioration of the dystrophic phenotype of mdx mice using a truncated utrophin transgene" Nature 384(6607):349-353 (1996).
Tsao et al. "The Three-Dimensional Structure of Canine Parvovirus and its Functional Implications" Science 251(5000):1456-1464 (1991).
Urabe et al. "Insect Cells as a Factory to Produce Adeno-Associated Virus Type 2 Vectors" Human Gene Therapy 13:1935-1943 (2002).
Vincent et al. "Long-term correction of mouse dystrophic degeneration by adenovirus-mediated transfer of a minidystrophin gene" Nature Genetics 5:130-134 (1993).
Walters et al. "Structure of Adeno-Associated Virus Serotype 5" Journal of Virology 78(7).:3361-3371 (2004).
Wang et al. "Adeno-associated virus vector carrying human minidystrophin genes effectively ameliorates muscular dystrophy in mdx mouse model" Proceedings of the National Academy of Sciences 97(25):13714-13719 (2000).
Wang et al. "Expanding the genetic code" *Annual Review of Biophysics and Biomolecular Structure* 35:225-249 (2006).
Xiao et al. "Gene Therapy Vectors Based on Adeno-Associated Virus Type 1" Journal of Virology 73(5).:3994-4003 (1999).
Xie et al. "Canine Parvovirus Capsid Structure, Analyzed at 2.9 A Resolution" Journal of Molecular Biology 264(3).:497-420 (1996).
Xie et al. "The atomic structure of adeno-associated virus (AAV-2)., a vector for human gene therapy" Proceeding of the National Academy of Sciences 99(16).:10405-1041O (2002).
Zhang et al. "Recombinant adenovirus expressing adeno-associated virus cap and rep proteins supports production of high-titer recombinant adeno-associated virus" Gene Therapy 8:704-712 (2001).
Zolotukhin et al. "Recombinant adeno-associated virus purification using novel methods improves infectious titer and yield" Gene Therapy6:973-985 (1999).
Office Action issued by the European Patent Office for Application No. 16737901.5, dated Sep. 23, 2019, 4 pages.
ACS on STN, BD Registry, 1182714-97-1 [online] [retrieved on Apr. 30, 2019], US2009215879, Aug. 27, 2009, SEQ ID No. 210.
SEQ ID No. 7 on p. 43 of U.S. Patent Publication No. US2009215879 (1 page) (published Aug. 27, 2009).
SEQ ID No. 210 on p. 80 of U.S. Patent Publication No. US2009215879 (1 page) (published Aug. 27, 2009).
DataBase GenBank: ABS91093.1, Aug. 10, 2007, [online] [retrieved on Feb. 14, 2020] Retrieved from Internet: https://www.ncbi.nlm.nih.gov/protein/ABS91093.1.

(56) References Cited

OTHER PUBLICATIONS

DataBase GenBank: ACW56705.1, Sep. 24, 2009, [online] [retrieved on May 7, 2019] Retrieved from Internet<https://www.ncbi.nlm.nih.gov/protein/ACW56705.1?report=genbank&log$=prottop&blast_rank=1&RID=D2CZ8TP9014>, 1 page.

* cited by examiner

| Common antigenic motifs chosen for library generation (Refer Table 5) | Number of randomized amino acids within the motif | Theoretical Diversities |
| --- | --- | --- |
| CAM4 | 4 | $1.60 \times 10^{5}$ |
| CAM5 | 7 | $1.28 \times 10^{9}$ |
| CAM8 | 8 | $2.56 \times 10^{10}$ |
| CAM9 | 9 | $5.12 \times 10^{11}$ |

Figure 7
ELISA (ADK1a antibody)
Ration to WT
0
0.2
0.4
0.6
0.8
1
1.2
1.4
1.6
1.8
2
AAV1-WT
AAV1-N447S
AAV1-S472R
AAV1-V473D
AAV1-N500E
AAV1-T502S
AAV1-W503A
AAV1e27
AAV1e28
AAV1e29

A.

B.

C.

METHODS AND COMPOSITIONS FOR ANTIBODY-EVADING VIRUS VECTORS

STATEMENT OF PRIORITY

This application is a 35 U.S.C. § 371 national phase application of International Application Serial No. PCT/US2016/054143, filed Sep. 28, 2016, which claims the benefit, under 35 U.S.C. § 119(e), of U.S. Provisional Application No. 62/234,016, filed Sep. 28, 2015, the entire contents of each of which are incorporated by reference herein.

STATEMENT OF GOVERNMENT SUPPORT

This invention was made with government funding under Grant Nos. HL112761, HL089221 and GM082946 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-752_ST25.txt, 344,842 bytes in size, generated on May 24, 2019 and filed via EFS-Web, is provided in lieu of a paper copy. This Sequence Listing is incorporated by reference into the specification for its disclosures.

FIELD OF THE INVENTION

The present invention relates to modified capsid proteins from adeno-associated virus (AAV) and virus capsids and virus vectors comprising the same. In particular, the invention relates to modified AAV capsid proteins and capsids comprising the same that can be incorporated into virus vectors to confer a phenotype of evasion of neutralizing antibodies without decreased transduction efficiency.

BACKGROUND OF THE INVENTION

Host-derived pre-existing antibodies generated upon natural encounter of AAV or recombinant AAV vectors prevent first time as well as repeat administration of AAV vectors as vaccines and/or for gene therapy. Serological studies reveal a high prevalence of antibodies in the human population worldwide with about 67% of people having antibodies against AAV1, 72% against AAV2, and about 40% against AAV5 through AAV9.

Furthermore, in gene therapy, certain clinical scenarios involving gene silencing or tissue degeneration may require multiple AAV vector administrations to sustain long term expression of the transgene. To circumvent these issues, recombinant AAV vectors which evade antibody recognition (AAVe) are required. This invention will help a) expand the eligible cohort of patients suitable for AAV-based gene therapy and b) allow multiple, repeat administrations of AAV-based gene therapy vectors.

The present invention overcomes previous shortcomings in the art by providing methods and compositions comprising an adeno-associated virus (AAV) capsid protein, comprising one or more amino acid substitutions, wherein the substitutions introduce into an AAV vector comprising these modified capsid proteins the ability to evade host antibodies.

SUMMARY OF THE INVENTION

In one aspect, the present invention provides an adeno-associated virus (AAV) capsid protein, comprising one or more amino acids substitutions, wherein the substitutions modify one or more previously existing antigenic sites on the AAV capsid protein.

In some embodiments, the amino acid substitutions are in antigenic footprints identified by peptide epitope mapping or cryo-electron microscopy studies of AAV-Antibody complexes containing capsids based on AAV1, AAV3, AAV4, AAV5, AAV6, AAV7, AAV 8, AAV9, AAV10, AAV11, AAV12, AAVrh8, AAVrh10, AAVrh32.33, Avian AAV or Bovine AAV.

In some embodiments, the modified antigenic site can prevent antibodies from binding or recognizing or neutralizing AAV capsids, wherein the antibody is an IgG (including IgG1, IgG2a, IgG2b, IgG3), IgM, IgE or IgA.

In some embodiments, the modified antigenic site can prevent binding or recognition or neutralization of AAV capsids by antibodies from different animal species, wherein the animal is human, canine, feline or equine.

In some embodiments, the modified antigenic site is a common antigenic motif, wherein a specific antibody or a cross-reactive antibody can bind, recognize or neutralize the AAV capsid.

In some embodiments, the substitutions introduce a modified antigenic site from a first AAV serotype into the capsid protein of a second AAV serotype that is different from said first AAV serotype.

The present invention also provides an AAV capsid comprising the AAV capsid protein of this invention. Further provided herein is a viral vector comprising the AAV capsid of this invention as well as a composition comprising the AAV capsid protein, AAV capsid and/or viral vector of this invention in a pharmaceutically acceptable carrier.

The present invention additionally provides a method of introducing a nucleic acid into a cell in the presence of antibodies against the AAV capsid, comprising contacting the cell with the viral vector of this invention. The cell can be in a subject and in some embodiments, the subject can be a human subject.

These and other aspects of the invention are addressed in more detail in the description of the invention set forth below.

BRIEF DESCRIPTION OF THE DRAWINGS

FIG. 2 discloses SEQ ID NO:494.

FIG. 13A discloses SEQ ID NOs:22, 23, 25, 483 and 527. FIG. 13B discloses SEQ ID NOs:485, 501 and 502. FIG. 13C discloses SEQ ID NOs:309, 486, 510. FIG. 13D discloses SEQ ID NOs:309 and 487. FIG. 13E discloses SEQ ID NOs:22-25, 483 and 495-500. FIG. 13F discloses SEQ ID NOs:485 and 501-509. FIG. 13G discloses SEQ ID NOs: 32, 37, 38 and 510-515. FIG. 13H discloses SEQ ID NOs:309-487 and 516-523.

FIG. 21 discloses SEQ ID NOs:534-527.

DETAILED DESCRIPTION OF THE INVENTION

Figure 1:
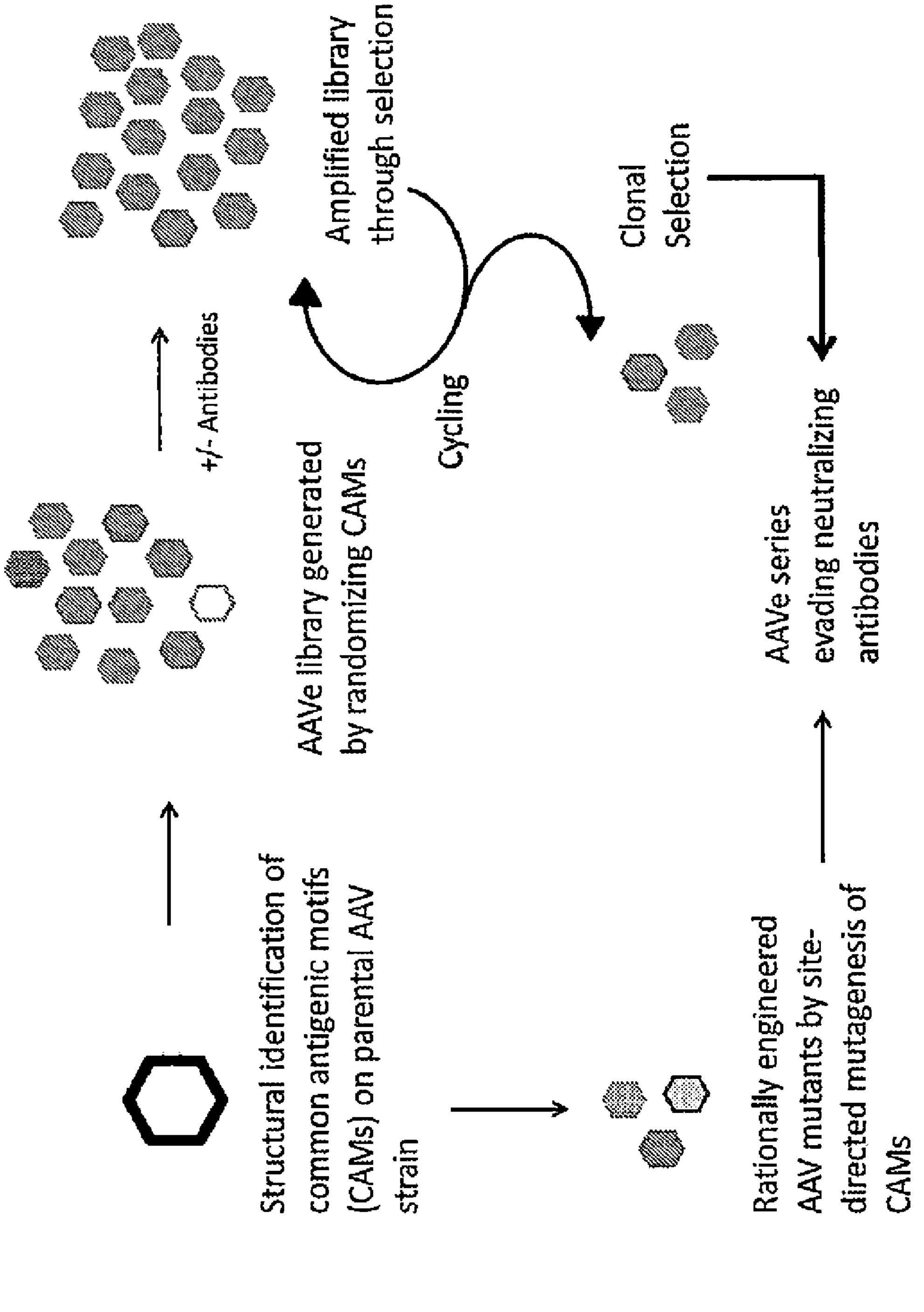
FIG. 1. Methods for generating AAVe strains through structural determination of common antigenic motifs (CAMs) listed in Table 5 and the generation of antibody evading AAV capsids (AAVe) by rational or combinatorial engineering of antigenic motifs followed by amplification and selection.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, GenBank accession numbers and other references mentioned herein are incorporated by reference herein in their entirety.

The designation of all amino acid positions in the AAV capsid proteins in the description of the invention and the appended claims is with respect to VP1 capsid subunit numbering. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 10%, 15%, 20%, 25%, 35%, 50%, 75%, 80%, 85%, 90%, 95%, 97% or more.

As used herein, the terms "enhance," "enhances," "enhancement" and similar terms indicate an increase of at least about 10%, 15%, 20%, 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Protoparvovirus, Erythroparvovirus, Bocaparvirus, and Densovirus subfamily. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers; Cotmore et al. Archives of Virology DOI 10.1007/s00705-013-1914-I).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, avian AAV, bovine AAV, canine AAV, equine AAV, ovine AAV, and any other AAV now known or later discovered. See, e.g., BERNARD N. FIELDS et al., *VIROLOGY*, volume 2, chapter 69 (4th ed., Lippincott-Raven Publishers). A number of AAV serotypes and clades have been identified (see, e.g., Gao et al., (2004) *J. Virology* 78:6381-6388; Moris et al., (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad Sci. USA* 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. The capsid structures of autonomous parvoviruses and AAV are described in more detail in BERNARD N. FIELDS et al., *VIROLOGY*, volume 2, chapters 69 & 70 (4th ed., Lippincott-Raven Publishers). See also, description of the crystal structure of AAV2 (Xie et al., (2002) *Proc. Nat. Acad Sci.* 99:10405-10), AAV9 (DiMattia et al., (2012) *J. Virol.* 86:6947-6958), AAV8 (Nam et al., (2007) *J. Virol.* 81:12260-12271), AAV6 (Ng et al., (2010) *J. Virol.* 84:12945-12957), AAV5 (Govindasamy et al., (2013) *J. Virol.* 87, 11187-11199), AAV4 (Govindasamy et al., (2006) *J. Virol.* 80:11556-11570), AAV3B (Lerch et al., (2010) *Virology* 403: 26-36), BPV (Kailasan et al., (2015) *J. Virol.* 89:2603-2614) and CPV (Xie et al., (1996) *J. Mol. Biol.* 6:497-520 and Tsao et al., (1991) *Science* 251: 1456-64).

TABLE 1

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |

TABLE 1-continued

| AAV Serotypes/Isolates | GenBank Accession Number |
|---|---|
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |

TABLE 1-continued

| AAV Serotypes/Isolates | GenBank Accession Number |
|---|---|
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the invention exhibits tropism for or transduces, respectively, tissues throughout the body (e.g., brain, lung, skeletal muscle, heart, liver, kidney and/or pancreas). In embodiments of the invention, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically).

Unless indicated otherwise, "efficient transduction" or "efficient tropism," or similar terms, can be determined by reference to a suitable control (e.g., at least about 50%, 60%, 70%, 80%, 85%, 90%, 95% or more of the transduction or tropism, respectively, of the control). In particular embodiments, the virus vector efficiently transduces or has efficient tropism for skeletal muscle, cardiac muscle, diaphragm muscle, pancreas (including n-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, the invention can be practiced to identify viral vectors of the invention that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the invention may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion.

Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) *Curr. Topics Microbiol.*

*Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, 12, 13 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2).

TABLE 2

| | Abbreviation | |
|---|---|---|
| Amino Acid Residue | Three-Letter Code | One-Letter Code |
| Alanine | Ala | A |
| Arginine | Arg | R |

TABLE 2-continued

| | Abbreviation | |
|---|---|---|
| Amino Acid Residue | Three-Letter Code | One-Letter Code |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |

TABLE 3-continued

| Modified Amino Acid Residue | Abbreviation |
|---|---|
| Phenylglycine | Phg |
| Beta-2-thienylalanine | Thi |

Further, the non-naturally occurring amino acid can be an "unnatural" amino acid as described by Wang et al., *Annu Rev Biophys Biomol Struct.* 35:225-49 (2006)). These unnatural amino acids can advantageously be used to chemically link molecules of interest to the AAV capsid protein.

Modified AAV Capsid Proteins and Virus Capsids and Virus Vectors Comprising the Same.

The present invention provides AAV capsid proteins (VP1, VP2 and/or VP3) comprising a modification (e.g., a substitution) in the amino acid sequence and virus capsids and virus vectors comprising the modified AAV capsid protein. The inventors have discovered that modifications of this invention can confer one or more desirable properties to virus vectors comprising the modified AAV capsid protein including without limitation, the ability to evade neutralizing antibodies. Thus, the present invention addresses some of the limitations associated with conventional AAV vectors.

Accordingly, in one aspect, the present invention provides an adeno-associated virus (AAV) capsid protein, comprising one or more amino acid substitutions, wherein the one or more substitutions modify one or more antigenic sites on the AAV capsid protein. The modification of the one or more antigenic sites results in inhibition of binding by an antibody to the one or more antigenic sites and/or inhibition of neutralization of infectivity of a virus particle comprising said AAV capsid protein. The one or more amino acid substitutions can be in one or more antigenic footprints identified by peptide epitope mapping and/or cryo-electron microscopy studies of AAV-antibody complexes containing AAV capsid proteins. In some embodiments, the one or more antigenic sites are common antigenic motifs or CAMs (see, e.g., Table 5). The capsid proteins of this invention are modified to produce an AAV capsid that is present in an AAV virus particle or AAV virus vector that has a phenotype of evading neutralizing antibodies. The AAV virus particle or vector of this invention can also have a phenotype of enhanced or maintained transduction efficiency in addition to the phenotype of evading neutralizing antibodies.

In some embodiments, the one or more substitutions of the one or more antigenic sites can introduce one or more antigenic sites from a capsid protein of a first AAV serotype into the capsid protein of a second AAV serotype that is different from said first AAV serotype.

The AAV capsid protein of this invention can be a capsid protein of an AAV serotype selected from AAV1, AAV2, AAV3, AAV3B, AAV4, AAV5, AAV6, AAV7, AAV8, AAV9, AAV10, AAV11, AAV12, AAVrh.8, AAVrh.10, AAVrh.32.33, bovine AAV, avian AAV or any other AAV now known or later identified.

Several examples of a modified AAV capsid protein of this invention are provided herein. In the following examples, the capsid protein can comprise the specific substitutions described and in some embodiments can comprise fewer or more substitutions than those described. For example in some embodiments, a capsid protein of this invention can comprise at least 1, 2, 3, 4, 5, 6, 7, 8, 9, 10, etc., substitutions.

Furthermore, in the embodiments described herein wherein an amino acid residue is substituted by any amino acid residue other than the amino acid residue present in the wild type or native amino acid sequence, said any other amino acid residue can be any natural or non-natural amino acid residue known in the art (see, e.g., Tables 2 and 3). In some embodiments, the substitution can be a conservative substitution and in some embodiments, the substitution can be a nonconservative substitution.

In some embodiments, the capsid protein of this invention can comprise a substitution at one or more (e.g., 2, 3, 4, 5, 6, or 7) of amino acid residues 262-268 of AAV1 (VP1 numbering; CAM1), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6, 7, 8, 9, or 10) of amino acid residues 370-379 of AAV1 (VP1 numbering; CAM 3), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6, 7, 8 or 9) of amino acid residues 451-459 of AAV1 (VP1 numbering; CAM 4-1), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2) of amino acid residues 472-473 of AAV1 (VP1 numbering; CAM 4-2) or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6, 7, or 8) of amino acid residues 493-500 of AAV1 (VP1 numbering; CAM 5), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6, or 7) of amino acid residues 528-534 of AAV1 (VP1 numbering; CAM 6), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, or 6) of amino acid residues 547-552 of AAV1 (VP1 numbering; CAM 7), in any combination, or the equivalent amino acid residues in AAV2, AAV3, AAV4, AAV5, AAV6, AAV7, AAV8, AAV9, AAV10, AAV1, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6, 7, 8, 9 or 10) of amino acid residues 588-597 of AAV1 (VP1 numbering; CAM 8), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2) of amino acid residues 709-710 of AAV1 (VP1 numbering; CAM 9-1), or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In some embodiments, the capsid protein of this invention can comprise a substitution at one or more (e.g., 2, 3, 4, 5, 6 or 7) of amino acid residues 716-722 of AAV1 (VP1 numbering; CAM 9-2), in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV.

In particular embodiments of this invention, an adeno-associated virus (AAV) capsid protein is provided herein, wherein the capsid protein comprises one or more substitution at all positions or in any combination of fewer than all positions, resulting in the amino acid sequence: $X^1$-$X^2$-$X^3$-$X^4$-$X^5$-$X^6$-$X^7$ (SEQ ID NO:18) at the amino acids corresponding to amino acid positions 262 to 268 (VP1 numbering) of the native AAV1 capsid protein, wherein $X^1$ is any amino acid other than S; wherein $X^2$ is any amino acid other than A; wherein $X^3$ is any amino acid other than S; wherein $X^4$ is any amino acid other than T; wherein $X^5$ is any amino acid other than G; wherein $X^6$ is any amino acid other than A; and wherein $X^7$ is any amino acid other than S. In embodiments wherein any of $X^1$ through $X^7$ is not substituted, the amino acid residue at the unsubstituted position is the wild type amino acid residue.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9X^{10}$ (SEQ ID NO:19) at the amino acids corresponding to amino acid positions 370 to 379 (VP1 numbering) of the native AAV1 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$ (SEQ ID NO:20) at the amino acids corresponding to amino acid positions 451 to 459 (VP1 numbering) of the native AAV1 capsid protein, wherein $X^1$ is any amino acid other than N; wherein $X^2$ is any amino acid other than Q; wherein $X^3$ is any amino acid other than S; wherein $X^4$ is any amino acid other than G; wherein $X^5$ is any amino acid other than S; wherein $X^6$ is any amino acid other than A; wherein $X^7$ is any amino acid other than Q; $X^1$ is any amino acid other than N and $X^9$ is any amino acid other than K. In particular embodiments, $X^6$-$X^7$-$X^8$-$X^9$ (SEQ ID NO:21) can be: (a) QVRG (SEQ ID NO:22); (b) ERPR (SEQ ID NO:23); (c) GRGG (SEQ ID NO:24); (d) SGGR (SEQ ID NO:25); (e) SERR (SEQ ID NO:26); or (f) LRGG (SEQ ID NO:27).

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:28) at the amino acids corresponding to amino acid positions 493 to 500 (VP1 numbering) of the native AAV1 capsid protein, wherein $X^1$ is any amino acid other than K; wherein $X^2$ is any amino acid other than T; wherein $X^3$ is any amino acid other than D; wherein X is any amino acid other than N; wherein $X^5$ is any amino acid other than N; wherein $X^6$ is any amino acid other than N; wherein $X^7$ is any amino acid other than S; and $X^8$ is any amino acid other than N. In particular embodiments, $X^1$-$X^2$-$X^3$-$X^4$-$X^5$-$X^6$-$X^7$ (SEQ ID NO:29) can be PGGNATR (SEQ ID NO:30).

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:31) at the amino acids corresponding to amino acid positions 588 to 597 (VP1 numbering) of the native AAV1 capsid protein, wherein $X^1$ is any amino acid other than S; wherein $X^2$ is any amino acid other than T; wherein $X^3$ is any amino acid other than D; wherein $X^4$ is any amino acid other than P; wherein $X^5$ is any amino acid other than A; wherein $X^6$ is any amino acid other than T; wherein $X^7$ is any amino acid other than G; wherein $X^8$ is any amino acid other than D; wherein $X^9$ is any amino acid other than V; and wherein $X^{1'}$ is any amino acid other than H. In particular embodiments, $X^1$-$X^2$-$X^3$-$X^4$-$X^5$-$X^6$-$X^7$-$X^8$-$X^9$-$X^{10}$ (SEQ ID NO:31) can be: (a) TADHDTKGVL (SEQ ID NO:32); (b) VVDPDKKGVL (SEQ ID NO:33); (c) AKDTGPLNVM (SEQ ID NO:34); (d) QTDAKDNGVQ (SEQ ID NO:35); (e) DKDPWLNDVI (SEQ ID NO:36); (f) TRDGSTESVL (SEQ ID NO:37); (g) VIDPDQKGVL (SEQ ID NO:38); or (h) VNDMSNYMVH (SEQ ID NO:39).

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native AAV1 capsid protein, wherein $X^1$ is any amino acid other than A; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:40) at the amino acids corresponding to amino acid positions 716 to 722 (VP1 numbering) of the native AAV1 capsid protein, wherein $X^1$ is any amino acid other than D; wherein $X^2$ is any amino acid other than N; wherein $X^3$ is any amino acid other than N; wherein $X^4$ is any amino acid other than G; wherein $X^5$ is any amino acid other than L; wherein $X^6$ is any amino acid other than Y; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$ (SEQ ID NO:41) at the amino acids corresponding to amino acid positions 262 to 267 (VP1 numbering) of the native AAV2 capsid protein, wherein $X^1$ is any amino acid other than S; wherein $X^2$ is any amino acid other than Q; wherein $X^3$ is any amino acid other than S; wherein $X^4$ is any amino acid other than G; wherein $X^5$ is any amino acid other than A; and wherein $X^6$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:42) at the amino acids corresponding to amino acid positions 369 to 378 (VP1 numbering) of the native AAV2 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:43) at the amino acids corresponding to amino acid positions 455 to 458 (VP1 numbering) of the native AAV2 capsid protein, wherein $X^1$ is any amino acid other than T; wherein $X^2$ is any amino acid other than T; wherein $X^3$ is any amino acid other than Q; and wherein $X^4$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:44) at the amino acids corresponding to amino acid positions 492 to 498 (VP1 numbering) of the native AAV2 capsid protein, wherein $X^1$ is any amino acid other than S; wherein $X^2$ is any amino acid other than A; wherein $X^3$ is any amino acid other than D; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:45) at the amino acids corresponding to amino acid positions 587 to 596 (VP1 numbering) of the native AAV2 capsid protein, wherein $X^1$ is any amino acid other than N; wherein $X^2$ is any amino acid other than R; wherein $X^3$ is any amino acid other than Q; wherein $X^4$ is any amino acid other than A; wherein $X^5$ is any amino acid other than A; wherein $X^6$ is any amino acid other than T; wherein $X^7$ is any amino acid other than A; wherein $X^8$ is any amino acid other than D; wherein $X^9$ is any amino acid other than V; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 708 to 709 (VP1 numbering) of the native AAV12 capsid protein, wherein $X^1$ is any amino acid other than V; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:46) at the amino acids corresponding to amino acid positions 715 to 721 (VP1 numbering) of the native AAV2 capsid protein, wherein $X^1$ is any amino acid other than D; wherein $X^2$ is any amino acid other than T; wherein $X^3$ is any amino acid other than N; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$ (SEQ ID NO:47) at the amino acids corresponding to amino acid positions 262 to 267 (VP1 numbering) of the native AAV3 capsid protein, wherein $X^1$ is any amino acid other than S; wherein $X^2$ is any amino acid other than Q; wherein $X^3$ is any amino acid other than S; wherein $X^4$ is any amino acid other than G; wherein $X^5$ is any amino acid other than A; and wherein $X^6$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:48) at the amino acids corresponding to amino acid positions 369 to 378 (VP1 numbering) of the native AAV3 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:49) at the amino acids corresponding to amino acid positions 456 to 459 (VP1 numbering) of the native AAV3 capsid protein, wherein $X^1$ is any amino acid other than T; wherein $X^2$ is any amino acid other than N; wherein $X^3$ is any amino acid other than Q; and wherein $X^4$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:50) at the amino acids corresponding to amino acid positions 493 to 499 (VP1 numbering) of the native AAV3 capsid protein, wherein $X^1$ is any amino acid other than A; wherein $X^2$ is any amino acid other than N; wherein X is any amino acid other than D; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-6-$X^7$-$X^8$-$X^9$-$X^{10}$ (SEQ ID NO:57) at the amino acids corresponding to amino acid positions 588 to 597 (VP1 numbering) of the native AAV3 capsid protein, wherein $X^1$ is any amino acid other than N; wherein $X^2$ is any amino acid other than T; wherein $X^3$ is any amino acid other than A; wherein $X^4$ is any amino acid other than P; wherein $X^5$ is any amino acid other than T; wherein $X^6$ is any amino acid other than T; wherein $X^7$ is any amino acid other than G; wherein $X^8$ is any amino acid other than T; wherein $X^9$ is any amino acid other than V; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native AAV3 capsid protein, wherein $X^1$ is any amino acid other than V; and wherein $X^2$ is any amino acid other than N.

An adeno-associated virus (AAV) capsid protein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:52) at the amino acids corresponding to amino acid positions 716 to 722 (VP1 numbering) of the native AAV3 capsid protein, wherein $X^1$ is any amino acid other than D; wherein $X^2$ is any amino acid other than T; wherein $X^3$ is any amino acid other than N; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:53) at the amino acids corresponding to amino acid positions 253 to 260 (VP1 numbering) of the native AAV4 capsid protein, wherein $X^1$ is any amino acid other than R; wherein $X^2$ is any amino acid other than L; wherein $X^3$ is any amino acid other than G; wherein $X^4$ is any amino acid other than E; wherein $X^5$ is any amino acid other than S; wherein $X^6$ is any amino acid other than L; wherein $X^7$ is any amino acid other than Q; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:54) at the amino acids corresponding to amino acid positions 360 to 369 (VP1 numbering) of the native AAV4 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y: and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:55) at the amino acids corresponding to amino acid positions 450 to 453 (VP1 numbering) of the native AAV4 capsid protein, wherein $X^1$ is any amino acid other than A; wherein $X^2$ is any amino acid other than G; wherein $X^3$ is any amino acid other than T; and wherein $X^4$ is any amino acid other than A.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:56) at the amino acids corresponding to amino acid positions 487 to 498 (VP1 numbering) of the native AAV4 capsid protein, wherein $X^1$ is any amino acid other than A; wherein $X^2$ is any amino acid other than N; wherein $X^3$ is any amino acid other than Q; wherein $X^4$ is any amino acid other than N; wherein $X^5$ is any amino acid other than Y; wherein $X^6$ is any amino acid other than K; wherein $X^7$ is any amino acid other than I; wherein $X^8$ is any amino acid other than P; wherein $X^9$ is any amino acid other than A; wherein $X^{10}$ is any amino acid other than T; wherein $X^{11}$ is any amino acid other than G; and wherein $X^{12}$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:57) at the amino acids corresponding to amino acid positions 586 to 595 (VP1 numbering) of the native AAV4 capsid protein, wherein $X^1$ is any amino acid other than S; wherein $X^2$ is any amino acid other than N; wherein $X^3$ is any amino acid other than L; wherein $X^4$ is any amino acid other than P; wherein $X^5$ is any amino acid other than T; wherein $X^6$ is any amino acid other than V; wherein $X^7$ is any amino acid other than D; wherein $X^8$ is any amino acid other than R; wherein $X^9$ is any amino acid other than L; and wherein $X^{10}$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 707 to 708 (VP1 numbering) of the native AAV4 capsid protein, wherein $X^1$ is any amino acid other than N; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:58) at the amino acids corresponding to amino acid positions 714 to 720 (VP1 numbering) of the native AAV4 capsid protein, wherein $X^1$ is any amino acid other than D; wherein $X^2$ is any amino acid other than A; wherein $X^3$ is any amino acid other than A; wherein $X^4$ is any amino acid other than G; wherein $X^5$ is any amino acid other than K; wherein $X^6$ is any amino acid other than Y; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:59) at the amino acids corresponding to amino acid positions 249 to 258 (VP1 numbering) of the native AAV5 capsid protein, wherein $X^1$ is any amino acid other than E; wherein $X^2$ is any amino acid other than I; wherein $X^3$ is any amino acid other than K; wherein $X^4$ is any amino acid other than S; wherein $X^5$ is any amino acid other than G; wherein $X^6$ is any amino acid other than S; wherein $X^7$ is any amino acid other than V; wherein $X^8$ is any amino acid other than D; wherein $X^9$ is any amino acid other than G; and wherein $X^{10}$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:60) at the amino acids corresponding to amino acid positions 360 to 369 (VP1 numbering) of the native AAV5 capsid protein, wherein $X^1$ is any amino acid other than V; wherein $X^2$ is any amino acid other than F; wherein $X^3$ is any amino acid other than T; wherein $X^4$ is any amino acid other than L; wherein $X^5$ is any amino acid other than P wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than A.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:61) at the amino acids corresponding to amino acid positions 443 to 446 (VP1 numbering) of the native AAV5 capsid protein, wherein $X^1$ is any amino acid other than N; wherein $X^2$ is any amino acid other than T; wherein $X^3$ is any amino acid other than G; and wherein $X^4$ is any amino acid other than G.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:62) at the amino acids corresponding to amino acid positions 479 to 485 (VP1 numbering) of the native AAV5 capsid protein, wherein $X^1$ is any amino acid other than S; wherein $X^2$ is any amino acid other than G; wherein $X^3$ is any amino acid other than V; wherein $X^4$ is any amino acid other than N wherein $X^5$ is any amino acid other than R; wherein $X^6$ is any amino acid other than A; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:63) at the amino acids corresponding to amino acid positions 577 to 586 (VP1 numbering) of the native AAV5 capsid protein, wherein $X^1$ is any amino acid other than T; wherein $X^2$ is any amino acid other than T; wherein $X^3$ is any amino acid other than A; wherein $X^4$ is any amino acid other than P; wherein $X^5$ is any amino acid other than A; wherein $X^6$ is any amino acid other than T; wherein $X^7$ is any amino acid other than G; wherein $X^8$ is any amino acid other than T; wherein $X^9$ is any amino acid other than Y; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 697 to 698 (VP1 numbering) of the native AAV5 capsid protein, wherein $X^1$ is any amino acid other than Q; and wherein $X^2$ is any amino acid other than F.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:64) at the amino acids corresponding to amino acid positions 704 to 710 (VP1 numbering) of the native AAV5 capsid protein, wherein $X^1$ is any amino acid other than D; wherein $X^2$ is any amino acid other than S; wherein X is any amino acid other than T; wherein $X^4$ is any amino acid other than G; wherein $X^5$ is any amino acid other than E; wherein $X^6$ is any amino acid other than Y; and wherein $X^7$ is any amino acid other than R.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:65) at the amino acids corresponding to amino acid positions 262 to 268 (VP1 numbering) of the native AAV6 capsid protein, wherein $X^1$ is any amino acid other than S; wherein $X^2$ is any amino acid other than A; wherein $X^3$ is any amino acid other than S; wherein $X^4$ is any amino acid other than T; wherein $X^5$ is any amino acid other than G; wherein $X^6$ is any amino acid other than A; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:66) at the amino acids corresponding to amino acid positions 370 to 379 (VP1 numbering) of the native AAV6 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:67) at the amino acids corresponding to amino acid positions 456 to 459 (VP1 numbering) of the native AAV6 capsid protein, wherein $X^1$ is any amino acid other than A; wherein $X^2$ is any amino acid other than Q; wherein $X^3$ is any amino acid other than N; and wherein $X^4$ is any amino acid other than K.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:68) at the amino acids corresponding to amino acid positions 493 to 499 (VP1 numbering) of the native AAV6 capsid protein, wherein $X^1$ is any amino acid other than K; wherein $X^2$ is any amino acid other than T; wherein $X^3$ is any amino acid other than D; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:69) at the amino acids corresponding to amino acid positions 588 to 597 (VP1 numbering) of the native AAV6 capsid protein, wherein $X^1$ is any amino acid other than S; wherein $X^2$ is any amino acid other than T; wherein $X^3$ is any amino acid other than D; wherein $X^4$ is any amino acid other than P; wherein $X^5$ is any amino acid other than A; wherein $X^6$ is any amino acid other than T; wherein $X^7$ is any amino acid other than G; wherein $X^8$ is any amino acid other than D; wherein $X^9$ is any amino acid other than V; and wherein $X^{10}$ is any amino acid other than H.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native AAV6 capsid protein, wherein $X^1$ is any amino acid other than A; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:70) at the amino acids corresponding to amino acid positions 716 to 722 (VP1 numbering) of the native AAV6 capsid protein, wherein $X^1$ is any amino acid other than D; wherein $X^2$ is any amino acid other than N; wherein $X^3$ is any amino acid other than N; wherein $X^4$ is any amino acid other than G; wherein $X^5$ is any amino acid other than L; wherein $X^6$ is any amino acid other than Y; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:71) at the amino acids corresponding to amino acid positions 263 to 269 (VP1 numbering) of the native AAV7 capsid protein, wherein $X^1$ is any amino acid other than S; wherein $X^2$ is any amino acid other than E; wherein $X^3$ is any amino acid other than T; wherein $X^4$ is any amino acid other than A; wherein $X^5$ is any amino acid other than G; wherein $X^6$ is any amino acid other than S; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:72) at the amino acids corresponding to amino acid positions 371 to 380 (VP1 numbering) of the native AAV7 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:73) at the amino acids corresponding to amino acid positions 458 to 461 (VP1 numbering) of the native AAV7 capsid protein, wherein $X^1$ is any amino acid other than A; wherein $X^2$ is any amino acid other than G; wherein $X^3$ is any amino acid other than N; and wherein $X^4$ is any amino acid other than R.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:74) at the amino acids corresponding to amino acid positions 495 to 501 (VP1 numbering) of the native AAV7 capsid protein, wherein $X^1$ is any amino acid other than L; wherein $X^2$ is any amino acid other than D; wherein $X^3$ is any amino acid other than Q; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:75) at the amino acids corresponding to amino acid positions 589 to 598 (VP1 numbering) of the native AAV7 capsid protein, wherein $X^1$ is any amino acid other than N; wherein $X^2$ is any amino acid other than T; wherein $X^3$ is any amino acid other than A; wherein $X^4$ is any amino acid other than A; wherein $X^5$ is any amino acid other than Q; wherein $X^6$ is any amino acid other than T; wherein $X^7$ is any amino acid other than Q; wherein $X^8$ is any amino acid other than V; wherein $X^9$ is any amino acid other than V; and wherein $X^{10}$ is any amino acid other than N.

An adeno-associated virus (AAV) capsid protein is also provided herein, wherein the capsid protein comprises a substitution resulting in the amino acid sequence: $X^1$-$X^2$ at the amino acids corresponding to amino acid positions 710 to 711 (VP1 numbering) of the native AAV7 capsid protein, wherein $X^1$ is any amino acid other than T; and wherein $X^2$ is any amino acid other than G;

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:76) at the amino acids corresponding to amino acid positions 717 to 723 (VP1 numbering) of the native AAV7 capsid protein, wherein $X^1$ is any amino acid other than D; wherein $X^2$ is any amino acid other than S; wherein $X^3$ is any amino acid other than Q; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:77) at the amino acids corresponding to amino acid positions 263 to 270 (VP1 numbering) of the native AAV8 capsid protein, wherein $X^1$ is any amino acid other than N; wherein $X^2$ is any amino acid other than G; wherein $X^3$ is any amino acid other than T; wherein $X^4$ is any amino acid other than S; wherein $X^5$ is any amino acid other than G; wherein $X^6$ is any amino acid other than G; wherein $X^7$ is any amino acid other than A; and wherein $X^8$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:78) at the amino acids corresponding to amino acid positions 372 to 381 (VP1 numbering) of the native AAV8 capsid protein, wherein $X^1$ is any amino acid other than V; wherein $X^2$ is any amino acid other than F; wherein $X^3$ is any amino acid other than M; wherein $X^4$ is any amino acid other than I;

wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:79) at the amino acids corresponding to amino acid positions 458 to 461 (VP1 numbering) of the native AAV8 capsid protein, wherein $X^1$ is any amino acid other than A; wherein $X^2$ is any amino acid other than N; wherein $X^3$ is any amino acid other than T; and wherein $X^4$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:80) at the amino acids corresponding to amino acid positions 495 to 501 (VP1 numbering) of the native AAV8 capsid protein, wherein $X^1$ is any amino acid other than T; wherein $X^2$ is any amino acid other than G; wherein $X^3$ is any amino acid other than Q; wherein $X^4$ is any amino acid other than N wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$ (SEQ ID NO:81) at the amino acids corresponding to amino acid positions 590 to 600 (VP1 numbering) of the native AAV8 capsid protein, wherein $X^1$ is any amino acid other than N; wherein $X^2$ is any amino acid other than T; wherein $X^3$ is any amino acid other than A; wherein $X^4$ is any amino acid other than P; wherein $X^5$ is any amino acid other than Q; wherein $X^6$ is any amino acid other than I; wherein $X^7$ is any amino acid other than G; wherein $X^8$ is any amino acid other than T; wherein $X^9$ is any amino acid other than V; wherein $X^{10}$ is any amino acid other than N; and wherein $X^{11}$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 711 to 712 (VP1 numbering) of the native AAV8 capsid protein, wherein $X^1$ is any amino acid other than T; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:82) at the amino acids corresponding to amino acid positions 718 to 724 (VP1 numbering) of the native AAV8 capsid protein, wherein $X^1$ is any amino acid other than N; wherein $X^2$ is any amino acid other than T; wherein $X^3$ is any amino acid other than E; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:83) at the amino acids corresponding to amino acid positions 262 to 269 (VP1 numbering) of the native AAV9 capsid protein, wherein $X^1$ is any amino acid other than N; wherein $X^2$ is any amino acid other than S; wherein $X^3$ is any amino acid other than T; wherein $X^4$ is any amino acid other than S; wherein $X^5$ is any amino acid other than G; wherein $X^6$ is any amino acid other than G; wherein $X^7$ is any amino acid other than S; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:84) at the amino acids corresponding to amino acid positions 371 to 380 (VP1 numbering) of the native AAV9 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:85) at the amino acids corresponding to amino acid positions 456 to 459 (VP1 numbering) of the native AAV9 capsid protein, wherein $X^1$ is any amino acid other than Q; wherein $X^2$ is any amino acid other than N; wherein $X^3$ is any amino acid other than Q; and wherein $X^4$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:86) at the amino acids corresponding to amino acid positions 493 to 499 (VP1 numbering) of the native AAV9 capsid protein, wherein $X^1$ is any amino acid other than V; wherein $X^2$ is any amino acid other than T; wherein $X^3$ is any amino acid other than Q; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:87) at the amino acids corresponding to amino acid positions 588 to 597 (VP1 numbering) of the native AAV9 capsid protein, wherein $X^1$ is any amino acid other than Q; wherein $X^2$ is any amino acid other than A; wherein $X^3$ is any amino acid other than Q; wherein $X^4$ is any amino acid other than A; wherein $X^5$ is any amino acid other than Q; wherein $X^6$ is any amino acid other than T; wherein $X^7$ is any amino acid other than G; wherein $X^8$ is any amino acid other than W; wherein $X^9$ is any amino acid other than V; and wherein $X^{10}$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native AAV9 capsid protein, wherein $X^1$ is any amino acid other than N; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:88) at the amino acids corresponding to amino acid positions 716 to 722 (VP1 numbering) of the native AAV9 capsid protein, wherein $X^1$ is any amino acid other than N; wherein $X^2$ is any amino acid other than T; wherein $X^3$ is any amino acid other than E; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:89) at the amino acids corresponding to amino acid positions 263 to 270 (VP1 numbering) of the native AAVrh10 capsid protein, wherein $X^1$ is any amino acid other than N; wherein $X^2$ is any amino acid other than G; wherein $X^3$ is any amino acid other than T; wherein $X^4$ is any amino acid other than S; wherein $X^5$ is any amino acid other than G; wherein $X^6$ is any amino acid other than G; wherein $X^7$ is any amino acid other than S; and wherein $X^8$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:90) at the amino acids corresponding to amino acid positions 372 to 381 (VP1 numbering) of the native AAVrh10 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:91) at the amino acids corresponding to amino acid positions 458 to 461 (VP1 numbering) of the native AAVrh10 capsid protein, wherein $X^1$ is any amino acid other than A; wherein $X^2$ is any amino acid other than G; wherein $X^3$ is any amino acid other than T; and wherein $X^4$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:92) at the amino acids corresponding to amino acid positions 495 to 501 (VP1 numbering) of the native AAVrh10 capsid protein, wherein $X^1$ is any amino acid other than L; wherein $X^2$ is any amino acid other than S; wherein $X^3$ is any amino acid other than Q; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:93) at the amino acids corresponding to amino acid positions 590 to 599 (VP1 numbering) of the native AAVrh10 capsid protein, wherein $X^1$ is any amino acid other than N; wherein $X^2$ is any amino acid other than A; wherein $X^3$ is any amino acid other than A; wherein $X^4$ is any amino acid other than P; wherein $X^5$ is any amino acid other than I; wherein $X^6$ is any amino acid other than V; wherein $X^7$ is any amino acid other than G; wherein $X^8$ is any amino acid other than A; wherein $X^9$ is any amino acid other than V; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 711 to 712 (VP1 numbering) of the native AAVrh10 capsid protein, wherein $X^1$ is any amino acid other than T; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:94) at the amino acids corresponding to amino acid positions 718 to 724 (VP1 numbering) of the native AAVrh10 capsid protein, wherein $X^1$ is any amino acid other than N; wherein $X^2$ is any amino acid other than T; wherein $X^3$ is any amino acid other than D; wherein $X^4$ is any amino acid other than G; wherein $X^5$ is any amino acid other than T; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:95) at the amino acids corresponding to amino acid positions 262 to 269 (VP1 numbering) of the native AAVrh8 capsid protein, wherein $X^1$ is any amino acid other than N; wherein $X^2$ is any amino acid other than G; wherein $X^3$ is any amino acid other than T; wherein X is any amino acid other than S; wherein $X^5$ is any amino acid other than G; wherein $X^6$ is any amino acid other than G; wherein $X^7$ is any amino acid other than S; and wherein $X^8$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:96) at the amino acids corresponding to amino acid positions 371 to 380 (VP1 numbering) of the native AAVrh8 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^5$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:97) at the amino acids corresponding to amino acid positions 456 to 459 (VP1 numbering) of the native AAVrh8 capsid protein, wherein $X^1$ is any amino acid other than G; wherein $X^2$ is any amino acid other than G; wherein $X^3$ is any amino acid other than T; and wherein $X^4$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:98) at the amino acids corresponding to amino acid positions 493 to 499 (VP1 numbering) of the native AAVrh8 capsid protein, wherein $X^1$ is any amino acid other than T; wherein $X^2$ is any amino acid other than N; wherein $X^3$ is any amino acid other than Q; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:99) at the amino acids corresponding to amino acid positions 588 to 597 (VP1 numbering) of the native AAVrh8 capsid protein, wherein $X^1$ is any amino acid other than N; wherein $X^2$ is any amino acid other than T; wherein $X^3$ is any amino acid other than Q; wherein $X^4$ is any amino acid other than A; wherein $X^5$ is any amino acid other than Q; wherein $X^6$ is any amino acid other than T; wherein $X^7$ is any amino acid other than G; wherein $X^8$ is any amino acid other than L; wherein $X^9$ is any amino acid other than V; and wherein $X^{10}$ is any amino acid other than H.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native AAVrh8 capsid protein, wherein $X^1$ is any amino acid other than T; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:100) at the amino acids corresponding to amino acid positions 716 to 722 (VP1 numbering) of the native AAVrh8 capsid protein, wherein $X^1$ is any amino acid other than N; wherein $X^2$ is any amino acid other than T; wherein $X^3$ is any amino acid other than E; wherein $X^4$ is any amino acid other than G; wherein $X^5$ is any amino acid other than V; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:101) at the amino acids corresponding to amino acid positions 263 to 270 (VP1 numbering) of the native AAV10 capsid protein, wherein $X^1$ is any amino acid other than N; wherein $X^2$ is any amino acid other than G; wherein $X^3$ is any amino acid other than T; wherein $X^4$ is any amino acid other than S; wherein $X^5$ is any amino acid other than G; wherein $X^6$ is any amino acid other than G; wherein $X^7$ is any amino acid other than S; and wherein $X^8$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:102) at the amino acids corresponding to amino acid positions 372 to 381 (VP1 numbering) of the native AAV10 capsid protein, wherein $X^1$ is any amino acid other than V; wherein $X^2$ is any amino acid other than F; wherein $X^3$ is any amino acid other than M; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than L.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:103) at the amino acids corresponding to amino acid positions 458 to 461 (VP1 numbering) of the native AAV10 capsid protein, wherein $X^1$ is any amino acid other than Q; wherein $X^2$ is any amino acid other than G; wherein $X^3$ is any amino acid other than T; and wherein $X^4$ is any amino acid other than Q.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:104) at the amino acids corresponding to amino acid positions 495 to 501 (VP1 numbering) of the native AAV10 capsid protein, wherein $X^1$ is any amino acid other than L; wherein $X^2$ is any amino acid other than S; wherein $X^3$ is any amino acid other than Q; wherein $X^4$ is any amino acid other than N; wherein $X^5$ is any amino acid other than N; wherein $X^6$ is any amino acid other than N; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:105) at the amino acids corresponding to amino acid positions 590 to 599 (VP1 numbering) of the native AAV10 capsid protein, wherein $X^1$ is any amino acid other than N; wherein $X^2$ is any amino acid other than T; wherein $X^3$ is any amino acid other than G; wherein $X^4$ is any amino acid other than P; wherein $X^5$ is any amino acid other than I; wherein $X^6$ is any amino acid other than V; wherein $X^7$ is any amino acid other than G; wherein $X^8$ is any amino acid other than N; wherein $X^9$ is any amino acid other than V; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 711 to 712 (VP1 numbering) of the native AAV10 capsid protein, wherein $X^1$ is any amino acid other than T; and wherein $X^2$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:106) at the amino acids corresponding to amino acid positions 718 to 724 (VP1 numbering) of the native AAV10 capsid protein, wherein $X^1$ is any amino acid other than N; wherein $X^2$ is any amino acid other than T; wherein $X^3$ is any amino acid other than E; wherein $X^4$ is any amino acid other than G; wherein $X^5$ is any amino acid other than T; wherein $X^6$ is any amino acid other than Y; and wherein $X^7$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:107) at the amino acids corresponding to amino acid positions 253 to 260 (VP1 numbering) of the native AAV11 capsid protein, wherein $X^1$ is any amino acid other than R; wherein $X^2$ is any amino acid other than L; wherein $X^3$ is any amino acid other than G; wherein $X^4$ is any amino acid other than T; wherein $X^5$ is any amino acid other than T; wherein $X^6$ is any amino acid other than S; wherein $X^7$ is any amino acid other than S; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:108) at the amino acids corresponding to amino acid positions 360 to 369 (VP1 numbering) of the native AAV11 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:109) at the amino acids corresponding to amino acid positions 449 to 452 (VP1 numbering) of the native AAV11 capsid protein, wherein $X^1$ is any amino acid other than Q; wherein $X^2$ is any amino acid other than G; wherein $X^3$ is any amino acid other than N; and wherein $X^4$ is any amino acid other than A.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:110) at the amino acids corresponding to amino acid positions 486 to 497 (VP1 numbering) of the native AAV11 capsid protein, wherein $X^1$ is any amino acid other than A; wherein $X^2$ is any amino acid other than S; wherein $X^3$ is any amino acid other than Q; wherein $X^4$ is any amino acid other than N; wherein $X^5$ is any amino acid other than Y; wherein $X^6$ is any amino acid other than K; wherein $X^7$ is any amino acid other than I; wherein $X^8$ is any amino acid other than P; wherein $X^9$ is any amino acid other than A; wherein $X^{10}$ is any amino acid other than S; wherein $X^{11}$ is any amino acid other than G; and wherein $X^{12}$ is any amino acid other than G.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:111) at the amino acids corresponding to amino acid positions 585 to 594 (VP1 numbering) of the native AAV11 capsid protein, wherein $X^1$ is any amino acid other than T; wherein $X^2$ is any amino acid other than T; wherein $X^3$ is any amino acid other than A; wherein $X^4$ is any amino acid other than P; wherein $X^5$ is any amino acid other than I; wherein $X^6$ is any amino acid other than T; wherein $X^7$ is any amino acid other than G; wherein $X^8$ is any amino acid other than N; wherein $X^9$ is any amino acid other than V; and wherein $X^{10}$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 706 to 707 (VP1 numbering) of the native AAV11 capsid protein, wherein $X^1$ is any amino acid other than S; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:112) at the amino acids corresponding to amino acid positions 713 to 719 (VP1 numbering) of the native AAV11 capsid protein, wherein $X^1$ is any amino acid other than D; wherein $X^2$ is any amino acid other than T; wherein $X^3$ is any amino acid other than T; wherein $X^4$ is any amino acid other than G; wherein $X^5$ is any amino acid other than K; wherein $X^6$ is any amino acid other than Y; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:113) at the amino acids corresponding to amino acid positions 262 to 269 (VP1 numbering) of the native AAV12 capsid protein, wherein $X^1$ is any amino acid other than R; wherein $X^2$ is any amino acid other than I; wherein $X^3$ is any amino acid other than G; wherein $X^4$ is any amino acid other than T; wherein $X^5$ is any amino acid other than T; wherein $X^6$ is any amino acid other than A; wherein $X^7$ is any amino acid other than N; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:114) at the amino acids corresponding to amino acid positions 369 to 378 (VP1 numbering) of the native AAV12 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:115) at the amino acids corresponding to amino acid positions 458 to 461 (VP1 numbering) of the native AAV12 capsid protein, wherein $X^1$ is any amino acid other than Q; wherein $X^2$ is any amino acid other than G; wherein $X^3$ is any amino acid other than T; and wherein $X^4$ is any amino acid other than A.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:116) at the amino acids corresponding to amino acid positions 495 to 506 (VP1 numbering) of the native AAV12 capsid protein, wherein $X^1$ is any amino acid other than A; wherein $X^2$ is any amino acid other than N; wherein $X^3$ is any amino acid other than Q; wherein $X^4$ is any amino acid other than N; wherein $X^5$ is any amino acid other than Y; wherein $X^6$ is any amino acid other than K; wherein $X^7$ is any amino acid other than I; wherein $X^8$ is any amino acid other than P; wherein $X^9$ is any amino acid other than A; wherein $X^{10}$ is any amino acid other than S; wherein $X^{11}$ is any amino acid other than G; and wherein $X^{12}$ is any amino acid other than G.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:117) at the amino acids corresponding to amino acid positions 594 to 601 (VP1 numbering) of the native AAV12 capsid protein, wherein $X^1$ is any amino acid other than T; wherein $X^2$ is any amino acid other than T; wherein $X^3$ is any amino acid other than A; wherein $X^4$ is any amino acid other than P; wherein $X^5$ is any amino acid other than H; wherein $X^6$ is any amino acid other than I; wherein $X^7$ is any amino acid other than A; wherein $X^8$ is any amino acid other than N; wherein $X^9$ is any amino acid other than L; and wherein $X^{10}$ is any amino acid other than D.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 715 to 716 (VP1 numbering) of the native AAV12 capsid protein, wherein $X^1$ is any amino acid other than N; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:118) at the amino acids corresponding to amino acid positions 722 to 728 (VP1 numbering) of the native AAV12 capsid protein, wherein $X^1$ is any amino acid other than D; wherein $X^2$ is any amino acid other than N; wherein $X^3$ is any amino acid other than A; wherein $X^4$ is any amino acid other than G; wherein $X^5$ is any amino acid other than N; wherein $X^6$ is any amino acid other than Y; and wherein $X^7$ is any amino acid other than H.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:119) at the amino acids corresponding to amino acid positions 253 to 260 (VP1 numbering) of the native AAVrh32.33 capsid protein, wherein $X^1$ is any amino acid other than R; wherein $X^2$ is any amino acid other than L; wherein $X^3$ is any amino acid other than G; wherein $X^4$ is any amino acid other than T; wherein $X^5$ is any amino acid other than T; wherein $X^6$ is any amino acid other than S; wherein $X^7$ is any amino acid other than N; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:120) at the amino acids corresponding to amino acid positions 360 to 369 (VP1 numbering) of the native AAVrh32.33 capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:121) at the amino acids corresponding to amino acid positions 449 to 452 (VP1 numbering) of the native AAVrh32.33 capsid protein, wherein $X^1$ is any amino acid other than Q; wherein $X^2$ is any amino acid other than G; wherein $X^3$ is any amino acid other than N; and wherein $X^4$ is any amino acid other than A.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:122) at the amino acids corresponding to amino acid positions 486 to 497 (VP1 numbering) of the native AAVrh32.33 capsid protein, wherein $X^1$ is any amino acid other than A; wherein $X^2$ is any amino acid other than S; wherein $X^3$ is any amino acid other than Q; wherein $X^4$ is any amino acid other than N; wherein $X^5$ is any amino acid other than Y; wherein $X^6$ is any amino acid other than K; wherein $X^7$ is any amino acid other than I; wherein $X^8$ is any amino acid other than P; wherein $X^9$ is any amino acid other than A; wherein $X^{10}$ is any amino acid other than S; wherein $X^{11}$ is any amino acid other than G; and wherein $X^{12}$ is any amino acid other than G.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:123) at the amino acids corresponding to amino acid positions 585 to 594 (VP1 numbering) of the native AAVrh32.33 capsid protein, wherein $X^1$ is any amino acid other than T; wherein $X^2$ is any amino acid other than T; wherein $X^3$ is any amino acid other than A; wherein $X^4$ is any amino acid other than P; wherein $X^5$ is any amino acid other than I; wherein $X^6$ is any amino acid other than T; wherein $X^7$ is any amino acid other than G; wherein $X^8$ is any amino acid other than N; wherein $X^9$ is any amino acid other than V; and wherein $X^{10}$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 706 to 707 (VP1 numbering) of the native AAVrh32.33 capsid protein, wherein $X^1$ is any amino acid other than S; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:124) at the amino acids corresponding to amino acid positions 713 to 719 (VP1 numbering) of the native AAVrh32.33 capsid protein, wherein $X^1$ is any amino acid other than D; wherein $X^2$ is any amino acid other than T; wherein $X^3$ is any amino acid other than T; wherein $X^4$ is any amino acid other than G; wherein $X^5$ is any amino acid other than K; wherein $X^6$ is any amino acid other than Y; and wherein $X^7$ is any amino acid other than T.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:125) at the amino acids corresponding to amino acid positions 255 to 262 (VP1 numbering) of the native bovine AAV capsid protein, wherein $X^1$ is any amino acid other than R; wherein $X^2$ is any amino acid other than L; wherein $X^3$ is any amino acid other than G; wherein $X^4$ is any amino acid other than S; wherein $X^5$ is any amino acid other than S; wherein $X^6$ is any amino acid other than N; wherein $X^7$ is any amino acid other than A; and wherein $X^8$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:126) at the amino acids corresponding to amino acid positions 362 to 371 (VP1 numbering) of the native bovine AAV capsid protein, wherein $X^1$ is any amino acid other than V; wherein $X^2$ is any amino acid other than F; wherein $X^3$ is any amino acid other than M; wherein $X^4$ is any amino acid other than V; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:127) at the amino acids corresponding to amino acid positions 452 to 455 (VP1 numbering) of the native bovine AAV capsid protein, wherein $X^1$ is any amino acid other than Q; wherein $X^2$ is any amino acid other than G; wherein $X^3$ is any amino acid other than N; and wherein $X^4$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:128) at the amino acids corresponding to amino acid positions 489 to 500 (VP1 numbering) of the native bovine AAV capsid protein, wherein $X^1$ is any amino acid other than A; wherein $X^2$ is any amino acid other than S; wherein $X^3$ is any amino acid other than Q; wherein $X^4$ is any amino acid other than N; wherein $X^5$ is any amino acid other than Y; wherein $X^6$ is any amino acid other than K; wherein $X^7$ is any amino acid other than I; wherein $X^8$ is any amino acid other than P; wherein $X^9$ is any amino acid other than Q; wherein $X^{10}$ is any amino acid other than G; wherein $X^{11}$ is any amino acid other than R; and wherein $X^{12}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:129) at the amino acids corresponding to amino acid positions 588 to 597 (VP1 numbering) of the native bovine AAV capsid protein, wherein $X^1$ is any amino acid other than T; wherein $X^2$ is any amino acid other than T; wherein $X^3$ is any amino acid other than V; wherein $X^4$ is any amino acid other than P; wherein $X^5$ is any amino acid other than T; wherein $X^6$ is any amino acid other than V; wherein $X^7$ is any amino acid other than D; wherein $X^8$ is any amino acid other than D; wherein $X^9$ is any amino acid other than V; and wherein $X^{10}$ is any amino acid other than D.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 709 to 710 (VP1 numbering) of the native bovine AAV capsid protein, wherein $X^1$ is any amino acid other than D; and wherein $X^2$ is any amino acid other than S.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO: 130) at the amino acids corresponding to amino acid positions 716 to 722 (VP1 numbering) of the native bovine AAV capsid protein, wherein $X^1$ is any amino acid other than D; wherein $X^2$ is any amino acid other than N; wherein $X^3$ is any amino acid other than A; wherein $X^4$ is any amino acid other than G; wherein $X^5$ is any amino acid other than A; wherein $X^6$ is any amino acid other than Y; and wherein $X^7$ is any amino acid other than K.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$ (SEQ ID NO:131) at the amino acids corresponding to amino acid positions 265 to 272 (VP1 numbering) of the native avian AAV capsid protein, wherein $X^1$ is any amino acid other than R; wherein $X^2$ is any amino acid other than I; wherein $X^3$ is any amino acid other than Q; wherein $X^4$ is any amino acid other than G; wherein $X^5$ is any amino acid other than P; wherein $X^6$ is any amino acid other than S; wherein $X^7$ is any amino acid other than G; and wherein $X^8$ is any amino acid other than G.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:132) at the amino acids corresponding to amino acid positions 375 to 384 (VP1 numbering) of the native avian AAV capsid protein, wherein $X^1$ is any amino acid other than I; wherein $X^2$ is any amino acid other than Y; wherein $X^3$ is any amino acid other than T; wherein $X^4$ is any amino acid other than I; wherein $X^5$ is any amino acid other than P; wherein $X^6$ is any amino acid other than Q; wherein $X^7$ is any amino acid other than Y; wherein $X^8$ is any amino acid other than G; wherein $X^9$ is any amino acid other than Y; and wherein $X^{10}$ is any amino acid other than C.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$ (SEQ ID NO:133) at the amino acids corresponding to amino acid positions 459 to 462 (VP1 numbering) of the native avian AAV capsid protein, wherein $X^1$ is any amino acid other than S; wherein $X^2$ is any amino acid other than S; wherein $X^3$ is any amino acid other than G; and wherein $X^4$ is any amino acid other than R.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$-$X^{11}$-$X^{12}$ (SEQ ID NO:134) at the amino acids corresponding to amino acid positions 496 to 507 (VP1 numbering) of the native avian AAV capsid protein, wherein $X^1$ is any amino acid other than A; wherein $X^2$ is any amino acid other than S; wherein $X^3$ is any amino acid other than N; wherein $X^4$ is any amino acid other than I; wherein $X^5$ is any amino acid other than T; wherein $X^6$ is any amino acid other than K; wherein $X^7$ is any amino acid other than N; wherein $X^8$ is any amino acid other than N; wherein $X^9$ is any amino acid other than V; wherein $X^{10}$ is any amino acid other than F; wherein $X^{11}$ is any amino acid other than S; and wherein $X^{12}$ is any amino acid other than V.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$-$X^8$-$X^9$-$X^{10}$ (SEQ ID NO:135) at the amino acids corresponding to amino acid positions 595 to 604 (VP1 numbering) of the native avian AAV capsid protein, wherein $X^1$ is any amino acid other than V; wherein $X^2$ is any amino acid other than T; wherein $X^3$ is any amino acid other than P; wherein $X^4$ is any amino acid other than G; wherein $X^5$ is any amino acid other than T; wherein $X^6$ is any amino acid other than R; wherein $X^7$ is any amino acid other than A; wherein $X^8$ is any amino acid other than A; wherein $X^9$ is any amino acid other than V; and wherein $X^{10}$ is any amino acid other than N.

An adeno-associated virus (AAV) capsid protein is also provided herein, wherein the capsid protein comprises a substitution at all positions or in any combination of fewer than all positions, resulting in the amino acid sequence: $X^1$-$X^2$ at the amino acids corresponding to amino acid positions 716 to 717 (VP1 numbering) of the native avian AAV capsid protein, wherein $X^1$ is any amino acid other than A; and wherein $X^2$ is any amino acid other than D.

An adeno-associated virus (AAV) capsid protein is also provided herein, wherein the capsid protein comprises a substitution at all positions or in any combination of fewer than all positions, resulting in the amino acid sequence: $X^1$-$X^2$-$X^3$-$X^4$-$X^5$-$X^6$-$X^7$ (SEQ ID NO:136) at the amino acids corresponding to amino acid positions 723 to 729 (VP1 numbering) of the native avian AAV capsid protein, wherein $X^1$ is any amino acid other than S; wherein $X^2$ is any amino acid other than D; wherein $X^3$ is any amino acid other than T; wherein $X^4$ is any amino acid other than G; wherein $X^5$ is any amino acid other than S; wherein $X^6$ is any amino acid other than Y; and wherein $X^7$ is any amino acid other than S.

In embodiments wherein any amino acid residue identified as $X^1$ through $X^{10}$ is not substituted, the amino acid residue at the unsubstituted position is the wild type amino acid residue of the reference amino acid sequence.

An AAV capsid protein is also provided herein, comprising an amino acid substitution at residues 488R, 450Q, 453S, 454G, 455S, 456A, 457Q and/or 500N of SEQ ID NO:1 (AAV1 capsid protein; VP1 numbering) in any combination.

An AAV capsid protein is also provided herein, comprising an amino acid substitution at residues 256L, 258K, 259Q, 261S, 263A, 264S, 265T, 266G, 272H, 385S, 386Q, 547S, 709A, 710N, 716D, 717N, 718N, 720L and/or 722T of SEQ ID NO:1 (AAV1 capsid protein; VP1 numbering) in any combination.

An AAV capsid protein is also provided herein, comprising an amino acid substitution at residues 244N, 246Q, 248R, 249E, 2501, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of SEQ ID NO:5 (AAV5 capsid protein; VP1 numbering).

An AAV capsid protein is also provided herein, comprising an amino acid substitution at residues 248R, 316V, 317Q, 318D, 319S, 443N, 530N, 531S, 532Q 533P, 534A, 535N, 540A, 541T, 542Y, 543L, 545G, 546N, 697Q, 704D, 706T, 708E, 709Y and/or 710R of SEQ ID NO:5 (AAV5 capsid protein; VP1 numbering) in any combination.

An AAV capsid protein is also provided herein, comprising an amino acid substitution at residues 264S, 266G, 269N, 272H, 457Q, 588S and/or 589T of SEQ ID NO:6 (AAV6 capsid protein; VP1 numbering) in any combination.

An AAV capsid protein is also provided herein, comprising an amino acid substitution at residues 457T, 459N, 496G, 499N, 500N, 589Q, 590N and/or 592A of SEQ ID NO:8 (AAV8 capsid protein; VP1 numbering) in any combination.

An AAV capsid protein is also provided herein, comprising an amino acid substitution at residues 451, 452N, 453G, 454S, 455G, 456Q, 457N and/or 458Q of SEQ ID NO:9 (AAV9 capsid protein; VP1 numbering) in any combination.

An AAV capsid protein is also provided herein, comprising a S472R substitution in the amino acid sequence of SEQ ID NO:1 (AAV1 capsid protein; VP1 numbering).

An AAV capsid protein is also provided herein, comprising a V473D substitution in the amino acid sequence of SEQ ID NO:1 (AAV1 capsid protein; VP1 numbering).

An AAV capsid protein is also provided herein, comprising a N500E substitution in the amino acid sequence of SEQ ID NO:1 (AAV1 capsid protein; VP1 numbering).

An AAV capsid protein is also provided herein, comprising an A456T, Q457T, N458Q and K459S substation in the amino acid sequence of SEQ ID NO:1 (AAV1 capsid protein; VP1 numbering).

An AAV capsid protein is also provided herein, comprising a T492S and K493A substitution in the amino acid sequence of SEQ ID NO:1 (AAV1 capsid protein; VP1 numbering).

An AAV capsid protein is also provided herein, comprising a S586R, S587G, S588N and T589R substitution in the amino acid sequence of SEQ ID NO:1 (AAV1 capsid protein; VP1 numbering).

An AAV capsid protein is also provided herein, comprising an A456T, Q457T, N458Q, K459S, T492S and K493A substitution in the amino acid sequence of SEQ ID NO:1 (AAV1 capsid protein; VP1 numbering).

An AAV capsid protein is also provided herein, comprising an A456T, Q457T, N458Q, K459S, S586R, S587G, S588N and T589R substitution in the amino acid sequence of SEQ ID NO:1 (AAV1 capsid protein; VP1 numbering).

An AAV capsid protein is also provided herein, comprising a T492S, K493A, S586R, S587G, S588N and T589R substitution in the amino acid sequence of SEQ ID NO:1 (AAV1 capsid protein; VP1 numbering).

An AAV capsid protein is also provided herein, comprising an A456T, Q457T, N458Q, K459S, T492S, K493A, S586R, S587G, S588N and T589R substitution in the amino acid sequence of SEQ ID NO:1 (AAV1 capsid protein; VP1 numbering).

The present invention further provides an AAV capsid protein comprising one or more amino acid substitutions of this invention, in any combination. For example, an AAV capsid protein of any given serotype described herein can comprise substitutions at the amino acid residues identified for CAM1, CAM3, CAM4-1, CAM4-2, CAM5, CAM6, CAM7, CAM8, CAM9-1 and/or CAM9-2 (listed in Table 5), singly or in any combination. As a further example, an AAV capsid of a first serotype can comprise amino acid substitutions that introduce residues that define a CAM region of a different AAV serotype, which can be a second, third, fourth AAV serotype, etc. The CAM regions of different AAV serotypes can be present on a first AAV serotype in any combination. This cumulative approach generates novel AAVe strains, which present variable antigenic surface topologies that would evade neutralizing antibodies. As a particular, nonlimiting example, an AAV1 serotype capsid protein can comprise an endogenous or mutated CAM1 region from a different second AAV serotype and an endogenous or mutated CAM3 region of a different third serotype and an endogenous or mutated CAM4 region of a different fourth serotype, etc., in any combination, as would be recognized by one of ordinary skill in the art.

In particular embodiments, the modified virus capsid proteins of the invention are not limited to AAV capsid proteins in which amino acids from one AAV capsid protein are substituted into another AAV capsid protein, and the substituted and/or inserted amino acids can be from any source, and can further be naturally occurring or partially or completely synthetic.

As described herein, the nucleic acid and amino acid sequences of the capsid proteins from a number of AAV are known in the art. Thus, the amino acids "corresponding" to amino acid positions of the native AAV capsid protein can be readily determined for any other AAV (e.g., by using sequence alignments).

The invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). Such AAV capsid proteins are also within the scope of the present invention.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the invention) as compared with the native AAV capsid protein sequence.

Thus, for example, the term "AAV2 capsid protein" includes AAV capsid proteins having the native AAV2 capsid protein sequence (see GenBank Accession No. AAC03780) as well as those comprising substitutions, insertions and/or deletions (as described in the preceding paragraph) in the native AAV2 capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence. For example, in particular embodiments, an "AAV2" capsid protein encompasses the native AAV2 capsid protein sequence as well as sequences that are at least about 90%, 95%, 97%, 98% or 99% similar or identical to the native AAV2 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad Sci. USA* 90, 5873-5787 (1993). A particularly useful BLAST program is the WU-BLAST-2 program which was obtained from Altschul et al., *Methods in Enzymology,* 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

The invention also provides a virus capsid comprising, consisting essentially of, or consisting of the modified AAV capsid protein of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV capsid, avian AAV capsid or any other AAV now known or later identified. A nonlimiting list of AAV serotypes is shown in Table 1 an AAV capsid of this invention can be any AAV serotype listed in Table 1 or derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The modified virus capsids of the invention also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present invention. Further, the invention provides compositions and pharmaceutical formulations comprising the inventive modified virus capsids; optionally, the composition also comprises a modified virus vector of the invention.

The invention also provides nucleic acids (optionally, isolated nucleic acids) encoding the modified virus capsids and capsid proteins of the invention. Further provided are vectors comprising the nucleic acids, and cells (in vivo or in culture) comprising the nucleic acids and/or vectors of the invention. As one example, the present invention provides a virus vector comprising: (a) a modified AAV capsid of this invention; and (b) a nucleic acid comprising at least one terminal repeat sequence, wherein the nucleic acid is encapsidated by the AAV capsid.

Other suitable vectors include without limitation viral vectors (e.g., adenovirus, AAV, herpesvirus, vaccinia, poxviruses, baculoviruses, and the like), plasmids, phage, YACs, BACs, and the like. Such nucleic acids, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al., (1994) *Virology* 198:477-488).

The modifications to the AAV capsid protein according to the present invention are "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 20, 18, 15, 12, 10, 9, 8, 7, 6, 5, 4 or 3 contiguous amino acids.

The modified capsid proteins and capsids of the invention can further comprise any other modification, now known or later identified.

For example, the AAV capsid proteins and virus capsids of the invention can be chimeric in that they can comprise all or a portion of a capsid subunit from another virus, optionally another parvovirus or AAV, e.g., as described in international patent publication WO 00/28004.

In some embodiments of this invention, the virus capsid can be a targeted virus capsid, comprising a targeting sequence (e.g., substituted or inserted in the viral capsid) that directs the virus capsid to interact with cell-surface molecules present on desired target tissue(s) (see, e.g., international patent publication WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

For example, a virus capsid of this invention may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., *Annu Rev Biophys Biomol Struct.* 35:225-49 (2006)) can be incorporated into an AAV capsid subunit of this invention at an orthogonal site as a means of redirecting a low-transduction vector to desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques,* 1$^{st}$ edition, Academic Press, 1996).

In some embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV4, AAV5) to confer heparin binding to the resulting mutant.

B19 infects primary erythroid progenitor cells using globoside as its receptor (Brown et al., (1993) Science 262: 114). The structure of B19 has been determined to 8 Å resolution (Agbandje-McKenna et al., (1994) *Virology* 203: 106). The region of the B19 capsid that binds to globoside has been mapped between amino acids 399-406 (Chapman et al., (1993) *Virology* 194:419), a looped out region between n3-barrel structures E and F (Chipman et al., (1996) *Proc. Nat. Acad Sci. USA* 93:7502). Accordingly, the globoside receptor binding domain of the B19 capsid may be substituted into an AAV capsid protein of this invention to target a virus capsid or virus vector comprising the same to erythroid cells.

In some embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP (SEQ ID NO:162) peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV capsid that otherwise does not bind to HS or heparin). It is known in the art that HS/heparin binding is mediated by a "basic patch" that is rich in arginines and/or lysines. In exemplary embodiments, a sequence following the motif BXXB (SEQ ID NO:163), where "B" is a basic residue and X is neutral and/or hydrophobic can be employed. As a nonlimiting example, BXXB can be RGNR (SEQ ID NO:164). As another nonlimiting example, BXXB is substituted for amino acid positions 262 through 265 in the native AAV2 capsid protein or at the corresponding position(s) in the capsid protein of another AAV serotype.

Other nonlimiting examples of suitable targeting sequences include the peptides targeting coronary artery endothelial cells identified by Mller et al., *Nature Biotechnology* 21:1040-1046 (2003) (consensus sequences NSVRDL(G/S) (SEQ ID NO:165), PRSVTVP (SEQ ID NO:166), NSVSSX(S/A) (SEQ ID NO:167); tumor-targeting peptides as described by Grifman et al., *Molecular Therapy* 3:964-975 (2001) (e.g., NGR, NGRAHA, SEQ ID NO:168); lung or brain targeting sequences as described by Work et al., *Molecular Therapy* 13:683-693 (2006) (QPEHSST; SEQ ID NO:169, VNTANST; SEQ ID NO:170, HGPMQKS; SEQ ID NO:171, PHKPPLA; SEQ ID NO:172, IKNNEMW; SEQ ID NO:173, RNLDTPM; SEQ ID NO:174, VDSHRQS; SEQ ID NO:175, YDSKTKT; SEQ ID NO:176, SQLPHQK; SEQ ID NO:177, STMQQNT; SEQ ID NO:178, TERYMTQ; SEQ ID NO:179, QPEHSST; SEQ ID NO:180, DASLSTS; SEQ ID NO:181, DLPNKKT; SEQ ID NO:182, DLTAARL; SEQ ID NO:183, EPHQFNY; SEQ ID NO:184, EPQSNHT; SEQ ID NO:185, MSSWPSQ; SEQ ID NO:186, NPKHNAT; SEQ ID NO:187, PDGMRTT; SEQ ID NO:188, PNNNKTT; SEQ ID NO:189, QSTTHDS; SEQ ID NO:190, TGSKQKQ; SEQ ID NO:191, SLKHQAL; SEQ ID NO:192 and SPIDGEQ; SEQ ID NO:193); vascular targeting sequences described by Hajitou et al., *TCM* 16:80-88 (2006)

(WIFPWIQL; SEQ ID NO:194, CDCRGDCFC; SEQ ID NO:195, CNGRC; SEQ ID NO:196, CPRECES; SEQ ID NO:197, GSL, CTTHWGFTLC; SEQ ID NO:198, CGRRAGGSC; SEQ ID NO:199, CKGGRAKDC; SEQ ID NO:200, and CVPELGHEC; SEQ ID NO:201); targeting peptides as described by Koivunen et al., *J. Nucl. Med* 40:883-888 (1999) (CRRETAWAK; SEQ ID NO:202, KGD, VSWFSHRYSPFAVS; SEQ ID NO:203, GYRDGYAGPILYN; SEQ ID NO:204, XXXY*XXX (SEQ ID NO:205) [where Y* is phospho-Tyr], Y*E/MNW; SEQ ID NO:206, RPLPPLP; SEQ ID NO:207, APPLPPR; SEQ ID NO:208, DVFYPYPYASGS; SEQ ID NO:209, MYWYPY; SEQ ID NO:210, DITWDQLWDLMK; SEQ ID NO:211, CWDD(G/L)WLC; SEQ ID NO:212, EWCEYLGGYLRCYA; SEQ ID NO:213, YXCXXGPXTWXCXP; SEQ ID NO:214, IEGPTLRQWLAARA; SEQ ID NO:215, LWXX(Y/W/F/H); SEQ ID NO:216, XFXXYLW; SEQ ID NO:217, SSIISHFRWGLCD; SEQ ID NO:218, MSRPACPPNDKYE; SEQ ID NO:219, CLRSGRGC; SEQ ID NO:220, CHWMFSPWC; SEQ ID NO:221, WXXF; SEQ ID NO:222, CSSRLDAC; SEQ ID NO:223, CLPVASC; SEQ ID NO:224, CGFECVRQCPERC; SEQ ID NO:225, CVALCREACGEGC; SEQ ID NO:226, SWCEPGWCR; SEQ ID NO:227, YSGKWGW; SEQ ID NO:228, GLSGGRS; SEQ ID NO:229, LMLPRAD; SEQ ID NO:230, CSCFRDVCC; SEQ ID NO:231, CRDVVSVIC; SEQ ID NO:232, CNGRC; SEQ ID NO:233, and GSL); and tumor targeting peptides as described by Newton & Deutscher, Phage Peptide Display in Handbook of Experimental Pharmacology, pages 145-163, Springer-Verlag, Berlin (2008) (MARSGL; SEQ ID NO:234, MARAKE; SEQ ID NO:235, MSRTMS; SEQ ID NO:236, KCCYSL; SEQ ID NO:237, WRR, WKR, WVR, WVK, WIK, WTR, WVL, WLL, WRT, WRG, WVS, WVA, MYWGDSHWLQYWYE; SEQ ID NO:238, MQLPLAT; SEQ ID NO:239, EWLS; SEQ ID NO:240, SNEW; SEQ ID NO:241, TNYL; SEQ ID NO:242, WIFPWIQL; SEQ ID NO:243, WDLAWMFRLPVG; SEQ ID NO:244, CTVALPGGYVRVC; SEQ ID NO:245, CVPELGHEC; SEQ ID NO:246, CGRRAGGSC; SEQ ID NO:247, CVAYCIEHHCWTC; SEQ ID NO:248, CVFAHNYDYLVC; SEQ ID NO:249, and CVFTSNYAFC; SEQ ID NO:250, VHSPNKK; SEQ ID NO:251, CDCRGDCFC; SEQ ID NO:252, CRGDGWC; SEQ ID NO:253, XRGCDX; SEQ ID NO:254, PXX(S/T); SEQ ID NO:255, CTTHWGFTLC; SEQ ID NO:256, SGKGPRQITAL; SEQ ID NO:257, A(A/Q)(N/AX)(IY)(TN/V/M/RXR/K); SEQ ID NO:258, VYMSPF; SEQ ID NO:259, MQLPLAT; SEQ ID NO:260, ATWLPPR; SEQ ID NO:261, HTMYYHHYQHHL; SEQ ID NO:262, SEVGCRAGPLQWLCEKYFG; SEQ ID NO:263, CGLLPVGRPDRNVWRWLC; SEQ ID NO:264, CKGQCDRFKGLPWEC; SEQ ID NO:265, SGRSA; SEQ ID NO:266, WGFP; SEQ ID NO:267, LWXXAr [Ar=Y, W, F, H); SEQ ID NO:216, XFXXYLW; SEQ ID NO:268, AEPMPHSLNFSQYLWYT; SEQ ID NO:269, WAY(W/F)SP; SEQ ID NO:270, IELLQAR; SEQ ID NO:271, DITWDQLWDLMK; SEQ ID NO:272, AYTKCSRQWRTCMTTH; SEQ ID NO:273, PQNSKIPGPTFLDPH; SEQ ID NO:274, SMEPALPDWWWKMFK; SEQ ID NO:275, ANTPCGPYTHDCPVKR; SEQ ID NO:276, TACHQHVRMVRP; SEQ ID NO:277, VPWMEPAYQRFL; SEQ ID NO:278, DPRATPGS; SEQ ID NO:279, FRPNRAQDYNTN; SEQ ID NO:280, CTKNSYLMC; SEQ ID NO:281, C(R/Q)L/RT(G/N)XXG(A/V)GC; SEQ ID NO:282, CPIEDRPMC; SEQ ID NO:283, HEWSYLAPYPWF; SEQ ID NO:284, MCPKHPLGC; SEQ ID NO:285, RMWPSSTVNLSAGRR; SEQ ID NO:286, SAKTAVSQRVWLPSHRGGEP; SEQ ID NO:287, KSREHVNNSACPSKRITAAL; SEQ ID NO:288, EGFR; SEQ ID NO:289, RVS, AGS, AGLGVR; SEQ ID NO:290, GGR, GGL, GSV, GVS, GTRQGHTMRLGVSDG; SEQ ID NO:291, IAGLATPGWSHWLAL; SEQ ID NO:292, SMSIARL; SEQ ID NO:293, HTFEPGV; SEQ ID NO:294, NTSLKRISNKRIRRK; SEQ ID NO:295, LRIKRKRRKKTRK; SEQ ID NO:296, GGG, GFS, LWS, EGG, LLV, LSP, LBS, AGG, GRR, GGH and GTV).

As yet a further embodiment, the targeting sequence may be a peptide that can be used for chemical coupling (e.g., can comprise arginine and/or lysine residues that can be chemically coupled through their R groups) to another molecule that targets entry into a cell.

As another embodiment, the AAV capsid protein or virus capsid of the invention can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV serotype.

Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By “directly following amino acid position X” it is intended that the insertion immediately follows the indicated amino acid position (for example, “following amino acid position 264” indicates a point insertion at position 265 or a larger insertion, e.g., from positions 265 to 268, etc.).

Furthermore, in representative embodiments, the capsid protein, virus capsid or vector of this invention can comprise amino acid modifications such as described in PCT Publication No. WO 2010/093784 (e.g., 2i8) and/or in PCT Publication No. WO 2014/144229 (e.g., dual glycan).

In some embodiments of this invention, the capsid protein, virus capsid or vector of this invention can have equivalent or enhanced transduction efficiency relative to the transduction efficiency of the AAV serotype from which the capsid protein, virus capsid or vector of this invention originated. In some embodiments of this invention, the capsid protein, virus capsid or vector of this invention can have reduced transduction efficiency relative to the transduction efficiency of the AAV serotype from which the capsid protein, virus capsid or vector of this invention originated. In some embodiments of this invention, the capsid protein, virus capsid or vector of this invention can have equivalent or enhanced tropism relative to the tropism of the AAV serotype from which the capsid protein, virus capsid or vector of this invention originated. In some embodiments of this invention, the capsid protein, virus capsid or vector of this invention can have an altered or different tropism relative to the tropism of the AAV serotype from which the capsid protein, virus capsid or vector of this invention originated.

In some embodiments of this invention, the capsid protein, virus capsid or vector of this invention can have or be engineered to have tropism for brain tissue.

The foregoing embodiments of the invention can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B

[N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2 (see, e.g., Table 4). As discussed elsewhere herein, the corresponding amino acid position(s) will be readily apparent to those skilled in the art using well-known techniques.

Nonlimiting examples of corresponding positions in a number of other AAV are shown in Table 4 (Position 2). In particular embodiments, the amino acid insertion or substitution is a threonine, aspartic acid, glutamic acid or phenylalanine (excepting AAV that have a threonine, glutamic acid or phenylalanine, respectively, at this position).

In other representative embodiments, the modified capsid proteins or virus capsids of the invention further comprise one or more mutations as described in WO 2007/089632 (e.g., an E→K mutation at amino acid position 531 of the AAV2 capsid protein or the corresponding position of the capsid protein from another AAV).

In further embodiments, the modified capsid protein or capsid can comprise a mutation as described in WO 2009/108274.

As another, possibility, the AAV capsid protein can comprise a mutation as described by Zhong et al. (*Virology* 381: 194-202 (2008); *Proc. Nat. Acad Sci.* 105: 7827-32 (2008)). For example, the AAV capsid protein can comprise a Y→F mutation at amino acid position 730.

The modifications described above can be incorporated into the capsid proteins or capsids of the invention in combination with each other and/or with any other modification now known or later discovered.

TABLE 4

| Serotype | Position 1 | Position 2 |
|---|---|---|
| AAV1 | A263X | T265X |
| AAV2 | Q263X | —265X |
| AAV3A | Q263X | —265X |
| AAV3B | Q263X | —265X |
| AAV4 | S257X | —259X |
| AAV5 | G253X | V255X |
| AAV6 | A263X | T265X |
| AAV7 | E264X | A266X |
| AAV8 | G264X | S266X |
| AAV9 | S263X | S265X |

Where, (X) → mutation to any amino acid; (—) → insertion of any amino acid
Note:
Position 2 inserts are indicated by the site of insertion The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the invention (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), and/or (v) reduced transduction of brain tissues (e.g., neurons) as compared with the level of transduction by a virus vector without the modified capsid protein. In particular embodiments, the virus vector has systemic transduction toward muscle, e.g., transduces multiple skeletal muscle groups throughout the body and optionally transduces cardiac muscle and/or diaphragm muscle.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants).

Methods of Producing Virus Vectors.

The present invention further provides methods of producing the inventive virus vectors. Thus, in one embodiment, the present invention provides a method of producing an AAV vector that evades neutralizing antibodies, comprising: a) identifying contact amino acid residues that form a three dimensional antigenic footprint on an AAV capsid protein; b) generating a library of AAV capsid proteins comprising amino acid substitutions of the contact amino acid residues identified in (a); c) producing AAV particles comprising capsid proteins from the library of AAV capsid proteins of (b); d) contacting the AAV particles of (c) with cells under conditions whereby infection and replication can occur; e) selecting AAV particles that can complete at least one infectious cycle and replicate to titers similar to control AAV particles; f) contacting the AAV particles selected in (e) with neutralizing antibodies and cells under conditions whereby infection and replication can occur; and g) selecting AAV particles that are not neutralized by the neutralizing antibodies of (f) Nonlimiting examples of methods for identifying contact amino acid residues include peptide epitope mapping and/or cryo-electron microscopy.

Resolution and identification of the antibody contact residues within the three dimensional antigenic footprint allows for their subsequent modification through random, rational and/or degenerate mutagenesis to generate antibody-evading AAV capsids that can be identified through further selection and/or screening.

Thus, in a further embodiment, the present invention provides a method of producing an AAV vector that evades neutralizing antibodies, comprising: a) identifying contact amino acid residues that form a three dimensional antigenic footprint on an AAV capsid protein; b) generating AAV capsid proteins comprising amino acid substitutions of the contact amino acid residues identified in (a) by random, rational and/or degenerate mutagenesis; c) producing AAV particles comprising capsid proteins from the AAV capsid proteins of (b); d) contacting the AAV particles of (c) with cells under conditions whereby infection and replication can occur, e) selecting AAV particles that can complete at least one infectious cycle and replicate to titers similar to control AAV particles; f) contacting the AAV particles selected in (e) with neutralizing antibodies and cells under conditions whereby infection and replication can occur, and g) selecting AAV particles that are not neutralized by the neutralizing antibodies of (f)

Nonlimiting examples of methods for identifying contact amino acid residues include peptide epitope mapping and/or cryo-electron microscopy. Methods of generating AAV capsid proteins comprising amino acid substitutions of contact amino acid residues by random, rational and/or degenerate mutagenesis are known in the art.

This comprehensive approach presents a platform technology that can be applied to modifying any AAV capsid. Application of this platform technology yields AAV antigenic variants derived from the original AAV capsid template without loss of transduction efficiency. As one advantage and benefit, application of this technology will expand the cohort of patients eligible for gene therapy with AAV vectors.

In one embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) Nature Med 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377.

As a further alternative, the virus vectors of the invention can be produced in insect cells using baculovirus vectors to deliver the rep/cap genes and rAAV template as described, for example, by Urabe et al., (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al., (1993) Nature Genetics 5:130; U.S. Patent Publication No. 2003/017131; International publication WO/2008/088895, Wang et al., *Proc. Natl. Acad Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SW), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al, (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (ß-globin), anemia (erythropoietin) and other blood disorders, Alzheimer's disease (GDF; neprilysin), multiple sclerosis (ß-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tay-Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (omithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vive or by using ex vive methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration.

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid and/or capsid protein and/or virus particle of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

Thus, the present invention provides a method of administering a nucleic acid to a cell, the method comprising contacting the cell with the virus vector, virus particle and/or composition of this invention.

A further aspect of the invention is a method of administering the virus vector, virus particle and/or virus capsid of this invention to a subject. Thus, the present invention also provides a method of delivering a nucleic acid to a subject, comprising administering to the subject a virus particle, virus vector and/or composition of this invention. Administration of the virus vectors, virus particles and/or capsids according to the present invention to a human subject or an animal in need thereof can be by any means known in the art. Optionally, the virus vector, virus particle and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-$\alpha$2, $\alpha$-sarcoglycan, $\beta$-sarcoglycan, $\gamma$-sarcoglycan, $\delta$-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent publication US 2002/0192189.

Thus, as one aspect, the invention further encompasses a method of treating and/or preventing a metabolic disorder in a subject in need thereof, the method comprising: administering a treatment or prevention effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle is described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

EXAMPLES

Example 1. Combinatorial Engineering and Selection of Antibody-Evading AAV Vectors (AAV1e Clones 1-26)

Figure 2:
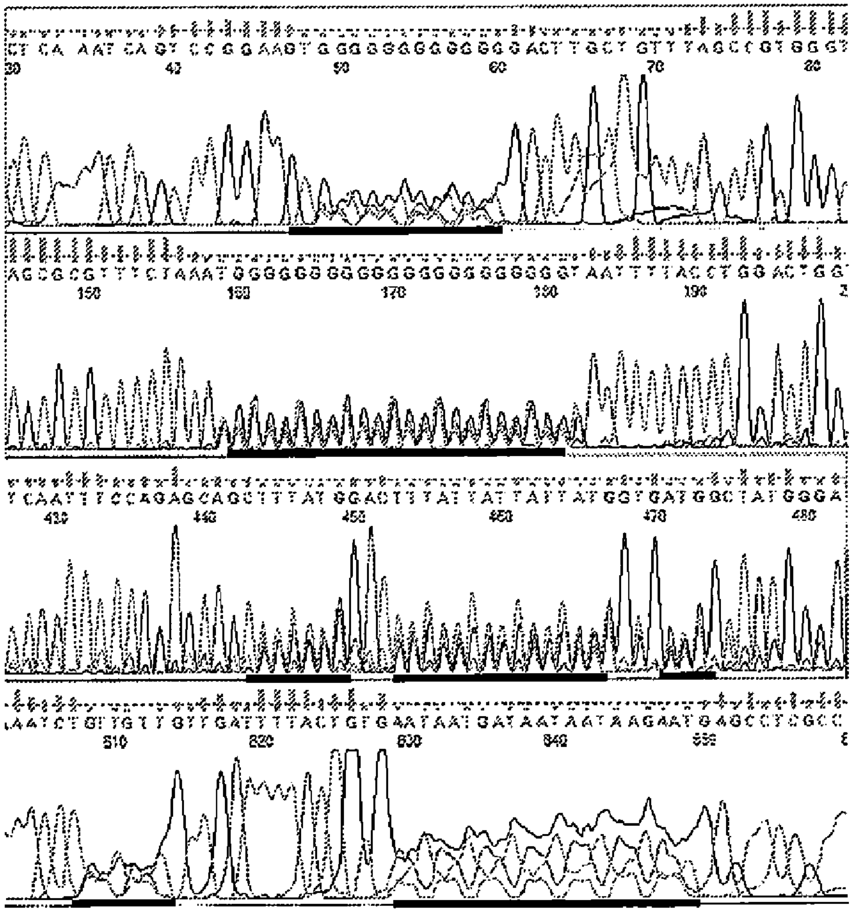
FIG. 2. Generation of AAVe libraries by random mutagenesis of amino acid residues within common antigenic motifs (CAMs) listed in Table 5. Theoretical diversities of different libraries generated by randomizing the different amino acid residues within each common antigenic motif. Successful generation of AAV1e libraries was confirmed via DNA sequencing of the AAV1e plasmids (SEQ ID NOS: 439-442). Black solid bar represents the position of the randomized sequences of different AAV1e libraries. Theoretical diversities were calculated by the following equation: Theoretical diversities=20^n, where n is the number of randomized amino acids within the indicated CAM.

The method for generating antibody evading AAVe mutants is as follows. A general schematic description of the approach is provided in FIG. 1. As an example, the first step involves identification of conformational 3D antigenic epitopes on the AAV capsid surface from cryo-electron microscopy. Selected residues within antigenic motifs are then subjected to mutagenesis using degenerate primers with each codon substituted by nucleotides NNK and gene fragments combined together by Gibson assembly and/or multistep PCR. Capsid-encoding genes containing a degenerate library of mutated antigenic motifs are cloned into a wild type AAV genome to replace the original Cap encoding DNA sequence yielding a plasmid library. Plasmid libraries are then transfected into 293 producer cell lines to generate AAV capsid libraries, which can then be subjected to selection. Successful generation of AAV libraries is confirmed via DNA sequencing (FIG. 2). In order to select for new AAV strains that can escape neutralizing antibodies (NAbs), AAV libraries are subjected to multiple rounds of infection in specific cells or tissues in the presence of a helper virus such as adenovirus with or without different monoclonal antibodies, polyclonal antibodies or serum containing anti-AAV antibodies. Cell lysates harvested from at least one round of successful infection and replication are sequenced to identify single AAV isolates escaping antibody neutralization.

As a nonlimiting specific example, common antigenic motifs on the AAV1 capsid protein (VP1) were subjected to mutagenesis as described above. The degenerate libraries were then subjected to infection in endothelial cells in culture for five cycles of infection and replication. Cells were infected with AAV1 libraries on day 0, infected with adenovirus at day 1 and cell lysates as well as supernatant were obtained at day 7 post-infection for repeating the cycle of infection and replication. This procedure was repeated five times following which, fifteen to twenty isolated clones from each library were subjected to DNA sequence analysis (FIG. 2). Each unique sequence was labeled as AAV1e(# number), where the number depicts the specific clonal isolate (Tables 6.1 to 6.4).

Figure 3:
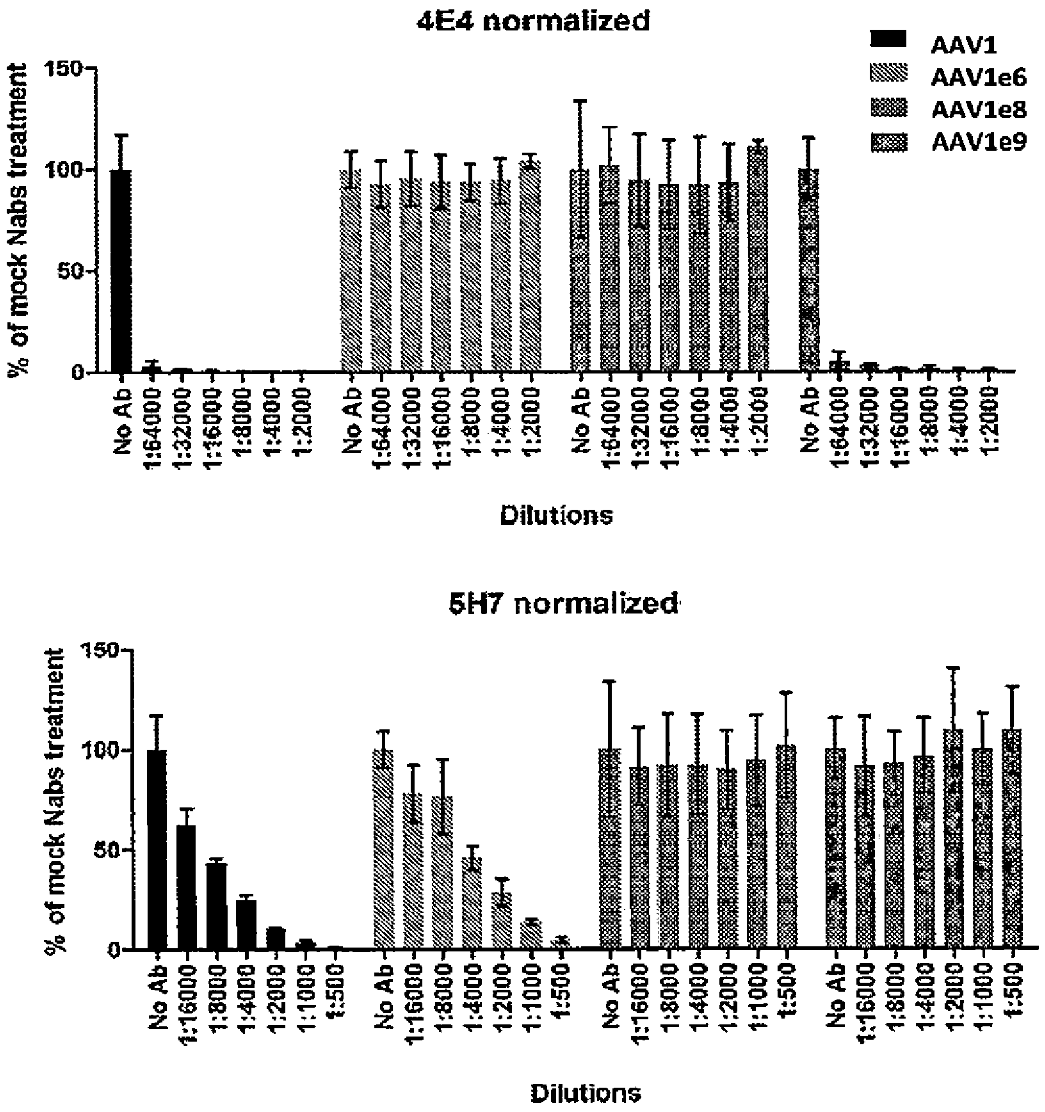
FIG. 3. In vitro antibody neutralization assay of AAV1e-series. Transduction efficiency was measured by luciferase activity. AAV1 (far left) is neutralized by both 4E4 (top) and 5H7 (bottom) and the 50% inhibition concentration of the two antibodies are <1:64000 and 1:16000 respectively. 4E4 and 5H7 are antibodies that neutralize parental AAV1. Clone AAV1e6 (middle left) is completely resistant to 4E4 neutralization (no reduction in transduction level at the highest antibody concentration) and partially resistant to 5H7 (50% inhibition concentration reduced to 1:4000). Clone AAV1e8 (middle right) showed complete resistance to both 4E4 and 5H7 neutralization where the highest antibody concentration showed no effect on the transduction level. AAV1e9 (far right) showed resistance to 5H7; however, it is as sensitive to 4E4 as AAV1.

For validation of AAV1e mutants and their ability to escape neutralization, AAV1 neutralizing antibodies, 4E4 (FIG. 3 top) and 5H7 (FIG. 3 bottom) were serially diluted in DMEM+5% FBS on a 96 well plate. AAV1 and AAV1e clones packaging a CBA-Luc cassette (5e7 vg/well) were added and incubated with antibody on a 96 well plate for 30 min at room temperature. 293 cells (4e5 cells/well) were added into the virus+antibody mix and incubated at 37° C., 5% $CO_2$ incubator for 48 h. Final volume of antibody, virus and cell mixture is 100 ul. Medium was then discarded from individual wells and replaced with 25 ul of passive lysis buffer. After 30 min incubation at room temperature, 25 ul of luciferin was added and reporter transgene expression (transduction efficiency) was assayed using a Victor3 illuminometer.

For validation of AAV1e mutants in mouse models in vivo (FIG. 4), a dose of 1e9 vg/ul was pre-incubated with neutralizing antibodies 4E4 (1:500) or 5H7 (1:10), or with PBS for 1 h at room temperature. Each mouse (6-8 weeks old, BALB/c, female) was injected with 20 ul of the virus and antibody mixture into each gastrocnemius muscle in the hind leg (2e10 vg/leg) through an intramuscular injection.

Figure 4:
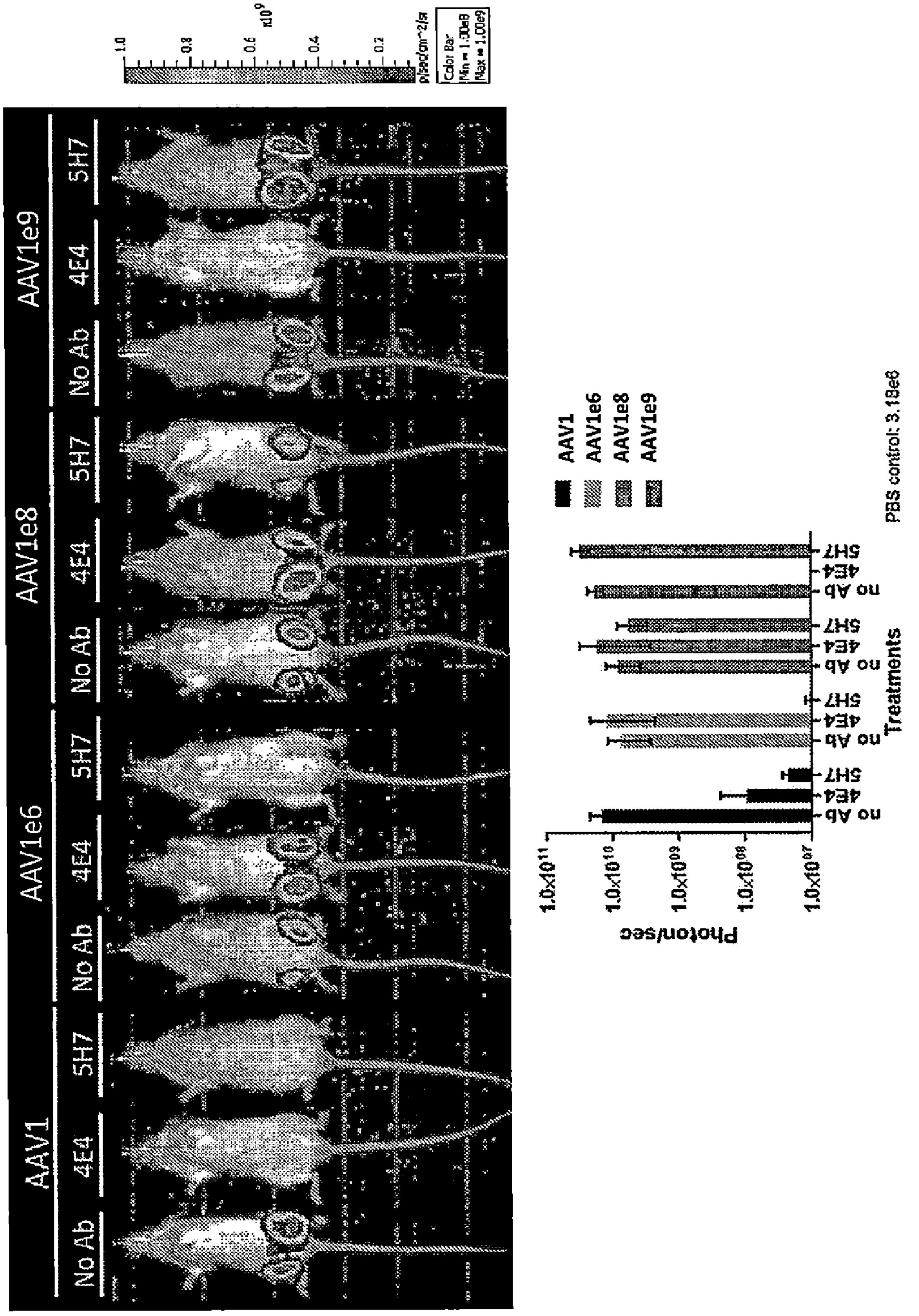
FIG. 4. In vivo antibody neutralization assay of AAV1e-series at 4 weeks post-injection into skeletal muscle of mice. Representative images of each virus and treatment group are shown. All viruses showed a similar level of transduction efficiency without antibody addition. AAV1e6 and AAV1e8 show resistance to 4E4 and AAV1e9 shows resistance to 5H7. AAV1e8 also shows partial resistance to 5H7. 4E4 and 5H7 are antibodies that completely neutralize parental AAV1. Luciferase activities were quantified and summarized in the bar graph (AAV1 is far left; AAV1e6 is middle left; AAV1e8 is middle right; AAV1e9 is far right). These results confirm that the AAV1e series can escape subsets of neutralizing antibodies. Other AAV strains can be subjected to this engineering and selection protocol and similar AAVe vector series can be generated from any capsid template using this approach.

Mice were anesthetized with isoflurane and injected with 150 ul of RediJect D-lucifercin intraperitoneally (IP) at different time intervals for live animal imaging and luciferase reporter expression. Luciferase activities of each mouse were imaged 1 min after the injection using a Xenogen IVIS Lumina® system. Live animal luciferase imaging was performed at 1 week and 4 weeks post-injection and luciferase activities quantified to determine differences in the ability of AAV1e clones to evade neutralizing antibodies (FIG. 4).

Figure 5:
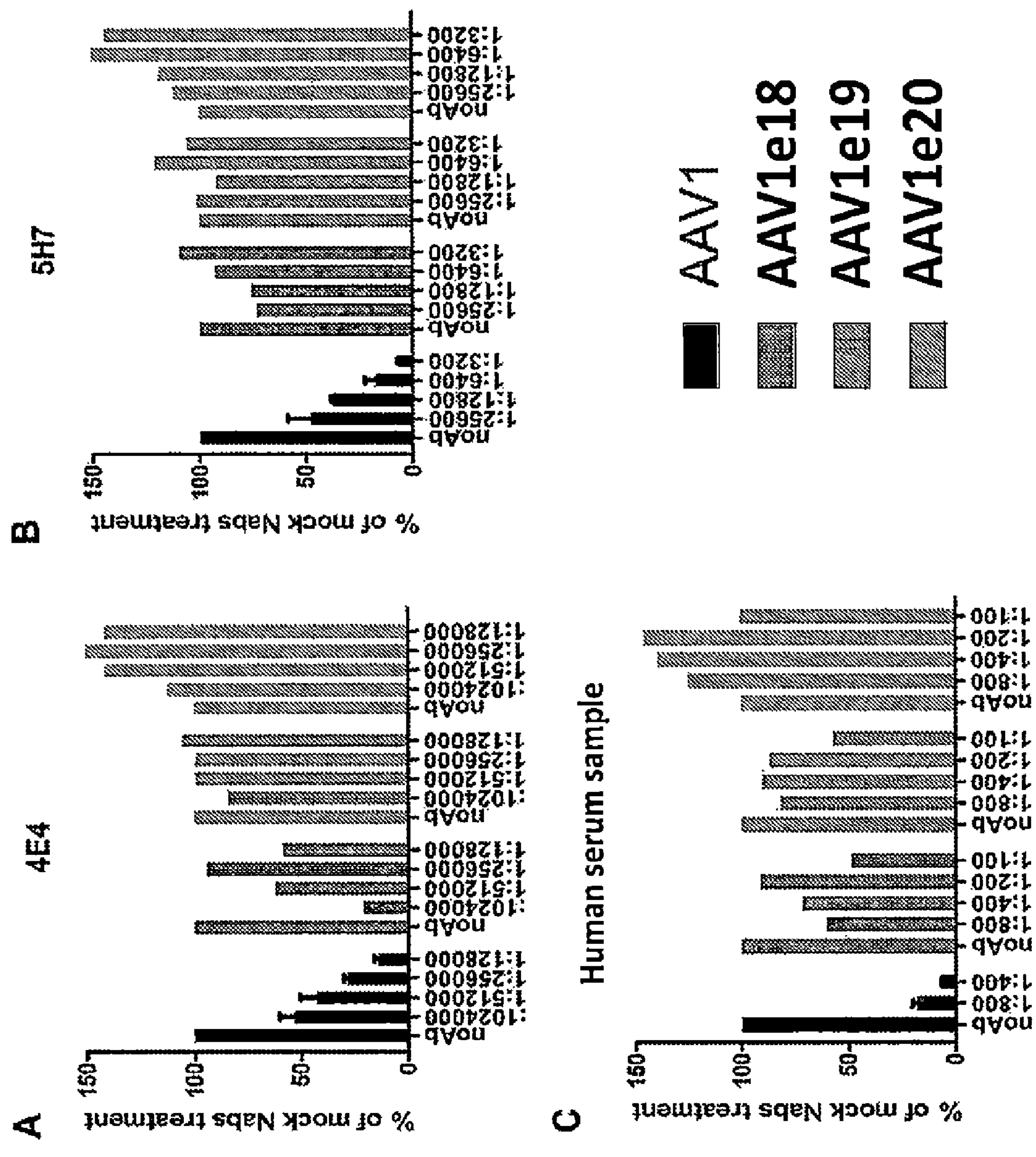
FIG. 5. In vitro antibody neutralization assay of AAV1e clones derived by rational combination of amino acid residues obtained from AAV1e6, AAv1e8 and AAV1e9. Transduction efficiency was measured by luciferase activity. AAV1 (far left) is completely neutralized by both 4E4 (top) and 5H7 (bottom) as well as the human serum sample containing polyclonal antibodies. The 50% inhibition dilution of human serum sample >1:800 fold dilution. 4E4 and 5H7 are antibodies that neutralize parental AAV1. Clone AAV1e18 (middle left) is partially resistant to 4E4, 5H7 as well as human serum. Clones AAV1e19 and AAV1e20 (middle and far right) showed complete resistance to both 4E4 and 5H7 neutralization as well as the human serum sample.
Figure 6:
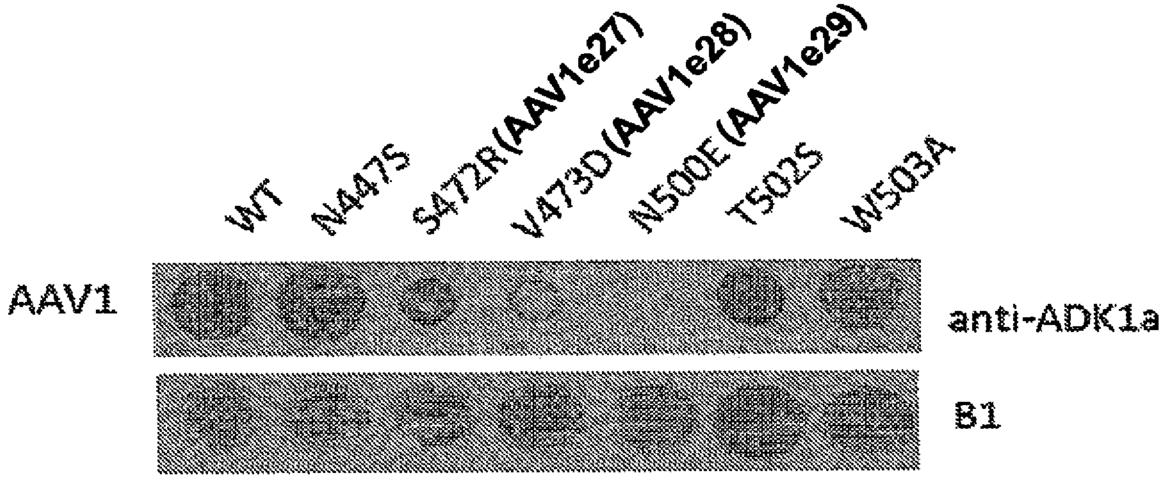
FIG. 6. Native dot blot assay comparing the parental AAV1 and AAV1e clones 27, 28 and 29 derived by rational, site-specific mutagenesis of residues S472R, V473D and N500E within CAM regions listed in Table 5. Assay determines the ability of AAV1e clones to escape antibody detection. ADK1a is a monoclonal antibody that detects parental AAV1 capsids.
Figure 7:
FIG. 7. ELISA assay comparing the parental AAV1 and AAV1e clones 27, 28 and 29 derived by rational, site-specific mutagenesis of residues S472R, V473D and N500E within CAM regions listed in Table 5. Assay determines the ability of AAV1e clones to escape antibody detection. ADK1a is a monoclonal antibody that detects parental AAV1 capsids.

For further enhancement of antibody evading properties, mutations discovered in AAV1e clones were combined on capsids to generate new AAV1e strains (clones 18 through 20). These clones were subjected to in vitro transduction assays in order to determine their ability to evade antibody neutralization. Clones AAV1e18-20 demonstrated the ability to escape both monoclonal antibodies against AAV1 or human serum sample containing polyclonal antibodies (FIG. 5).

Example 2. Rational Engineering of Antibody-Evading AAV Vectors (AAV1e Series 27-36, AAV9e1, and AAV9e2)

Current WT AAV vectors are likely to have pre-existing antibodies targeted against the capsid surface, which prevents efficient transduction. Vectors of this invention overcome these limitations.

This invention provides AAV antibody escape variants that retain transduction efficiency. They are engineered to overcome pre-existing antibody responses based on capsid interaction sites and capsid-antibody structures, and can be further engineered to target specific tissues.

Figure 8:
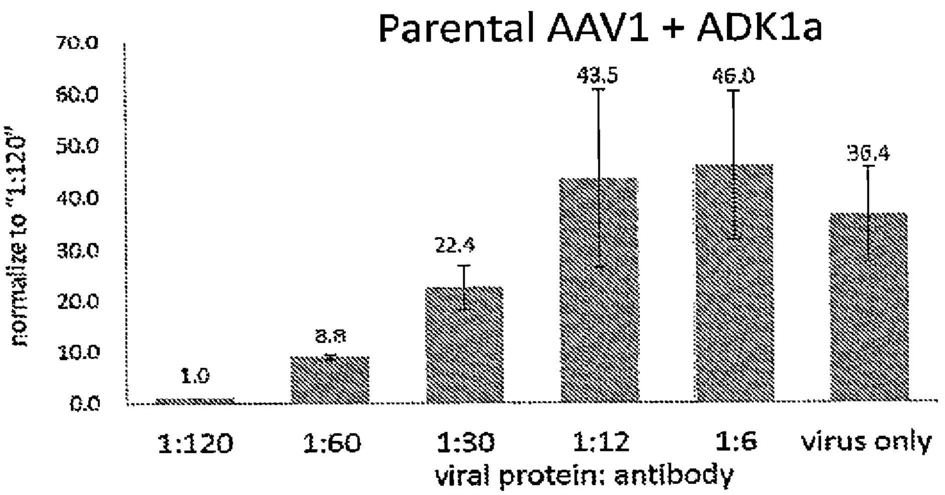
FIG. 8. Transduction assay showing ability of AAV1e27 clone to evade neutralization by ADK1a, which is an anti-capsid antibody against parental AAV1.
Figure 8:
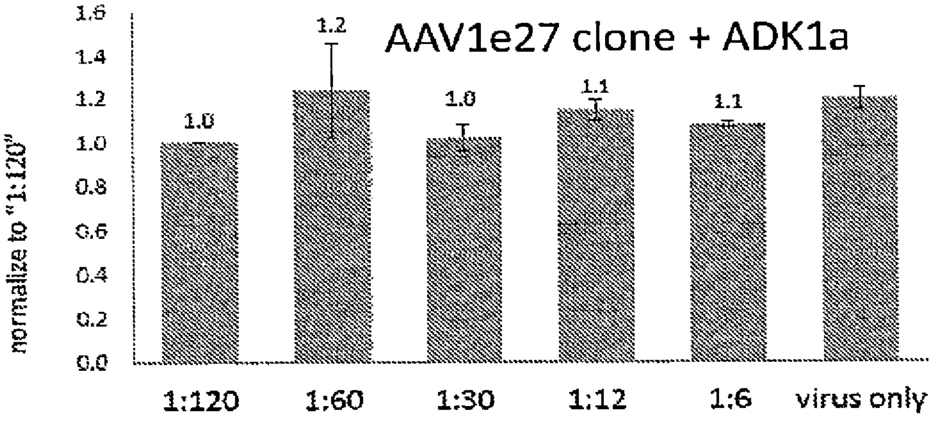
Figure 9:
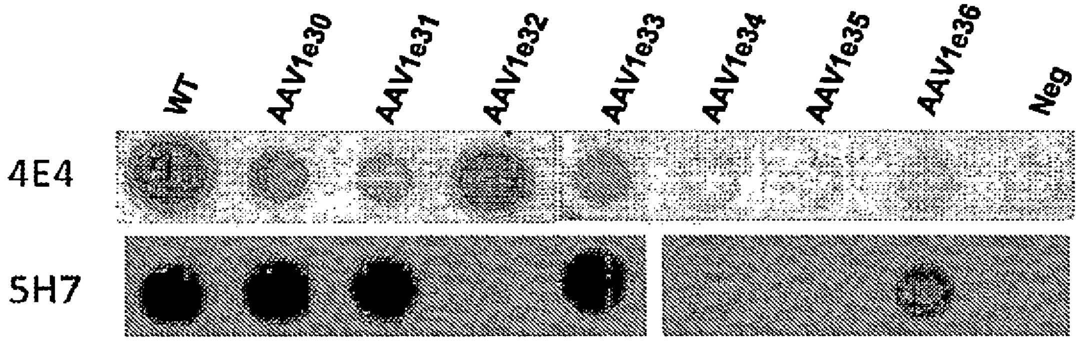
FIG. 9. Native dot blot assay comparing the parental AAV1 and clones AAV1e30-36 derived by rational, multiple site-specific mutagenesis within the CAM regions outlined in Table 5. Assay determines the ability of AAV1e clones to escape antibody detection. 4E4 and 5H7 are anti-AAV1 capsid antibodies.
Figure 10:
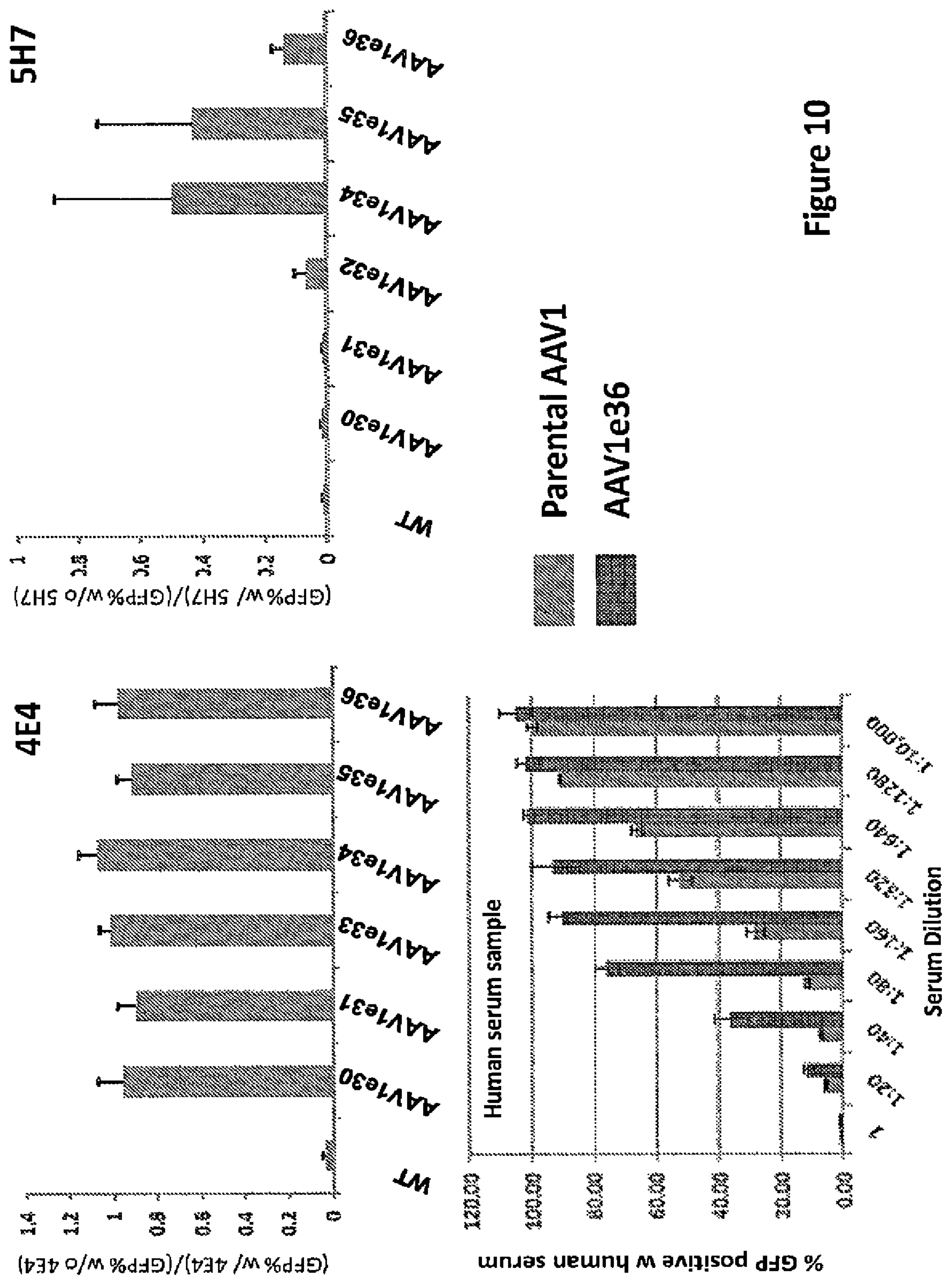
FIG. 10. Transduction assay comparing the parental AAV1 and clones AAV1e30-36 derived by rational, multiple site-specific mutagenesis within the CAM regions outlined in Table 5. Assay determines the ability of AAV1e clones to escape antibody detection. 4E4 and 5H7 are monoclonal antibodies against the parental AAV1 capsid and the human serum sample contains polyclonal antibodies against AAV1. Clones AAV1e30-36 completely escape 4E4, while parental AAV1 is neutralized. Clones AAV1e34 and AAV1e35 show substantial ability to escape 5H7, while AAV1e36 displays a partial ability for evading 5H7. Clone AAV1e36 escapes polyclonal antibodies in a human patient serum sample (50% neutralization for parental AAV1 is 1:320 dilution, while AAV1e36 is shifted to between 1:40 and 1:80 dilution range.
Figure 11:
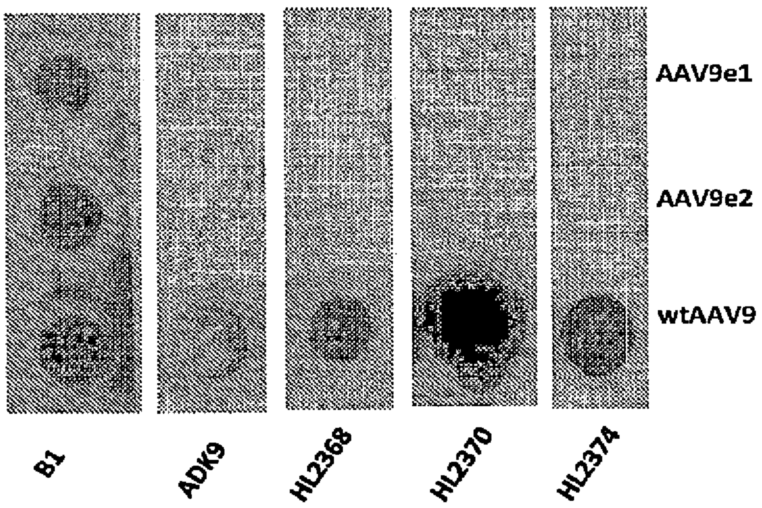
FIG. 11. Native dot blot assay comparing the parental AAV9 and clones AAV9e1 and AAV9e2 derived by rational, site-specific mutagenesis of residues listed within the CAM regions outlined in Table 5. Assay establishes the ability to engineer another serotype AAV9 to evade antibodies and the ability of AAV9e clones to escape antibody detection. ADK9, HL2368, HL2370 and HL2372 are monoclonal antibodies that detect parental AAV9 capsids.

We have designed AAV1 as well as AAV9 variants to escape anti-AAV capsid monoclonal binding and host antibody neutralization based on antigenic epitope information attained from 3D structural characterization of AAV capsids, receptor binding sites, and AAV-antibody complex structures determined by cryo-electron microscopy and image reconstruction. These vectors contain amino acid alterations in variable regions of the capsid, which have been established as common antigenic motifs (CAMs; Table 5). Amino acid residues within these CAMs have been modified to generate novel AAV strains that can escape neutralizing antibodies (AAVe series) in order to overcome pre-existing immunity (Tables 7 and 8), which has been reported to be detrimental to AAV transduction efficacy in pre-clinical animal studies and in human clinical trials. We have tested the mutants described herein and observe, using biochemical approaches including dot blots and ELISA (FIGS. 6, 7, 9 and 11), that these mutants escape recognition by antibodies targeted at the parental capsid, escape neutralization in the presence of anti-capsid antibodies (FIGS. 8 and 10), and display significantly reduced recognition by sera obtained from patients participating in a clinical trial utilizing AAV1 as the gene delivery vector (FIG. 10).

TABLE 5

Representative list of common antigenic motifs (CAMs) found on different AAV serotypes and isolates (respective VP1 numbering of residues and different amino acid residues is shown).

| | CAM1 (SEQ ID NO:) | CAM3 (SEQ ID NO:) | CAM4-1 (SEQ ID NO:) | CAM4-2 | CAM5 (SEQ ID NO:) |
|---|---|---|---|---|---|
| AAV1 | 262-SASTGAS-268 (303) | 370-VFMIPQYGYL-379 (304) | 451-NQSGSAQNK-459 (305) | 472-SV-473 | 493-KTDNNNSN-500 (306) |
| AAV2 | 262-SQSGAS-267 (311) | 369-VFMVPQYGYL-378 (312) | 450-TPSGTTTQS-458 (313) | 471-RD-472 | 492-SADNN1SE-499 (314) |
| AAV3 | 262-SQSGAS-267 (319) | 369-VFMVPQYGYL-378 (320) | 451-TTSGTTNQS-459 (321) | 472-SL-473 | 493-ANDNNNSN-500 (322) |
| AAV4 | 253-RLGESLQS-260 (327) | 360-VFMVPQYGYC-369 (328) | 445-GTTLNAGTA-453 (329) | 466-SN-467 | 487-ANQNYKIPATGS-498 (330 |
| AAV5 | 249-EIKSGSVDGS-258 (335) | 360-VFTLPQYGYA-369 (336) | 440-STNNTGGVQ-448 (337) | 458-AN-459 | 479-SG'VNRAS-485 (338) |
| AAV6 | 262-SASTGAS-268 (343) | 370-VFMIPQYGYL-379 (344) | 45I-NQSGSAQNK-459 (345) | 472-SV-473 | 493-KTDNNNSN-500 (346) |
| AAV7 | 263-SETAGST-269 (351) | 371-VFMIPQYGYL-380 (352) | 453-NPGGTAGNR-461 (353) | 474-AE-475 | 495-LDQNNNSN-502 (354) |
| AAV8 | 263-NGTSGGAT-270 (359) | 372-VFMIPQYGYL-381 (360) | 453-TTGGTANTQ-461 (361) | 474-AN-475 | 495-TGQNNNSN-502 (362) |
| AAV9 | 262-NSTSGGSS-269 (367) | 371-VFMIPQYGYL-380 (368) | 45I-INGSGQNQQ-459 (369) | 472-AV-473 | 493-VTQNNNSE-500 (370) |
| AAVrh8 | 262-NGTSGGST-269 (375) | 371-VFMVPQYGYL-380 (376) | 45I-QTTGTGGTQ-459 (377) | 472-AN-473 | 493-TNQNNNSN-500 (378) |
| AAVrh10 | 263-NGTSGGST-270 (383) | 372-VFMIPQYGYL-381 (384) | 453-STGGTAGTQ-461 (385) | 474-SA-475 | 495-LSQNNNSN-502 (386) |
| AAV10 | 263-NGTSGGST-270 (391) | 372-VFMIPQYGYL-381 (392) | 453-STGGTQGTQ-461 (393) | 474-SA-475 | 495-LSQNNNSN-502 (394) |
| AAV11 | 253-RLGTTSSS-260 (399) | 360-VFMVPQYGYC-369 (400) | 444-GETLNQGNA-452 (401) | 465-AF-466 | 486-ASQNYKIPASGG-497 (402) |
| AAV12 | 262-RIGTTANS-269 (407) | 369-VFMVPQYGYC-378 (408) | 453-GNSLNQGTA-461 (409) | 474-AY-475 | 495-ANQNYKIPASGG-506 (410) |
| AAVrh32.33 | 253-RLGTTSNS-260 (415) | 360-VFMVPQYGYC-369 (416) | 444-GETLNQGNA-452 (417) | 465-AF-466 | 486-ASQNYKIPASGG-497 (418) |
| Bovine AAV | 255-RLGSSNAS-262 (423) | 362-VFMVPQYGYC-371 (424) | 447-GGTLNQGNS-455 (425) | 468-SG-469 | 489-ASQNYKIPQGRN-500 (426) |
| Avian AAV | 265-RIQGPSGG-272 (431) | 375-IYTIPQYGYC-384 (432) | 454-VSQAGSSGR-462 (433) | 475-AA-476 | 496-ASNITKNNVFSV-507 (434) |

| | CAM6 (SEQ ID NO:) | CAM7 (SEQ ID NO:) | CAM8 (SEQ ID NO:) | CAM9-1 | CAM9-2 (SEQ ID NO:) |
|---|---|---|---|---|---|
| AAVI | 528-KDDEDKF-534 (307) | 547-SAGASN-552 (308) | 588-STDPATGDVH-597 (309) | 709-AN-710 | 716-DNNGLYT-722 (310) |
| AAV2 | 527-KDDEEKF-533 (315) | 546-GSEKTN-551 (316) | 587-NRQAATADVN-596 (317) | 708-VN-709 | 715-DTNGVYS-721 (318) |
| AAV3 | 528-KDDEEKF-534 (323) | 547-GTTASN-552 (324) | 588-NTAPTTGTVN-597 (325) | 709-VN-710 | 716-DTNGVYS-722 (326) |
| AAV4 | 527-GPADSKF-533 (331) | 545-QNGNTA-560 (332) | 586-SNLPTVDRLT-595 (333) | 707-NS-708 | 714-DAAGKYT-720 (334) |
| AAV5 | 515-LQGSNTY-521 (339) | 534-ANPGTTAT-541 (340) | 577-TTAPATGTYN-586 (341) | 697-QF-698 | 704-DSTGEYR-710 (342) |

TABLE 5-continued

| Representative list of common antigenic motifs (CAMs) found on different AAV serotypes and isolates (respective VP1 numbering of residues and different amino acid residues is shown). | | | | | |
|---|---|---|---|---|---|
| AAV6 | 528-KDDKDKF-534 (347) | 547-SAGASN-552 (348) | 588-STDPATGDVH-597 (349) | 709-AN-710 | 716-DNNGLYT-722 (350) |
| AAV7 | 530-KDDEDRF-536 (355) | 549-GATNKT-554 (356) | 589-NTAAQTQVVN-598 (357) | 710-TG-711 | 717-DSQGVYS-723 (358) |
| AAV8 | 530-KDDEERF-536 (363) | 549-NAARDN-554 (364) | 590-NTAPQIGTVNS-600 (365) | 711-TS-712 | 718-NTEGVYS-724 (366) |
| AAV9 | 528-KEGEDRF-534 (371) | 547-GTGRDN-552 (372) | 588-QAQAQTGWVQ-597 (373) | 709-NN-710 | 716-NTEGVYS-722 (374) |
| AAVrh8 | 528-KDDDDRF-534 (379) | 547-GAGNDG-552 (380) | 588-NTQAQTGLVH-597 (381) | 709-TN-710 | 716-NTEGVYS-722 (382) |
| AAVrh10 | 530-KDDEERF-536 (387) | 549-GAGKDN-554 (388) | 590-NAAPIVGAVN-599 (389) | 711-TN-712 | 718-NTDGTYS-724 (390) |
| AAV10 | 530-KDDEERF-536 (395) | 549-GAGRDN-554 (396) | 590-NTGPIVGNVN-599 (397) | 711-TN-712 | 718-NTEGTYS-724 (398) |
| AAV11 | 526-GPSDGDF-532 (403) | 544-VTGNTT-549 (404) | 585-TTAPITGNVT-594 (405) | 706-SS-707 | 713-DTTGKYT-719 (406) |
| AAV12 | 535-GAGDSDF-541 (411) | 553-PSGNTT-558 (412) | 594-TTAPHIANLD-603 (413) | 715-NS-716 | 722-DNAGNYH-728 (414) |
| AAVrh32.33 | 526-GPSDGDF-532 (419) | 544-VTGNTT-549 (420) | 585-TTAPITGNVT-594 (421) | 706-SS-707 | 713-DTTGKYT-719 (422) |
| Bovine AAV | 529-ANDATDF-535 (427) | 547-ITGNTT-552 (428) | 588-TTVPTVDDVD-597 (429) | 709-DS-710 | 716-DNAGAYK-722 (430) |
| Avian AAV | 533-FSGEPDR-539 (435) | 552-VYDQTTAT-559 (436) | 595-VTPGTRAAVN-604 (437) | 716-AD-717 | 723-SDTGSYS-729 (438) |

TABLE 6.1

AAV1e1-7. List of novel neutralizing antibody evading AAV1e strains isolated after screening and selection. Each strain is labeled as AAV1eN, where N is the strain number. Amino acid residues that were selected by this approach within the different common antigenic motifs are listed with VPI capsid protein numbering. In each case, 15-25 clones isolated from the library screen were sent for sequence analysis the relative frequencies of each strain is also listed.

| Nab Evading AAV1e strains | Novel amino acid sequence identified in corresponding AAV1e isolate | Frequency |
|---|---|---|
| AAV1e1 | 456-QVRG-459 (SEQ ID NO: 22) | 10/19 |
| AAV1e2 | 456-GRGG-459 (SEQ ID NO: 24) | 1/19 |
| AAV1e3 | 456-SGGR-459 (SEQ ID NO: 25) | 1/19 |
| AAV1e4 | 456-ERPR-459 (SEQ ID NO: 23) | 1/19 |
| AAV1e5 | 456-SERR-459 (SEQ ID NO: 26) | 1/19 |
| AAV1e6 | 456-LRGG-459 (SEQ ID NO: 27) | 1/19 |
| AAV1e7 | 456-ERPR-459 (SEQ ID NO: 23), D595N | 4/19 |

TABLE 6.2

AAV1e8-16. List of novel neutralizing antibody evading AAV1e strains isolated after screening and selection (Cont'd)

| Nab Evading AAV1e strains | Novel amino acid sequence identified in corresponding AAV1e isolate | Frequency |
|---|---|---|
| AAV1e8 | 493-PGGNATR-499 (SEQ ID NO: 30) | 15/15 |
| AAV1e9 | 588-TADHDTKGVL-597 (SEQ ID NO: 32) | 15/24 |
| AAV1e10 | 588-VVDPDKKGVL-597 (SEQ ID NO: 33) | 1/24 |
| AAV1e11 | 588-AKDTGPLNVM-597 (SEQ ID NO: 34) | 2/24 |
| AAV1e12 | 588-QTDAKDNGVQ-597 (SEQ ID NO: 35) | 1/24 |
| AAV1e13 | 588-DKDPWLNDVI-597 (SEQ ID NO: 36) | 1/24 |
| AAV1e14 | 588-TRDGSTESVL-597 (SEQ ID NO: 37) | 2/24 |
| AAV1e15 | 588-VIDPDQKGVL-597 (SEQ ID NO: 38) | 1/24 |
| AAV1e16 | 588-VNDMSNYMVH-597 (SEQ ID NO: 39) | 1/24 |

TABLE 6.3

(AAV1e17-20). List of novel neutralizing antibody evading AAV1e generated by making various rationally engineered permutations and combinations of amino acid sequences derived from AAV1e6, AAV1e8 and AAV1e9.

| Nab Evading AAV1e strains (Combination mutant strains) | Amino acid sequences combined by rational mutagenesis |
|---|---|
| AAV1e17 | (456-LRGG-459, SEQ ID NO: 27) + (493-PGGNATR-499, SEQ ID NO: 30) |
| AAV1e18 | (456-LRGG-459, SEQ ID NO: 27) + (588-TADHDTKGVL-597, SEQ ID NO: 32) |
| AAV1e19 | (493-PGGNATR-499, SEQ ID NO: 30) + (588-TADHDTKGVL-597, SEQ ID NO: 32) |
| AAV1e20 | (456-LRGG-459, SEQ ID NO: 27) + (493-PGGNATR-499, SEQ ID NO: 30) + (588-TADHDTKGVL-597, SEQ ID NO: 32) |

TABLE 6.4

AAV1e21-26. List of novel neutralizing antibody evading AAV1e strains isolated after screening and selection (Cont'd.) These novel AAV1e strains contain new sequences listed below in addition to the AAV1e8 sequence 493-PGGNATR-499. Briefly, an AAV1e capsid library was generated using AAV1e8 as the template capsid and randomizing common antigenic motif CAM8 (residues 588-597). These were subjected similar screening and isolation protocols to obtain different novel AAV1e isolates.

| Nab Evading AAV1e strains engineered using AAV1e8 as a template | Novel amino acid sequence identified in corresponding AAV1e isolate | Frequency |
|---|---|---|
| AAV1e21 | 588-CNDEMQVQVN-597 (SEQ ID NO: 297) | 2/9 |
| AAV1e22 | 588-SPDIVYADVC-597 (SEQ ID NO: 298) | 1/9 |
| AAV1e23 | 588-LDDCHNIDVN-597 (SEQ ID NO: 299) | 1/9 |
| AAV1e24 | 588-SCDCVTNSVS-597 (SEQ ID NO: 300) | 1/9 |
| AAV1e25 | 588-TVDSNPYEVN-597 (SEQ ID NO: 301) | 1/9 |
| AAV1e26 | 588-GDDHPNPDVL-597 (SEQ ID NO: 302) | 1/9 |

TABLE 7

AAV1e27-36. List of novel neutralizing antibody evading AAV1e strains generated by making various rationally determined, site-specific mutations on the AAV capsid protein. Single mutants and multiple site mutants are shown.

| Nab Evading AAV1e strains | Site-specific amino acid mutations generated by rational mutagenesis |
|---|---|
| AAV1e27 | S472R |
| AAV1e28 | V473D |
| AAV1e29 | N500E |
| AAV1e30 | A456T + Q457T + N458Q + K459S |
| AAV1e31 | T492S + K493A |
| AAV1e32 | S586R + S587G + S588N + T589R |
| AAV1e33 | A456T + Q457T + N458Q + K459S + T492S + K493A |
| AAV1e34 | A456T + Q457T + N458Q + K459S + S586R + S587G + S588N + T589R |
| AAV1e35 | T492S + K493A + S586R + S587G + S588N + T589R |
| AAV1e36 | A456T + Q457T + N458Q + K459S + T492S + K493A + S586R + S587G + S588N + T589R |

TABLE 8

AAV9e1 & AAV9e2. Proof of concept studies establishing the rational design of novel neutralizing antibody evading AAV9e strains. Table lists the different site-specific point mutations made in AAV9 by rational mutagenesis.

| Antibody Evading AAV1e strains | Site-specific amino acid mutations generated by rational mutagenesis |
|---|---|
| AAV9e1 | S454V + Q456V |
| AAV9e2 | I451Q + G453Q + Q456S + N457A + N459 insertion |

Example 3. Structure-Based Iterative Evolution of Antigenically Advanced AAV Variants for Therapeutic Gene Transfer Cells, viruses and antibodies. HEK293 and MB114 cells were maintained in Dulbecco's modified Eagle's medium (DMEM) supplemented with 10% fetal bovine serum (FBS) (ThermoFisher, Waltham, Mass.), 100 units/ml of penicillin and 101±g/ml of streptomycin (P/S) (ThermoFisher, Waltham, Mass.) in 5% $CO_2$ at 37° C. Murine adenovirus 1 (MAV-1) was purchased from American Type Culture Collection (ATCC, Mannassas, Va.) and amplified by infecting MB114 cells at a multiplicity of infection (MOI) of 1. At day 6 post-infection (approximately 50% cytopathic effect (CPE)), media containing progeny MAV-1 viruses were harvested and centrifuged at 3000 g for 5 min, and the supernatant stored at −80° C. for subsequent evolution studies. Mouse anti-AAV1 monoclonal antibodies ADK1a, 4E4 and 5H7 have been described previously. De-identified and naïve human serum samples were purchased from Valley Biomedical, Winchester, Va. Naïve serum from rhesus macaques was from the Yerkes National Primate Center. Antisera against AAV1 capsids, generated by immunizing rhesus macaques intramuscularly (I.M.) with AAV1 capsids was from the Oregon National Primate Center. All mouse, human and non-human primate serum used in this study were heat inactivated at 55° C. for 15 min prior to use.

Recombinant AAV Production, Purification and Quantification.

Recombinant AAV vectors were produced by transfecting four 150 mm dishes containing HEK293 cells at 70-80% confluence using polyethylenimine (PEI) according to the triple plasmid protocol. Recombinant vectors packaging single stranded genomes encoding firefly luciferase driven by the chicken beta-actin promoter (ssCBA-Luc) or self-complementary green fluorescence protein driven by a hybrid chicken beta-actin promoter (scCBh-GFP) were generated using this method. Subsequent steps involving harvesting of recombinant AAV vectors and downstream purification were carried out as described previously. Recombinant AAV vector titers were determined by quantitative PCR (qPCR) with primers that amplify AAV2 inverted terminal repeat (ITR) regions, 5'-AACATGCTACGCAGAGAGGGAGTGG-3' (SEQ ID NO:477), 5'-CATGAGACAAGGAACCCCTAGTGATGGAG-3' (SEQ ID NO:478).

Structural Modeling and Analysis of AAV Antigenic Footprints.

Antigenic footprints of AAV serotypes 1/6, AAV2, AAV5, AAV8 and AAV9 were determined using previously resolved structures of AAV capsids complexed with different mouse monoclonal antibodies. To restrict diversity and maximize efficiency of AAV library generation, only amino acid residues directly in contact with antibodies were included for analysis. Contact surface residues on each serotype were either aligned by Clustal Omega software or structurally superimposed using PyMOL (Schrödinger, New York City, N.Y.). Structural alignment revealed that antibody footprints from multiple serotypes overlap in close proximity to the 3-fold symmetry axis, around the 5-fold pore and at the 2-fold depression. Of these so-called common antigenic motifs (CAMs), we determined that 12/18 of the antibodies analyzed have direct contact at the 3-fold symmetry supporting the notion that this region is a critical antigenic determinant. For the current study, antigenic footprints for three distinct monoclonal antibodies (4E4, 5H7 and ADK1a) were visualized on the AAV1 capsid (PDB ID: 3ng9) and roadmap images were generated using the RIVEM program.

Generation of AAV Capsid Libraries.

AAV libraries were engineered through saturation mutagenesis of amino acid residues within different antigenic footprints associated with distinct monoclonal antibodies described above. Briefly, for Gibson assembly, twelve oligos with an average length of 70 nucleotides were ordered from IDT (Coralville, Iowa). Each oligo contains at least 15-20 nt overlapping homology to the neighboring oligos. Three oligos contained degenerate nucleotides (NNK) within genomic regions coding for different antigenic footprints. Plasmid libraries were then generated by in vitro assembly of multiple oligos using High Fidelity Gibson Assembly Mix (NEB, Ipswich, Mass.) according to manufacturer instructions. The assembled fragments were either PCR amplified for 10 cycles using Phusion HF (NEB, Ipswich, Mass.) or directly cloned into pTR-AAV1 plasmids between the BspEI and SbfI restriction sites. Plasmid pTR-AAV1 contains genes encoding AAV2 Rep and AAV1 Cap with 2 stop codons at positions 490 and 491 (AAV1 VP1 numbering) introduced by site directed mutagenesis (Agilent, Santa Clara, Calif.). The entire construct is flanked by AAV2 inverted terminal repeats (ITRs) to enable packaging and replication of pseudotyped AAV1 libraries upon helper virus co-infection. It is noteworthy to mention that the AAV1** capsid gene was incorporated prior to library cloning in order to reduce wild type AAV1 contamination within the different libraries. Ligation reactions were then concentrated and purified by ethanol precipitation. Purified ligation products were electroporated into DHIOB electroMax (Invitrogen, Carlsbad, Calif.) and directly plated on multiple 5245 $mm^2$ bioassay dishes (Corning, Corning, N.Y.) to avoid bias from bacterial suspension cultures. Plasmid DNA from pTR-AAV1CAM libraries was purified from pooled colonies grown on LB agar plates using a Maxiprep kit (Invitrogen, Carlsbad, Calif.).

Directed Evolution of Novel AAV CAM Strains.

Equal amounts (15 μg each) of each pTR-AAV1CAM library and the Ad helper plasmid, pXX680, were transfected onto HEK293 cells at 70-80% confluency on each 150 mm dish using PEI to generate CAM viral libraries. AAV CAM libraries were purified using standard procedures described earlier. MB114 cells were seeded on a 100 mm tissue culture dish overnight to reach 60-70% confluence before inoculation with AAV CAM libraries at an MOI ranging from 1000-10,000. After 24 h post-transduction, MAV-1 was added as helper virus to promote AAV replication. At 6 days post-infection with MAV-1 (50% CPE), the supernatant was harvested and DNase I resistant vector genomes were quantified on day 7. Media containing replicating AAV strains and MAV-1 obtained from each round of infection were then used as inoculum for each subsequent cycle for a total of 5 rounds of evolution. Subsequent iterative rounds of evolution were carried out in a similar fashion with AAV capsid libraries containing different permutations and combinations of newly evolved antigenic footprints.

Identification of Newly Evolved AAV Strains.

To analyze sequence diversity of the parental and evolved AAV CAM libraries, DNase I resistant vector genomes were isolated from media and amplified by Q5 polymerase for 10-18 cycles (NEB, Ipswich, Mass.) using primers, 5'-CCCTACACGACGCTCTTCCGATCTNNNNNeagaact a ggaagt-3' (SEQ ID NO:479) and 5'-GACTGGAGTTCA-GACGTGTGCTCTTCCGATCTNNNNNgccaggtaatgctc-ccatagc-3' (SEQ ID NO:480). Illumina MiSeq sequencing adaptor for multiplexing was added through a second round of PCR using Q5 Polymerase with P5 and P7 primers. After each round of PCR, the products were purified using a PureLink PCR Micro Kit (ThermoFisher, Waltham, Mass.). Quality of the amplicons was verified using a Bioanalyzer (Agilent), and concentrations quantified using a Qubit spectrometer (ThermoFisher, Waltham, Mass.). Libraries were then prepared for sequencing with a MiSeq 300 Kit v2, following manufacturer instructions, and sequenced on the MiSeq system (Illumina).

Sequencing Data Analysis.

De-multiplexed reads were analyzed via a custom Perl script. Briefly, raw sequencing files were probed for mutagenized regions of interest, and the frequencies of different nucleotide sequences in this region were counted and ranked for each library. Nucleotide sequences were also translated, and these amino acid sequences were similarly counted and ranked. Amino acid sequence frequencies across libraries were then plotted in R.

Isolation of AAV CAM Variants for Characterization.

To characterize selected clones from each library, DNase I resistant vector genomes were isolated from media and amplified by Phusion HF (NEB, Ipswich, Mass.) using primers flanking the BspEI and SbfI sites. The PCR products were gel purified, sub-cloned into TOPO cloning vectors (ThermoFisher, Waltham, Mass.) and sent out for standard Sanger sequencing (Eton Bioscience, San Diego, Calif.). Unique sequences were sub-cloned into an AAV helper plasmid backbone, pXR, using BspEI and SbfI sites. Unique recombinant AAV CAM variants were produced following a standard rAAV production protocol as described above.

In Vitro Antibody and Serum Neutralization Assays.

Twenty-five microliters of antibodies or antisera (as specified for individual experiments) was mixed with an equal volume containing recombinant AAV vectors (MOI 1,000-10,000) in tissue culture treated, black, glass bottom 96 well plates (Corning, Corning, N.Y.) and incubated at room temperature (RT°) for 30 min. A total of $5\times10^4$ HEK293 cells in 50 μl of media was then added to each well and the plates incubated in 5% $CO_2$ at 37° C. for 48 h. Cells were then lysed with 25 μl of 1× passive lysis buffer (Promega, Madison, Wis.) for 30 min at RT. Luciferase activity was measured on a Victor 3 multilabel plate reader (Perkin Elmer, Waltham, Mass.) immediately after addition of 25 μl of luciferin (Promega, Madison, Wis.). All read outs were normalized to controls with no antibody/antisera treatment. Recombinant AAV vectors packaging ssCBA-Luc transgenes and pre diluted in DMEM+5% FBS+P/S were utilized in this assay.

In Vive Antibody Neutralization Assay.

Each hind limb of 6-8 week old female BAlb/c mice (Jackson Laboratory, Bay Harbor, Me.) was injected intramuscularly (I.M.) with $2\times10^{10}$ AAV packaging CBA-Luc pre-mixed with three different monoclonal antibodies, 4E4, 5H7 and ADK1a, at 1:500, 1:50 and 1:5 dilutions, respectively, in a final volume of 20 µl. After 4 wk post-injection, luciferase activity was measured using a Xenogen IVIS Lumina system (PerkinElmer Life Sciences/Caliper Life Sciences, Waltham, Mass.) at 5 min post-intraperitoneal (I.P.) injection of 175 µl of in vivo D-luciferin (120 mg/kg Nanolight, Pinetop, Ariz.) per mouse. Luciferase activity was measured as photons/sec/cm$^2$/sr and analyzed using Living Image 3.2 software (Caliper Life Sciences, Waltham, Mass.).

Generation of Anti-AAV1 Mouse Serum by Immunization.

1×10$^{10}$ vg of wtAAV1 in 20 µl of PBS was injected intramuscularly into each hind leg of 6-8 week old, female Balb/c mice. Whole blood was collected by cardiac puncture at 4 wk post-injection and serum was isolated using standard coagulation and centrifugation protocols. Briefly, mouse blood was coagulated at RT for 30 min and centrifuged at 2000 g for 10 min at 4° C. All serum was heat-inactivated at 55° C. for 15 min and stored at −80° C.

In Vivo Characterization of AAV CAM Variants in Mice.

A dose of 1×10$^{11}$ vg of AAV vectors packaging the scCBh-GFP transgene cassette in 200 µl of PBS was injected into C57/B16 mice intravenously (I.V.) via the tail vein. Mice were sacrificed after 3 wk post-injection and perfused with 4% paraformaldehyde (PFA) in PBS. Multiple organs, including heart, brain, liver and kidney, were harvested. Tissues were sectioned to 50 µm thin slices by vibratome VT1200S (Leica, Welzlar, Germany) and stained for GFP with standard immunohistochemistry 3,3'-Diaminobenzidine (DAB) stain procedures described previously. At least 3 sections per organ from 3 different mice were submitted for slide scanning. For bio-distribution analysis, 1×10$^{11}$ vg of AAV vectors packaging ssCBA-Luc were injected I.V. as mentioned above in Balb/C mice. After 2 wk post-injection, mice were sacrificed and perfused with 1×PBS. Multiple organs, including heart, brain, lung, liver, spleen, kidney and muscle, were harvested. DNA was harvested using DNeasy kit (Qiagen, Hilden, Germany) according to the manufacturer's instructions. Vector genome copy numbers were determined by quantitative PCR (qPCR) using as described previously using luciferase transgene primers, 5'-CCTTCGCITCAAAAAATGGAAC-3' (SEQ ID NO:481), and 5'-AAAAGCACTCTGATTGACAAATAC-3' (SEQ ID NO:482). Viral genome copy numbers were normalized to mouse genomic DNA in each sample. Tissue samples were also processed for luciferase activity assays by homogenization in 1×PLB (Promega, Madison, Wis.) using a Qiagen TissueLyserII at a frequency of 20 hz for three 45 s pulses. The homogenate was spun down, and 20 µl of supernatant mixed with 50 µl of luciferin (Promega, Madison, Wis.) and immediately measured using a Victor 3 multilabel plate reader (Perkin Elmer, Waltham, Mass.).

Intracerebroventricular (I.C.V.) Injections.

Postnatal day 0 (P0) C57/B16 pups which were anesthetized on ice for 2 minutes followed by stereotaxic I.C.V. injections with AAV vectors packaging the scCBh-GFP transgene cassette. A dose of 3×10$^9$ vg in 3 µl of PBS was injected into the left lateral ventricle using a Hamilton 700 series syringe with a 26 s gauge needle (Sigma-Aldrich, St. Louis, Mo.), attached to a KOPF-900 small animal stereotaxic instrument (KOPF instruments, Tujunga, Calif.). All neonatal injections were performed 0.5 mm relative to the sagittal sinus, 2 mm rostral to transverse sinus and 1.5 mm deep. After vector administration, mice were revived under a heat lamp and rubbed in the bedding before being placed back with the dam. Mouse brains were harvested at 2 wk post vector administrations (P14). Brains were post fixed and immunostained as described previously.

Western Blots and Electron Microscopy.

A total of 5×10$^9$ viral genomes were re-suspended in NuPAGE LDS sample buffer (Invitrogen, Carlsbad, Calif.). +50 mM 1,4-Dithiothreitol (DTT). Samples were ran on NuPAGE 4-12% Bis-Tris Gel and transferred onto polyvinylidene fluoride (PVDF) membrane. (Invitrogen, Carlsbad, Calif.). AAV capsid proteins were detected using mouse monoclonal antibody B1 (1:50) and secondary goat anti-mouse conjugated to horseradish peroxidase (HRP) (Jackson Immuno Research Labs, West Grove, Pa.). For EM studies, 1×10$^9$ vg/l of virus was prepared in PBS and absorbed on a Formvar/Carbon 400 mesh, Cu grid (TED Pella, Redding, Calif.). Samples were negative stained with 2% uranyl acetate and analyzed using a Zeiss Supra 25 field emission scanning electron microscope.

Structural Analysis of AAV-Antibody Complexes Enables an Iterative Approach to Evolve Novel AAV Variants.

Figures 12A, 12B, 12C, 12D:
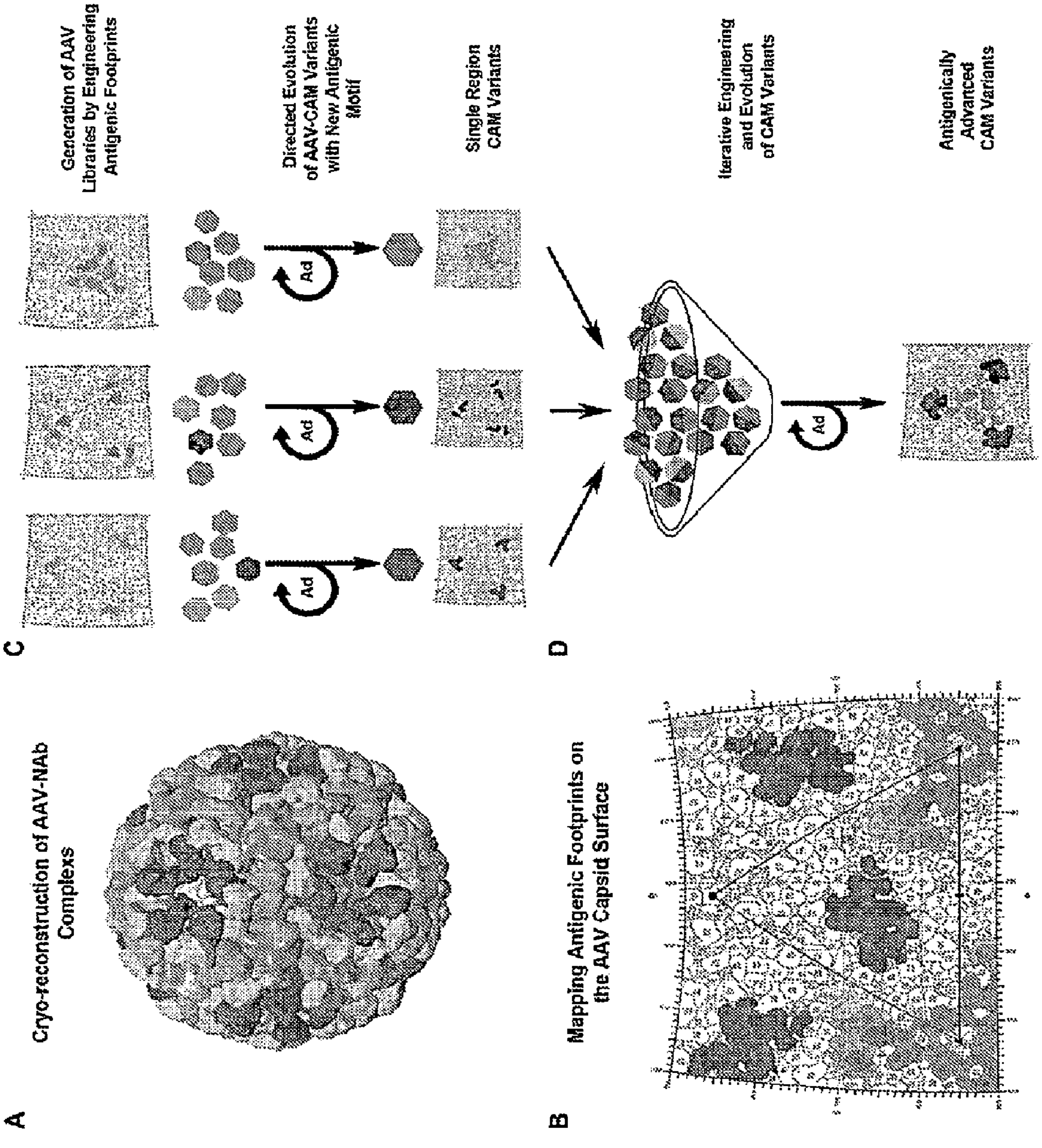
FIGS. 12A-12D. Roadmap for structure-based evolution of antigenically advanced AAV variants. (A) Three-dimensional model of cryo-reconstructed AAV1 capsid complexed to multiple monoclonal antibodies. The model depicts AAV1 complexed with the Fab regions of 4 different monoclonal antibodies viewed along the 2-fold axis, ADK1a, ADK1b, 4E4, 5H7. (B) Contact residues and common antigenic motifs (CAMs) for four anti-AAV1 antibodies on the capsid generated by RIVEM are shown. Color codes of each antibody are same as above, in addition, overlapping residues between antibodies were colored individually, ADK1a and 4E4, 4E4 and 5H7. (C) Individual antigenic footprints on the AAV1 capsid selected for engineering and AAV library generation. Three different AAV libraries were subjected to five rounds of evolution on vascular endothelial cells co-infected with adenovirus to yield single region AAV-CAM variants. (D) Newly evolved antigenic footprints from each library were then combined and re-engineered through an iterative process, pooled and subjected to a second round of directed evolution for 3 cycles. This approach yields antigenically advanced AAV-CAM variants with new footprints that have not yet emerged in nature.

We analyzed previously resolved, cryo-reconstructed structures of AAV1 capsids complexed with four different fragment antigen binding (Fab) regions of anti-AAV1 monoclonal antibodies. Three-dimensional reconstruction revealed that this subset of antibodies nearly masks the entire AAV1 capsid surface (FIG. 12A). We then identified a subset of capsid surface residues (through construction of roadmap images) that lie within these antigenic footprints and are implicated in direct contact with the different antibodies (FIG. 12B). Further analysis and comparison with different AAV serotypes revealed a prominent clustering of common antigenic footprints at the 3-fold symmetry axis on the capsid surface. Specifically, amino acid residues within three surface regions, common antigenic motif 4 (CAM4; 456-AQNK-459, SEQ ID NO:483), common antigenic motif 5 (CAM5; 493-KTDNNNS-499, SEQ ID NO:484) and common antigenic motif 8 (CAM8; 588-STDPATGDVH-597, SEQ ID NO:309) were selected for saturation mutagenesis and generation of different AAV libraries. It is important to note that the different CAMs listed above are subsets of variable regions (VRs) 4, 5 and 8 outlined previously. Each AAV capsid library was then subjected to five rounds of directed evolution in vascular endothelial cells, which are highly permissive to the parental AAV1 strain (FIG. 12C). Novel AAV variants were identified and combination AAV libraries were engineered using the latter as templates. Iterative rounds of evolution and capsid engineering yielded novel antigenically advanced AAV strains characterized in the current study (FIG. 12D).

Antigenic Footprints on the AAV Capsid Surface are Remarkably Plastic and Evolvable.

Figures 13A, 13B, 13C, 13D, 13E, 13F, 13G, 13H:
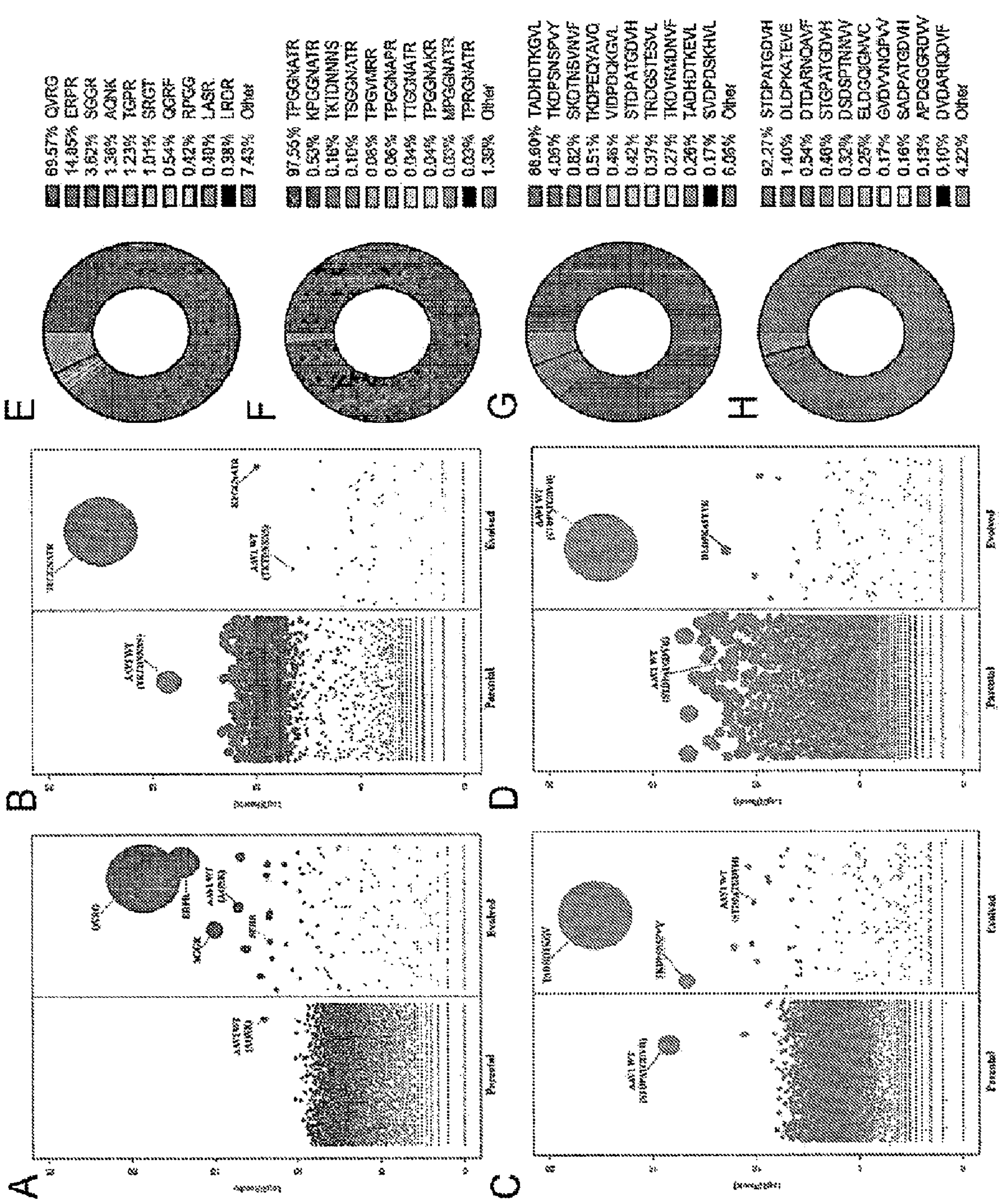
FIGS. 13A-13H. Analysis of library diversity, directed evolution and enrichment of novel antigenic footprints. Parental and evolved libraries were subjected to high-throughput sequencing using the Illumina MiSeq platform. Following analysis with a custom Perl script, enriched amino acid sequences were plotted in R for both the parental and evolved libraries of (A) region 4, (B) region 5, (C) region 8 and (D) combined regions 5+8. Each bubble represents a distinct capsid amino acid sequence with the area proportional to the number of reads for that variant in the respective library. (E-H) Amino acid sequence representation was calculated for the top ten variants with the highest representation in each library after subjecting to evolution. Percentages represent the number of reads for the variant in the evolved library normalized to the total number of reads containing the antigenic region of interest. "Other" sequences represent all other evolved library amino acid sequences not contained in the top ten hits.
Figure 20:
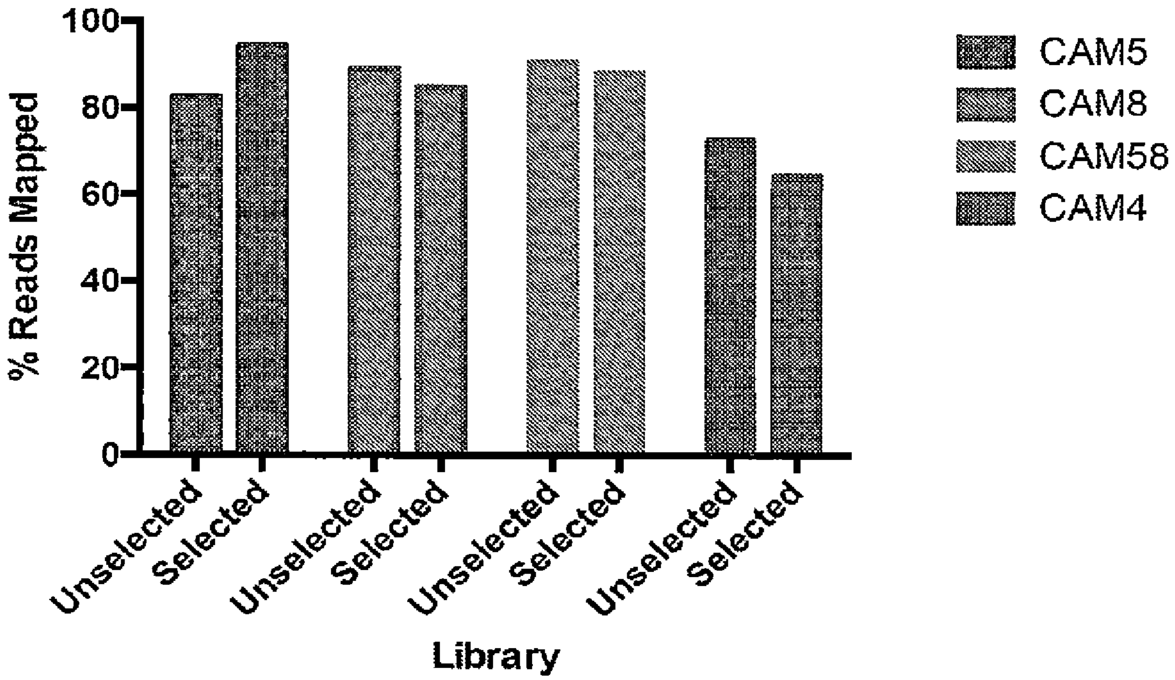
FIG. 20. Sequencing Reads Mapped to Region of Interest. Percentage of sequencing reads mapped to the mutagenized region of interest for unselected and selected libraries CAM5, CAM8, CAM58, and CAM4. Demultiplexed FASTQ files were processed and mapped with a custom Perl script.
Figure 21:
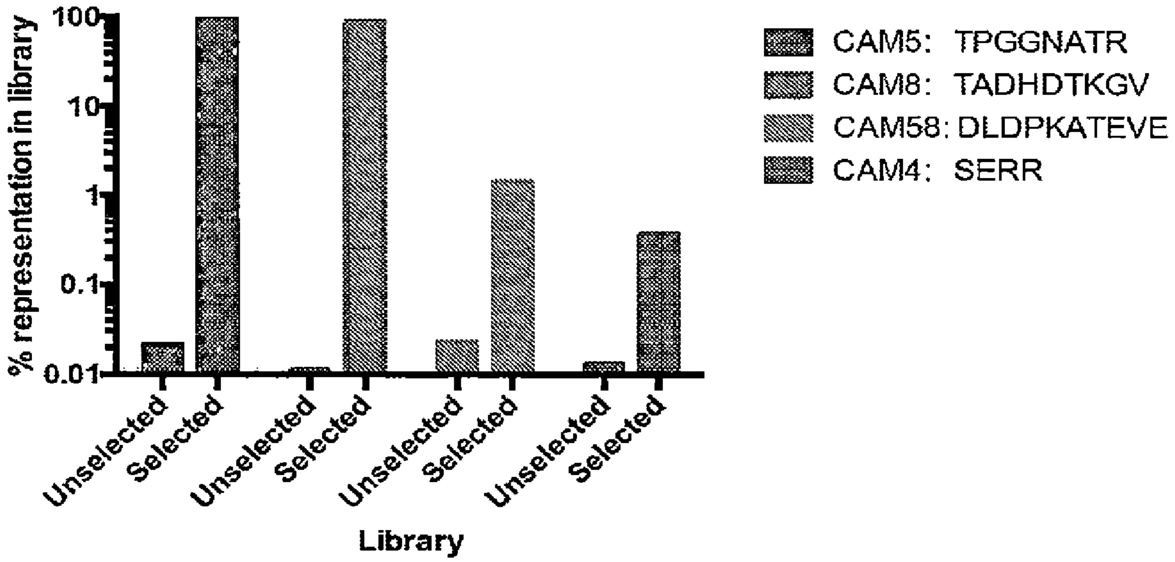
FIG. 21. Representation of lead variants in unselected and selected libraries. Percentage representation of amino acid sequences for lead variants in unselected and selected libraries, calculated by dividing the reads containing a sequence of interest by the total reads containing the mutagenized region.

As outlined above, the AAV CAM4, CAM5, and CAM8 libraries were subjected to 5 rounds of directed evolution. Libraries were then sequenced using the MiSeq system (Illumina), wherein each unselected (parental) library was sequenced at ~2×10$^6$ reads and selected (evolved) libraries sequenced at ~2×10$^5$ reads. De-multiplexed reads were probed for mutagenized regions of interest with a custom Perl script, with a high percentage of reads mapping to these regions for all libraries (FIGS. 20-21). At both the nucleotide and amino acid level, all unselected libraries demonstrated high diversity and minimal bias towards any particular sequence, while evolved libraries showed dramatic enhancement in representation of one or more lead variants (FIGS. 13A-C, E-G). Further, within the top ten selected variants for each library, many amino acid sequences showed similarities at multiple residues (FIGS. 13E-G). For instance, in the evolved CAM5 library 97.55% of sequences spanning the mutagenized region of interest read TPGGNATR (SEQ ID NO:485), while minor variants largely mimicked this sequence (FIG. 13F). In case of CAM8, we observed significant enrichment (86.6%) for a variant with amino acid residues TADHDTKGV (SEQ ID NO:486) (FIG. 13G). The evolved CAM4 library demonstrated higher plasticity (QVRG (SEQ ID NO:22), 69.57%; ERPR (SEQ ID NO:23), 14.05%; SGGR (SEQ ID NO:25), 3.62%) as evidenced by the range of amino acid residues tolerated within that antigenic region (FIG. 13A). We then generated a combination AAV library (CAM58, FIG. 13D), which carries the lead epitope from the evolved CAM5 library and a randomized CAM8 region. Interestingly, subjecting this library to directed evolution yielded the wild type AAV1 sequence in the CAM8 region (92.27%), i.e., STDPATGDVH (SEQ ID NO:309) (FIG. 13H). Although a secondary variant with the sequence DLDPKATEVE (SEQ IDNO:487) was also enriched (1.4%) (FIG. 13D), the latter observation demonstrates the evolutionary and structural constraints imposed by the interaction between CAM5 and CAM8 regions. These constraints were further evaluated by rational combination of different epitopes derived from these novel CAM4, 5 or 8 variants. Nevertheless, these results corroborate the notion that antigenic footprints on the AAV capsid surface are mutable and can be evolved into novel footprints, while maintaining infectivity.

Individually Evolved AAV CAM Variants are Similar to the Parental AAV1 Serotype.

Figures 19A, 19B, 19C:
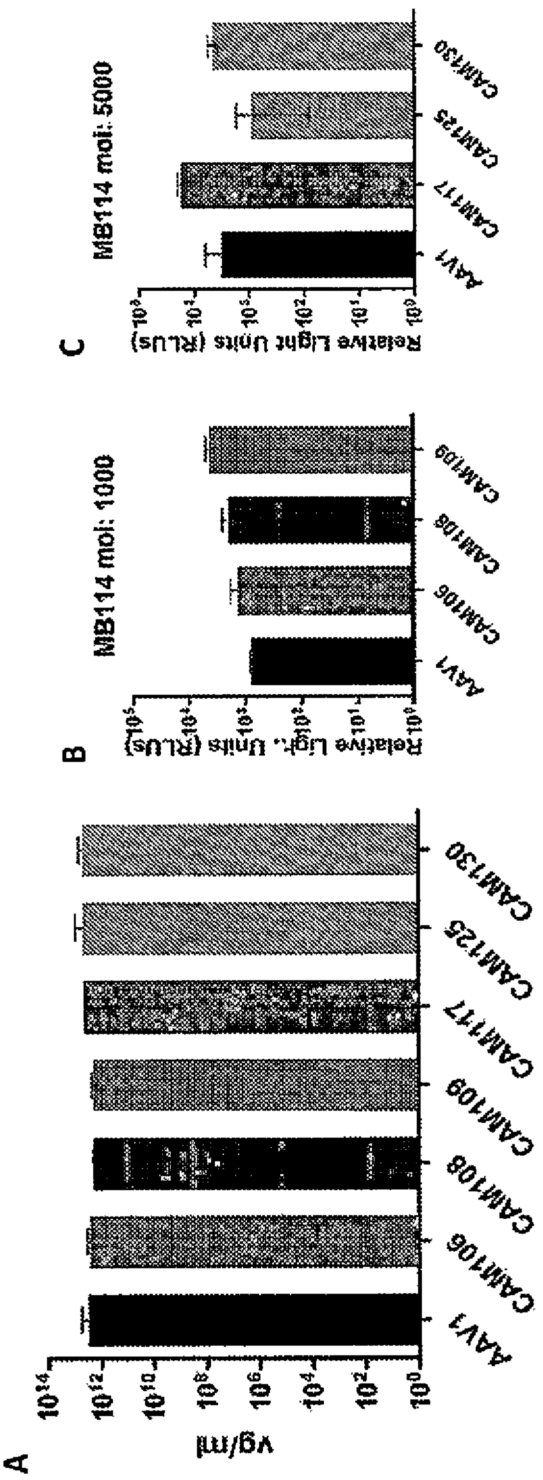
FIGS. 19A-19C. Physical and biological properties of CAM variants compared to AAV1. (A) Titers of purified CAM variants produced using the triple plasmid transfection protocol in HEK293 cells (four 150 mm culture dishes). Transduction profile of (B) single CAM variants and (C) combined CAM variants compared to AAV1 on vascular endothelial cells (MB114).

Multiple, evolved AAV variants were selected from each library for subsequent characterization, specifically, CAM101-107 (region 4), CAM108 (region 5) and CAM109-116 (region 8). All CAM variants packaging the ssCBA-Luc genome were produced and their transduction efficiencies assessed in vascular endothelial cells (FIGS. 19A-19C). A single CAM variant from each evolved library that displayed the highest transduction efficiency was shortlisted for further characterization. Specifically, CAM106 (456-SERR-459, SEQ ID NO:26), CAM108 (492-TPGGNATR-499, SEQ ID NO:485) and CAM109 (588-TADHDTKGVL-597, SEQ ID NO:32)) showed similar to modestly improved transduction efficiency compared to parental AAV1 on vascular endothelial cells. These observations support the notion that antigenic footprints can be re-engineered and evolved, while maintaining or improving upon the endogenous attributes of the corresponding parental AAV strain. Further evaluation of the physical properties of these lead CAM variants confirmed that yield (vector genome titers), capsid morphology (EM), and packaging efficiency (proportion of full-to-empty particles) were comparable to parental AAV1 vectors (FIGS. 19A-19C).

Individual CAM Variants Evade Neutralization by Monoclonal Antibodies.

Figures 14A, 14B, 14C, 14D, 14E, 14F, 14G, 14H, 14I:
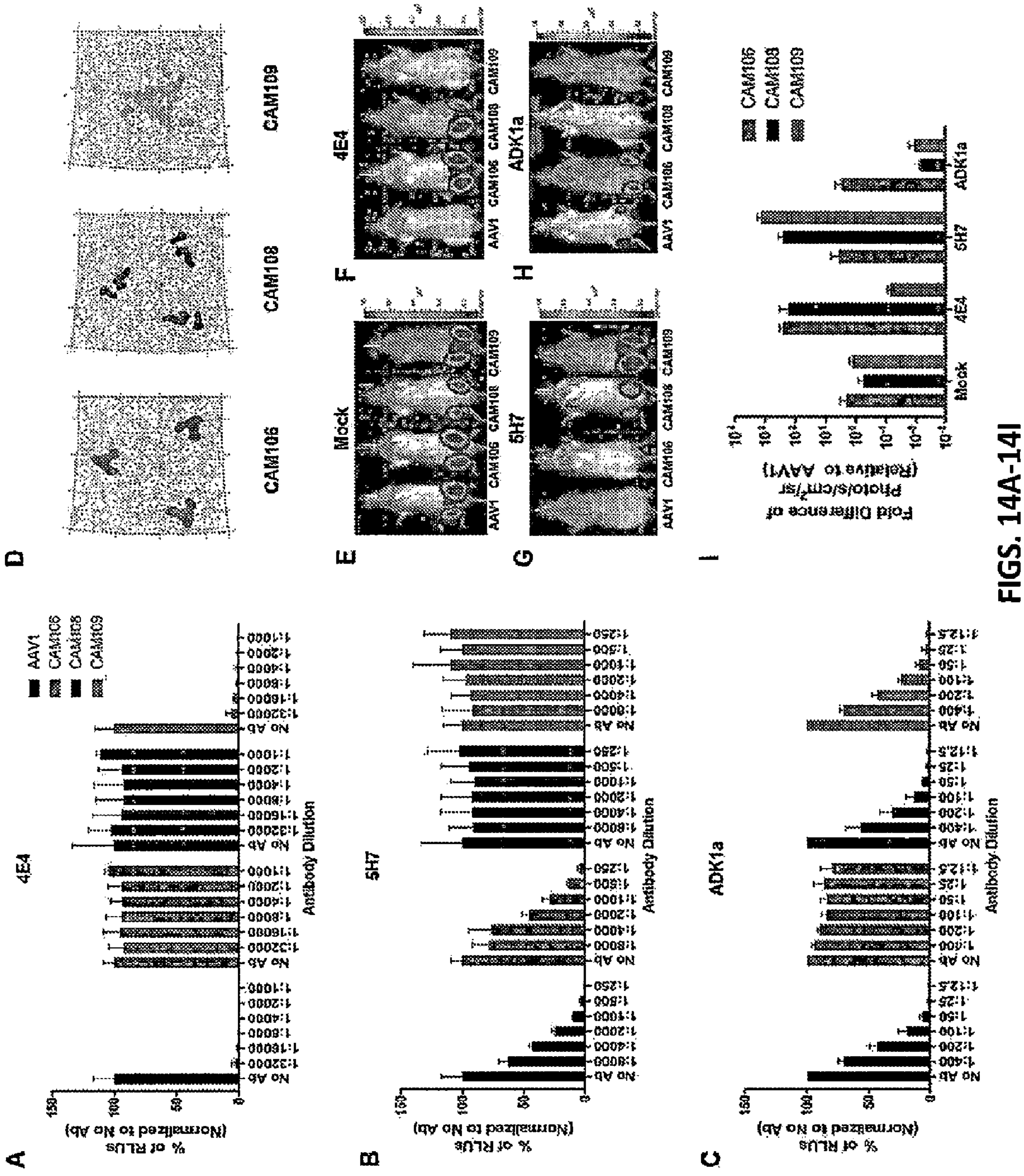
FIGS. 14A-14I. Neutralization profile of AAV1 and single region CAM variants against mouse monoclonal antibodies (MAbs) in vitro and in vivo. (A-C) Different AAV strains, AAV1, CAM106, CAM108 and CAM109 evaluated against MAbs 4E4, 5H7 and ADK1a at different dilutions of hybridoma media. Relative luciferase transgene expression mediated by different vectors mixed with MAbs was normalized to no antibody controls. Error bars represent standard deviation (n=4). (D) Roadmap images of the 3-fold axis of each CAM mutant showing the location of newly evolved antigenic footprints—CAM106, CAM108 and CAM109. (E-H) Luciferase expression in mouse hind limb muscles injected with a dose of $2\times10^{10}$ vg of AAV1, CAM106, CAM108 and CAM109 vectors packaging ssCBA-Luc and mixed with different MAbs. Representative live animal images at 4 wks post-injection are shown in the following subgroups (E) no antibody control, (F) 4E4 (1:500), (G) 5H7 (1:50) and (H) ADK1a (1:5). (I) Quantitation of luciferase activity mediated by different CAM variants relative to parental AAV1. Luciferase activity is expressed as photons/sec/cm2/sr as calculated by Living Image 3.2 software. Error bars represent S.D. (n=3).

We first evaluated the ability of single region CAM variants to escape neutralization by mouse monoclonal antibodies, ADK1a, 4E4 and 5H7 described previously. As shown in FIGS. 14A-C, each CAM variant shows a distinct NAb escape profile. As expected, parental AAV1 was neutralized by all MAbs tested at different dilutions. The CAM106 and CAM108 variants were resistant to neutralization by 4E4, while CAM109 was completely neutralized similar to AAV1 (FIG. 14A). Next, we determined that CAM108 and CAM109 both escape neutralization by 5H7, whereas CAM106 was significantly affected by 5H7 similar to AAV1 (FIG. 14B). With ADK1a, CAM106 was completely resistant to neutralization, while CAM108 and CAM109 were both effectively neutralized (FIG. 14C).

In Vivo Neutralization Profile of CAM Variants Against Monoclonal Antibodies.

To further test whether the ability of CAM variants to escape neutralization can be reproduced in vivo, AAV1 and CAM variants packaging ssCBA-Luc were mixed with the corresponding MAbs and injected intramuscularly into mice. In the absence of MAbs, all CAM variants and AAV1 showed similar luciferase transgene expression in mouse muscle (FIG. 14E). In the presence of antibodies, the neutralization profiles of the CAM variants corroborated results from in vitro studies. Briefly, CAM106 was resistant to ADK1a and 4E4, while CAM108 efficiently transduces mouse muscle in the presence of 4E4 or 5H7 and CAM109 evades 5H7 with high efficiency. Importantly, AAV1 transduction of mouse muscle was completely abolished when co-administered with any of these antibodies (FIGS. 14F-H). Quantitative analysis of luciferase transgene expression by CAM variants normalized to AAV1 confirmed these observations (FIG. 14I).

Iterative Engineering of Complex Antigenic Footprints on Single Region CAM Variants.

Figures 15A, 15B, 15C, 15D, 15E:
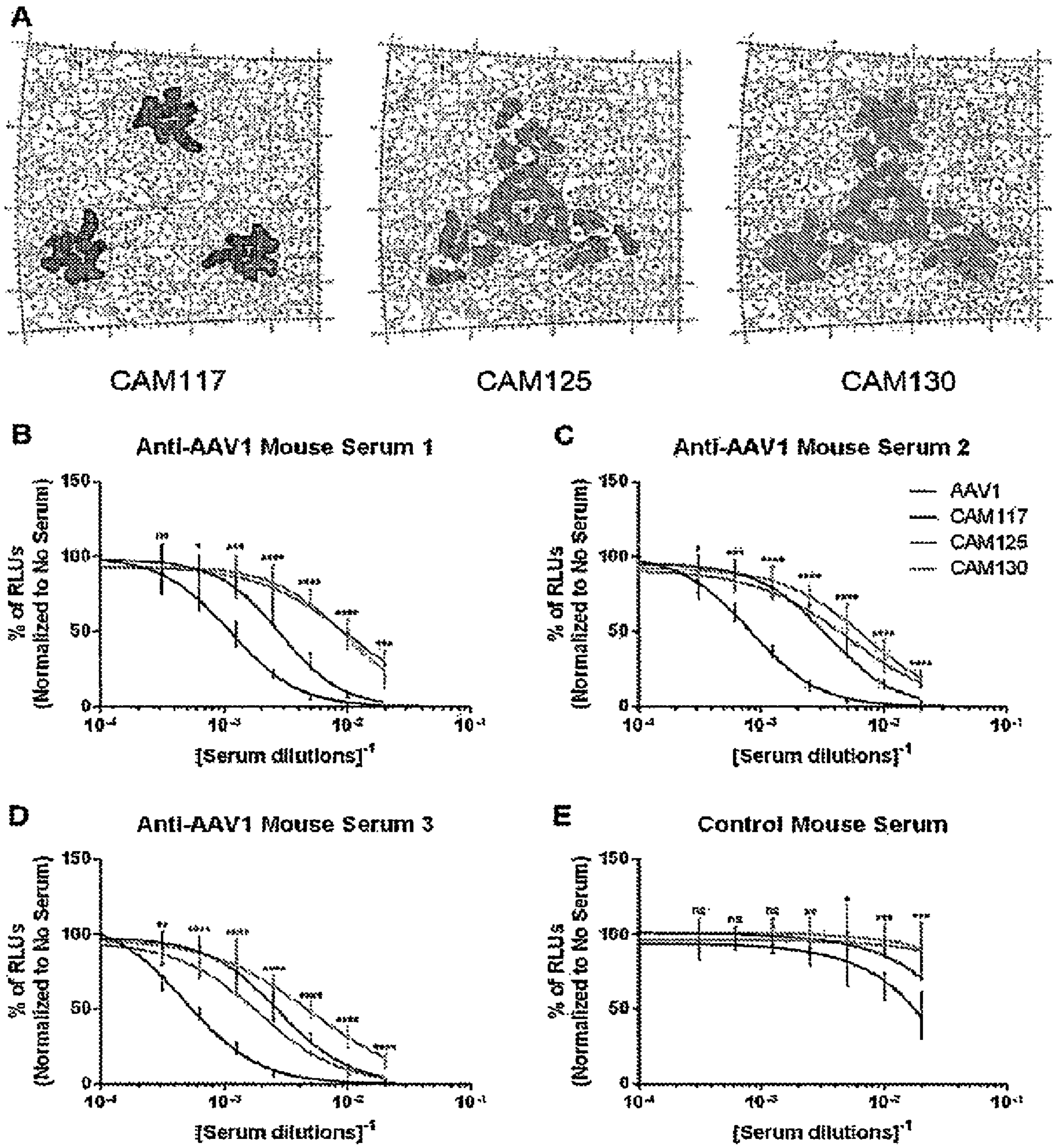
FIGS. 15A-15E. Neutralization profiles of AAV1 and CAM variants in pre-immunized mouse antisera. (A) Roadmap images of each antigenically advanced CAM variant showing newly evolved footprints at the 3-fold symmetry axis—CAM117 (regions 4+5), CAM125 (regions 5+8, cyan) and CAM130 (regions 4+5+8). (B-D) Anti-AAV1 mouse serum from three individual animals and (E) control mouse serum were serially diluted in 2-fold increments from 1:50-1:3200 and co-incubated with AAV vectors in vitro. The dotted line represents NAb-mediated inhibition of AAV transduction by 50%. Solid lines represent relative transduction efficiencies of AAV1, CAM117, CAM125 and CAM130 at different dilutions of antisera. Error bars represented S.D. (n=3).

Based on promising results from MAb neutralization studies, we hypothesized that combining different, evolved antigenic footprints will allow better NAb evasion. To achieve such, we generated four variants through a combination of rational mutagenesis, library generation and iterative evolution. First, we observed that rational combination of antigenic footprints from CAM106 and CAM108 yielded a functional and stable AAV variant, dubbed CAM117 (FIG. 15A). However, we observed that amino acid residues constituting antigenically advanced footprints on CAM108 and CAM109 were not structurally compatible (reduced viral titer) In order to facilitate structural compatibility, we generated a new AAV capsid library using CAM108 as a template and by carrying out saturation mutagenesis of amino acid residues in region 8. After 3 iterative cycles of directed evolution on vascular endothelial cells, several viable variants were generated (FIG. 15A). After initial characterization, CAM125 (region 5, 492-TPGGNATR-499 (SEQ ID NO:485); region 8, 588-DLDPKATEVE-597 (SEQ ID NO:487)) was selected for further analysis. We then iteratively engineered a third variant (CAM130) by grafting the evolved antigenic footprint from CAM106 onto CAM125. The CAM130 variant contains the following amino acid residues in three distinct antigenic footprints—region 4, 456-SERR-459 (SEQ ID NO:26; region 5, 492-TPGGNATR-499 (SEQ ID NO:485) and region 8, 588-DLDPKATEVE-597 (SEQ ID NO:487) (FIG. 15A). All three iteratively engineered variants, CAM117, CAM125 and CAM130 show similar physical attributes compared to parental AAV1 with regard to titer and proportion of full-to-empty particles (FIGS. 19A-19C).

CAM117, CAM 125 and CAM130 Escape Neutralizing Antisera from Pre-Immunized Mice.

To test whether antigenically advanced CAM variants can demonstrate escape from polyclonal neutralizing antibodies found in serum, we sero-converted mice by immunization with wild type AAV1 capsids. Overall, while antisera obtained from individual mice efficiently neutralized AAV1, CAM117, CAM125 and CAM130 display increased resistance to neutralization (FIGS. 15B-D). Briefly, we tested antisera dilutions ranging over two orders of magnitude (1:3200 to 1:50) to generate sigmoidal neutralization curves. As seen in FIGS. 15B-D, when compared to AAV1, the CAM variants show a dramatic shift to the right indicating improved ability to evade anti-AAV1 serum. In particular, the serum concentration required for 50% neutralization of transduction ($ND_{50}$) is significantly higher in case of each CAM variant compared to parental AAV1 in each individual subject (FIGS. 15B-D). Furthermore, we observed an incremental ability to evade NAbs with each iterative engineering/evolution step. Specifically, the most antigenically advanced variant, CAM130 displays a 8-16 fold improvement in $ND_{50}$ values (FIGS. 15B-D). These results corroborate the notion that antigenic footprints on AAV capsid are modular and cumulative in their ability to mediate NAb evasion. A similar, but less robust trend was observed with regard to the neutralizing potential of serum obtained from naïve mice as control (FIG. 15E).

CAM130 Efficiently Evades Neutralization by Non-Human Primate Antisera.

Figures 16A, 16B, 16C, 16D, 16E, 16F, 16G, 16H, 16I:
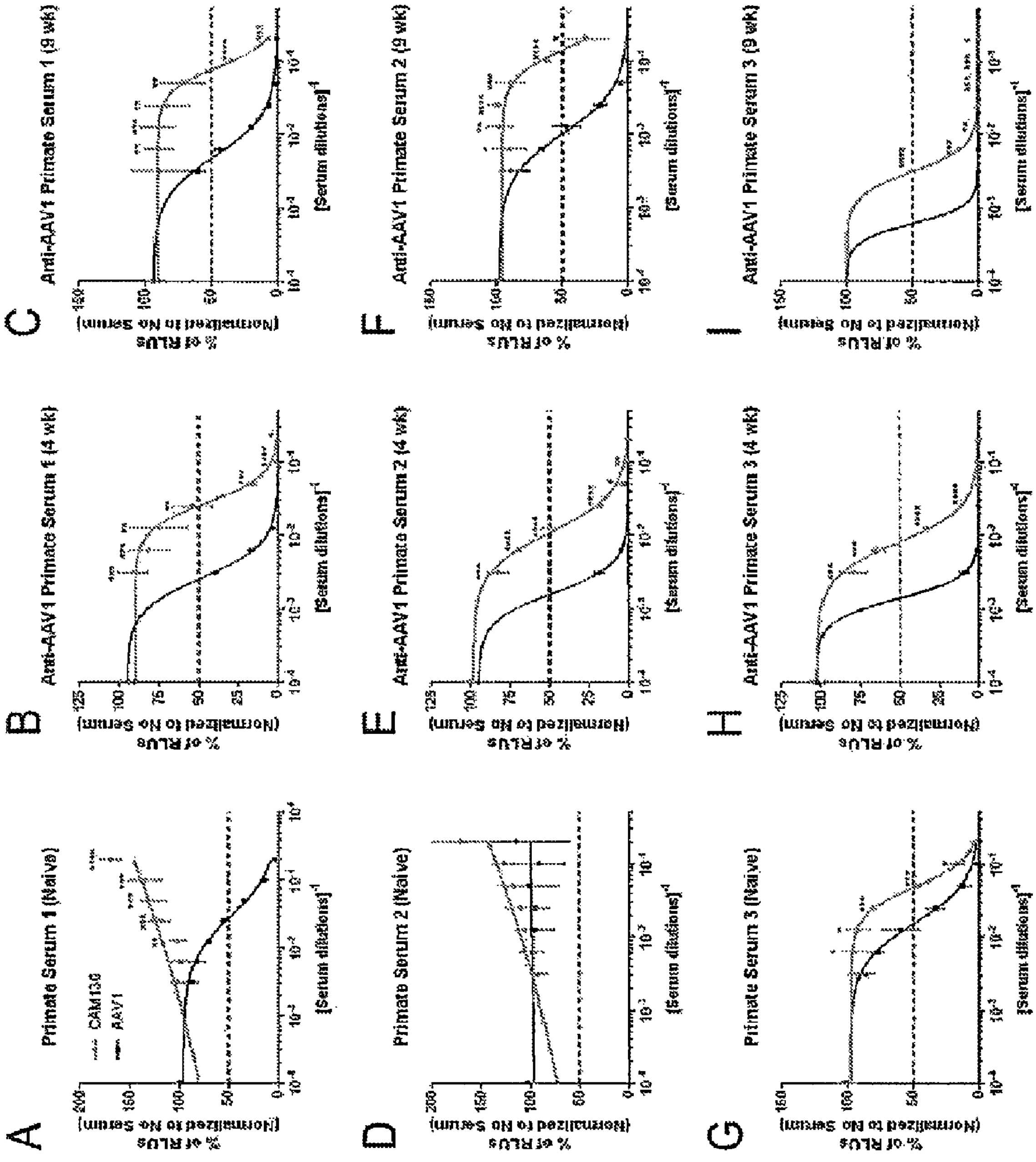
FIGS. 16A-16I. Neutralization profiles of AAV1 and CAM130 in non-human primate antisera. Serum samples collected from three individual rhesus macaques collected at pre-(naïve) and post-immunization (at 4 wks and 9 wks) were serially diluted at 2-fold increments from 1:5-1:320 and co-incubated with AAV vectors in vitro. The dotted line represents NAb-mediated inhibition of AAV transduction by 50%. Solid lines represent relative transduction efficiencies of AAV1 and CAM130 at different dilutions of antisera. Error bars represented S.D. (n=3).

To validate whether our approach can be translated in larger animal models, we tested the ability of AAV1 and the lead variant, CAM130 to evade NAbs generated in non-human primates. Briefly, we subjected AAV vectors to neutralization assays using serum collected at three different time points—pre-immunization (naïve), 4 wks and 9 wks post-immunization. All macaques sero-converted after immunization with NAb titers at the highest levels in week 4 and declining at week 9 in subjects 1 and 2, and increased potency at week 9 in subject 3 (FIGS. 16A-I). Moreover, naïve sera from subjects 1 and 3 prior to immunization were able to neutralize AAV1 effectively (FIGS. 16A and 16G). We tested antisera dilutions ranging over two orders of magnitude (1:320 to 1:5) to generate neutralization curves as described earlier. Antisera obtained at 4 wks after immunization neutralized AAV1 effectively at $ND_{50}$>1:320. In contrast, CAM130 displayed a significant shift to the right and improved resistance to neutralization compared to AAV1 by 4-16 fold (FIGS. 16B, 16E, 16H). A similar trend and enhancement in resistance to NAbs was observed in the case of CAM130 when evaluating antisera obtained at 9 wks post-immunization (FIGS. 16C, 16F, 16I). Further, these results strongly support the notion that antigenicity of AAV capsids can be re-engineered to escape broadly neutralizing antibodies from different animal species on the basis of structural cues obtained from mouse MAb footprints.

CAM130 Efficiently Evades NAbs in Primate and Human Sera.

Figures 17A, 17B:
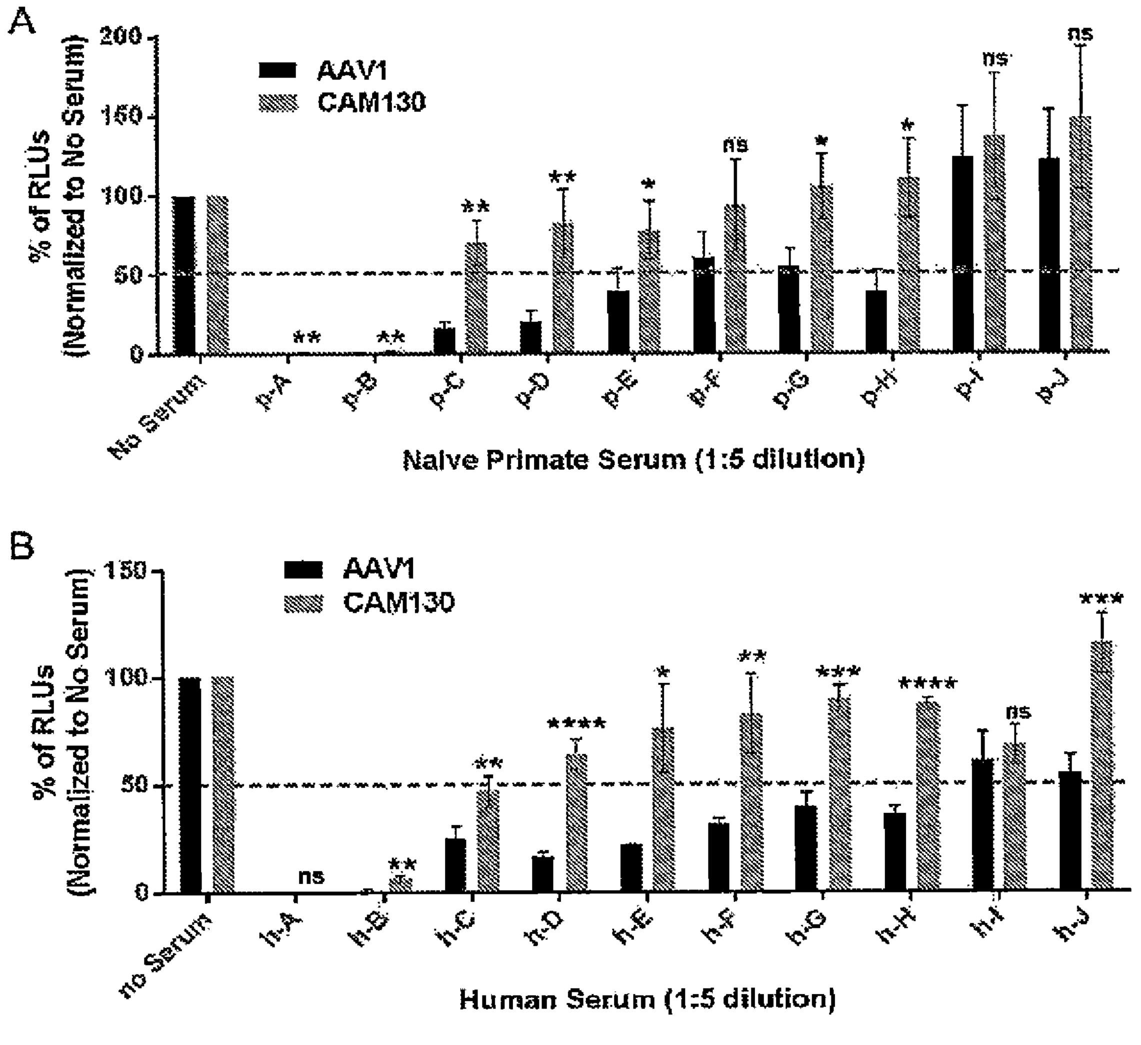
FIGS. 17A and 17B. Neutralization profile of AAV1 and CAM130 against individual primate and human serum samples. AAV1 and CAM130 packaging CBA-Luc (MOI 10,000) were tested against (A) primate and (B) human sera at a 1:5 dilution to reflect clinically relevant exclusion criteria. The dotted line represents NAb-mediated inhibition of AAV transduction by 50%. Solid bars represent relative transduction efficiencies of AAV1 and CAM130. Error bars represented S.D. (n=3).

To test whether CAM130 can evade NAbs in the general non-human primate and human population, we tested serum samples obtained from a cohort of 10 subjects each. We evaluated a fixed serum dilution of 1:5 to reflect currently mandated exclusion criteria employed in ongoing clinical trials for hemophilia and other indications requiring systemic AAV administration. As seen in FIG. 17A, primate subjects p-A and p-B displayed high NAb titers that completely neutralized both AAV1 and CAM130. At the other end of the spectrum, subjects p-I and p-J showed no pre-existing immunity to AAV capsids and did not effectively neutralize AAV1 or CAM130. However, serum samples for subjects p-C through p-H efficiently neutralized AAV1 and reduced transduction efficiency below 50% of untreated controls. In contrast, serum samples p-C through p-H were unable to neutralize the antigenically advanced CAM130 variant. Thus, CAM130 shows exceptional NAb evasion in this cohort by evading 8 out of 10 serum samples (FIG. 17A). We then utilized a similar approach to test serum from 10 human subjects. Using clinically relevant exclusion criteria (1:5 dilution), we segregated the human sera into two high titer (h-A and h-B), six intermediate titer (h-C through h-H) and two modest titer sub-groups that neutralized AAV1 effectively. Strikingly, CAM130 was able to evade polyclonal NAbs in human sera for 8/10 samples tested (FIG. 17B). Taken together, these studies strongly support the notion that the antigenically advanced CAM130 variant can significantly expand the patient cohort.

CAM130 Displays a Favorable Transduction Profile In Vivo.

Figures 18A, 18B, 18C, 18D:
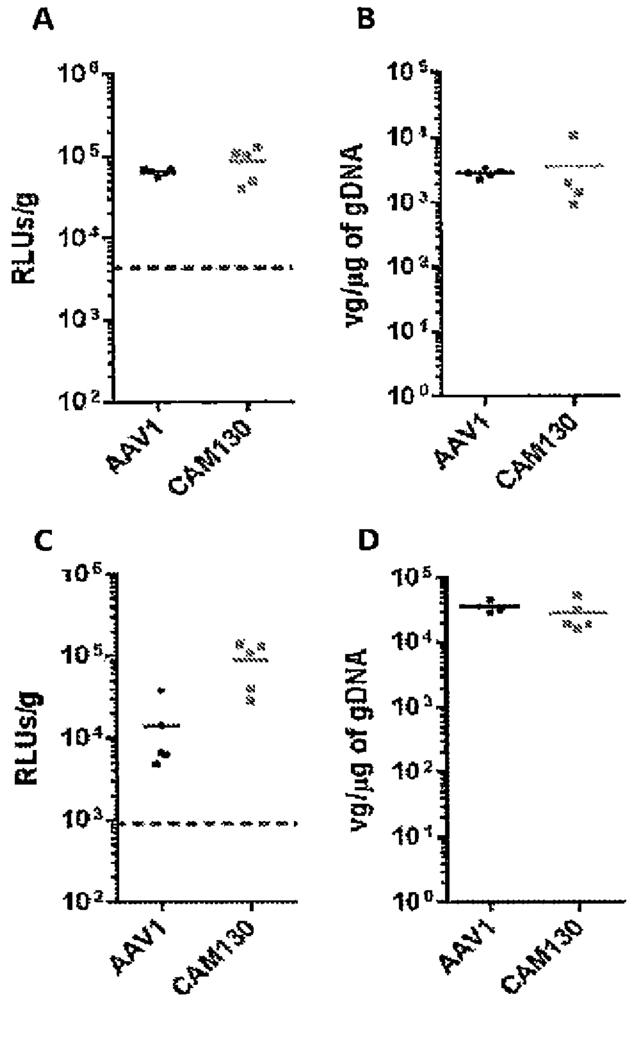
FIG. 18A-18D. In vive characterization of the CAM130 variant. Luciferase transgene expression profiles of AAV1 and CAM130 in (A) heart and (C) liver at 2 wks post-intravenous administration of $1\times10^{11}$ vg/mouse (n=5). Dotted lines show background levels of luciferase activity in mock injection controls. Biodistribution of AAV1 and CAM130 vector genomes in (B) heart and (D) liver. Vector genome copy numbers per cell were calculated and values from mock injection controls were subtracted to obtain final values. Each dot represented a duplicated experiment from a single animal (n=5) and the dash represents the mean value.

We compared the in vivo tissue tropism, transduction efficiency and biodistribution of CAM130 to the parental AAV1 strain in mice. A dose of $1\times10^{11}$ vg/mouse of AAV vectors packaging scCBh-GFP was injected intravenously into 6-8 week old female BALB/c mice via the tail vein. At 2 wks post injection, CAM130 showed an enhanced cardiac GFP expression profile compared to AAV1, while differences in the liver were unremarkable. In particular, more GFP-positive cardiac myofibers are detectable in CAM130 treated animals compared to the AAV1 cohort. We then administered $1\times10^{11}$ vg/mouse of AAV vectors packaging ssCBA-Luc genomes intravenously as described above. In contrast to GFP expression from self-complementary CAM130 vectors, no significant differences were noted in luciferase activity within the heart for ssCAM130 vs. AAV1-treated mice (FIG. 18A). However, a modest, albeit statistically insignificant increase in luciferase expression was observed within the liver (FIG. 18C). Transduction efficiencies in other major organs, i.e., lung, brain, kidney and spleen, were low. Importantly, no differences were noted in the systemic biodistribution of CAM130 and AAV1 vectors. Consistent with earlier reports, ~10-fold higher vector genome copy numbers were detected in the liver compared to cardiac tissue for both CAM130 and AAV1 vectors (FIGS. 18B and 18D).

To further compare the potency and tropism of CAM130 to AAV1, we evaluated the transduction profiles of the latter two strains following CNS administration. A dose of $3\times10^{9}$ vg/mouse of AAV1 or CAM130 packaging scCBh-GFP genomes was injected by intra-CSF administration in neonatal mice. Both AAV1 and CAM130 spread well within the brain with a general preference for transducing the ipsilateral side more readily than the contralateral hemisphere. Similar to cardiac tissue, a greater number of GFP-positive cells are observed in the case of CAM130 compared to AAV1. In particular, CAM130 appears to transduce a greater number of neurons, particularly within the motor cortex, cortex and most prominently in the hippocampus. The potential mechanism(s) for the improved transduction profile displayed by CAM130 in cardiac and CNS tissue could potentially arise from post-entry trafficking events that are currently under investigation. More importantly, these in vivo results confirm that antigenic footprints on AAV capsids can be engineered to effectively evade NAbs, while simultaneously controlling cellular/tissue tropism as well as biodistribution profile and improving potency.

Similarly, AAV1e mutants demonstrate robust and neuron-specific gene expression in the brain following intracranial administration. Different AAV1e vectors packaging an scGFP expression cassette were administered into the cerebrospinal fluid of P0 mice by stereotaxic injection into lateral ventricles. The vector dose administered was $3\times10^{9}$ vector genomes/animal. Mice were sacrificed at 3 weeks post-injection and brains processed using DAB immunohistochemistry and image reporter gene expression in cerebellum, olfactory bulb, cortex and hippocampus.

Example 4: AAV8e Antibody Evading Mutants

Figure 22:
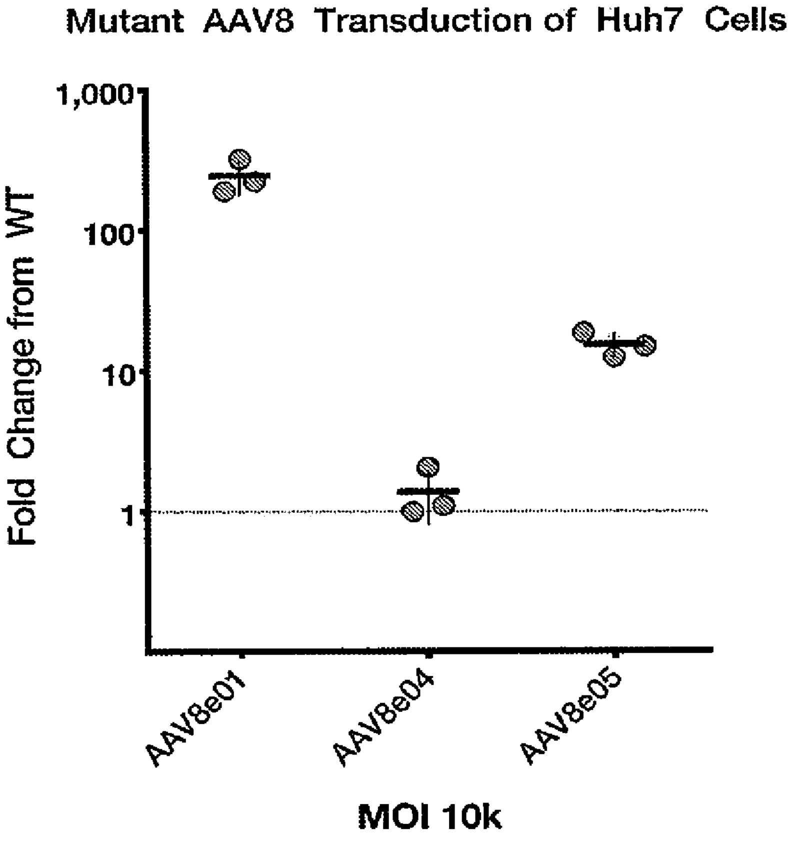
FIG. 22. Transduction of human hepatocarcinoma cells Huh7 by AAV8e mutants. Transduction efficiency of AAV8e mutants AAV8e01, AAV8e04 and AAV8e05 of Huh7 cells was determined and compared to the transduction of Huh7 cells by wild-type AAV8.

Evolved mutants AAV8e01, AAV8e04 and AAV8e05 demonstrate improved transduction in comparison with parental AAV8 isolate in human hepatocarcinoma cells (Huh7). Briefly, cells were incubated with different AAV8 derived variants at 10,000 vector genomes per cell for 24 hours. Quantitation of luciferase transgene activity revealed over 2 log increase in transduction efficiency of AAV8e01 over AAV8 (dotted line); over 1 log order increase for AAV8e05 and ~2-fold increase in the case of AAV8e04. These results corroborate the generation of novel AAV8 variants that demonstrate robust transduction of transformed human hepatocytes in culture compared to the state-of-the-art natural isolate. These results are shown in FIG. 22.

Figure 23A:
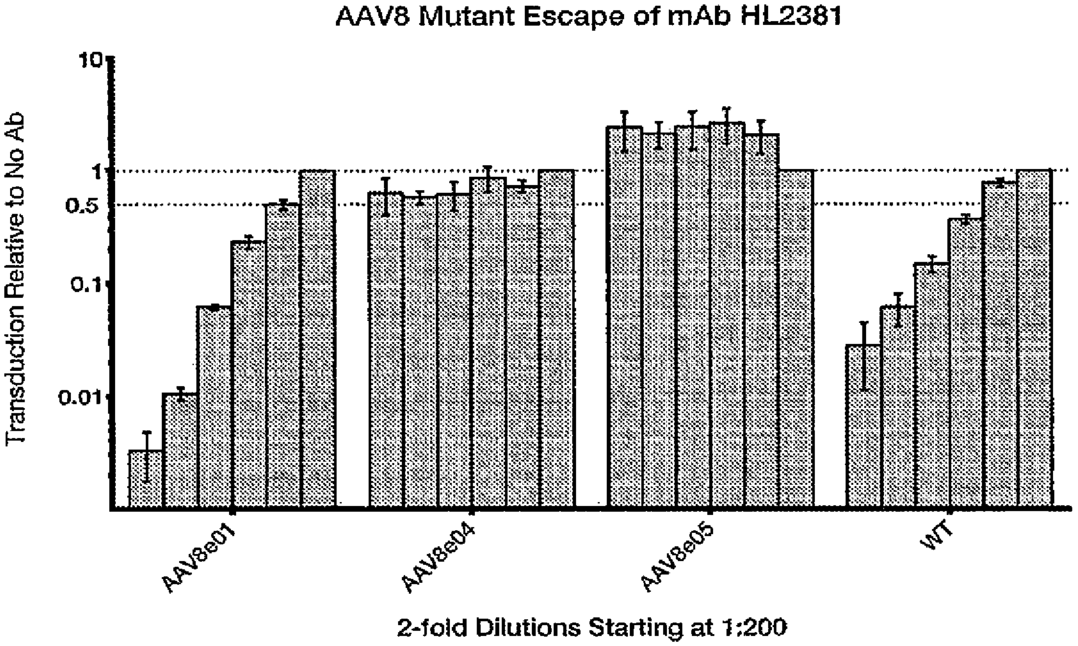
FIGS. 23A-23C. Escape of AAV8e mutants from neutralization by mouse monoclonal antibodies against AAV8. The ability of AAV8e mutants to escape neutralization was examined using mAbs HL2381 (A), HL2383 (B) and ADK8 (C).
Figure 23B:
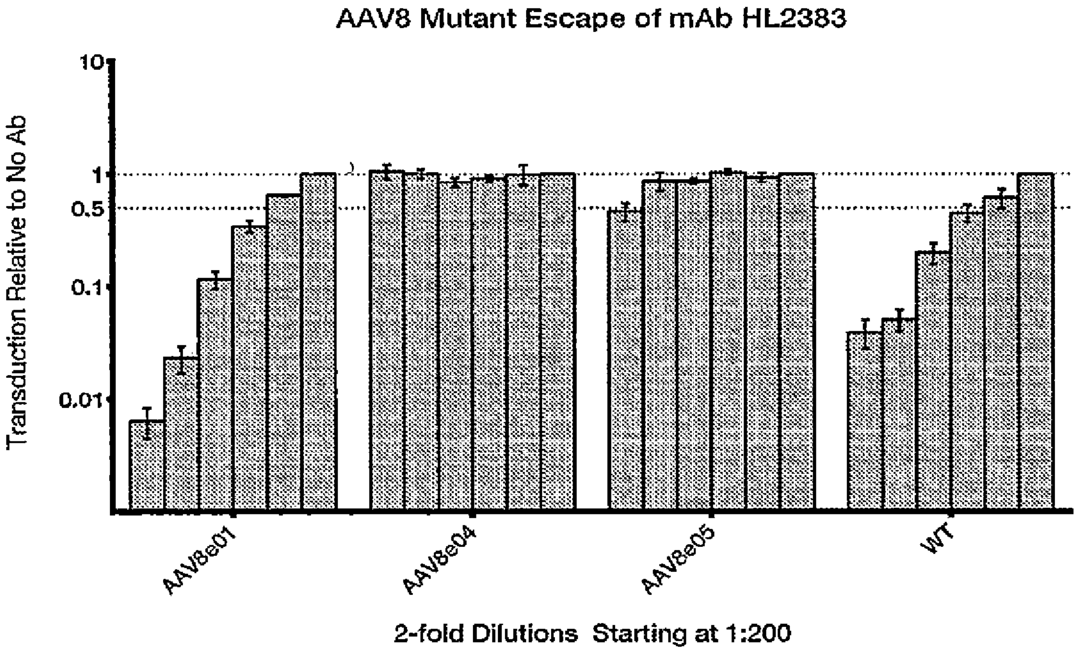
Figure 23C:
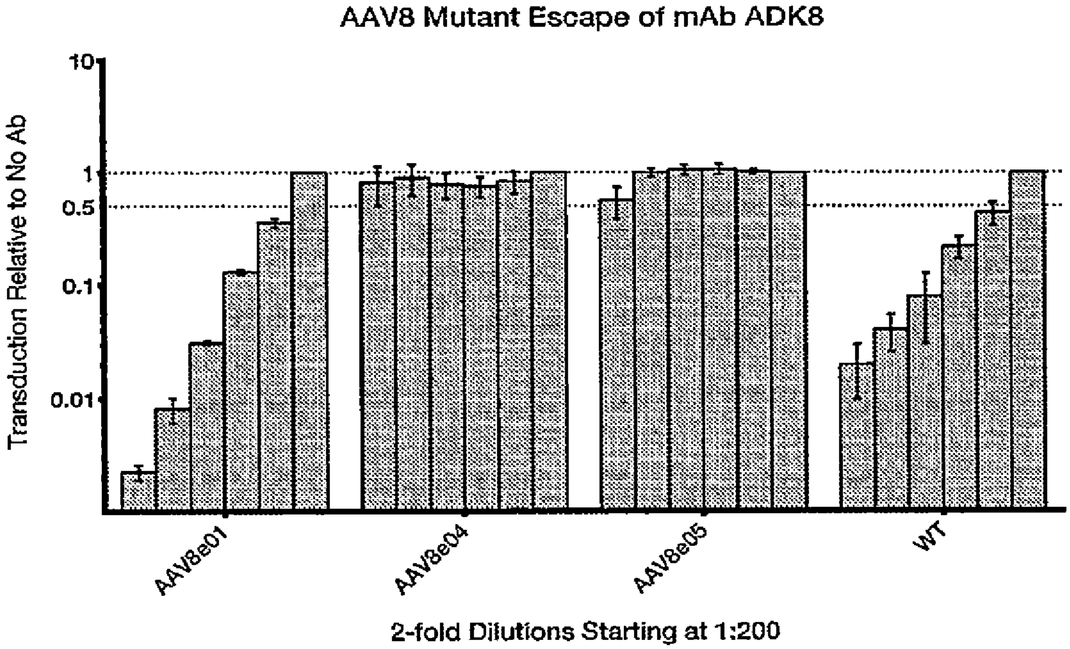

AAV8e mutants demonstrate the ability to escape neutralization by mouse monoclonal antibodies generated specifically against AAV8. Briefly, human hepatocarcinoma cells were incubated with different AAV8e mutants or wild type (WT) AAV8 vectors packaging luciferase transgene cassettes with or without neutralizing antibodies. Each monoclonal antibody (mAb) was directed against different antigenic epitopes located on the AAV8 capsid surface. As shown in FIGS. 23A-23C, AAV8e04 and AAV8e05 escape neutralization by mAbs HL2381 (FIG. 23A), HL2383 (FIG. 23B) and ADK8 (FIG. 23C) tested at different dilutions. In contrast, the parental AAV8 strain is neutralized effectively under these conditions.

Nonlimiting examples of AAV8e mutants of this invention are listed in Table 9.

TABLE 9

AAV8e mutants

| Name | Clone | Sequence | Description |
|---|---|---|---|
| AAV8e01 | CAM84a | 455-SNGRGV-460 (SEQ ID NO: 488) | Single 8CAM-4a |
| AAV8e02 | CAM84b | 455-VNTSING-461 (SEQ ID NO: 489) | Single 8CAM-4b |
| AAV8e03 | CAM84c | 455-IRGAGAV-461 (SEQ ID NO: 490) | Single 8CAM-4c |
| AAV8e04 | CAM85a | 494-YPGGNYK-501 (SEQ ID NO: 491) | Single 8CAM-5a |
| AAV8e05 | CAM88a | 586-KQKNVN-591 (SEQ ID NO: 492) | Single 8CAM-8a |
| AAV8e06 | CAM88b | 586-RMSSIK-591 (SEQ ID NO: 493) | Single 8CAM-8b |
| AAV8e07 | CAM845a | 455-SNGRGV-460 (SEQ ID NO: 488) + 494-YPGGNYK-501 (SEQ ID NO: 491) | Double 8CAM-4a-5a |
| AAV8e08 | CAM848a | 455-SNGRGV-460 (SEQ ID NO:488) + 586-KQKNVN-591 (SEQ ID NO: 492) | Double 8CAM-4a-8a |

The foregoing is illustrative of the present invention, and is not to be construed as limiting thereof. The invention is defined by the following claims, with equivalents of the claims to be included therein.

Sequences

SEQUENCES

AAV1 capsid protein (GenBank Accession No. AAD27757) (SEQ ID NO: 1)

```
  1  MAADGYLPDW LEDNLSEGIR EWWDLKPGAP KPKANQQKQD DGRGLVLPGY KYLGPFNGLD
 61  KGEPVNAADA AALEHDKAYD QQLKAGDNPY LRYNHADAEF QERLQEDTSF GGNLGRAVFQ
121  AKKRVLEPLG LVEEGAKTAP GKKRPVEQSP QEPDSSSGIG KTGQQPAKKR LNFGQTGDSE
181  SVPDPQPLGE PPATPAAVGP TTMASGGGAP MADNNEGADG VGNASGNWHC DSTWLGDRVI
241  TTSTRTWALP TYNNHLYKQI SSASTGASND NHYFGYSTPW GYFDFNRFHC HFSPRDWQRL
301  INNNWGFRPK RLNFKLENIQ VKEVTTNDGV TTIANNLTST VQVFSDSEYQ LPYVLGSAHQ
361  GCLPPFPADV FMIPQYGYLT LNNGSQAVGR SSFYCLEYFP SQMLRTGNNF TFSYTFEEVP
421  FHSSYAHSQS LDRLMNPLID QYLYYLNRTQ NQSGSAQNKD LLFSRGSPAG MSVQPKNWLP
481  GPCYRQQRVS KTKTDNNNSN FTWTGASKYN LNGRESIINP GTAMASHKDD EDKFFPMSGV
541  MIFGKESAGA SNTALDNVMI TDEEEIKATN PVATERFGTV AVNFQSSSTD PATGDVHAMG
601  ALPGMVWQDR DVYLQGPIWA KIPHTDGHFH PSPLMGGFGL KNPPPQILIK NTPVPANPPA
661  EFSATKFASF ITQYSTGQVS VEIEWELQKE NSKRWNPEVQ YTSNYAKSAN VDFTVDNNGL
721  YTEPRPIGTR YLTRPL
```

AAV2 capsid protein (GenBank Accession No. YP_680426) (SEQ ID NO: 2)

```
  1  MAADGYLPDW LEDTLSEGIR QWWKLKPGPP PPKPAERHKD DSRGLVLPGY KYLGPFNGLD
```

-continued

| SEQUENCES |
|---|
| 61 KGEPVNEADA AALEHDKAYD RQLDSGDNPY LKYNHADAEF QERLKEDTSF GGNLGRAVFQ |
| 121 AKKRVLEPLG LVEEPVKTAP GKKRPVEHSP VEPDSSSGTG KAGQQPARKR LNFGQTGDAD |
| 181 SVPDPQPLGQ PPAAPSGLGT NTMATGSGAP MADNNEGADG VGNSSGNWHC DSTWMGDRVI |
| 241 TTSTRTWALP TYNNHLYKQI SSQSGASNDN HYFGYSTPWG YFDFNRFHCH FSPRDWQRLI |
| 301 NNNWGFRPKR LNFKLFNIQV KEVTQNDGTT TIANNLTSTV QVFTDSEYQL PYVLGSAHQG |
| 361 CLPPFPADVF MVPQYGYLTL NNGSQAVGRS SFYCLEYFPS QMLRTGNNFT FSYTFEDVPF |
| 421 HSSYAHSQSL DRLMNPLIDQ YLYYLSRTNT PSGTTTQSRL QFSQAGASDI RDQSRNWLPG |
| 481 PCYRQQRVSK TSADNNNSEY SWTGATKYHL NGRDSLVNPG PAMASHKDDE EKFFPQSGVL |
| 541 IFGKQGSEKT NVDIEKVMIT DEEEIRTTNP VATEQYGSVS TNLQRGNRQA ATADVNTQGV |
| 601 LPGMVWQDRD VYLQGPIWAK IPHTDGHFHP SPLMGGFGLK HPPPQILIKN TPVPANPSTT |
| 661 FSAAKFASFI TQYSTGQVSV EIEWELQKEN SKRWNPEIQY TSNYNKSVNV DFTVDTNGVY |
| 721 SEPRPIGTRY LTRNL |
| AAV3 capsid protein (GenBank Accession No. AAC55049) (SEQ ID NO: 3) |
| 1 MAADGYLPDW LEDNLSEGIR EWWALKPGVP QPKANQQHQD NRRGLVLPGY KYLGPGNGLD |
| 61 KGEPVNEADA AALEHDKAYD QQLKAGDNPY LKYNHADAEF QERLQEDTSF GGNLGRAVFQ |
| 121 AKKRILEPLG LVEEAAKTAP GKKGAVDQSP QEPDSSSGVG KSGKQPARKR LNFGQTGDSE |
| 181 SVPDPQPLGE PPAAPTSLGS NTMASGGGAP MADNNEGADG VGNSSGNWHC DSQWLGDRVI |
| 241 TTSTRTWALP TYNNHLYKQI SSQSGASNDN HYFGYSTPWG YFDFNRFHCH FSPRDWQRLI |
| 301 NNNWGFRPKK LSFKLFNIQV RGVTQNDGTT TIANNLTSTV QVFTDSEYQL PYVLGSAHQG |
| 361 CLPPFPADVF MVPQYGYLTL NNGSQAVGRS SFYCLEYFPS QMLRTGNNFQ FSYTFEDVPF |
| 421 HSSYAHSQSL DRLMNPLIDQ YLYYLNRTQG TTSGTTNQSR LLFSQAGPQS MSLQARNWLP |
| 481 GPCYRQQRLS KTANDNNNSN FPWTAASKYH LNGRDSLVNP GPAMASHKDD EEKFFPMHGN |
| 541 LIFGKEGTTA SNAELDNVMI TDEEEIRTTN PVATEQYGTV ANNLQSSNTA PTTGTVNHQG |
| 601 ALPGMVWQDR DVYLQGPIWA KIPHTDGHFH PSPLMGGFGL KHPPPQIMIK NTPVPANPPT |
| 661 TFSPAKFASF ITQYSTGQVS VEIEWELQKE NSKRWNPEIQ YTSNYNKSVN VDFTVDTNGV |
| 721 YSEPRPIGTR YLTRNL |
| AAV4 capsid protein (GenBank Accession No. NP_044927) (SEQ ID NO: 4) |
| 1 MTDGYLPDWL EDNLSEGVRE WWALQPGAPK PKANQQHQDN ARGLVLPGYK YLGPGNGLDK |
| 61 GEPVNAADAA ALEHDKAYDQ QLKAGDNPYL KYNHADAEFQ QRLQGDTSFG GNLGRAVFQA |
| 121 KKRVLEPLGL VEQAGETAPG KKRPLIESPQ QPDSSTGIGK KGKQPAKKKL VFEDETGAGD |
| 181 GPPEGSTSGA MSDDSEMRAA AGGAAVEGGQ GADGVGNASG DWHCDSTWSE GHVTTTSTRT |
| 241 WVLPTYNNHL YKRLGESLQS NTYNGFSTPW GYFDFNRFHC HFSPRDWQRL INNNWGMRPK |
| 301 AMRVKIFNIQ VKEVTTSNGE TTVANNLTST VQIFADSSYE LPYVMDAGQE GSLPPFPNDV |
| 361 FMVPQYGYCG LVTGNTSQQQ TDRNAFYCLE YFPSQMLRTG NNFEITYSFE KVPFHSMYAH |
| 421 SQSLDRLMNP LIDQYLWGLQ STTTGTTLNA GTATTNFTKL RPTNFSNFKK NWLPGPSIKQ |
| 481 QGFSKTANQN YKIPATGSDS LIKYETHSTL DGRWSALTPG PPMATAGPAD SKFSNSQLIF |
| 541 AGPKQNGNTA TVPGTLIFTS EEELAATNAT DTDMWGNLPG GDQSNSNLPT VDRLTALGAV |
| 601 PGMVWQNRDI YYQGPIWAKI PHTDGHFHPS PLIGGFGLKH PPPQIFIKNT PVPANPATTF |
| 661 SSTPVNSFIT QYSTGQVSVQ IDWEIQKERS KRWNPEVQFT SNYGQQNSLL WAPDAAGKYT |
| 721 EPRAIGTRYL THHL |

-continued

| SEQUENCES |
|---|

AAV5 capsid protein (GenBank Accession No. AAD13756) (SEQ ID NO: 5)

```
  1   MSFVDHPPDW LEEVGEGLRE FLGLEAGPPK PKPNQQHQDQ ARGLVLPGYN YLGPGNGLDR

 61   GEPVNRADEV AREHDISYNE QLEAGDNPYL KYNHADAEFQ EKLADDTSFG GNLGKAVFQA

121   KKRVLEPFGL VEEGAKTAPT GKRIDDHFPK RKKARTEEDS KPSTSSDAEA GPSGSQQLQI

181   PAQPASSLGA DTMSAGGGGP LGDNNQGADG VGNASGDWHC DSTWMGDRVV TKSTRTWVLP

241   SYNNHQYREI KSGSVDGSNA NAYFGYSTPW GYFDFNRFHS HWSPRDWQRL INNYWGFRPR

301   SLRVK1FNIQ VKEVTVQDST TTIANNLTST VQVFTDDDYQ LPYVVGNGTE GCLPAFPPQV

361   FTLPQYGYAT LNRDNTENPT ERSSFFCLEY FPSKMLRTGN NFEFTYNFEE VPFHSSFAPS

421   QNLFKLANPL VDQYLYRFVS TNNTGGVQFN KNLAGRYANT YKNWFPGPMG RTQGWNLGSG

481   VNRASVSAFA TTNRMELEGA SYQVPPQPNG MTNNLQGSNT YALENTMIFN SQPANPGTTA

541   TYLEGNMLIT SESETQPVNR VAYNVGGQMA TNNQSSTTAP ATGTYNLQEI VPGSVWMERD

601   VYLQGPIWAK IPETGAHFHP SPAMGGFOLK HPPPMMLIKN TPVPGNITSF SDVPVSSFIT

661   QYSTGQVTVE MEWELKKENS KRWNPEIQYT NNYNDPQFVD FAPDSTGEYR TTRPIGTRYL

721   TRPL
```

AAV6 capsid protein (GenBank Accession No. AAB95450) (SEQ ID NO: 6)

```
  1   MAADGYLPDW LEDNLSEGIR EWWDLKPGAP KPKANQQKQD DGRGLVLPGY KYLGPFNGLD

 61   KGEPVNAADA AALEHDKAYD QQLKAGDNPY LRYNHADAEF QERLQEDTSF GGNLGRAVFQ

121   AKKRVLEPFG LVEEGAKTAP GKKRPVEQSP QEPDSSSGIG KTGQQPAKKR LNFGQTGDSE

181   SVPDPQPLGE PPATPAAVGP TTMASGGGAP MADNNEGADG VGNASGNWHC DSTWLGDRVI

241   TTSTRTWALP TYNNHLYKQI SSASTGASND NHYFGYSTPW GYFDFNRFHC HFSPRDWQRL

301   INNNWGFRPK RLNFKLFNIQ VKEVTTNDGV TTIANNLTST VQVFSDSEYQ LPYVLGSAHQ

361   GCLPPFPADV FMIPQYGYLT LNNGSQAVGR SSFYCLEYFP SQMLRTGNNF TFSYTFEDVP

421   FHSSYAHSQS LDRLMNPLID QYLYYLNRTQ NQSGSAQNKD LLFSRGSPAG MSVQPKNWLP

481   GPCYRQQPVS KTKTDNNNSN FTWTGASKYN LNGRESIINP GTAMASHKDD KDKFFPMSGV

541   MIFGKESAGA SNTALDNVMI TDEEEIKATN PVATERFGTV AVNLQSSSTD PATGDVHVMG

601   ALPGMVWQDR DVYLQGPIWA KIPHTDGHFH PSPLMGGFGL KHPPPQILIK NTPVPANPPA

661   EFSATKFASF ITQYSTGQVS VEIEWELQKE NSKRWNPEVQ YTSNYAKSAN VDFTVDNNGL

721   YTEPRPIGTR YLTRPL
```

AAV7 capsid protein (GenBank Accession No. AAN03855) (SEQ ID NO: 7)

```
  1   MAADGYLPDW LEDNLSEGIR EWWDLKPGAP KPKANQQKQD NGRGLVLPGY KYLGPFNGLD

 61   KGEPVNAADA AALEHDKAYD QQLKAGDNPY LRYNHADAEF QERLQEDTSF GGNLGRAVFQ

121   AKKRVLEPLG LVEEGAKTAP AKKRPVEPSP QRSPDSSTGI GKKGQQPARK RLNFGQTGDS

181   ESVPDPQPLG EPPAAPSSVG SGTVAAGGGA PMADNNEGAD GVGNASGNWH CDSTWLGDRV

241   ITTSTRTWAL PTYNNHLYKQ ISSETAGSTN DNTYFGYSTP WGYFDFNRFH CHFSPRDWQR

301   LINNNWGFRP KKLRFKLFNI QVKEVTTNDG VTTIANNLTS TIQVFSDSEY QLPYVLGSAH

361   QGCLPPFPAD VFMIPQYGYL TLNNGSQSVG RSSFYCLEYF PSQMLRTGNN FEFSYSFEDV

421   PFHSSYAHSQ SLDRLMNPLI DQYLYYLART QSNPGGTAGN RELQFYQGGP STMAEQAKNW

481   LPGPCFRQQR VSKTLDQNNN SNFAWTGATK YHLNGRNSLV NPGVAMATHK DDEDRFFPSS

541   GVLIFGKTGA TNKTTLENVL MTNEEEIRPT NPVATEEYGI VSSNLQAANT AAQTQVVNNQ

601   GALPGMVWQN RDVYLQGPIW AKIPHTDGNF HPSPLMGGFG LKHPPPQILI KNTPVPANPP
```

| SEQUENCES |
|---|
| 661 EVFTPAKFAS FITQYSTGQV SVEIEWELQK ENSKRWNPEI QYTSNFEKQT GVDFAVDSQG |
| 721 VYSEPRPIGT RYLTRNL |
| AAV8 capsid protein (GenBank Accession No. AAN03857) (SEQ ID NO: 8) |
| 1 MAADGYLPDW LEDNLSEGIR EWWALKPGAP KPKANQQKQD DGRGLVLPGY KYLGPFNGLD |
| 61 KGEPVNAADA AALEHDKAYD QQLQAGDNPY LRYNHADAEF QERLQEDTSF GGNLGRAVFQ |
| 121 AKKRVLEPLG LVEEGAKTAP GKKRPVEPSP QRSPDSSTGI GKKGQQPARK RLNFGQTGDS |
| 181 ESVPDPQPLG EPPAAPSGVG PNTMAAGGGA PMADNNEGAD GVGSSSGNWH CDSTWLGDRV |
| 241 ITTSTRTWAL PTYNNHLYKQ ISNGTSGGAT NDNTYFGYST PWGYFDFNRF HCHFSPRDWQ |
| 301 RLINNNWGFR PKRLSFKLFN IQVKEVTQNE GTKTIANNLT STIQVFTDSE YQLPYVLGSA |
| 361 HQGCLPPFPA DVFMIPQYGY LTLNNGSQAV GRSSFYCLEY FPSQMLRTGN NFQFTYTFED |
| 421 VPFHSSYAHS QSLDRLMNPL IDQYLYYLSR TQTTGGTANT QTLGFSQGGP NTMANQAKNW |
| 481 LPGPCYRQQR VSTTTGQNNN SNFAWTAGTK YHLNGRNSLA NPGIAMATHK DDEERFFPSN |
| 541 GILIFGKQNA ARDNADYSDV MLTSEEEIKT TNPVATEEYG IVADNLQQQN TAPQIGTVNS |
| 601 QGALPGMVWQ NRDVYLQGPI WAKIPHTDGN FHPSPLMGGF GLKHPPPQIL IKNTPVPADP |
| 661 PTTFNQSKLN SFITQYSTGQ VSVEIEWELQ KENSKRWNPE IQYTSNYYKS TSVDFAVNTE |
| 721 GVYSEPRPIG TRYLTRNL |
| AAV9 capsid protein (GenBank Accession No. AAS99264) (SEQ ID NO: 9) |
| 1 MAADGYLPDW LEDNLSEGIR EWWALKPGAP QPKANQQHQD NARGLVLPGY KYLGPGNGLD |
| 61 KGEPVNAADA AALEHDKAYD QQLKAGDNPY LKYNHADAEF QERLKEDTSF GGNLGRAVFQ |
| 121 AKKRLLEPLG LVEEAAKTAP GKKRPVEQSP QEPDSSAGIG KSGAQPAKKR LNFGQTGDTE |
| 181 SVPDPQPIGE PPAAPSGVGS LTMASGGGAP VADNNEGADG VGSSSGNWHC DSQWLGDRVI |
| 241 TTSTRTWALP TYNNHLYKQI SNSTSGGSSN DNAYFGYSTP WGYFDFNRFH CHFSPRDWQR |
| 301 LINNNWGFRP KRLNFKLENT QVKEVTDNNG VKTIANNLTS TVQVFTDSDY QLPYVLGSAH |
| 361 EGCLPPFPAD VFMIPQYGYL TLNDGSQAVG RSSFYCLEYF PSQMLRTGNN FQFSYEFENV |
| 421 PFHSSYAHSQ SLDRLMNPLI DQYLYYLSKT INGSGQNQQT LKFSVAGPSN MAVQGRNYIP |
| 481 GPSYRQQRVS TTVTQNNNSE FAWPGASSWA LNGRNSLMNP GPAMASHKEG EDRFFPLSGS |
| 541 LIFGKQGTGR DNVDADKVMI TNEEEIKTTN PVATESYGQV ATNHQSAQAQ AQTGWVQNQG |
| 601 ILPGMVWQDR DVYLQGPIWA KIPHTDGNFH PSPLMGGFGM KHPPPQILIK NTPVPADPPT |
| 661 AFNKDKLNSF ITQYSTGQVS VEIEWELQKE NSKRWNPEIQ YTSNYYKSNN VEFAVNTEGV |
| 721 YSEPRPIGTR YLTRNL |
| AAVrh.8 capsid protein (GenBank Accession No. AAO88183) (SEQ ID NO: 10) |
| 1 MAADGYLPDW LEDNLSEGIR EWWDLKPGAP KPKANQQKQD DGRGLVLPGY KYLGPFNGLD |
| 61 KGEPVNAADA AALEHDKAYD QQLKAGDNPY LRYNHADAEF QERLQEDTSF GGNLGRAVFQ |
| 121 AKKRVLEPLG LVEEGAKTAP GKKRPVEQSP QEPDSSSGIG KTGQQPAKKR LNFGQTGDSE |
| 181 SVPDPQPLGE PPAAPSGLGP NTMASGGGAP MADNNEGADG VGNSSGNWHC DSTWLGDRVI |
| 241 TTSTRTWALP TYNNHLYKQI SNGTSGGSTN DNTYFGYSTP WGYFDFNRFH CHFSPRDWQR |
| 301 LINNNWGFRP KRLNFKLFNI QVKEVTTNEG TKTIANNLTS TVQVFTDSEY QLPYVLGSAH |
| 361 QGCLPPFPAD VFMVPQYGYL TLNNGSQALG RSSFYCLEYF PSQMLRTGNN FQFSYTFEDV |
| 421 PFHSSYAHSQ SLDRLMNPLI DQYLYYLVRT QTTGTGGTQT LAFSQAGPSS MANQARNWVP |
| 481 GPCYRQQRVS TTTNQNNNSN FAWTGAAKFK LNGRDSLMNP GVAMASHKDD DDRFFPSSGV |

-continued

| SEQUENCES |
|---|

541 LIFGKQGAGN DGVDYSQVLI TDEEEIKATN PVATEEYGAV AINNQAANTQ AQTGLVHNQG

601 VIPGMVWQNR DVYLQGPIWA KIPHTDGNFH PSPLMGGFGL KHPPPQILIK NTPVPADPPL

661 TFNQAKLNSF ITQYSTGQVS VEIEWELQKE NSKRWNPEIQ YTSNYYKSTN VDFAVNTEGV

721 YSEPRPIGTR YLTRNL

AAVrh.10 capsid protein (GenBank Accession No. AA088201) (SEQ ID NO: 11)
1 MAADGYLPDW LEDNLSEGIR EWWDLKPGAP KPKANQQKQD DGRGLVLPGY KYLGPFNGLD

61 KGEPVNAADA AALEHDKAYD QQLKAGDNPY LRYNHADAEF QERLQEDTSF GGNLGRAVFQ

121 AKKRVLEPLG LVEEGAKTAP GKKRPVEPSP QRSPDSSTGI GKKGQQPAKK RLNFGQTGDS

181 ESVPDPQPIG EPPAGPSGLG SGTMAAGGGA PMADNNEGAD GVGSSSGNWH CDSTWLGDRV

241 ITTSTRTWAL PTYNNHLYKQ ISNGTSGGST NDNTYFGYST PWGYFDFNRF HCHFSPRDWQ

301 RLINNNWGFR PKRLNFKLFN IQVKEVTQNE GTKTIANNLT STIQVFTDSE YQLPYVLGSA

361 HQGCLPPFPA DVFMIPQYGY LTLNNGSQAV GRSSFYCLEY FPSQMLRTGN NFEFSYQFED

421 VPFHSSYAHS QSLDRLMNPL IDQYLYYLSR TQSTGGTAGT QQLLFSQAGP NNMSAQAKNW

481 LPGPCYRQQR VSTTLSQNNN SNFAWTGATK YHLNGRDSLV NPGVAMATHK DDEERFFPSS

541 GVLMFGKQGA GKDNVDYSSV MLTSEEEIKT TNPVATEQYG VVADNLQQQN AAPIVGAVNS

601 QGALPGMVWQ NRDVYLQGPT WAKIPHTDGN FHPSPLMGGF GLKHPPPQIL IKNTPVPADP

661 PTTFSQAKLA SFITQYSTGQ VSVEIEWELQ KENSKRWNPE IQYTSNYYKS TNVDFAVNTD

721 GTYSEPRPIG TRYLTRNL

AAV10 capsid protein (GenBank Accession No. AAT46337) (SEQ ID NO: 12)
1 MAADGYLPDW LEDNLSEGIR EWWDLKPGAP KPKANQQKQD DGRGLVLPGY KYLGPFNGLD

61 KGEPVNAADA AALEHDKAYD QQLKAGDNPY LRYNHADAEF QERLQEDTSF GGNLGRAVFQ

121 AKKRVLEPLG LVEEAAKTAP GKKRPVEPSP QRSPDSSTGI GKKGQQPAKK RLNFGQTGES

181 ESVPDPQPIG EPPAGPSGLG SGTMAAGGGA PMADNNEGAD GVGSSSGNWH CDSTWLGDRV

241 ITTSTRTWAL PTYNNHLYKQ ISNGTSGGST NDNTYFGYST PWGYFDFNRF HCHFSPRDWQ

301 RLINNNWGFR PKRLSFKLFN IQVKEVTQNE GTKT1ANNLT STIQVFTDSE YQLPYVLGSA

361 HQGCLPPFPA DVFMIPQYGY LTLNNGSQAV GRSSFYCLEY FPSQMLRTGN NFEFSYTFED

421 VPFHSSYAHS QSLDRLMNPL IDQYLYYLSR TQSTGGTQGT QQLLFSQAGP ANMSAQAKNW

481 LPGPCYRQQR VSTTLSQNNN SNFAWTGATK YHLNGRDSLV NPGVAMATHK DDEERFFPSS

541 GVLMFGKQGA GRDNVDYSSV MLTSEEEIKT TNPVATEQYG VVADNLQQAN TGPIVGNVNS

601 QGALPGMVWQ NRDVYLQGPI WAKIPHTDGN FHPSPLMGGF GLKHPPPQIL IKNTPVPADP

661 PTTFSQAKLA SFITQYSTGQ VSVEIEWELQ KENSKRWNPE IQYTSNYYKS TNVDFAVNTE

721 GTYSEPRPIG TRYLTRNL

AAV11 capsid protein (GenBank Accession No. AAT46339) (SEQ ID NO: 13)
1 MAADGYLPDW LEDNLSEGIR EWWDLKPGAP KPKANQQKQD DGRGLVLPGY KYLGPFNGLD

61 KGEPVNAADA AALEHDKAYD QQLKAGDNPY LRYNHADAEF QERLQEDTSF GGNLGRAVFQ

121 AKKRVLEPLG LVEEGAKTAP GKKRPLESPQ EPDSSSGIGK KGKQPARKRL NFEEDTGAGD

181 GPPEGSDTSA MSSDIEMRAA PGGNAVDAGQ GSDGVGNASG DWHCDSTWSE GKVTTTSTRT

241 WVLPTYNNHL YLRLGTTSSS NTYNGFSTPW GYFDFNRFHC HFSPRDWQRL INNNWGLRPK

301 AMRVKIFNIQ VKEVTTSNGE TTVANNLTST VQIFADSSYE LPYVMDAGQE GSLPPFPNDV

361 FMVPQYGYCG IVTGENQNQT DRNAFYCLEY FPSQMLRTGN NFEMAYNFEK VPFHSMYAHS

-continued

| SEQUENCES |
|---|

421 QSLDRLMNPL LDQYLWHLQS TTSGETLNQG NAATTFGKIR SGDFAFYRKN WLPGPCVKQQ

481 RFSKTASQNY KIPASGGNAL LKYDTHYTLN NRWSNIAPGP PMATAGPSDG DFSNAQLIFP

541 GPSVTGNTTT SANNLLFTSE EEIAATNPRD TDMFGQIADN NQNATTAPIT GNVTAMGVLP

601 GMVWQNRDIY YQGPIWAKIP HADGHFHPSP LIGGFGLKHP PPQIFIKNTP VPANPATTFT

661 AARVDSFITQ YSTGQVAVQI EWEIEKERSK RWNPEVQFTS NYGNQSSMLW APDTTGKYTE

721 PRVIGSRYLT NHL

AAV12 capsid protein (GenBank Accession No. ABI16639) (SEQ ID NO: 14)
1 MAADGYLPDW LEDNLSEGIR EWWALKPGAP QPKANQQHQD NGRGLVLPGY KYLGPFNGLD

61 KGEPVNEADA AALEHDKAYD KQLEQGDNPY LKYNHADAEF QQRLATDTSF GGNLGRAVFQ

121 AKKRILEPLG LVEEGVKTAP GKKRPLEKTP NRPTNPDSGK APAKKKQKDG EPADSARRTL

181 DFEDSGAGDG PPEGSSSGEM SHDAEMRAAP GGNAVEAGQG ADGVGNASGD WHCDSTWSEG

241 RVTTTSTRTW VLPTYNNHLY LRIGTTANSN TYNGFSTPWG YFDFNRFHCH FSPRDWQRLI

301 NNNWGLRPKS MRVKIFNIQV KEVTTSNGET TVANNLTSTV QIFADSTYEL PYVMDAGQEG

361 SFPPFPNDVF MVPQYGYCGV VTGKNQNQTD RNAFYCLEYF PSQMLRTGNN FEVSYQFEKV

421 PFHSMYAHSQ SLDRMMNPLL DQYLWHLQST TTGNSLNQGT ATTTYGKITT GDFAYYRKNW

481 LPGACIKQQK FSKNANQNYK IPASGGDALL KYDTHTTLNG RWSNMAPGPP MATAGAGDSD

541 FSNSQLIFAG PNPSGNTTTS SNNLLFTSEE EIATTNPRDT DMFGQIADNN QNATTAPHIA

601 NLDAMGIVPG MVWQNRDIYY QGPIWAKVPH TDGHFHPSPL MGGFGLKHPP PQIFIKNTPV

661 PANPNTTFSA ARINSFLTQY STGQVAVQID WEIQKEHSKR WNPEVQFTSN YGTQNSMLWA

721 PDNAGNYHEL RAIGSRFLTH HL

AAVih.32.33 capsid protein (GenBank Accession No. ACB55318) (SEQ ID NO: 15)
1 MAADGYLPDW LEDNLSEGIR EWWDLKPGAP KPKANQQKQD DGRGLVLPGY KYLGPFNGLD

61 KGEPVNAADA AALEHDKAYD QQLKAGDNPY LRYNHADAEF QERLQEDTSF GGNLGRAVFQ

121 AKKRVLEPLG LVEEGAKTAP GKKRPLESPQ EPDSSSGIGK KGKQPAKKRL NFEEDTGAGD

181 GPPEGSDTSA MSSDIEMRAA PGGNAVDAGQ GSDGVGNASG DWHCDSTWSE GKVTTTSTRT

241 WVLPTYNNHL YLRLGTTSNS NTYNGFSTPW GYFDFNRFHC HFSPRDWQRL INNNWGLRPK

301 AMRVKIFNIQ VKEVTTSNGE TTVANNLTST VQIFADSSYE LPYVMDAGQE GSLPPFPNDV

361 FMVPQYGYCG IVTGENQNQT DRNAFYCLEY FPSQMLRTGN NFEMAYNFEK VPFHSMYAHS

421 QSLDRLMNPL LDQYLWHLQS TTSGETLNQG NAATTFGKIR SGDFAFYRKN WLPGPCVKQQ

481 RFSKTASQNY KIPASGGNAL LKYDTHYTLN NRWSNIAPGP PMATAGPSDG DFSNAQLIFP

541 GPSVTGNTTT SANNLLFTSE EEIAATNPRD TDMFGQIADN NQNATTAPIT GNVTAMGVLP

601 GMVWQNRDIY YQGPIWAKIP HADGHFHPSP LIGGFGLKHP PPQIFIKNTP VPANPATTFT

661 AARVDSFITQ YSTGQVAVQI EWEIEKERSK RWNPEVQFTS NYGNQSSMLW APDTTGKYTE

721 PRVIGSRYLT NHL

Bovine AAV capsid protein (GenBank Accession No. YP_024971) (SEQ ID NO: 16)
1 MSFVDHPPDW LESIODGFRE FLGLEAGPPK PKANQQKQDN ARGLVLPGYK YLGPGNGLDK

61 GDPVNFADEV AREHDLSYQK QLEAGDNPYL KYNHADAEFQ EKLASDTSFG GNLGKAVFQA

121 KKRILEPLGL VETPDKTAPA AKKRPLEQSP QEPDSSSGVG KKGKQPARKR LNFDDEPGAG

181 DGPPPEGPSS GAMSTETEMR AAAGGNGGDA GQGAEGVGNA SGDWHCDSTW SESHVTTTST

241 RTWVLPTYNN HLYLRLGSSN ASDTFNGFST PWGYFDFNRF HCHFSPRDWQ RLINNHWGLR

-continued

SEQUENCES

```
301    PKSMQVRIFN IQVKEVTTSN GETTVSNNLT STVQIFADST YELPYVMDAG QEGSLPPFPN

361    DVFMVPQYGY CGLVTGGSSQ NQTDRNAFYC LEYFPSQMLR TGNNFEMVYK FENVPFHSMY

421    AHSQSLDRLM NPLLDQYLWE LQSTTSGGTL NQGNSATNFA KLTKTNFSGY RKNWLPGPMM

481    KQQRFSKTAS QNYKIPQGRN NSLLHYETRT TLDGRWSNFA PGTAMATAAN DATDFSQAQL

541    IFAGPNITGN TTTDANNLMF TSEDELRATN PRDTDLFGHL ATNQQNATTV PTVDDVDGVG

601    VYPGMVWQDR DIYYQGPIWA KIPHTDGHFH PSPLIGGFGL KSPPPQIFIK NTPVPANPAT

661    TFSPARINSF ITQYSTGQVA VKIEWEIQKE RSKRWNPEVQ FTSNYGAQDS LLWAPDNAGA

721    YKEPRAIGSR YLTNHL
```

Avian AAV ATCC VR-865 capsid protein (GenBank Accession No. NP_852781) (SEQ ID NO: 17)

```
  1    MSLISDAIPD WLERLVKKGV NAAADFYHLE SGPPRPKANQ QTQESLEKDD SRGLVFPGYN

 61    YLGPFNGLDK GEPVNEADAA ALEHDKAYDL EIKDGHNPYF EYNEADRRFQ ERLKDDTSFG

121    GNLGKAIFQA KKRVLEPFGL VEDSKTAPTG DKRKGEDEPR LPDTSSQTPK KNKKPRKERP

181    SGGAEDPGEG TSSNAGAAAP ASSVGSSIMA EGGGGPVGDA GQGADGVGNS SGNWHCDSQW

241    LENGVVTRTT RTWVLPSYNN HLYKRIQGPS GGDNNNKFFG FSTPWGYFDY NRFHCHFSPR

301    DWQRLINNNW GIRPKAMRFR LFNIQVKEVT VQDFNTTIGN NLTSTVQVFA DKDYQLPYVL

361    GSATEGTFPP FPADIYTIPQ YGYCTLNYNN EAVDRSAFYC LDYFPSDMLR TGNNFEFTYT

421    FEDVPFHSMF AHNQTLDRLM NPLVDQYLWA FSSVSQAGSS GRALHYSRAT KTNMAAQYRN

481    WLPGPFFRDQ QIFTGASNIT KNNVFSVWEK GKQWELDNRT NLMQPGPAAA TTFSGEPDRQ

541    AMQNTLAFSR TVYDQTTATT DRNQILITNE DEIRPTNSVG IDAWGAVPTN NQSIVTPGTR

601    AAVNNQGALP GMVWQNRDIY PTGTHLAKIP DTDNHFHPSP LIGRFGCKHP PQIFIKNTP

661    VPANPSETFQ TAKVASFINQ YSTGQCTVEI FWELKKETSK RWNPEIQFTS NFGNAADIQF

721    AVSDTGSYSE PRPIGTRYLT KPL
```

That which is claimed is:

1. A recombinant adeno associated virus (AAV) vector, the vector comprising a capsid protein and a nucleic acid encapsidated by the capsid protein;

wherein the nucleic acid encodes a heterologous polypeptide or heterologous RNA sequence; and wherein the capsid protein comprises one or more of the following substitutions, wherein the amino acids are numbered according to the amino acid sequence of SEQ ID NO:8:

a) a substitution of the amino acids corresponding to amino acids 455-460 with the sequence SNGRGV (SEQ ID NO:488), a substitution of the amino acids corresponding to amino acids 455-461 with the sequence VNTSING (SEQ ID NO:489), or a substitution of the amino acids corresponding to amino acids 455-461 with the sequence IRGAGAV (SEQ ID NO:490);

b) a substitution of the amino acids corresponding to amino acids 494-501 with the sequence YPGGNYK (SEQ ID NO:491); and/or c) a substitution of the amino acids corresponding to amino acids 586-591 with the sequence KQKNVN (SEQ ID NO:492) or RMSSIK (SEQ ID NO:493).

2. The recombinant AAV vector of claim 1, wherein the one or more substitutions inhibit neutralization of infectivity of the AAV vector and/or inhibit binding of an antibody to the AAV vector, wherein the antibody binds to a capsid protein comprising the amino acid sequence of SEQ ID NO:8.

3. The recombinant AAV vector of claim 2, wherein the antibody is selected from the group consisting of HL2381, HL3283, and ADK8.

4. The recombinant AAV vector of claim 3, wherein the antibody is HL2381.

5. The recombinant AAV vector of claim 3, wherein the antibody is HL2383.

6. The recombinant AAV vector of claim 3, wherein the antibody is ADK8.

7. The recombinant AAV vector of claim 1, wherein the capsid protein further comprises a substitution at amino acid 453, 454, 502, 592, 593, 594, 595, 596, 597, 598, 599 and/or 600, in any combination.

8. The recombinant AAV vector of claim 1, wherein the capsid protein comprises a substitution of amino acids 455-460 with the sequence SNGRGV (SEQ ID NO:488).

9. The recombinant AAV vector of claim 1, wherein the capsid protein comprises a substitution of amino acids 455-460 with the sequence SNGRGV (SEQ ID NO:488) and a substitution of amino acids 494-501 with the sequence YPGGNYK (SEQ ID NO:491).

10. The recombinant AAV vector of claim 1, wherein the capsid protein comprises a substitution of amino acids 455-460 with the sequence SNGRGV (SEQ ID NO:488) and a substitution of amino acids 494-501 with the sequence KQKNVN (SEQ ID NO:492).

11. The recombinant AAV vector claim 1, wherein the heterologous polypeptide is a therapeutic polypeptide.

12. The recombinant AAV vector of claim 1, wherein the heterologous RNA is a functional RNA.

13. The recombinant AAV vector of claim 1, wherein the nucleic acid comprises terminal repeat (TR) sequences from AAV2 or AAV4.

14. A recombinant adeno-associated virus (AAV) vector, the vector comprising a capsid protein and a nucleic acid encapsidated by the capsid protein;

wherein the nucleic acid encodes a heterologous polypeptide or heterologous RNA sequence; and wherein the capsid protein comprises one or more of the following substitutions, wherein the amino acids are numbered according to the amino acid sequence of SEQ ID NO:8:

a) a substitution of the amino acids corresponding to amino acids 455-460 with the sequence SNGRGV (SEQ ID NO:488), a substitution of the amino acids corresponding to amino acids 455-461 with the sequence VNTSING (SEQ ID NO:489), or a substitution of the amino acids corresponding to amino acids 455-461 with the sequence IRGAGAV (SEQ ID NO:490);

b) a substitution of the amino acids corresponding to amino acids 494-501 with the sequence YPGGNYK (SEQ ID NO:491); and/or c) a substitution of the amino acids corresponding to amino acids 586-591 with the sequence KQKNVN (SEQ ID NO:492) or RMSSIK (SEQ ID NO:493), and wherein the capsid protein with the substitutions of one or more of a)-c) is at least about 90% identical to the amino acid sequence of SEQ ID NO:8.

15. The recombinant AAV vector of claim 14, wherein the capsid protein comprises a sequence at least about 95% identical to the amino acid sequence of SEQ ID NO:8.

16. The recombinant AAV vector of claim 14, wherein the capsid protein comprises a sequence at least about 97% identical to the amino acid sequence of SEQ ID NO:8.

17. The recombinant AAV vector of claim 14, wherein the capsid protein comprises a sequence at least about 98% identical to the amino acid sequence of SEQ ID NO:8.

18. The recombinant AAV vector of claim 14, wherein the capsid protein comprises a sequence at least about 99% identical to the amino acid sequence of SEQ ID NO:8.

19. The recombinant AAV vector of claim 14, wherein the one or more substitutions inhibit neutralization of infectivity of the AAV vector and/or inhibit binding of an antibody to the AAV vector, wherein the antibody binds to a capsid protein comprising the amino acid sequence of SEQ ID NO:8.

20. The recombinant AAV vector of claim 19, wherein the antibody is selected from the group consisting of HL2381, HL2383, and ADK8.

21. The recombinant AAV vector of claim 20, wherein the antibody is HL2381.

22. The recombinant AAV vector of claim 20, wherein the antibody is HL2383.

23. The recombinant AAV vector of claim 20, wherein the antibody is ADK8.

24. The recombinant AAV vector of claim 14, wherein the capsid protein comprises one or more substitutions at the amino acids corresponding to amino acids 453-461 and 495-502 of SEQ ID NO:8.

25. The recombinant AAV vector of claim 14, wherein the capsid protein comprises one or more substitutions at the amino acids corresponding to amino acids 453-461 and 590-600 of SEQ ID NO:8.

26. The recombinant AAV vector of claim 14, wherein the capsid protein comprises one or more substitutions at the amino acids corresponding to amino acids 495-502 and 590-600 of SEQ ID NO:8.

27. The recombinant AAV vector of claim 14, wherein the capsid protein comprises one or more substitutions at the amino acids corresponding to amino acids 453-461, 495-502 and 590-600 of SEQ ID NO:8.

28. The recombinant AAV vector of claim 14, wherein the capsid protein comprises a substitution of amino acids 455-460 of SEQ ID NO:8 with the sequence SNGRGV (SEQ ID NO:488).

29. The recombinant AAV vector of claim 14, wherein the capsid protein comprises a substitution of amino acids 455-460 of SEQ ID NO:8 with the sequence SNGRGV (SEQ ID NO:488) and a substitution of amino acids 494-501 of SEQ ID NO:8 with the sequence YPGGNYK (SEQ ID NO:491).

30. The recombinant AAV vector of claim 14, wherein the capsid protein comprises a substitution of amino acids 455-460 of SEQ ID NO:8 with the sequence SNGRGV (SEQ ID NO:488) and a substitution of amino acids 494-501 of SEQ ID NO:8 with the sequence KQKNVN (SEQ ID NO:492).

31. The recombinant AAV vector claim 14, wherein the heterologous polypeptide is a therapeutic polypeptide.

32. The recombinant AAV vector of claim 14, wherein the heterologous RNA is a functional RNA.

33. The recombinant AAV vector of claim 14, wherein the nucleic acid comprises terminal repeat (TR) sequences from AAV2 or AAV4.

* * * * *

SEQUENCE LISTING

```
<160> NUMBER OF SEQ ID NOS: 527

<210> SEQ ID NO 1
<211> LENGTH: 736
<212> TYPE: PRT
<213> ORGANISM: adeno-associated virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510
```

```
Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 2
<211> LENGTH: 735
<212> TYPE: PRT
<213> ORGANISM: adeno-associated virus

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160
```

-continued

```
Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575
```

```
Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 3
<211> LENGTH: 736
<212> TYPE: PRT
<213> ORGANISM: adeno-associated virus

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220
```

-continued

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640
```

-continued

```
Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735


<210> SEQ ID NO 4
<211> LENGTH: 734
<212> TYPE: PRT
<213> ORGANISM: adeno-associated virus

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285
```

-continued

```
Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
    690                 695                 700
```

```
Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730


<210> SEQ ID NO 5
<211> LENGTH: 724
<212> TYPE: PRT
<213> ORGANISM: adeno-associated virus

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350
```

```
Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 6
<211> LENGTH: 736
<212> TYPE: PRT
<213> ORGANISM: adeno-associated virus

<400> SEQUENCE: 6
```

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

-continued

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 7
<211> LENGTH: 737
<212> TYPE: PRT
<213> ORGANISM: adeno-associated virus

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

```
Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480
```

-continued

```
Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 8
<211> LENGTH: 738
<212> TYPE: PRT
<213> ORGANISM: adeno-associated virus

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
```

```
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 9
<211> LENGTH: 736
<212> TYPE: PRT
<213> ORGANISM: adeno-associated virus

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
```

-continued

```
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

Thr Gly Trp Val Gln Asn Gln Gly Ile Leu Pro Gly Met Val Trp Gln
595 600 605

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 10
<211> LENGTH: 736
<212> TYPE: PRT
<213> ORGANISM: adeno-associated virus

<400> SEQUENCE: 10

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Thr Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Ala Pro Ser Gly Leu Gly Pro Asn Thr Met Ala Ser Gly Gly Gly
195 200 205

Ala Pro Met Ala Asp Asn Asn Glu Gly Ala Asp Gly Val Gly Asn Ser
210 215 220

Ser Gly Asn Trp His Cys Asp Ser Thr Trp Leu Gly Asp Arg Val Ile

```
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655
```

```
Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 11
<211> LENGTH: 738
<212> TYPE: PRT
<213> ORGANISM: adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
```

```
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720
```

```
Gly Thr Tyr Ser Glu Pro Arg Pro Ile Gly Thr Arg Tyr Leu Thr Arg
                725                 730                 735

Asn Leu


<210> SEQ ID NO 12
<211> LENGTH: 738
<212> TYPE: PRT
<213> ORGANISM: adeno-associated virus

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350
```

```
Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 13
<211> LENGTH: 733
<212> TYPE: PRT
```

<213> ORGANISM: adeno-associated virus

<400> SEQUENCE: 13

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Leu Glu Ser Pro Gln Glu Pro Asp Ser Ser Ser Gly Ile Gly Lys
145 150 155 160

Lys Gly Lys Gln Pro Ala Arg Lys Arg Leu Asn Phe Glu Glu Asp Thr
165 170 175

Gly Ala Gly Asp Gly Pro Pro Glu Gly Ser Asp Thr Ser Ala Met Ser
180 185 190

Ser Asp Ile Glu Met Arg Ala Ala Pro Gly Gly Asn Ala Val Asp Ala
195 200 205

Gly Gln Gly Ser Asp Gly Val Gly Asn Ala Ser Gly Asp Trp His Cys
210 215 220

Asp Ser Thr Trp Ser Glu Gly Lys Val Thr Thr Thr Ser Thr Arg Thr
225 230 235 240

Trp Val Leu Pro Thr Tyr Asn Asn His Leu Tyr Leu Arg Leu Gly Thr
245 250 255

Thr Ser Ser Ser Asn Thr Tyr Asn Gly Phe Ser Thr Pro Trp Gly Tyr
260 265 270

Phe Asp Phe Asn Arg Phe His Cys His Phe Ser Pro Arg Asp Trp Gln
275 280 285

Arg Leu Ile Asn Asn Asn Trp Gly Leu Arg Pro Lys Ala Met Arg Val
290 295 300

Lys Ile Phe Asn Ile Gln Val Lys Glu Val Thr Thr Ser Asn Gly Glu
305 310 315 320

Thr Thr Val Ala Asn Asn Leu Thr Ser Thr Val Gln Ile Phe Ala Asp
325 330 335

Ser Ser Tyr Glu Leu Pro Tyr Val Met Asp Ala Gly Gln Glu Gly Ser
340 345 350

Leu Pro Pro Phe Pro Asn Asp Val Phe Met Val Pro Gln Tyr Gly Tyr
355 360 365

Cys Gly Ile Val Thr Gly Glu Asn Gln Asn Gln Thr Asp Arg Asn Ala
370 375 380

Phe Tyr Cys Leu Glu Tyr Phe Pro Ser Gln Met Leu Arg Thr Gly Asn
385 390 395 400

```
Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

<210> SEQ ID NO 14
<211> LENGTH: 742
<212> TYPE: PRT
<213> ORGANISM: adeno-associated virus

<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45
```

-continued

```
Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365

Val Phe Met Val Pro Gln Tyr Gly Tyr Cys Gly Val Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460
```

```
Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740


<210> SEQ ID NO 15
<211> LENGTH: 733
<212> TYPE: PRT
<213> ORGANISM: adeno-associated virus

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510
```

```
Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730


<210> SEQ ID NO 16
<211> LENGTH: 736
<212> TYPE: PRT
<213> ORGANISM: adeno-associated virus

<400> SEQUENCE: 16

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Ala Lys Lys Arg
    130                 135                 140

Pro Leu Glu Gln Ser Pro Gln Glu Pro Asp Ser Ser Ser Gly Val Gly
145                 150                 155                 160
```

```
Lys Lys Gly Lys Gln Pro Ala Arg Lys Arg Leu Asn Phe Asp Asp Glu
                165                 170                 175

Pro Gly Ala Gly Asp Gly Pro Pro Pro Glu Gly Pro Ser Ser Gly Ala
            180                 185                 190

Met Ser Thr Glu Thr Glu Met Arg Ala Ala Ala Gly Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
    290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Gly Ser Ser Gln Asn Gln Thr Asp
    370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
            420                 425                 430

Leu Leu Asp Gln Tyr Leu Trp Glu Leu Gln Ser Thr Thr Ser Gly Gly
        435                 440                 445

Thr Leu Asn Gln Gly Asn Ser Ala Thr Asn Phe Ala Lys Leu Thr Lys
    450                 455                 460

Thr Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
                485                 490                 495

Gln Gly Arg Asn Asn Ser Leu Leu His Tyr Glu Thr Arg Thr Thr Leu
            500                 505                 510

Asp Gly Arg Trp Ser Asn Phe Ala Pro Gly Thr Ala Met Ala Thr Ala
        515                 520                 525

Ala Asn Asp Ala Thr Asp Phe Ser Gln Ala Gln Leu Ile Phe Ala Gly
    530                 535                 540

Pro Asn Ile Thr Gly Asn Thr Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575
```

```
Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
        595                 600                 605

Asp Arg Asp Ile Tyr Tyr Gln Gly Pro Ile Trp Ala Lys Ile Pro His
    610                 615                 620

Thr Asp Gly His Phe His Pro Ser Pro Leu Ile Gly Gly Phe Gly Leu
625                 630                 635                 640

Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
        675                 680                 685

Lys Glu Arg Ser Lys Arg Trp Asn Pro Glu Val Gln Phe Thr Ser Asn
    690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735


<210> SEQ ID NO 17
<211> LENGTH: 743
<212> TYPE: PRT
<213> ORGANISM: adeno-associated virus

<400> SEQUENCE: 17

Met Ser Leu Ile Ser Asp Ala Ile Pro Asp Trp Leu Glu Arg Leu Val
1               5                   10                  15

Lys Lys Gly Val Asn Ala Ala Ala Asp Phe Tyr His Leu Glu Ser Gly
            20                  25                  30

Pro Pro Arg Pro Lys Ala Asn Gln Gln Thr Gln Glu Ser Leu Glu Lys
        35                  40                  45

Asp Asp Ser Arg Gly Leu Val Phe Pro Gly Tyr Asn Tyr Leu Gly Pro
    50                  55                  60

Phe Asn Gly Leu Asp Lys Gly Glu Pro Val Asn Glu Ala Asp Ala Ala
65                  70                  75                  80

Ala Leu Glu His Asp Lys Ala Tyr Asp Leu Glu Ile Lys Asp Gly His
                85                  90                  95

Asn Pro Tyr Phe Glu Tyr Asn Glu Ala Asp Arg Arg Phe Gln Glu Arg
            100                 105                 110

Leu Lys Asp Asp Thr Ser Phe Gly Gly Asn Leu Gly Lys Ala Ile Phe
        115                 120                 125

Gln Ala Lys Lys Arg Val Leu Glu Pro Phe Gly Leu Val Glu Asp Ser
    130                 135                 140

Lys Thr Ala Pro Thr Gly Asp Lys Arg Lys Gly Glu Asp Glu Pro Arg
145                 150                 155                 160

Leu Pro Asp Thr Ser Ser Gln Thr Pro Lys Lys Asn Lys Lys Pro Arg
                165                 170                 175

Lys Glu Arg Pro Ser Gly Gly Ala Glu Asp Pro Gly Glu Gly Thr Ser
            180                 185                 190

Ser Asn Ala Gly Ala Ala Ala Pro Ala Ser Ser Val Gly Ser Ser Ile
        195                 200                 205

Met Ala Glu Gly Gly Gly Gly Pro Val Gly Asp Ala Gly Gln Gly Ala
    210                 215                 220
```

-continued

```
Asp Gly Val Gly Asn Ser Ser Gly Asn Trp His Cys Asp Ser Gln Trp
225                 230                 235                 240

Leu Glu Asn Gly Val Val Thr Arg Thr Thr Arg Thr Trp Val Leu Pro
                245                 250                 255

Ser Tyr Asn Asn His Leu Tyr Lys Arg Ile Gln Gly Pro Ser Gly Gly
            260                 265                 270

Asp Asn Asn Asn Lys Phe Phe Gly Phe Ser Thr Pro Trp Gly Tyr Phe
        275                 280                 285

Asp Tyr Asn Arg Phe His Cys His Phe Ser Pro Arg Asp Trp Gln Arg
    290                 295                 300

Leu Ile Asn Asn Asn Trp Gly Ile Arg Pro Lys Ala Met Arg Phe Arg
305                 310                 315                 320

Leu Phe Asn Ile Gln Val Lys Glu Val Thr Val Gln Asp Phe Asn Thr
                325                 330                 335

Thr Ile Gly Asn Asn Leu Thr Ser Thr Val Gln Val Phe Ala Asp Lys
            340                 345                 350

Asp Tyr Gln Leu Pro Tyr Val Leu Gly Ser Ala Thr Glu Gly Thr Phe
        355                 360                 365

Pro Pro Phe Pro Ala Asp Ile Tyr Thr Ile Pro Gln Tyr Gly Tyr Cys
    370                 375                 380

Thr Leu Asn Tyr Asn Asn Glu Ala Val Asp Arg Ser Ala Phe Tyr Cys
385                 390                 395                 400

Leu Asp Tyr Phe Pro Ser Asp Met Leu Arg Thr Gly Asn Asn Phe Glu
                405                 410                 415

Phe Thr Tyr Thr Phe Glu Asp Val Pro Phe His Ser Met Phe Ala His
            420                 425                 430

Asn Gln Thr Leu Asp Arg Leu Met Asn Pro Leu Val Asp Gln Tyr Leu
        435                 440                 445

Trp Ala Phe Ser Ser Val Ser Gln Ala Gly Ser Ser Gly Arg Ala Leu
    450                 455                 460

His Tyr Ser Arg Ala Thr Lys Thr Asn Met Ala Ala Gln Tyr Arg Asn
465                 470                 475                 480

Trp Leu Pro Gly Pro Phe Phe Arg Asp Gln Gln Ile Phe Thr Gly Ala
                485                 490                 495

Ser Asn Ile Thr Lys Asn Asn Val Phe Ser Val Trp Glu Lys Gly Lys
            500                 505                 510

Gln Trp Glu Leu Asp Asn Arg Thr Asn Leu Met Gln Pro Gly Pro Ala
        515                 520                 525

Ala Ala Thr Thr Phe Ser Gly Glu Pro Asp Arg Gln Ala Met Gln Asn
    530                 535                 540

Thr Leu Ala Phe Ser Arg Thr Val Tyr Asp Gln Thr Thr Ala Thr Thr
545                 550                 555                 560

Asp Arg Asn Gln Ile Leu Ile Thr Asn Glu Asp Glu Ile Arg Pro Thr
                565                 570                 575

Asn Ser Val Gly Ile Asp Ala Trp Gly Ala Val Pro Thr Asn Asn Gln
            580                 585                 590

Ser Ile Val Thr Pro Gly Thr Arg Ala Ala Val Asn Asn Gln Gly Ala
        595                 600                 605

Leu Pro Gly Met Val Trp Gln Asn Arg Asp Ile Tyr Pro Thr Gly Thr
    610                 615                 620

His Leu Ala Lys Ile Pro Asp Thr Asp Asn His Phe His Pro Ser Pro
625                 630                 635                 640
```

-continued

```
Leu Ile Gly Arg Phe Gly Cys Lys His Pro Pro Pro Gln Ile Phe Ile
                645                 650                 655

Lys Asn Thr Pro Val Pro Ala Asn Pro Ser Glu Thr Phe Gln Thr Ala
            660                 665                 670

Lys Val Ala Ser Phe Ile Asn Gln Tyr Ser Thr Gly Gln Cys Thr Val
        675                 680                 685

Glu Ile Phe Trp Glu Leu Lys Lys Glu Thr Ser Lys Arg Trp Asn Pro
    690                 695                 700

Glu Ile Gln Phe Thr Ser Asn Phe Gly Asn Ala Ala Asp Ile Gln Phe
705                 710                 715                 720

Ala Val Ser Asp Thr Gly Ser Tyr Ser Glu Pro Arg Pro Ile Gly Thr
                725                 730                 735

Arg Tyr Leu Thr Lys Pro Leu
            740


<210> SEQ ID NO 18
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than A
<220> FEATURE:
<221> NAME/KEY: MISC_FEATURE
<222> LOCATION: (3)..(3)
<223> OTHER INFORMATION: Xaa can be any naturally occurring amino acid
      other than S
<220> FEATURE:
<221> NAME/KEY: MISC_FEATURE
<222> LOCATION: (4)..(4)
<223> OTHER INFORMATION: Xaa can be any naturally occurring amino acid
      other than T
<220> FEATURE:
<221> NAME/KEY: MISC_FEATURE
<222> LOCATION: (5)..(5)
<223> OTHER INFORMATION: Xaa can be any naturally occurring amino acid
      other than G
<220> FEATURE:
<221> NAME/KEY: MISC_FEATURE
<222> LOCATION: (6)..(6)
<223> OTHER INFORMATION: Xaa can be any naturally occurring amino acid
      other than A
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 18

Xaa Xaa Xaa Xaa Xaa Xaa Xaa
1               5


<210> SEQ ID NO 19
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
```

<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)
<223> OTHER INFORMATION: Xaa can be any naturally occurring amino acid other than I
<220> FEATURE:
<221> NAME/KEY: MISC_FEATURE
<222> LOCATION: (5)..(5)
<223> OTHER INFORMATION: Xaa can be any naturally occurring amino acid other than P
<220> FEATURE:
<221> NAME/KEY: MISC_FEATURE
<222> LOCATION: (6)..(6)
<223> OTHER INFORMATION: Xaa can be any naturally occurring amino acid other than Q
<220> FEATURE:
<221> NAME/KEY: MISC_FEATURE
<222> LOCATION: (7)..(7)
<223> OTHER INFORMATION: Xaa can be any naturally occurring amino acid other than Y
<220> FEATURE:
<221> NAME/KEY: MISC_FEATURE
<222> LOCATION: (8)..(8)
<223> OTHER INFORMATION: Xaa can be any naturally occurring amino acid other than G
<220> FEATURE:
<221> NAME/KEY: MISC_FEATURE
<222> LOCATION: (9)..(9)
<223> OTHER INFORMATION: Xaa can be any naturally occurring amino acid other than Y
<220> FEATURE:
<221> NAME/KEY: MISC_FEATURE
<222> LOCATION: (10)..(10)
<223> OTHER INFORMATION: Xaa can be any naturally occurring amino acid other than L

<400> SEQUENCE: 19

```
Xaa Xaa Xaa Xaa Xaa Xaa Xaa Xaa Xaa Xaa
1               5                   10
```

<210> SEQ ID NO 20
<211> LENGTH: 9
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N
<220> FEATURE:
<221> NAME/KEY: MISC_FEATURE
<222> LOCATION: (2)..(2)
<223> OTHER INFORMATION: Xaa can be any naturally occurring amino acid other than Q
<220> FEATURE:
<221> NAME/KEY: MISC_FEATURE
<222> LOCATION: (3)..(3)
<223> OTHER INFORMATION: Xaa can be any naturally occurring amino acid other than S
<220> FEATURE:

```
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than S
<220> FEATURE:
<221> NAME/KEY: MISC_FEATURE
<222> LOCATION: (6)..(6)
<223> OTHER INFORMATION: Xaa can be any naturally occurring amino acid
      other than A
<220> FEATURE:
<221> NAME/KEY: MISC_FEATURE
<222> LOCATION: (7)..(7)
<223> OTHER INFORMATION: Xaa can be any naturally occurring amino acid
      other than Q
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
      other than K

<400> SEQUENCE: 20

Xaa Xaa Xaa Xaa Xaa Xaa Xaa Xaa Xaa
1               5


<210> SEQ ID NO 21
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than Q
<220> FEATURE:
<221> NAME/KEY: MISC_FEATURE
<222> LOCATION: (3)..(3)
<223> OTHER INFORMATION: Xaa can be any naturally occurring amino acid
      other than N
<220> FEATURE:
<221> NAME/KEY: MISC_FEATURE
<222> LOCATION: (4)..(4)
<223> OTHER INFORMATION: Xaa can be any naturally occurring amino acid
      other than K

<400> SEQUENCE: 21

Xaa Xaa Xaa Xaa
1


<210> SEQ ID NO 22
<211> LENGTH: 4
<212> TYPE: PRT
<213> ORGANISM: Artificial
<220> FEATURE:
```

<223> OTHER INFORMATION: AAV capsid protein common antigenic motif (CAM)
      substitution sequence

<400> SEQUENCE: 22

Gln Val Arg Gly
1

<210> SEQ ID NO 23
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence

<400> SEQUENCE: 23

Glu Arg Pro Arg
1

<210> SEQ ID NO 24
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence

<400> SEQUENCE: 24

Gly Arg Gly Gly
1

<210> SEQ ID NO 25
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence

<400> SEQUENCE: 25

Ser Gly Gly Arg
1

<210> SEQ ID NO 26
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence

<400> SEQUENCE: 26

Ser Glu Arg Arg
1

<210> SEQ ID NO 27
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence

<400> SEQUENCE: 27

Leu Arg Gly Gly
1

<210> SEQ ID NO 28
<211> LENGTH: 8
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than D
<220> FEATURE:
<221> NAME/KEY: MISC_FEATURE
<222> LOCATION: (4)..(6)
<223> OTHER INFORMATION: Xaa can be any naturally occurring amino acid other than N
<220> FEATURE:
<221> NAME/KEY: MISC_FEATURE
<222> LOCATION: (5)..(5)
<223> OTHER INFORMATION: Xaa can be any naturally occurring amino acid other than N
<220> FEATURE:
<221> NAME/KEY: MISC_FEATURE
<222> LOCATION: (7)..(7)
<223> OTHER INFORMATION: Xaa can be any naturally occurring amino acid other than S
<220> FEATURE:
<221> NAME/KEY: MISC_FEATURE
<222> LOCATION: (8)..(8)
<223> OTHER INFORMATION: Xaa can be any naturally occurring amino acid other than N

<400> SEQUENCE: 28

```
Xaa Xaa Xaa Xaa Xaa Xaa Xaa Xaa
1               5
```

<210> SEQ ID NO 29
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than D
<220> FEATURE:
<221> NAME/KEY: MISC_FEATURE
<222> LOCATION: (4)..(6)
<223> OTHER INFORMATION: Xaa can be any naturally occurring amino acid other than N
<220> FEATURE:
<221> NAME/KEY: MISC_FEATURE
<222> LOCATION: (7)..(7)

<223> OTHER INFORMATION: Xaa can be any naturally occurring amino acid
other than S

<400> SEQUENCE: 29

Xaa Xaa Xaa Xaa Xaa Xaa Xaa
1 5

<210> SEQ ID NO 30
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 30

Pro Gly Gly Asn Ala Thr Arg
1 5

<210> SEQ ID NO 31
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than S
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than D
<220> FEATURE:
<221> NAME/KEY: MISC_FEATURE
<222> LOCATION: (4)..(4)
<223> OTHER INFORMATION: Xaa can be any naturally occurring amino acid
other than P
<220> FEATURE:
<221> NAME/KEY: MISC_FEATURE
<222> LOCATION: (5)..(5)
<223> OTHER INFORMATION: Xaa can be any naturally occurring amino acid
other than A
<220> FEATURE:
<221> NAME/KEY: MISC_FEATURE
<222> LOCATION: (6)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than D
<220> FEATURE:
<221> NAME/KEY: MISC_FEATURE
<222> LOCATION: (9)..(9)
<223> OTHER INFORMATION: Xaa can be any naturally occurring amino acid
other than V
<220> FEATURE:
<221> NAME/KEY: MISC_FEATURE
<222> LOCATION: (10)..(10)
<223> OTHER INFORMATION: Xaa can be any naturally occurring amino acid other than H

<400> SEQUENCE: 31

Xaa Xaa Xaa Xaa Xaa Xaa Xaa Xaa Xaa Xaa
1 5 10

<210> SEQ ID NO 32
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 32

Thr Ala Asp His Asp Thr Lys Gly Val Leu
1 5 10

<210> SEQ ID NO 33
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 33

Val Val Asp Pro Asp Lys Lys Gly Val Leu
1 5 10

<210> SEQ ID NO 34
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 34

Ala Lys Asp Thr Gly Pro Leu Asn Val Met
1 5 10

<210> SEQ ID NO 35
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 35

Gln Thr Asp Ala Lys Asp Asn Gly Val Gln
1 5 10

<210> SEQ ID NO 36
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 36

Asp Lys Asp Pro Trp Leu Asn Asp Val Ile
1 5 10

<210> SEQ ID NO 37

<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 37

Thr Arg Asp Gly Ser Thr Glu Ser Val Leu
1 5 10

<210> SEQ ID NO 38
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 38

Val Ile Asp Pro Asp Gln Lys Gly Val Leu
1 5 10

<210> SEQ ID NO 39
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 39

Val Asn Asp Met Ser Asn Tyr Met Val His
1 5 10

<210> SEQ ID NO 40
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than D
<220> FEATURE:
<221> NAME/KEY: MISC_FEATURE
<222> LOCATION: (2)..(3)
<223> OTHER INFORMATION: Xaa can be any naturally occurring amino acid
other than N
<220> FEATURE:
<221> NAME/KEY: MISC_FEATURE
<222> LOCATION: (4)..(4)
<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than L
<220> FEATURE:
<221> NAME/KEY: MISC_FEATURE
<222> LOCATION: (6)..(6)
<223> OTHER INFORMATION: Xaa can be any naturally occurring amino acid
other than Y
<220> FEATURE:
<221> NAME/KEY: MISC_FEATURE
<222> LOCATION: (7)..(7)
<223> OTHER INFORMATION: Xaa can be any naturally occurring amino acid
other than T

<400> SEQUENCE: 40

Xaa Xaa Xaa Xaa Xaa Xaa Xaa
1               5

<210> SEQ ID NO 41
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than S
<220> FEATURE:
<221> NAME/KEY: MISC_FEATURE
<222> LOCATION: (2)..(2)
<223> OTHER INFORMATION: Xaa can be any naturally occurring amino acid other than Q
<220> FEATURE:
<221> NAME/KEY: MISC_FEATURE
<222> LOCATION: (3)..(3)
<223> OTHER INFORMATION: Xaa can be any naturally occurring amino acid other than S
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than A
<220> FEATURE:
<221> NAME/KEY: MISC_FEATURE
<222> LOCATION: (5)..(5)
<223> OTHER INFORMATION: Xaa can be any naturally occurring amino acid other than S
<220> FEATURE:
<221> NAME/KEY: misc_feature
<222> LOCATION: (6)..(6)
<223> OTHER INFORMATION: Xaa can be any naturally occurring amino acid

<400> SEQUENCE: 41

Xaa Xaa Xaa Xaa Xaa Xaa
1               5

<210> SEQ ID NO 42
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)

<223> OTHER INFORMATION: Xaa can be any naturally occurring amino acid
      other than V
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than L

<400> SEQUENCE: 42

Xaa Xaa Xaa Xaa Xaa Xaa Xaa Xaa Xaa Xaa
1               5                   10

<210> SEQ ID NO 43
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than S

<400> SEQUENCE: 43

Xaa Xaa Xaa Xaa
1

<210> SEQ ID NO 44
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid

```
      other than S
<220> FEATURE:
<221> NAME/KEY: MISC_FEATURE
<222> LOCATION: (2)..(2)
<223> OTHER INFORMATION: Xaa can be any naturally occurring amino acid
      other than A
<220> FEATURE:
<221> NAME/KEY: MISC_FEATURE
<222> LOCATION: (3)..(3)
<223> OTHER INFORMATION: Xaa can be any naturally occurring amino acid
      other than D
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 44

Xaa Xaa Xaa Xaa Xaa Xaa Xaa
1               5


<210> SEQ ID NO 45
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than R
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(5)
<223> OTHER INFORMATION: Xaa can be any naturally occurring amino acid
      other than A
<220> FEATURE:
<221> NAME/KEY: MISC_FEATURE
<222> LOCATION: (6)..(6)
<223> OTHER INFORMATION: Xaa can be any naturally occurring amino acid
      other than T
<220> FEATURE:
<221> NAME/KEY: MISC_FEATURE
<222> LOCATION: (7)..(7)
<223> OTHER INFORMATION: Xaa can be any naturally occurring amino acid
      other than A
<220> FEATURE:
<221> NAME/KEY: MISC_FEATURE
<222> LOCATION: (8)..(8)
<223> OTHER INFORMATION: Xaa can be any naturally occurring amino acid
      other than D
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
```

other than N

<400> SEQUENCE: 45

Xaa Xaa Xaa Xaa Xaa Xaa Xaa Xaa Xaa Xaa
1 5 10

<210> SEQ ID NO 46
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than D
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than N
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than V
<220> FEATURE:
<221> NAME/KEY: MISC_FEATURE
<222> LOCATION: (6)..(6)
<223> OTHER INFORMATION: Xaa can be any naturally occurring amino acid other than Y
<220> FEATURE:
<221> NAME/KEY: MISC_FEATURE
<222> LOCATION: (7)..(7)
<223> OTHER INFORMATION: Xaa can be any naturally occurring amino acid other than S

<400> SEQUENCE: 46

Xaa Xaa Xaa Xaa Xaa Xaa Xaa
1 5

<210> SEQ ID NO 47
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than S
<220> FEATURE:
<221> NAME/KEY: MISC_FEATURE
<222> LOCATION: (2)..(2)
<223> OTHER INFORMATION: Xaa can be any naturally occurring amino acid other than Q
<220> FEATURE:
<221> NAME/KEY: MISC_FEATURE
<222> LOCATION: (3)..(3)
<223> OTHER INFORMATION: Xaa can be any naturally occurring amino acid other than S

```
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than A
<220> FEATURE:
<221> NAME/KEY: MISC_FEATURE
<222> LOCATION: (6)..(6)
<223> OTHER INFORMATION: Xaa can be any naturally occurring amino acid
      other than S

<400> SEQUENCE: 47

Xaa Xaa Xaa Xaa Xaa Xaa
1               5


<210> SEQ ID NO 48
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than V
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than L
```

<400> SEQUENCE: 48

Xaa Xaa Xaa Xaa Xaa Xaa Xaa Xaa Xaa Xaa
1               5                   10

<210> SEQ ID NO 49
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than T
<220> FEATURE:
<221> NAME/KEY: MISC_FEATURE
<222> LOCATION: (2)..(2)
<223> OTHER INFORMATION: Xaa can be any naturally occurring amino acid other than N
<220> FEATURE:
<221> NAME/KEY: MISC_FEATURE
<222> LOCATION: (3)..(3)
<223> OTHER INFORMATION: Xaa can be any naturally occurring amino acid other than Q
<220> FEATURE:
<221> NAME/KEY: MISC_FEATURE
<222> LOCATION: (4)..(4)
<223> OTHER INFORMATION: Xaa can be any naturally occurring amino acid other than S

<400> SEQUENCE: 49

Xaa Xaa Xaa Xaa
1

<210> SEQ ID NO 50
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than A
<220> FEATURE:
<221> NAME/KEY: MISC_FEATURE
<222> LOCATION: (2)..(2)
<223> OTHER INFORMATION: Xaa can be any naturally occurring amino acid other than N
<220> FEATURE:
<221> NAME/KEY: MISC_FEATURE
<222> LOCATION: (3)..(3)
<223> OTHER INFORMATION: Xaa can be any naturally occurring amino acid other than D
<220> FEATURE:
<221> NAME/KEY: MISC_FEATURE
<222> LOCATION: (4)..(6)
<223> OTHER INFORMATION: Xaa can be any naturally occurring amino acid other than N
<220> FEATURE:
<221> NAME/KEY: MISC_FEATURE
<222> LOCATION: (7)..(7)
<223> OTHER INFORMATION: Xaa can be any naturally occurring amino acid other than S

<400> SEQUENCE: 50

Xaa Xaa Xaa Xaa Xaa Xaa Xaa
1               5

<210> SEQ ID NO 51
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than A
<220> FEATURE:
<221> NAME/KEY: MISC_FEATURE
<222> LOCATION: (4)..(4)
<223> OTHER INFORMATION: Xaa can be any naturally occurring amino acid other than P
<220> FEATURE:
<221> NAME/KEY: MISC_FEATURE
<222> LOCATION: (5)..(6)
<223> OTHER INFORMATION: Xaa can be any naturally occurring amino acid other than T
<220> FEATURE:
<221> NAME/KEY: MISC_FEATURE
<222> LOCATION: (7)..(7)
<223> OTHER INFORMATION: Xaa can be any naturally occurring amino acid other than G
<220> FEATURE:
<221> NAME/KEY: MISC_FEATURE
<222> LOCATION: (8)..(8)
<223> OTHER INFORMATION: Xaa can be any naturally occurring amino acid other than T
<220> FEATURE:
<221> NAME/KEY: MISC_FEATURE
<222> LOCATION: (9)..(9)
<223> OTHER INFORMATION: Xaa can be any naturally occurring amino acid other than V
<220> FEATURE:
<221> NAME/KEY: MISC_FEATURE
<222> LOCATION: (10)..(10)
<223> OTHER INFORMATION: Xaa can be any naturally occurring amino acid other than N

<400> SEQUENCE: 51

```
Xaa Xaa Xaa Xaa Xaa Xaa Xaa Xaa Xaa Xaa
1               5                   10
```

<210> SEQ ID NO 52
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than D
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid
other than N
<220> FEATURE:
<221> NAME/KEY: MISC_FEATURE
<222> LOCATION: (4)..(4)
<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than V
<220> FEATURE:
<221> NAME/KEY: MISC_FEATURE
<222> LOCATION: (6)..(6)
<223> OTHER INFORMATION: Xaa can be any naturally occurring amino acid
other than Y
<220> FEATURE:
<221> NAME/KEY: MISC_FEATURE
<222> LOCATION: (7)..(7)
<223> OTHER INFORMATION: Xaa can be any naturally occurring amino acid
other than S

<400> SEQUENCE: 52

Xaa Xaa Xaa Xaa Xaa Xaa Xaa
1               5

<210> SEQ ID NO 53
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than R
<220> FEATURE:
<221> NAME/KEY: MISC_FEATURE
<222> LOCATION: (2)..(2)
<223> OTHER INFORMATION: Xaa can be any naturally occurring amino acid
other than L
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than E
<220> FEATURE:
<221> NAME/KEY: MISC_FEATURE
<222> LOCATION: (5)..(5)
<223> OTHER INFORMATION: Xaa can be any naturally occurring amino acid
other than S
<220> FEATURE:
<221> NAME/KEY: MISC_FEATURE
<222> LOCATION: (6)..(6)
<223> OTHER INFORMATION: Xaa can be any naturally occurring amino acid
other than L
<220> FEATURE:
<221> NAME/KEY: MISC_FEATURE
<222> LOCATION: (7)..(7)
<223> OTHER INFORMATION: Xaa can be any naturally occurring amino acid
other than Q
<220> FEATURE:
<221> NAME/KEY: MISC_FEATURE
<222> LOCATION: (8)..(8)
<223> OTHER INFORMATION: Xaa can be any naturally occurring amino acid
other than S

<400> SEQUENCE: 53

Xaa Xaa Xaa Xaa Xaa Xaa Xaa Xaa
1 5

<210> SEQ ID NO 54
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)
<223> OTHER INFORMATION: Xaa can be any naturally occurring amino acid other than V
<220> FEATURE:
<221> NAME/KEY: MISC_FEATURE
<222> LOCATION: (5)..(5)
<223> OTHER INFORMATION: Xaa can be any naturally occurring amino acid other than P
<220> FEATURE:
<221> NAME/KEY: MISC_FEATURE
<222> LOCATION: (6)..(6)
<223> OTHER INFORMATION: Xaa can be any naturally occurring amino acid other than Q
<220> FEATURE:
<221> NAME/KEY: MISC_FEATURE
<222> LOCATION: (7)..(7)
<223> OTHER INFORMATION: Xaa can be any naturally occurring amino acid other than Y
<220> FEATURE:
<221> NAME/KEY: MISC_FEATURE
<222> LOCATION: (8)..(8)
<223> OTHER INFORMATION: Xaa can be any naturally occurring amino acid other than G
<220> FEATURE:
<221> NAME/KEY: MISC_FEATURE
<222> LOCATION: (9)..(9)
<223> OTHER INFORMATION: Xaa can be any naturally occurring amino acid other than Y
<220> FEATURE:
<221> NAME/KEY: MISC_FEATURE
<222> LOCATION: (10)..(10)
<223> OTHER INFORMATION: Xaa can be any naturally occurring amino acid other than C

<400> SEQUENCE: 54

Xaa Xaa Xaa Xaa Xaa Xaa Xaa Xaa Xaa Xaa
1 5 10

<210> SEQ ID NO 55
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)

<223> OTHER INFORMATION: Xaa can be any naturally occurring amino acid
other than A
<220> FEATURE:
<221> NAME/KEY: MISC_FEATURE
<222> LOCATION: (2)..(2)
<223> OTHER INFORMATION: Xaa can be any naturally occurring amino acid
other than G
<220> FEATURE:
<221> NAME/KEY: MISC_FEATURE
<222> LOCATION: (3)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than A

<400> SEQUENCE: 55

Xaa Xaa Xaa Xaa
1

<210> SEQ ID NO 56
<211> LENGTH: 12
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than A
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(4)
<223> OTHER INFORMATION: Xaa can be any naturally occurring amino acid
other than N
<220> FEATURE:
<221> NAME/KEY: MISC_FEATURE
<222> LOCATION: (5)..(5)
<223> OTHER INFORMATION: Xaa can be any naturally occurring amino acid
other than Y
<220> FEATURE:
<221> NAME/KEY: MISC_FEATURE
<222> LOCATION: (6)..(6)
<223> OTHER INFORMATION: Xaa can be any naturally occurring amino acid
other than K
<220> FEATURE:
<221> NAME/KEY: MISC_FEATURE
<222> LOCATION: (7)..(7)
<223> OTHER INFORMATION: Xaa can be any naturally occurring amino acid
other than I
<220> FEATURE:
<221> NAME/KEY: MISC_FEATURE
<222> LOCATION: (8)..(8)
<223> OTHER INFORMATION: Xaa can be any naturally occurring amino acid
other than P
<220> FEATURE:
<221> NAME/KEY: MISC_FEATURE
<222> LOCATION: (9)..(9)
<223> OTHER INFORMATION: Xaa can be any naturally occurring amino acid
other than A
<220> FEATURE:
<221> NAME/KEY: MISC_FEATURE
<222> LOCATION: (10)..(10)

<223> OTHER INFORMATION: Xaa can be any naturally occurring amino acid
      other than T
<220> FEATURE:
<221> NAME/KEY: MISC_FEATURE
<222> LOCATION: (11)..(11)
<223> OTHER INFORMATION: Xaa can be any naturally occurring amino acid
      other than G
<220> FEATURE:
<221> NAME/KEY: MISC_FEATURE
<222> LOCATION: (12)..(12)
<223> OTHER INFORMATION: Xaa can be any naturally occurring amino acid
      other than S

<400> SEQUENCE: 56

Xaa Xaa Xaa Xaa Xaa Xaa Xaa Xaa Xaa Xaa Xaa Xaa
1               5                   10

<210> SEQ ID NO 57
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than N
<220> FEATURE:
<221> NAME/KEY: MISC_FEATURE
<222> LOCATION: (3)..(3)
<223> OTHER INFORMATION: Xaa can be any naturally occurring amino acid
      other than L
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(6)
<223> OTHER INFORMATION: Xaa can be any naturally occurring amino acid
      other than V
<220> FEATURE:
<221> NAME/KEY: MISC_FEATURE
<222> LOCATION: (7)..(7)
<223> OTHER INFORMATION: Xaa can be any naturally occurring amino acid
      other than D
<220> FEATURE:
<221> NAME/KEY: MISC_FEATURE
<222> LOCATION: (8)..(8)
<223> OTHER INFORMATION: Xaa can be any naturally occurring amino acid
      other than R
<220> FEATURE:
<221> NAME/KEY: MISC_FEATURE
<222> LOCATION: (9)..(9)
<223> OTHER INFORMATION: Xaa can be any naturally occurring amino acid
      other than L
<220> FEATURE:
<221> NAME/KEY: MISC_FEATURE
<222> LOCATION: (10)..(10)
<223> OTHER INFORMATION: Xaa can be any naturally occurring amino acid
      other than T

<400> SEQUENCE: 57

```
Xaa Xaa Xaa Xaa Xaa Xaa Xaa Xaa Xaa Xaa
1               5                   10


<210> SEQ ID NO 58
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than D
<220> FEATURE:
<221> NAME/KEY: MISC_FEATURE
<222> LOCATION: (2)..(3)
<223> OTHER INFORMATION: Xaa can be any naturally occurring amino acid
      other than A
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than K
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than T

<400> SEQUENCE: 58

Xaa Xaa Xaa Xaa Xaa Xaa Xaa
1               5


<210> SEQ ID NO 59
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than E
<220> FEATURE:
<221> NAME/KEY: MISC_FEATURE
<222> LOCATION: (2)..(2)
<223> OTHER INFORMATION: Xaa can be any naturally occurring amino acid
      other than I
<220> FEATURE:
<221> NAME/KEY: MISC_FEATURE
<222> LOCATION: (3)..(3)
<223> OTHER INFORMATION: Xaa can be any naturally occurring amino acid
      other than K
<220> FEATURE:
<221> NAME/KEY: MISC_FEATURE
<222> LOCATION: (4)..(4)
<223> OTHER INFORMATION: Xaa can be any naturally occurring amino acid
      other than S
<220> FEATURE:
<221> NAME/KEY: MISC_FEATURE
<222> LOCATION: (5)..(5)
<223> OTHER INFORMATION: Xaa can be any naturally occurring amino acid
```

```
      other than G
<220> FEATURE:
<221> NAME/KEY: MISC_FEATURE
<222> LOCATION: (6)..(6)
<223> OTHER INFORMATION: Xaa can be any naturally occurring amino acid
      other than S
<220> FEATURE:
<221> NAME/KEY: MISC_FEATURE
<222> LOCATION: (7)..(7)
<223> OTHER INFORMATION: Xaa can be any naturally occurring amino acid
      other than V
<220> FEATURE:
<221> NAME/KEY: MISC_FEATURE
<222> LOCATION: (8)..(8)
<223> OTHER INFORMATION: Xaa can be any naturally occurring amino acid
      other than D
<220> FEATURE:
<221> NAME/KEY: MISC_FEATURE
<222> LOCATION: (9)..(9)
<223> OTHER INFORMATION: Xaa can be any naturally occurring amino acid
      other than G
<220> FEATURE:
<221> NAME/KEY: MISC_FEATURE
<222> LOCATION: (10)..(10)
<223> OTHER INFORMATION: Xaa can be any naturally occurring amino acid
      other than S

<400> SEQUENCE: 59

Xaa Xaa Xaa Xaa Xaa Xaa Xaa Xaa Xaa Xaa
1               5                   10


<210> SEQ ID NO 60
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than L
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
```

```
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than A

<400> SEQUENCE: 60

Xaa Xaa Xaa Xaa Xaa Xaa Xaa Xaa Xaa Xaa
1               5                   10


<210> SEQ ID NO 61
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than V
<220> FEATURE:
<221> NAME/KEY: MISC_FEATURE
<222> LOCATION: (4)..(4)
<223> OTHER INFORMATION: Xaa can be any naturally occurring amino acid
      other than Q

<400> SEQUENCE: 61

Xaa Xaa Xaa Xaa
1


<210> SEQ ID NO 62
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than V
<220> FEATURE:
<221> NAME/KEY: MISC_FEATURE
<222> LOCATION: (4)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
      other than R
```

<220> FEATURE:
<221> NAME/KEY: MISC_FEATURE
<222> LOCATION: (6)..(6)
<223> OTHER INFORMATION: Xaa can be any naturally occurring amino acid
other than A
<220> FEATURE:
<221> NAME/KEY: MISC_FEATURE
<222> LOCATION: (7)..(7)
<223> OTHER INFORMATION: Xaa can be any naturally occurring amino acid
other than S

<400> SEQUENCE: 62

Xaa Xaa Xaa Xaa Xaa Xaa Xaa
1 5

<210> SEQ ID NO 63
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than A
<220> FEATURE:
<221> NAME/KEY: MISC_FEATURE
<222> LOCATION: (4)..(4)
<223> OTHER INFORMATION: Xaa can be any naturally occurring amino acid
other than P
<220> FEATURE:
<221> NAME/KEY: MISC_FEATURE
<222> LOCATION: (5)..(5)
<223> OTHER INFORMATION: Xaa can be any naturally occurring amino acid
other than A
<220> FEATURE:
<221> NAME/KEY: MISC_FEATURE
<222> LOCATION: (6)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than T
<220> FEATURE:
<221> NAME/KEY: MISC_FEATURE
<222> LOCATION: (9)..(9)
<223> OTHER INFORMATION: Xaa can be any naturally occurring amino acid
other than Y
<220> FEATURE:
<221> NAME/KEY: MISC_FEATURE
<222> LOCATION: (10)..(10)
<223> OTHER INFORMATION: Xaa can be any naturally occurring amino acid
other than N

<400> SEQUENCE: 63

Xaa Xaa Xaa Xaa Xaa Xaa Xaa Xaa Xaa Xaa
1 5 10

<210> SEQ ID NO 64
<211> LENGTH: 7
<212> TYPE: PRT

```
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than D
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than E
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than R

<400> SEQUENCE: 64

Xaa Xaa Xaa Xaa Xaa Xaa Xaa
1               5


<210> SEQ ID NO 65
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than A
<220> FEATURE:
<221> NAME/KEY: MISC_FEATURE
<222> LOCATION: (3)..(3)
<223> OTHER INFORMATION: Xaa can be any naturally occurring amino acid
      other than S
<220> FEATURE:
<221> NAME/KEY: MISC_FEATURE
<222> LOCATION: (4)..(4)
<223> OTHER INFORMATION: Xaa can be any naturally occurring amino acid
      other than T
<220> FEATURE:
<221> NAME/KEY: MISC_FEATURE
<222> LOCATION: (5)..(5)
<223> OTHER INFORMATION: Xaa can be any naturally occurring amino acid
      other than G
<220> FEATURE:
```

```
<221> NAME/KEY: MISC_FEATURE
<222> LOCATION: (6)..(6)
<223> OTHER INFORMATION: Xaa can be any naturally occurring amino acid
      other than A
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 65

Xaa Xaa Xaa Xaa Xaa Xaa Xaa
1               5


<210> SEQ ID NO 66
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than L

<400> SEQUENCE: 66

Xaa Xaa Xaa Xaa Xaa Xaa Xaa Xaa Xaa Xaa
1               5                   10
```

<210> SEQ ID NO 67
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than A
<220> FEATURE:
<221> NAME/KEY: MISC_FEATURE
<222> LOCATION: (2)..(2)
<223> OTHER INFORMATION: Xaa can be any naturally occurring amino acid other than Q
<220> FEATURE:
<221> NAME/KEY: MISC_FEATURE
<222> LOCATION: (3)..(3)
<223> OTHER INFORMATION: Xaa can be any naturally occurring amino acid other than N
<220> FEATURE:
<221> NAME/KEY: MISC_FEATURE
<222> LOCATION: (4)..(4)
<223> OTHER INFORMATION: Xaa can be any naturally occurring amino acid other than K

<400> SEQUENCE: 67

Xaa Xaa Xaa Xaa
1

<210> SEQ ID NO 68
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than D
<220> FEATURE:
<221> NAME/KEY: MISC_FEATURE
<222> LOCATION: (4)..(6)
<223> OTHER INFORMATION: Xaa can be any naturally occurring amino acid other than N
<220> FEATURE:
<221> NAME/KEY: MISC_FEATURE
<222> LOCATION: (7)..(7)
<223> OTHER INFORMATION: Xaa can be any naturally occurring amino acid other than S

<400> SEQUENCE: 68

Xaa Xaa Xaa Xaa Xaa Xaa Xaa
1               5

<210> SEQ ID NO 69
<211> LENGTH: 10
<212> TYPE: PRT
<213> ORGANISM: Artificial
<220> FEATURE:

<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than D
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than A
<220> FEATURE:
<221> NAME/KEY: MISC_FEATURE
<222> LOCATION: (6)..(6)
<223> OTHER INFORMATION: Xaa can be any naturally occurring amino acid
      other than T
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than D
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than H

<400> SEQUENCE: 69

Xaa Xaa Xaa Xaa Xaa Xaa Xaa Xaa Xaa Xaa
1               5                   10

<210> SEQ ID NO 70
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than D
<220> FEATURE:
<221> NAME/KEY: MISC_FEATURE
<222> LOCATION: (2)..(3)
<223> OTHER INFORMATION: Xaa can be any naturally occurring amino acid
      other than N
<220> FEATURE:
<221> NAME/KEY: MISC_FEATURE
<222> LOCATION: (4)..(4)

<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than L
<220> FEATURE:
<221> NAME/KEY: MISC_FEATURE
<222> LOCATION: (6)..(6)
<223> OTHER INFORMATION: Xaa can be any naturally occurring amino acid
other than Y
<220> FEATURE:
<221> NAME/KEY: MISC_FEATURE
<222> LOCATION: (7)..(7)
<223> OTHER INFORMATION: Xaa can be any naturally occurring amino acid
other than T

<400> SEQUENCE: 70

Xaa Xaa Xaa Xaa Xaa Xaa Xaa
1 5

<210> SEQ ID NO 71
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than S
<220> FEATURE:
<221> NAME/KEY: MISC_FEATURE
<222> LOCATION: (2)..(2)
<223> OTHER INFORMATION: Xaa can be any naturally occurring amino acid
other than E
<220> FEATURE:
<221> NAME/KEY: MISC_FEATURE
<222> LOCATION: (3)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than A
<220> FEATURE:
<221> NAME/KEY: MISC_FEATURE
<222> LOCATION: (5)..(5)
<223> OTHER INFORMATION: Xaa can be any naturally occurring amino acid
other than G
<220> FEATURE:
<221> NAME/KEY: MISC_FEATURE
<222> LOCATION: (6)..(6)
<223> OTHER INFORMATION: Xaa can be any naturally occurring amino acid
other than S
<220> FEATURE:
<221> NAME/KEY: MISC_FEATURE
<222> LOCATION: (7)..(7)
<223> OTHER INFORMATION: Xaa can be any naturally occurring amino acid
other than T

<400> SEQUENCE: 71

Xaa Xaa Xaa Xaa Xaa Xaa Xaa
1 5

<210> SEQ ID NO 72
<211> LENGTH: 10
<212> TYPE: PRT
<213> ORGANISM: Artificial
<220> FEATURE:
<223> OTHER INFORMATION: AAV capsid protein common antigenic motif (CAM)

```
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than L

<400> SEQUENCE: 72

Xaa Xaa Xaa Xaa Xaa Xaa Xaa Xaa Xaa Xaa
1               5                   10


<210> SEQ ID NO 73
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
```

other than N
<220> FEATURE:
<221> NAME/KEY: MISC_FEATURE
<222> LOCATION: (4)..(4)
<223> OTHER INFORMATION: Xaa can be any naturally occurring amino acid
other than R

<400> SEQUENCE: 73

Xaa Xaa Xaa Xaa
1

<210> SEQ ID NO 74
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than L
<220> FEATURE:
<221> NAME/KEY: MISC_FEATURE
<222> LOCATION: (2)..(2)
<223> OTHER INFORMATION: Xaa can be any naturally occurring amino acid
other than D
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S

<400> SEQUENCE: 74

Xaa Xaa Xaa Xaa Xaa Xaa Xaa
1 5

<210> SEQ ID NO 75
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than N
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(4)
<223> OTHER INFORMATION: Xaa can be any naturally occurring amino acid
other than A
<220> FEATURE:
<221> NAME/KEY: MISC_FEATURE
<222> LOCATION: (5)..(5)
<223> OTHER INFORMATION: Xaa can be any naturally occurring amino acid
other than Q

```
<220> FEATURE:
<221> NAME/KEY: MISC_FEATURE
<222> LOCATION: (6)..(6)
<223> OTHER INFORMATION: Xaa can be any naturally occurring amino acid
      other than T
<220> FEATURE:
<221> NAME/KEY: MISC_FEATURE
<222> LOCATION: (7)..(7)
<223> OTHER INFORMATION: Xaa can be any naturally occurring amino acid
      other than Q
<220> FEATURE:
<221> NAME/KEY: MISC_FEATURE
<222> LOCATION: (8)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than N

<400> SEQUENCE: 75

Xaa Xaa Xaa Xaa Xaa Xaa Xaa Xaa Xaa Xaa
1               5                   10


<210> SEQ ID NO 76
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than D
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than V
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 76

Xaa Xaa Xaa Xaa Xaa Xaa Xaa
1               5


<210> SEQ ID NO 77
<211> LENGTH: 8
<212> TYPE: PRT
```

<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N
<220> FEATURE:
<221> NAME/KEY: MISC_FEATURE
<222> LOCATION: (2)..(2)
<223> OTHER INFORMATION: Xaa can be any naturally occurring amino acid other than G
<220> FEATURE:
<221> NAME/KEY: MISC_FEATURE
<222> LOCATION: (3)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than S
<220> FEATURE:
<221> NAME/KEY: MISC_FEATURE
<222> LOCATION: (5)..(6)
<223> OTHER INFORMATION: Xaa can be any naturally occurring amino acid other than G
<220> FEATURE:
<221> NAME/KEY: MISC_FEATURE
<222> LOCATION: (7)..(7)
<223> OTHER INFORMATION: Xaa can be any naturally occurring amino acid other than A
<220> FEATURE:
<221> NAME/KEY: MISC_FEATURE
<222> LOCATION: (8)..(8)
<223> OTHER INFORMATION: Xaa can be any naturally occurring amino acid other than T

<400> SEQUENCE: 77

Xaa Xaa Xaa Xaa Xaa Xaa Xaa Xaa
1               5

<210> SEQ ID NO 78
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)
<223> OTHER INFORMATION: Xaa can be any naturally occurring amino acid other than I
<220> FEATURE:
<221> NAME/KEY: MISC_FEATURE
<222> LOCATION: (5)..(5)
<223> OTHER INFORMATION: Xaa can be any naturally occurring amino acid other than P
<220> FEATURE:

<221> NAME/KEY: MISC_FEATURE
<222> LOCATION: (6)..(6)
<223> OTHER INFORMATION: Xaa can be any naturally occurring amino acid
other than Q
<220> FEATURE:
<221> NAME/KEY: MISC_FEATURE
<222> LOCATION: (7)..(7)
<223> OTHER INFORMATION: Xaa can be any naturally occurring amino acid
other than Y
<220> FEATURE:
<221> NAME/KEY: MISC_FEATURE
<222> LOCATION: (8)..(8)
<223> OTHER INFORMATION: Xaa can be any naturally occurring amino acid
other than G
<220> FEATURE:
<221> NAME/KEY: MISC_FEATURE
<222> LOCATION: (9)..(9)
<223> OTHER INFORMATION: Xaa can be any naturally occurring amino acid
other than Y
<220> FEATURE:
<221> NAME/KEY: MISC_FEATURE
<222> LOCATION: (10)..(10)
<223> OTHER INFORMATION: Xaa can be any naturally occurring amino acid
other than L

<400> SEQUENCE: 78

Xaa Xaa Xaa Xaa Xaa Xaa Xaa Xaa Xaa Xaa
1 5 10

<210> SEQ ID NO 79
<211> LENGTH: 4
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than A
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than Q

<400> SEQUENCE: 79

Xaa Xaa Xaa Xaa
1

<210> SEQ ID NO 80
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than T
<220> FEATURE:
<221> NAME/KEY: MISC_FEATURE
<222> LOCATION: (2)..(2)
<223> OTHER INFORMATION: Xaa can be any naturally occurring amino acid
other than G
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S

<400> SEQUENCE: 80

Xaa Xaa Xaa Xaa Xaa Xaa Xaa
1 5

<210> SEQ ID NO 81
<211> LENGTH: 11
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than N
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than A
<220> FEATURE:
<221> NAME/KEY: MISC_FEATURE
<222> LOCATION: (4)..(4)
<223> OTHER INFORMATION: Xaa can be any naturally occurring amino acid
other than P
<220> FEATURE:
<221> NAME/KEY: MISC_FEATURE
<222> LOCATION: (5)..(5)
<223> OTHER INFORMATION: Xaa can be any naturally occurring amino acid
other than Q
<220> FEATURE:
<221> NAME/KEY: MISC_FEATURE
<222> LOCATION: (6)..(6)
<223> OTHER INFORMATION: Xaa can be any naturally occurring amino acid
other than I
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than T
<220> FEATURE:
<221> NAME/KEY: MISC_FEATURE
<222> LOCATION: (9)..(9)
<223> OTHER INFORMATION: Xaa can be any naturally occurring amino acid
other than V
<220> FEATURE:
<221> NAME/KEY: MISC_FEATURE

```
<222> LOCATION: (10)..(10)
<223> OTHER INFORMATION: Xaa can be any naturally occurring amino acid
      other than N
<220> FEATURE:
<221> NAME/KEY: MISC_FEATURE
<222> LOCATION: (11)..(11)
<223> OTHER INFORMATION: Xaa can be any naturally occurring amino acid
      other than S

<400> SEQUENCE: 81

Xaa Xaa Xaa Xaa Xaa Xaa Xaa Xaa Xaa Xaa Xaa
1               5                   10


<210> SEQ ID NO 82
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than E
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than V
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 82

Xaa Xaa Xaa Xaa Xaa Xaa Xaa
1               5


<210> SEQ ID NO 83
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
```

```
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than S
<220> FEATURE:
<221> NAME/KEY: MISC_FEATURE
<222> LOCATION: (5)..(6)
<223> OTHER INFORMATION: Xaa can be any naturally occurring amino acid
      other than G
<220> FEATURE:
<221> NAME/KEY: MISC_FEATURE
<222> LOCATION: (7)..(8)
<223> OTHER INFORMATION: Xaa can be any naturally occurring amino acid
      other than S

<400> SEQUENCE: 83

Xaa Xaa Xaa Xaa Xaa Xaa Xaa Xaa
1               5


<210> SEQ ID NO 84
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
```

```
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than L

<400> SEQUENCE: 84

Xaa Xaa Xaa Xaa Xaa Xaa Xaa Xaa Xaa Xaa
1               5                   10


<210> SEQ ID NO 85
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than Q
<220> FEATURE:
<221> NAME/KEY: MISC_FEATURE
<222> LOCATION: (2)..(2)
<223> OTHER INFORMATION: Xaa can be any naturally occurring amino acid
      other than N
<220> FEATURE:
<221> NAME/KEY: MISC_FEATURE
<222> LOCATION: (3)..(4)
<223> OTHER INFORMATION: Xaa can be any naturally occurring amino acid
      other than Q

<400> SEQUENCE: 85

Xaa Xaa Xaa Xaa
1


<210> SEQ ID NO 86
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 86

Xaa Xaa Xaa Xaa Xaa Xaa Xaa
```

1               5

<210> SEQ ID NO 87
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than Q
<220> FEATURE:
<221> NAME/KEY: MISC_FEATURE
<222> LOCATION: (2)..(2)
<223> OTHER INFORMATION: Xaa can be any naturally occurring amino acid other than A
<220> FEATURE:
<221> NAME/KEY: MISC_FEATURE
<222> LOCATION: (3)..(3)
<223> OTHER INFORMATION: Xaa can be any naturally occurring amino acid other than Q
<220> FEATURE:
<221> NAME/KEY: MISC_FEATURE
<222> LOCATION: (4)..(4)
<223> OTHER INFORMATION: Xaa can be any naturally occurring amino acid other than A
<220> FEATURE:
<221> NAME/KEY: MISC_FEATURE
<222> LOCATION: (5)..(5)
<223> OTHER INFORMATION: Xaa can be any naturally occurring amino acid other than Q
<220> FEATURE:
<221> NAME/KEY: MISC_FEATURE
<222> LOCATION: (6)..(6)
<223> OTHER INFORMATION: Xaa can be any naturally occurring amino acid other than T
<220> FEATURE:
<221> NAME/KEY: MISC_FEATURE
<222> LOCATION: (7)..(7)
<223> OTHER INFORMATION: Xaa can be any naturally occurring amino acid other than G
<220> FEATURE:
<221> NAME/KEY: MISC_FEATURE
<222> LOCATION: (8)..(8)
<223> OTHER INFORMATION: Xaa can be any naturally occurring amino acid other than W
<220> FEATURE:
<221> NAME/KEY: MISC_FEATURE
<222> LOCATION: (9)..(9)
<223> OTHER INFORMATION: Xaa can be any naturally occurring amino acid other than V
<220> FEATURE:
<221> NAME/KEY: MISC_FEATURE
<222> LOCATION: (10)..(10)
<223> OTHER INFORMATION: Xaa can be any naturally occurring amino acid other than Q

<400> SEQUENCE: 87

Xaa Xaa Xaa Xaa Xaa Xaa Xaa Xaa Xaa Xaa
1               5                   10

<210> SEQ ID NO 88
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N

```
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than E
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than V
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 88

Xaa Xaa Xaa Xaa Xaa Xaa Xaa
1               5


<210> SEQ ID NO 89
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than S
<220> FEATURE:
<221> NAME/KEY: MISC_FEATURE
<222> LOCATION: (5)..(6)
<223> OTHER INFORMATION: Xaa can be any naturally occurring amino acid
      other than G
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
      other than T
```

<400> SEQUENCE: 89

Xaa Xaa Xaa Xaa Xaa Xaa Xaa Xaa
1               5

<210> SEQ ID NO 90
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)
<223> OTHER INFORMATION: Xaa can be any naturally occurring amino acid other than I
<220> FEATURE:
<221> NAME/KEY: MISC_FEATURE
<222> LOCATION: (5)..(5)
<223> OTHER INFORMATION: Xaa can be any naturally occurring amino acid other than P
<220> FEATURE:
<221> NAME/KEY: MISC_FEATURE
<222> LOCATION: (6)..(6)
<223> OTHER INFORMATION: Xaa can be any naturally occurring amino acid other than Q
<220> FEATURE:
<221> NAME/KEY: MISC_FEATURE
<222> LOCATION: (7)..(7)
<223> OTHER INFORMATION: Xaa can be any naturally occurring amino acid other than Y
<220> FEATURE:
<221> NAME/KEY: MISC_FEATURE
<222> LOCATION: (8)..(8)
<223> OTHER INFORMATION: Xaa can be any naturally occurring amino acid other than G
<220> FEATURE:
<221> NAME/KEY: MISC_FEATURE
<222> LOCATION: (9)..(9)
<223> OTHER INFORMATION: Xaa can be any naturally occurring amino acid other than Y
<220> FEATURE:
<221> NAME/KEY: MISC_FEATURE
<222> LOCATION: (10)..(10)
<223> OTHER INFORMATION: Xaa can be any naturally occurring amino acid other than L

<400> SEQUENCE: 90

Xaa Xaa Xaa Xaa Xaa Xaa Xaa Xaa Xaa Xaa
1               5                   10

<210> SEQ ID NO 91
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:

<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than Q

<400> SEQUENCE: 91

Xaa Xaa Xaa Xaa
1

<210> SEQ ID NO 92
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than L
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 92

Xaa Xaa Xaa Xaa Xaa Xaa Xaa
1               5

<210> SEQ ID NO 93
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE

```
<222> LOCATION: (2)..(3)
<223> OTHER INFORMATION: Xaa can be any naturally occurring amino acid
      other than A
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than I
<220> FEATURE:
<221> NAME/KEY: MISC_FEATURE
<222> LOCATION: (6)..(6)
<223> OTHER INFORMATION: Xaa can be any naturally occurring amino acid
      other than V
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than A
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than N

<400> SEQUENCE: 93

Xaa Xaa Xaa Xaa Xaa Xaa Xaa Xaa Xaa Xaa
1               5                   10


<210> SEQ ID NO 94
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than D
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
```

<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 94

Xaa Xaa Xaa Xaa Xaa Xaa Xaa
1               5

<210> SEQ ID NO 95
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than S
<220> FEATURE:
<221> NAME/KEY: MISC_FEATURE
<222> LOCATION: (5)..(6)
<223> OTHER INFORMATION: Xaa can be any naturally occurring amino acid
      other than G
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
      other than T

<400> SEQUENCE: 95

Xaa Xaa Xaa Xaa Xaa Xaa Xaa Xaa
1               5

<210> SEQ ID NO 96
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)

<223> OTHER INFORMATION: Xaa can be any naturally occurring amino acid other than F
<220> FEATURE:
<221> NAME/KEY: MISC_FEATURE
<222> LOCATION: (3)..(3)
<223> OTHER INFORMATION: Xaa can be any naturally occurring amino acid other than M
<220> FEATURE:
<221> NAME/KEY: MISC_FEATURE
<222> LOCATION: (4)..(4)
<223> OTHER INFORMATION: Xaa can be any naturally occurring amino acid other than V
<220> FEATURE:
<221> NAME/KEY: MISC_FEATURE
<222> LOCATION: (5)..(5)
<223> OTHER INFORMATION: Xaa can be any naturally occurring amino acid other than P
<220> FEATURE:
<221> NAME/KEY: MISC_FEATURE
<222> LOCATION: (6)..(6)
<223> OTHER INFORMATION: Xaa can be any naturally occurring amino acid other than Q
<220> FEATURE:
<221> NAME/KEY: MISC_FEATURE
<222> LOCATION: (7)..(7)
<223> OTHER INFORMATION: Xaa can be any naturally occurring amino acid other than Y
<220> FEATURE:
<221> NAME/KEY: MISC_FEATURE
<222> LOCATION: (8)..(8)
<223> OTHER INFORMATION: Xaa can be any naturally occurring amino acid other than G
<220> FEATURE:
<221> NAME/KEY: MISC_FEATURE
<222> LOCATION: (9)..(9)
<223> OTHER INFORMATION: Xaa can be any naturally occurring amino acid other than Y
<220> FEATURE:
<221> NAME/KEY: MISC_FEATURE
<222> LOCATION: (10)..(10)
<223> OTHER INFORMATION: Xaa can be any naturally occurring amino acid other than L

<400> SEQUENCE: 96

```
Xaa Xaa Xaa Xaa Xaa Xaa Xaa Xaa Xaa Xaa
1               5                   10
```

<210> SEQ ID NO 97
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(2)
<223> OTHER INFORMATION: Xaa can be any naturally occurring amino acid other than G
<220> FEATURE:
<221> NAME/KEY: MISC_FEATURE
<222> LOCATION: (3)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than Q

<400> SEQUENCE: 97

```
Xaa Xaa Xaa Xaa
1
```

<210> SEQ ID NO 98

<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than T
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S

<400> SEQUENCE: 98

Xaa Xaa Xaa Xaa Xaa Xaa Xaa
1               5

<210> SEQ ID NO 99
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than N
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(4)
<223> OTHER INFORMATION: Xaa can be any naturally occurring amino acid
other than A
<220> FEATURE:
<221> NAME/KEY: MISC_FEATURE
<222> LOCATION: (5)..(5)
<223> OTHER INFORMATION: Xaa can be any naturally occurring amino acid
other than Q
<220> FEATURE:
<221> NAME/KEY: MISC_FEATURE
<222> LOCATION: (6)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid

```
      other than G
<220> FEATURE:
<221> NAME/KEY: MISC_FEATURE
<222> LOCATION: (8)..(8)
<223> OTHER INFORMATION: Xaa can be any naturally occurring amino acid
      other than L
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than H

<400> SEQUENCE: 99

Xaa Xaa Xaa Xaa Xaa Xaa Xaa Xaa Xaa Xaa
1               5                   10


<210> SEQ ID NO 100
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than E
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than V
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: —ISC_FEATURE
<222> LOCATION: (7)..(7)
<223> OTHER INFORMATION: Xaa can be any naturally occurring amino acid
      other than S

<400> SEQUENCE: 100

Xaa Xaa Xaa Xaa Xaa Xaa Xaa
1               5


<210> SEQ ID NO 101
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
```

```
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than S
<220> FEATURE:
<221> NAME/KEY: MISC_FEATURE
<222> LOCATION: (5)..(6)
<223> OTHER INFORMATION: Xaa can be any naturally occurring amino acid
      other than G
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
      other than T

<400> SEQUENCE: 101

Xaa Xaa Xaa Xaa Xaa Xaa Xaa Xaa
1               5


<210> SEQ ID NO 102
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
```

<220> FEATURE:
<221> NAME/KEY: MISC_FEATURE
<222> LOCATION: (7)..(7)
<223> OTHER INFORMATION: Xaa can be any naturally occurring amino acid
other than Y
<220> FEATURE:
<221> NAME/KEY: MISC_FEATURE
<222> LOCATION: (8)..(8)
<223> OTHER INFORMATION: Xaa can be any naturally occurring amino acid
other than G
<220> FEATURE:
<221> NAME/KEY: MISC_FEATURE
<222> LOCATION: (9)..(9)
<223> OTHER INFORMATION: Xaa can be any naturally occurring amino acid
other than Y
<220> FEATURE:
<221> NAME/KEY: MISC_FEATURE
<222> LOCATION: (10)..(10)
<223> OTHER INFORMATION: Xaa can be any naturally occurring amino acid
other than L

<400> SEQUENCE: 102

Xaa Xaa Xaa Xaa Xaa Xaa Xaa Xaa Xaa Xaa
1               5                   10

<210> SEQ ID NO 103
<211> LENGTH: 4
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than Q
<220> FEATURE:
<221> NAME/KEY: MISC_FEATURE
<222> LOCATION: (2)..(2)
<223> OTHER INFORMATION: Xaa can be any naturally occurring amino acid
other than G
<220> FEATURE:
<221> NAME/KEY: MISC_FEATURE
<222> LOCATION: (3)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than Q

<400> SEQUENCE: 103

Xaa Xaa Xaa Xaa
1

<210> SEQ ID NO 104
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than L
<220> FEATURE:
<221> NAME/KEY: MISC_FEATURE
<222> LOCATION: (2)..(2)
<223> OTHER INFORMATION: Xaa can be any naturally occurring amino acid
other than S
<220> FEATURE:

```
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S

<400> SEQUENCE: 104

Xaa Xaa Xaa Xaa Xaa Xaa Xaa
1               5


<210> SEQ ID NO 105
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than G
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than I
<220> FEATURE:
<221> NAME/KEY: MISC_FEATURE
<222> LOCATION: (6)..(6)
<223> OTHER INFORMATION: Xaa can be any naturally occurring amino acid
      other than V
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than N
```

<400> SEQUENCE: 105

Xaa Xaa Xaa Xaa Xaa Xaa Xaa Xaa Xaa Xaa
1 5 10

<210> SEQ ID NO 106
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than E
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than T
<220> FEATURE:
<221> NAME/KEY: MISC_FEATURE
<222> LOCATION: (6)..(6)
<223> OTHER INFORMATION: Xaa can be any naturally occurring amino acid other than Y
<220> FEATURE:
<221> NAME/KEY: MISC_FEATURE
<222> LOCATION: (7)..(7)
<223> OTHER INFORMATION: Xaa can be any naturally occurring amino acid other than S

<400> SEQUENCE: 106

Xaa Xaa Xaa Xaa Xaa Xaa Xaa
1 5

<210> SEQ ID NO 107
<211> LENGTH: 8
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than R
<220> FEATURE:
<221> NAME/KEY: MISC_FEATURE
<222> LOCATION: (2)..(2)
<223> OTHER INFORMATION: Xaa can be any naturally occurring amino acid other than L
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE

```
<222> LOCATION: (4)..(5)
<223> OTHER INFORMATION: Xaa can be any naturally occurring amino acid
      other than T
<220> FEATURE:
<221> NAME/KEY: MISC_FEATURE
<222> LOCATION: (6)..(8)
<223> OTHER INFORMATION: Xaa can be any naturally occurring amino acid
      other than S

<400> SEQUENCE: 107

Xaa Xaa Xaa Xaa Xaa Xaa Xaa Xaa
1               5


<210> SEQ ID NO 108
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than V
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than C

<400> SEQUENCE: 108

Xaa Xaa Xaa Xaa Xaa Xaa Xaa Xaa Xaa Xaa
1               5                   10
```

<210> SEQ ID NO 109
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than Q
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than N
<220> FEATURE:
<221> NAME/KEY: MISC_FEATURE
<222> LOCATION: (4)..(4)
<223> OTHER INFORMATION: Xaa can be any naturally occurring amino acid
      other than A

<400> SEQUENCE: 109

Xaa Xaa Xaa Xaa
1

<210> SEQ ID NO 110
<211> LENGTH: 12
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
      other than Y
<220> FEATURE:
<221> NAME/KEY: MISC_FEATURE
<222> LOCATION: (6)..(6)
<223> OTHER INFORMATION: Xaa can be any naturally occurring amino acid
      other than K
<220> FEATURE:
<221> NAME/KEY: MISC_FEATURE
<222> LOCATION: (7)..(7)
<223> OTHER INFORMATION: Xaa can be any naturally occurring amino acid
      other than I
<220> FEATURE:
<221> NAME/KEY: MISC_FEATURE
<222> LOCATION: (8)..(8)

<223> OTHER INFORMATION: Xaa can be any naturally occurring amino acid
      other than P
<220> FEATURE:
<221> NAME/KEY: MISC_FEATURE
<222> LOCATION: (9)..(9)
<223> OTHER INFORMATION: Xaa can be any naturally occurring amino acid
      other than A
<220> FEATURE:
<221> NAME/KEY: MISC_FEATURE
<222> LOCATION: (10)..(10)
<223> OTHER INFORMATION: Xaa can be any naturally occurring amino acid
      other than S
<220> FEATURE:
<221> NAME/KEY: MISC_FEATURE
<222> LOCATION: (11)..(12)
<223> OTHER INFORMATION: Xaa can be any naturally occurring amino acid
      other than G

<400> SEQUENCE: 110

Xaa Xaa Xaa Xaa Xaa Xaa Xaa Xaa Xaa Xaa Xaa Xaa
1               5                   10

<210> SEQ ID NO 111
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than A
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than I
<220> FEATURE:
<221> NAME/KEY: MISC_FEATURE
<222> LOCATION: (6)..(6)
<223> OTHER INFORMATION: Xaa can be any naturally occurring amino acid
      other than T
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than T

<400> SEQUENCE: 111

Xaa Xaa Xaa Xaa Xaa Xaa Xaa Xaa Xaa Xaa
1 5 10

<210> SEQ ID NO 112
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than D
<220> FEATURE:
<221> NAME/KEY: MISC_FEATURE
<222> LOCATION: (2)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than K
<220> FEATURE:
<221> NAME/KEY: MISC_FEATURE
<222> LOCATION: (6)..(6)
<223> OTHER INFORMATION: Xaa can be any naturally occurring amino acid other than Y
<220> FEATURE:
<221> NAME/KEY: MISC_FEATURE
<222> LOCATION: (7)..(7)
<223> OTHER INFORMATION: Xaa can be any naturally occurring amino acid other than T

<400> SEQUENCE: 112

Xaa Xaa Xaa Xaa Xaa Xaa Xaa
1 5

<210> SEQ ID NO 113
<211> LENGTH: 8
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than R
<220> FEATURE:
<221> NAME/KEY: MISC_FEATURE
<222> LOCATION: (2)..(2)
<223> OTHER INFORMATION: Xaa can be any naturally occurring amino acid other than I
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE
<222> LOCATION: (4)..(5)
<223> OTHER INFORMATION: Xaa can be any naturally occurring amino acid other than T
<220> FEATURE:
<221> NAME/KEY: MISC_FEATURE
<222> LOCATION: (6)..(6)
<223> OTHER INFORMATION: Xaa can be any naturally occurring amino acid

```
      other than A
<220> FEATURE:
<221> NAME/KEY: MISC_FEATURE
<222> LOCATION: (7)..(7)
<223> OTHER INFORMATION: Xaa can be any naturally occurring amino acid
      other than N
<220> FEATURE:
<221> NAME/KEY: MISC_FEATURE
<222> LOCATION: (8)..(8)
<223> OTHER INFORMATION: Xaa can be any naturally occurring amino acid
      other than S

<400> SEQUENCE: 113

Xaa Xaa Xaa Xaa Xaa Xaa Xaa Xaa
1               5


<210> SEQ ID NO 114
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than V
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than C

<400> SEQUENCE: 114

Xaa Xaa Xaa Xaa Xaa Xaa Xaa Xaa Xaa Xaa
```

1 5 10

<210> SEQ ID NO 115
<211> LENGTH: 4
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than Q
<220> FEATURE:
<221> NAME/KEY: MISC_FEATURE
<222> LOCATION: (2)..(2)
<223> OTHER INFORMATION: Xaa can be any naturally occurring amino acid other than G
<220> FEATURE:
<221> NAME/KEY: MISC_FEATURE
<222> LOCATION: (3)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than A

<400> SEQUENCE: 115

Xaa Xaa Xaa Xaa
1

<210> SEQ ID NO 116
<211> LENGTH: 12
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than N
<220> FEATURE:
<221> NAME/KEY: MISC_FEATURE
<222> LOCATION: (2)..(2)
<223> OTHER INFORMATION: Xaa can be any naturally occurring amino acid other than N
<220> FEATURE:
<221> NAME/KEY: MISC_FEATURE
<222> LOCATION: (3)..(3)
<223> OTHER INFORMATION: Xaa can be any naturally occurring amino acid other than Q
<220> FEATURE:
<221> NAME/KEY: MISC_FEATURE
<222> LOCATION: (4)..(4)
<223> OTHER INFORMATION: Xaa can be any naturally occurring amino acid other than N
<220> FEATURE:
<221> NAME/KEY: MISC_FEATURE
<222> LOCATION: (5)..(5)
<223> OTHER INFORMATION: Xaa can be any naturally occurring amino acid other than Y
<220> FEATURE:
<221> NAME/KEY: MISC_FEATURE
<222> LOCATION: (6)..(6)
<223> OTHER INFORMATION: Xaa can be any naturally occurring amino acid other than K
<220> FEATURE:
<221> NAME/KEY: MISC_FEATURE
<222> LOCATION: (7)..(7)
<223> OTHER INFORMATION: Xaa can be any naturally occurring amino acid other than I
<220> FEATURE:
<221> NAME/KEY: MISC_FEATURE
<222> LOCATION: (8)..(8)
<223> OTHER INFORMATION: Xaa can be any naturally occurring amino acid
other than P
<220> FEATURE:
<221> NAME/KEY: MISC_FEATURE
<222> LOCATION: (9)..(9)
<223> OTHER INFORMATION: Xaa can be any naturally occurring amino acid
other than A
<220> FEATURE:
<221> NAME/KEY: MISC_FEATURE
<222> LOCATION: (10)..(10)
<223> OTHER INFORMATION: Xaa can be any naturally occurring amino acid
other than S
<220> FEATURE:
<221> NAME/KEY: MISC_FEATURE
<222> LOCATION: (11)..(12)
<223> OTHER INFORMATION: Xaa can be any naturally occurring amino acid
other than G

<400> SEQUENCE: 116

Xaa Xaa Xaa Xaa Xaa Xaa Xaa Xaa Xaa Xaa Xaa Xaa
1               5                   10

<210> SEQ ID NO 117
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than A
<220> FEATURE:
<221> NAME/KEY: MISC_FEATURE
<222> LOCATION: (4)..(4)
<223> OTHER INFORMATION: Xaa can be any naturally occurring amino acid
other than H
<220> FEATURE:
<221> NAME/KEY: MISC_FEATURE
<222> LOCATION: (5)..(5)
<223> OTHER INFORMATION: Xaa can be any naturally occurring amino acid
other than H
<220> FEATURE:
<221> NAME/KEY: MISC_FEATURE
<222> LOCATION: (6)..(6)
<223> OTHER INFORMATION: Xaa can be any naturally occurring amino acid
other than I
<220> FEATURE:
<221> NAME/KEY: MISC_FEATURE
<222> LOCATION: (7)..(7)
<223> OTHER INFORMATION: Xaa can be any naturally occurring amino acid
other than A
<220> FEATURE:
<221> NAME/KEY: MISC_FEATURE
<222> LOCATION: (8)..(8)
<223> OTHER INFORMATION: Xaa can be any naturally occurring amino acid
other than N
<220> FEATURE:
<221> NAME/KEY: MISC_FEATURE
<222> LOCATION: (9)..(9)
<223> OTHER INFORMATION: Xaa can be any naturally occurring amino acid
other than L
<220> FEATURE:
<221> NAME/KEY: MISC_FEATURE
<222> LOCATION: (10)..(10)
<223> OTHER INFORMATION: Xaa can be any naturally occurring amino acid
other than D

<400> SEQUENCE: 117

Xaa Xaa Xaa Xaa Xaa Xaa Xaa Xaa Xaa Xaa
1 5 10

<210> SEQ ID NO 118
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than D
<220> FEATURE:
<221> NAME/KEY: MISC_FEATURE
<222> LOCATION: (2)..(2)
<223> OTHER INFORMATION: Xaa can be any naturally occurring amino acid other than N
<220> FEATURE:
<221> NAME/KEY: MISC_FEATURE
<222> LOCATION: (3)..(3)
<223> OTHER INFORMATION: Xaa can be any naturally occurring amino acid other than A
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than N
<220> FEATURE:
<221> NAME/KEY: MISC_FEATURE
<222> LOCATION: (6)..(6)
<223> OTHER INFORMATION: Xaa can be any naturally occurring amino acid other than Y
<220> FEATURE:
<221> NAME/KEY: MISC_FEATURE
<222> LOCATION: (7)..(7)
<223> OTHER INFORMATION: Xaa can be any naturally occurring amino acid other than H

<400> SEQUENCE: 118

Xaa Xaa Xaa Xaa Xaa Xaa Xaa
1 5

<210> SEQ ID NO 119
<211> LENGTH: 8
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than R
<220> FEATURE:
<221> NAME/KEY: MISC_FEATURE
<222> LOCATION: (2)..(2)
<223> OTHER INFORMATION: Xaa can be any naturally occurring amino acid other than L
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:

<221> NAME/KEY: MISC_FEATURE
<222> LOCATION: (4)..(5)
<223> OTHER INFORMATION: Xaa can be any naturally occurring amino acid
other than T
<220> FEATURE:
<221> NAME/KEY: MISC_FEATURE
<222> LOCATION: (6)..(6)
<223> OTHER INFORMATION: Xaa can be any naturally occurring amino acid
other than S
<220> FEATURE:
<221> NAME/KEY: MISC_FEATURE
<222> LOCATION: (7)..(7)
<223> OTHER INFORMATION: Xaa can be any naturally occurring amino acid
other than N
<220> FEATURE:
<221> NAME/KEY: MISC_FEATURE
<222> LOCATION: (8)..(8)
<223> OTHER INFORMATION: Xaa can be any naturally occurring amino acid
other than S

<400> SEQUENCE: 119

Xaa Xaa Xaa Xaa Xaa Xaa Xaa Xaa
1 5

<210> SEQ ID NO 120
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than V
<220> FEATURE:
<221> NAME/KEY: MISC_FEATURE
<222> LOCATION: (2)..(2)
<223> OTHER INFORMATION: Xaa can be any naturally occurring amino acid
other than F
<220> FEATURE:
<221> NAME/KEY: MISC_FEATURE
<222> LOCATION: (3)..(3)
<223> OTHER INFORMATION: Xaa can be any naturally occurring amino acid
other than M
<220> FEATURE:
<221> NAME/KEY: MISC_FEATURE
<222> LOCATION: (4)..(4)
<223> OTHER INFORMATION: Xaa can be any naturally occurring amino acid
other than V
<220> FEATURE:
<221> NAME/KEY: MISC_FEATURE
<222> LOCATION: (5)..(5)
<223> OTHER INFORMATION: Xaa can be any naturally occurring amino acid
other than P
<220> FEATURE:
<221> NAME/KEY: MISC_FEATURE
<222> LOCATION: (6)..(6)
<223> OTHER INFORMATION: Xaa can be any naturally occurring amino acid
other than Q
<220> FEATURE:
<221> NAME/KEY: MISC_FEATURE
<222> LOCATION: (7)..(7)
<223> OTHER INFORMATION: Xaa can be any naturally occurring amino acid
other than Y
<220> FEATURE:
<221> NAME/KEY: MISC_FEATURE
<222> LOCATION: (8)..(8)
<223> OTHER INFORMATION: Xaa can be any naturally occurring amino acid
other than G
<220> FEATURE:
<221> NAME/KEY: MISC_FEATURE
<222> LOCATION: (9)..(9)
<223> OTHER INFORMATION: Xaa can be any naturally occurring amino acid
other than Y
<220> FEATURE:

```
<221> NAME/KEY: MISC_FEATURE
<222> LOCATION: (10)..(10)
<223> OTHER INFORMATION: Xaa can be any naturally occurring amino acid
      other than C

<400> SEQUENCE: 120

Xaa Xaa Xaa Xaa Xaa Xaa Xaa Xaa Xaa Xaa
1               5                   10


<210> SEQ ID NO 121
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than Q
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than N
<220> FEATURE:
<221> NAME/KEY: MISC_FEATURE
<222> LOCATION: (4)..(4)
<223> OTHER INFORMATION: Xaa can be any naturally occurring amino acid
      other than A

<400> SEQUENCE: 121

Xaa Xaa Xaa Xaa
1


<210> SEQ ID NO 122
<211> LENGTH: 12
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
      other than Y
<220> FEATURE:
<221> NAME/KEY: MISC_FEATURE
```

```
<222> LOCATION: (6)..(6)
<223> OTHER INFORMATION: Xaa can be any naturally occurring amino acid
      other than K
<220> FEATURE:
<221> NAME/KEY: MISC_FEATURE
<222> LOCATION: (7)..(7)
<223> OTHER INFORMATION: Xaa can be any naturally occurring amino acid
      other than I
<220> FEATURE:
<221> NAME/KEY: MISC_FEATURE
<222> LOCATION: (8)..(8)
<223> OTHER INFORMATION: Xaa can be any naturally occurring amino acid
      other than P
<220> FEATURE:
<221> NAME/KEY: MISC_FEATURE
<222> LOCATION: (9)..(9)
<223> OTHER INFORMATION: Xaa can be any naturally occurring amino acid
      other than A
<220> FEATURE:
<221> NAME/KEY: MISC_FEATURE
<222> LOCATION: (10)..(10)
<223> OTHER INFORMATION: Xaa can be any naturally occurring amino acid
      other than S
<220> FEATURE:
<221> NAME/KEY: MISC_FEATURE
<222> LOCATION: (11)..(12)
<223> OTHER INFORMATION: Xaa can be any naturally occurring amino acid
      other than G

<400> SEQUENCE: 122

Xaa Xaa Xaa Xaa Xaa Xaa Xaa Xaa Xaa Xaa Xaa Xaa
1               5                   10


<210> SEQ ID NO 123
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than A
<220> FEATURE:
<221> NAME/KEY: MISC_FEATURE
<222> LOCATION: (4)..(4)
<223> OTHER INFORMATION: Xaa can be any naturally occurring amino acid
      other than P
<220> FEATURE:
<221> NAME/KEY: MISC_FEATURE
<222> LOCATION: (5)..(5)
<223> OTHER INFORMATION: Xaa can be any naturally occurring amino acid
      other than I
<220> FEATURE:
<221> NAME/KEY: MISC_FEATURE
<222> LOCATION: (6)..(6)
<223> OTHER INFORMATION: Xaa can be any naturally occurring amino acid
      other than T
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
```

<222> LOCATION: (9)..(9)
<223> OTHER INFORMATION: Xaa can be any naturally occurring amino acid
other than V
<220> FEATURE:
<221> NAME/KEY: MISC_FEATURE
<222> LOCATION: (10)..(10)
<223> OTHER INFORMATION: Xaa can be any naturally occurring amino acid
other than T

<400> SEQUENCE: 123

Xaa Xaa Xaa Xaa Xaa Xaa Xaa Xaa Xaa Xaa
1 5 10

<210> SEQ ID NO 124
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than D
<220> FEATURE:
<221> NAME/KEY: MISC_FEATURE
<222> LOCATION: (2)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than K
<220> FEATURE:
<221> NAME/KEY: MISC_FEATURE
<222> LOCATION: (6)..(6)
<223> OTHER INFORMATION: Xaa can be any naturally occurring amino acid
other than Y
<220> FEATURE:
<221> NAME/KEY: MISC_FEATURE
<222> LOCATION: (7)..(7)
<223> OTHER INFORMATION: Xaa can be any naturally occurring amino acid
other than T

<400> SEQUENCE: 124

Xaa Xaa Xaa Xaa Xaa Xaa Xaa
1 5

<210> SEQ ID NO 125
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than R
<220> FEATURE:
<221> NAME/KEY: MISC_FEATURE
<222> LOCATION: (2)..(2)
<223> OTHER INFORMATION: Xaa can be any naturally occurring amino acid
other than L
<220> FEATURE:
<221> NAME/KEY: MISC_FEATURE
<222> LOCATION: (3)..(3)

<223> OTHER INFORMATION: Xaa can be any naturally occurring amino acid
      other than G
<220> FEATURE:
<221> NAME/KEY: MISC_FEATURE
<222> LOCATION: (4)..(5)
<223> OTHER INFORMATION: Xaa can be any naturally occurring amino acid
      other than S
<220> FEATURE:
<221> NAME/KEY: MISC_FEATURE
<222> LOCATION: (6)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than A
<220> FEATURE:
<221> NAME/KEY: MISC_FEATURE
<222> LOCATION: (8)..(8)
<223> OTHER INFORMATION: Xaa can be any naturally occurring amino acid
      other than S

<400> SEQUENCE: 125

Xaa Xaa Xaa Xaa Xaa Xaa Xaa Xaa
1               5

<210> SEQ ID NO 126
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than F
<220> FEATURE:
<221> NAME/KEY: MISC_FEATURE
<222> LOCATION: (3)..(3)
<223> OTHER INFORMATION: Xaa can be any naturally occurring amino acid
      other than M
<220> FEATURE:
<221> NAME/KEY: MISC_FEATURE
<222> LOCATION: (4)..(4)
<223> OTHER INFORMATION: Xaa can be any naturally occurring amino acid
      other than V
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)

```
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than C

<400> SEQUENCE: 126

Xaa Xaa Xaa Xaa Xaa Xaa Xaa Xaa Xaa Xaa
1               5                   10


<210> SEQ ID NO 127
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than Q
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than N
<220> FEATURE:
<221> NAME/KEY: MISC_FEATURE
<222> LOCATION: (4)..(4)
<223> OTHER INFORMATION: Xaa can be any naturally occurring amino acid
      other than S

<400> SEQUENCE: 127

Xaa Xaa Xaa Xaa
1


<210> SEQ ID NO 128
<211> LENGTH: 12
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
```

other than Y
<220> FEATURE:
<221> NAME/KEY: MISC_FEATURE
<222> LOCATION: (6)..(6)
<223> OTHER INFORMATION: Xaa can be any naturally occurring amino acid
other than K
<220> FEATURE:
<221> NAME/KEY: MISC_FEATURE
<222> LOCATION: (7)..(7)
<223> OTHER INFORMATION: Xaa can be any naturally occurring amino acid
other than I
<220> FEATURE:
<221> NAME/KEY: MISC_FEATURE
<222> LOCATION: (8)..(8)
<223> OTHER INFORMATION: Xaa can be any naturally occurring amino acid
other than P
<220> FEATURE:
<221> NAME/KEY: MISC_FEATURE
<222> LOCATION: (9)..(9)
<223> OTHER INFORMATION: Xaa can be any naturally occurring amino acid
other than Q
<220> FEATURE:
<221> NAME/KEY: MISC_FEATURE
<222> LOCATION: (10)..(10)
<223> OTHER INFORMATION: Xaa can be any naturally occurring amino acid
other than G
<220> FEATURE:
<221> NAME/KEY: MISC_FEATURE
<222> LOCATION: (11)..(11)
<223> OTHER INFORMATION: Xaa can be any naturally occurring amino acid
other than R
<220> FEATURE:
<221> NAME/KEY: MISC_FEATURE
<222> LOCATION: (12)..(12)
<223> OTHER INFORMATION: Xaa can be any naturally occurring amino acid
other than N

<400> SEQUENCE: 128

Xaa Xaa Xaa Xaa Xaa Xaa Xaa Xaa Xaa Xaa Xaa Xaa
1 5 10

<210> SEQ ID NO 129
<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than V
<220> FEATURE:
<221> NAME/KEY: MISC_FEATURE
<222> LOCATION: (4)..(4)
<223> OTHER INFORMATION: Xaa can be any naturally occurring amino acid
other than P
<220> FEATURE:
<221> NAME/KEY: MISC_FEATURE
<222> LOCATION: (5)..(5)
<223> OTHER INFORMATION: Xaa can be any naturally occurring amino acid
other than T
<220> FEATURE:
<221> NAME/KEY: MISC_FEATURE
<222> LOCATION: (6)..(6)
<223> OTHER INFORMATION: Xaa can be any naturally occurring amino acid
other than V
<220> FEATURE:
<221> NAME/KEY: MISC_FEATURE
<222> LOCATION: (7)..(7)
<223> OTHER INFORMATION: Xaa can be any naturally occurring amino acid

```
      other than D
<220> FEATURE:
<221> NAME/KEY: MISC_FEATURE
<222> LOCATION: (8)..(8)
<223> OTHER INFORMATION: Xaa can be any naturally occurring amino acid
      other than D
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than D

<400> SEQUENCE: 129

Xaa Xaa Xaa Xaa Xaa Xaa Xaa Xaa Xaa Xaa
1               5                   10


<210> SEQ ID NO 130
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than D
<220> FEATURE:
<221> NAME/KEY: MISC_FEATURE
<222> LOCATION: (2)..(2)
<223> OTHER INFORMATION: Xaa can be any naturally occurring amino acid
      other than N
<220> FEATURE:
<221> NAME/KEY: MISC_FEATURE
<222> LOCATION: (3)..(3)
<223> OTHER INFORMATION: Xaa can be any naturally occurring amino acid
      other than A
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than A
<220> FEATURE:
<221> NAME/KEY: MISC_FEATURE
<222> LOCATION: (6)..(6)
<223> OTHER INFORMATION: Xaa can be any naturally occurring amino acid
      other than Y
<220> FEATURE:
<221> NAME/KEY: MISC_FEATURE
<222> LOCATION: (7)..(7)
<223> OTHER INFORMATION: Xaa can be any naturally occurring amino acid
      other than K

<400> SEQUENCE: 130

Xaa Xaa Xaa Xaa Xaa Xaa Xaa
1               5


<210> SEQ ID NO 131
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
```

```
<220> FEATURE:
<221> NAME/KEY: MISC_FEATURE
<222> LOCATION: (1)..(1)
<223> OTHER INFORMATION: Xaa can be any naturally occurring amino acid
      other than R
<220> FEATURE:
<221> NAME/KEY: MISC_FEATURE
<222> LOCATION: (2)..(2)
<223> OTHER INFORMATION: Xaa can be any naturally occurring amino acid
      other than I
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than S
<220> FEATURE:
<221> NAME/KEY: MISC_FEATURE
<222> LOCATION: (7)..(8)
<223> OTHER INFORMATION: Xaa can be any naturally occurring amino acid
      other than G

<400> SEQUENCE: 131

Xaa Xaa Xaa Xaa Xaa Xaa Xaa Xaa
1               5


<210> SEQ ID NO 132
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than I
<220> FEATURE:
<221> NAME/KEY: MISC_FEATURE
<222> LOCATION: (2)..(2)
<223> OTHER INFORMATION: Xaa can be any naturally occurring amino acid
      other than Y
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than P
<220> FEATURE:
<221> NAME/KEY: MISC_FEATURE
<222> LOCATION: (6)..(6)
<223> OTHER INFORMATION: Xaa can be any naturally occurring amino acid
      other than Q
```

```
<220> FEATURE:
<221> NAME/KEY: MISC_FEATURE
<222> LOCATION: (7)..(7)
<223> OTHER INFORMATION: Xaa can be any naturally occurring amino acid
      other than Y
<220> FEATURE:
<221> NAME/KEY: MISC_FEATURE
<222> LOCATION: (8)..(8)
<223> OTHER INFORMATION: Xaa can be any naturally occurring amino acid
      other than G
<220> FEATURE:
<221> NAME/KEY: MISC_FEATURE
<222> LOCATION: (9)..(9)
<223> OTHER INFORMATION: Xaa can be any naturally occurring amino acid
      other than Y
<220> FEATURE:
<221> NAME/KEY: MISC_FEATURE
<222> LOCATION: (10)..(10)
<223> OTHER INFORMATION: Xaa can be any naturally occurring amino acid
      other than C

<400> SEQUENCE: 132

Xaa Xaa Xaa Xaa Xaa Xaa Xaa Xaa Xaa Xaa
1               5                   10


<210> SEQ ID NO 133
<211> LENGTH: 4
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than G
<220> FEATURE:
<221> NAME/KEY: MISC_FEATURE
<222> LOCATION: (4)..(4)
<223> OTHER INFORMATION: Xaa can be any naturally occurring amino acid
      other than R

<400> SEQUENCE: 133

Xaa Xaa Xaa Xaa
1


<210> SEQ ID NO 134
<211> LENGTH: 12
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than N
<220> FEATURE:
```

```
<221> NAME/KEY: MISC_FEATURE
<222> LOCATION: (4)..(4)
<223> OTHER INFORMATION: Xaa can be any naturally occurring amino acid
      other than I
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(6)
<223> OTHER INFORMATION: Xaa can be any naturally occurring amino acid
      other than K
<220> FEATURE:
<221> NAME/KEY: MISC_FEATURE
<222> LOCATION: (7)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than V
<220> FEATURE:
<221> NAME/KEY: MISC_FEATURE
<222> LOCATION: (10)..(10)
<223> OTHER INFORMATION: Xaa can be any naturally occurring amino acid
      other than F
<220> FEATURE:
<221> NAME/KEY: MISC_FEATURE
<222> LOCATION: (11)..(11)
<223> OTHER INFORMATION: Xaa can be any naturally occurring amino acid
      other than S
<220> FEATURE:
<221> NAME/KEY: MISC_FEATURE
<222> LOCATION: (12)..(12)
<223> OTHER INFORMATION: Xaa can be any naturally occurring amino acid
      other than V

<400> SEQUENCE: 134

Xaa Xaa Xaa Xaa Xaa Xaa Xaa Xaa Xaa Xaa Xaa Xaa
1               5                   10


<210> SEQ ID NO 135
<211> LENGTH: 10
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than V
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(3)
<223> OTHER INFORMATION: Xaa can be any naturally occurring amino acid
      other than P
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
```

<221> NAME/KEY: MISC_FEATURE
<222> LOCATION: (6)..(6)
<223> OTHER INFORMATION: Xaa can be any naturally occurring amino acid other than R
<220> FEATURE:
<221> NAME/KEY: MISC_FEATURE
<222> LOCATION: (7)..(8)
<223> OTHER INFORMATION: Xaa can be any naturally occurring amino acid other than A
<220> FEATURE:
<221> NAME/KEY: MISC_FEATURE
<222> LOCATION: (9)..(9)
<223> OTHER INFORMATION: Xaa can be any naturally occurring amino acid other than V
<220> FEATURE:
<221> NAME/KEY: MISC_FEATURE
<222> LOCATION: (10)..(10)
<223> OTHER INFORMATION: Xaa can be any naturally occurring amino acid other than N

<400> SEQUENCE: 135

Xaa Xaa Xaa Xaa Xaa Xaa Xaa Xaa Xaa Xaa
1               5                   10

<210> SEQ ID NO 136
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than S
<220> FEATURE:
<221> NAME/KEY: MISC_FEATURE
<222> LOCATION: (2)..(2)
<223> OTHER INFORMATION: Xaa can be any naturally occurring amino acid other than D
<220> FEATURE:
<221> NAME/KEY: MISC_FEATURE
<222> LOCATION: (3)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than G
<220> FEATURE:
<221> NAME/KEY: MISC_FEATURE
<222> LOCATION: (5)..(5)
<223> OTHER INFORMATION: Xaa can be any naturally occurring amino acid other than S
<220> FEATURE:
<221> NAME/KEY: MISC_FEATURE
<222> LOCATION: (6)..(6)
<223> OTHER INFORMATION: Xaa can be any naturally occurring amino acid other than Y
<220> FEATURE:
<221> NAME/KEY: MISC_FEATURE
<222> LOCATION: (7)..(7)
<223> OTHER INFORMATION: Xaa can be any naturally occurring amino acid other than S

<400> SEQUENCE: 136

Xaa Xaa Xaa Xaa Xaa Xaa Xaa
1               5

<210> SEQ ID NO 137
<211> LENGTH: 9
<212> TYPE: PRT
<213> ORGANISM: Artificial

-continued

<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than T
<220> FEATURE:
<221> NAME/KEY: MISC_FEATURE
<222> LOCATION: (2)..(2)
<223> OTHER INFORMATION: Xaa can be any naturally occurring amino acid
      other than P
<220> FEATURE:
<221> NAME/KEY: MISC_FEATURE
<222> LOCATION: (3)..(3)
<223> OTHER INFORMATION: Xaa can be any naturally occurring amino acid
      other than S
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(7)
<223> OTHER INFORMATION: Xaa can be any naturally occurring amino acid
      other than T
<220> FEATURE:
<221> NAME/KEY: MISC_FEATURE
<222> LOCATION: (8)..(8)
<223> OTHER INFORMATION: Xaa can be any naturally occurring amino acid
      other than Q
<220> FEATURE:
<221> NAME/KEY: MISC_FEATURE
<222> LOCATION: (9)..(9)
<223> OTHER INFORMATION: Xaa can be any naturally occurring amino acid
      other than S

<400> SEQUENCE: 137

Xaa Xaa Xaa Xaa Xaa Xaa Xaa Xaa Xaa
1               5

<210> SEQ ID NO 138
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than A
<220> FEATURE:
<221> NAME/KEY: MISC_FEATURE
<222> LOCATION: (3)..(3)
<223> OTHER INFORMATION: Xaa can be any naturally occurring amino acid
      other than D
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
other than E

<400> SEQUENCE: 138

Xaa Xaa Xaa Xaa Xaa Xaa Xaa Xaa
1 5

<210> SEQ ID NO 139
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than S
<220> FEATURE:
<221> NAME/KEY: MISC_FEATURE
<222> LOCATION: (4)..(4)
<223> OTHER INFORMATION: Xaa can be any naturally occurring amino acid
other than G
<220> FEATURE:
<221> NAME/KEY: MISC_FEATURE
<222> LOCATION: (5)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid
other than N
<220> FEATURE:
<221> NAME/KEY: MISC_FEATURE
<222> LOCATION: (8)..(8)
<223> OTHER INFORMATION: Xaa can be any naturally occurring amino acid
other than Q
<220> FEATURE:
<221> NAME/KEY: MISC_FEATURE
<222> LOCATION: (9)..(9)
<223> OTHER INFORMATION: Xaa can be any naturally occurring amino acid
other than S

<400> SEQUENCE: 139

Xaa Xaa Xaa Xaa Xaa Xaa Xaa Xaa Xaa
1 5

<210> SEQ ID NO 140
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than A
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)

<223> OTHER INFORMATION: Xaa can be any naturally occurring amino acid
other than D
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S
<220> FEATURE:
<221> NAME/KEY: MISC_FEATURE
<222> LOCATION: (8)..(8)
<223> OTHER INFORMATION: Xaa can be any naturally occurring amino acid
other than N

<400> SEQUENCE: 140

Xaa Xaa Xaa Xaa Xaa Xaa Xaa Xaa
1 5

<210> SEQ ID NO 141
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid
other than L
<220> FEATURE:
<221> NAME/KEY: MISC_FEATURE
<222> LOCATION: (5)..(5)
<223> OTHER INFORMATION: Xaa can be any naturally occurring amino acid
other than N
<220> FEATURE:
<221> NAME/KEY: MISC_FEATURE
<222> LOCATION: (6)..(6)
<223> OTHER INFORMATION: Xaa can be any naturally occurring amino acid
other than A
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than T
<220> FEATURE:
<221> NAME/KEY: MISC_FEATURE
<222> LOCATION: (9)..(9)
<223> OTHER INFORMATION: Xaa can be any naturally occurring amino acid
other than A

<400> SEQUENCE: 141

Xaa Xaa Xaa Xaa Xaa Xaa Xaa Xaa Xaa
1 5

<210> SEQ ID NO 142

<211> LENGTH: 9
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than V
<220> FEATURE:
<221> NAME/KEY: MISC_FEATURE
<222> LOCATION: (9)..(9)
<223> OTHER INFORMATION: Xaa can be any naturally occurring amino acid
      other than Q

<400> SEQUENCE: 142

Xaa Xaa Xaa Xaa Xaa Xaa Xaa Xaa Xaa
1               5

<210> SEQ ID NO 143
<211> LENGTH: 9
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than N
<220> FEATURE:
<221> NAME/KEY: MISC_FEATURE
<222> LOCATION: (2)..(2)
<223> OTHER INFORMATION: Xaa can be any naturally occurring amino acid
      other than Q
<220> FEATURE:
<221> NAME/KEY: MISC_FEATURE
<222> LOCATION: (3)..(3)
<223> OTHER INFORMATION: Xaa can be any naturally occurring amino acid
      other than S
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid other than S
<220> FEATURE:
<221> NAME/KEY: MISC_FEATURE
<222> LOCATION: (6)..(6)
<223> OTHER INFORMATION: Xaa can be any naturally occurring amino acid
other than A
<220> FEATURE:
<221> NAME/KEY: MISC_FEATURE
<222> LOCATION: (7)..(7)
<223> OTHER INFORMATION: Xaa can be any naturally occurring amino acid
other than Q
<220> FEATURE:
<221> NAME/KEY: MISC_FEATURE
<222> LOCATION: (8)..(8)
<223> OTHER INFORMATION: Xaa can be any naturally occurring amino acid
other than N
<220> FEATURE:
<221> NAME/KEY: MISC_FEATURE
<222> LOCATION: (9)..(9)
<223> OTHER INFORMATION: Xaa can be any naturally occurring amino acid
other than K

<400> SEQUENCE: 143

Xaa Xaa Xaa Xaa Xaa Xaa Xaa Xaa Xaa
1               5

<210> SEQ ID NO 144
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than K
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than D
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S
<220> FEATURE:
<221> NAME/KEY: MISC_FEATURE
<222> LOCATION: (8)..(8)
<223> OTHER INFORMATION: Xaa can be any naturally occurring amino acid
other than N

<400> SEQUENCE: 144

Xaa Xaa Xaa Xaa Xaa Xaa Xaa Xaa
1               5

<210> SEQ ID NO 145
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence <220> FEATURE:
<221> NAME/KEY: MISC_FEATURE
<222> LOCATION: (1)..(1)
<223> OTHER INFORMATION: Xaa can be any naturally occurring amino acid
other than N
<220> FEATURE:
<221> NAME/KEY: MISC_FEATURE
<222> LOCATION: (2)..(2)
<223> OTHER INFORMATION: Xaa can be any naturally occurring amino acid
other than P
<220> FEATURE:
<221> NAME/KEY: MISC_FEATURE
<222> LOCATION: (3)..(4)
<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than T
<220> FEATURE:
<221> NAME/KEY: MISC_FEATURE
<222> LOCATION: (6)..(6)
<223> OTHER INFORMATION: Xaa can be any naturally occurring amino acid
other than A
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than N
<220> FEATURE:
<221> NAME/KEY: MISC_FEATURE
<222> LOCATION: (9)..(9)
<223> OTHER INFORMATION: Xaa can be any naturally occurring amino acid
other than R

<400> SEQUENCE: 145

Xaa Xaa Xaa Xaa Xaa Xaa Xaa Xaa Xaa
1               5

<210> SEQ ID NO 146
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than L
<220> FEATURE:
<221> NAME/KEY: MISC_FEATURE
<222> LOCATION: (2)..(2)
<223> OTHER INFORMATION: Xaa can be any naturally occurring amino acid
other than D
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S

```
<220> FEATURE:
<221> NAME/KEY: MISC_FEATURE
<222> LOCATION: (8)..(8)
<223> OTHER INFORMATION: Xaa can be any naturally occurring amino acid
      other than N

<400> SEQUENCE: 146

Xaa Xaa Xaa Xaa Xaa Xaa Xaa Xaa
1               5


<210> SEQ ID NO 147
<211> LENGTH: 9
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(2)
<223> OTHER INFORMATION: Xaa can be any naturally occurring amino acid
      other than T
<220> FEATURE:
<221> NAME/KEY: MISC_FEATURE
<222> LOCATION: (3)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(6)
<223> OTHER INFORMATION: Xaa can be any naturally occurring amino acid
      other than A
<220> FEATURE:
<221> NAME/KEY: MISC_FEATURE
<222> LOCATION: (7)..(7)
<223> OTHER INFORMATION: Xaa can be any naturally occurring amino acid
      other than N
<220> FEATURE:
<221> NAME/KEY: MISC_FEATURE
<222> LOCATION: (8)..(8)
<223> OTHER INFORMATION: Xaa can be any naturally occurring amino acid
      other than T
<220> FEATURE:
<221> NAME/KEY: misc_feature
<222> LOCATION: (9)..(9)
<223> OTHER INFORMATION: Xaa can be any naturally occurring amino acid

<400> SEQUENCE: 147

Xaa Xaa Xaa Xaa Xaa Xaa Xaa Xaa Xaa
1               5


<210> SEQ ID NO 148
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than t
<220> FEATURE:
<221> NAME/KEY: MISC_FEATURE
<222> LOCATION: (2)..(2)
<223> OTHER INFORMATION: Xaa can be any naturally occurring amino acid
      other than G
<220> FEATURE:
<221> NAME/KEY: MISC_FEATURE
```

<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S
<220> FEATURE:
<221> NAME/KEY: MISC_FEATURE
<222> LOCATION: (8)..(8)
<223> OTHER INFORMATION: Xaa can be any naturally occurring amino acid
other than N

<400> SEQUENCE: 148

Xaa Xaa Xaa Xaa Xaa Xaa Xaa Xaa
1 5

<210> SEQ ID NO 149
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than i
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than S
<220> FEATURE:
<221> NAME/KEY: MISC_FEATURE
<222> LOCATION: (5)..(5)
<223> OTHER INFORMATION: Xaa can be any naturally occurring amino acid
other than G
<220> FEATURE:
<221> NAME/KEY: MISC_FEATURE
<222> LOCATION: (6)..(6)
<223> OTHER INFORMATION: Xaa can be any naturally occurring amino acid
other than Q
<220> FEATURE:
<221> NAME/KEY: MISC_FEATURE
<222> LOCATION: (7)..(7)
<223> OTHER INFORMATION: Xaa can be any naturally occurring amino acid
other than N
<220> FEATURE:
<221> NAME/KEY: MISC_FEATURE
<222> LOCATION: (8)..(9)
<223> OTHER INFORMATION: Xaa can be any naturally occurring amino acid
other than Q

<400> SEQUENCE: 149

Xaa Xaa Xaa Xaa Xaa Xaa Xaa Xaa Xaa
1 5

<210> SEQ ID NO 150
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than V
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S
<220> FEATURE:
<221> NAME/KEY: MISC_FEATURE
<222> LOCATION: (8)..(8)
<223> OTHER INFORMATION: Xaa can be any naturally occurring amino acid
other than E

<400> SEQUENCE: 150

Xaa Xaa Xaa Xaa Xaa Xaa Xaa Xaa
1               5

<210> SEQ ID NO 151
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than S
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(4)
<223> OTHER INFORMATION: Xaa can be any naturally occurring amino acid
other than G
<220> FEATURE:
<221> NAME/KEY: MISC_FEATURE
<222> LOCATION: (5)..(5)
<223> OTHER INFORMATION: Xaa can be any naturally occurring amino acid
other than T
<220> FEATURE:
<221> NAME/KEY: MISC_FEATURE
<222> LOCATION: (6)..(6)
<223> OTHER INFORMATION: Xaa can be any naturally occurring amino acid
other than A
<220> FEATURE:
<221> NAME/KEY: MISC_FEATURE
<222> LOCATION: (7)..(7)

<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than T
<220> FEATURE:
<221> NAME/KEY: MISC_FEATURE
<222> LOCATION: (9)..(9)
<223> OTHER INFORMATION: Xaa can be any naturally occurring amino acid
other than Q

<400> SEQUENCE: 151

Xaa Xaa Xaa Xaa Xaa Xaa Xaa Xaa Xaa
1 5

<210> SEQ ID NO 152
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than L
<220> FEATURE:
<221> NAME/KEY: MISC_FEATURE
<222> LOCATION: (2)..(2)
<223> OTHER INFORMATION: Xaa can be any naturally occurring amino acid
other than S
<220> FEATURE:
<221> NAME/KEY: MISC_FEATURE
<222> LOCATION: (3)..(3)
<223> OTHER INFORMATION: Xaa can be any naturally occurring amino acid
other than Q
<220> FEATURE:
<221> NAME/KEY: MISC_FEATURE
<222> LOCATION: (4)..(6)
<223> OTHER INFORMATION: Xaa can be any naturally occurring amino acid
other than N
<220> FEATURE:
<221> NAME/KEY: MISC_FEATURE
<222> LOCATION: (7)..(7)
<223> OTHER INFORMATION: Xaa can be any naturally occurring amino acid
other than S
<220> FEATURE:
<221> NAME/KEY: MISC_FEATURE
<222> LOCATION: (8)..(8)
<223> OTHER INFORMATION: Xaa can be any naturally occurring amino acid
other than N

<400> SEQUENCE: 152

Xaa Xaa Xaa Xaa Xaa Xaa Xaa Xaa
1 5

<210> SEQ ID NO 153
<211> LENGTH: 9
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than Q
<220> FEATURE:
<221> NAME/KEY: MISC_FEATURE
<222> LOCATION: (2)..(3)
<223> OTHER INFORMATION: Xaa can be any naturally occurring amino acid

```
      other than T
<220> FEATURE:
<221> NAME/KEY: MISC_FEATURE
<222> LOCATION: (4)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than T
<220> FEATURE:
<221> NAME/KEY: MISC_FEATURE
<222> LOCATION: (9)..(9)
<223> OTHER INFORMATION: Xaa can be any naturally occurring amino acid
      other than Q

<400> SEQUENCE: 153

Xaa Xaa Xaa Xaa Xaa Xaa Xaa Xaa Xaa
1               5


<210> SEQ ID NO 154
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than T
<220> FEATURE:
<221> NAME/KEY: MISC_FEATURE
<222> LOCATION: (2)..(2)
<223> OTHER INFORMATION: Xaa can be any naturally occurring amino acid
      other than N
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(6)
<223> OTHER INFORMATION: Xaa can be any naturally occurring amino acid
      other than N
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
      other than N

<400> SEQUENCE: 154

Xaa Xaa Xaa Xaa Xaa Xaa Xaa Xaa
1               5


<210> SEQ ID NO 155
<211> LENGTH: 9
```

<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than S
<220> FEATURE:
<221> NAME/KEY: MISC_FEATURE
<222> LOCATION: (2)..(2)
<223> OTHER INFORMATION: Xaa can be any naturally occurring amino acid
      other than T
<220> FEATURE:
<221> NAME/KEY: MISC_FEATURE
<222> LOCATION: (3)..(4)
<223> OTHER INFORMATION: Xaa can be any naturally occurring amino acid
      other than G
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than T
<220> FEATURE:
<221> NAME/KEY: MISC_FEATURE
<222> LOCATION: (9)..(9)
<223> OTHER INFORMATION: Xaa can be any naturally occurring amino acid
      other than Q

<400> SEQUENCE: 155

Xaa Xaa Xaa Xaa Xaa Xaa Xaa Xaa Xaa
1               5

<210> SEQ ID NO 156
<211> LENGTH: 8
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than L
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than Q
<220> FEATURE:
<221> NAME/KEY: MISC_FEATURE
<222> LOCATION: (4)..(6)
<223> OTHER INFORMATION: Xaa can be any naturally occurring amino acid
      other than N

```
<220> FEATURE:
<221> NAME/KEY: MISC_FEATURE
<222> LOCATION: (7)..(7)
<223> OTHER INFORMATION: Xaa can be any naturally occurring amino acid
      other than S
<220> FEATURE:
<221> NAME/KEY: MISC_FEATURE
<222> LOCATION: (8)..(8)
<223> OTHER INFORMATION: Xaa can be any naturally occurring amino acid
      other than N

<400> SEQUENCE: 156

Xaa Xaa Xaa Xaa Xaa Xaa Xaa Xaa
1               5


<210> SEQ ID NO 157
<211> LENGTH: 9
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (1)..(1)
<223> OTHER INFORMATION: Xaa can be any naturally occurring amino acid
      other than G
<220> FEATURE:
<221> NAME/KEY: MISC_FEATURE
<222> LOCATION: (2)..(2)
<223> OTHER INFORMATION: Xaa can be any naturally occurring amino acid
      other than E
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than L
<220> FEATURE:
<221> NAME/KEY: MISC_FEATURE
<222> LOCATION: (5)..(5)
<223> OTHER INFORMATION: Xaa can be any naturally occurring amino acid
      other than N
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than A

<400> SEQUENCE: 157

Xaa Xaa Xaa Xaa Xaa Xaa Xaa Xaa Xaa
1               5


<210> SEQ ID NO 158
<211> LENGTH: 9
<212> TYPE: PRT
<213> ORGANISM: Artificial
```

<220> FEATURE:
<223> OTHER INFORMATION: Targeting peptide sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than S
<220> FEATURE:
<221> NAME/KEY: MISC_FEATURE
<222> LOCATION: (4)..(4)
<223> OTHER INFORMATION: Xaa can be any naturally occurring amino acid
other than L
<220> FEATURE:
<221> NAME/KEY: MISC_FEATURE
<222> LOCATION: (5)..(5)
<223> OTHER INFORMATION: Xaa can be any naturally occurring amino acid
other than N
<220> FEATURE:
<221> NAME/KEY: MISC_FEATURE
<222> LOCATION: (6)..(6)
<223> OTHER INFORMATION: Xaa can be any naturally occurring amino acid
other than Q
<220> FEATURE:
<221> NAME/KEY: MISC_FEATURE
<222> LOCATION: (7)..(7)
<223> OTHER INFORMATION: Xaa can be any naturally occurring amino acid
other than G
<220> FEATURE:
<221> NAME/KEY: MISC_FEATURE
<222> LOCATION: (8)..(8)
<223> OTHER INFORMATION: Xaa can be any naturally occurring amino acid
other than T
<220> FEATURE:
<221> NAME/KEY: MISC_FEATURE
<222> LOCATION: (9)..(9)
<223> OTHER INFORMATION: Xaa can be any naturally occurring amino acid
other than A

<400> SEQUENCE: 158

Xaa Xaa Xaa Xaa Xaa Xaa Xaa Xaa Xaa
1               5

<210> SEQ ID NO 159
<211> LENGTH: 9
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(2)
<223> OTHER INFORMATION: Xaa can be any naturally occurring amino acid
other than E
<220> FEATURE:
<221> NAME/KEY: MISC_FEATURE
<222> LOCATION: (3)..(3)
<223> OTHER INFORMATION: Xaa can be any naturally occurring amino acid
other than T
<220> FEATURE:
<221> NAME/KEY: MISC_FEATURE
<222> LOCATION: (4)..(4)
<223> OTHER INFORMATION: Xaa can be any naturally occurring amino acid other than L
<220> FEATURE:
<221> NAME/KEY: MISC_FEATURE
<222> LOCATION: (5)..(5)
<223> OTHER INFORMATION: Xaa can be any naturally occurring amino acid
      other than N
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than A

<400> SEQUENCE: 159

Xaa Xaa Xaa Xaa Xaa Xaa Xaa Xaa Xaa
1               5

<210> SEQ ID NO 160
<211> LENGTH: 9
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (1)..(2)
<223> OTHER INFORMATION: Xaa can be any naturally occurring amino acid
      other than G
<220> FEATURE:
<221> NAME/KEY: MISC_FEATURE
<222> LOCATION: (3)..(3)
<223> OTHER INFORMATION: Xaa can be any naturally occurring amino acid
      other than T
<220> FEATURE:
<221> NAME/KEY: MISC_FEATURE
<222> LOCATION: (4)..(4)
<223> OTHER INFORMATION: Xaa can be any naturally occurring amino acid
      other than L
<220> FEATURE:
<221> NAME/KEY: MISC_FEATURE
<222> LOCATION: (5)..(5)
<223> OTHER INFORMATION: Xaa can be any naturally occurring amino acid
      other than N
<220> FEATURE:
<221> NAME/KEY: MISC_FEATURE
<222> LOCATION: (6)..(6)
<223> OTHER INFORMATION: Xaa can be any naturally occurring amino acid
      other than Q
<220> FEATURE:
<221> NAME/KEY: MISC_FEATURE
<222> LOCATION: (7)..(7)
<223> OTHER INFORMATION: Xaa can be any naturally occurring amino acid
      other than G
<220> FEATURE:
<221> NAME/KEY: MISC_FEATURE
<222> LOCATION: (8)..(8)
<223> OTHER INFORMATION: Xaa can be any naturally occurring amino acid
      other than N
<220> FEATURE:
<221> NAME/KEY: MISC_FEATURE
<222> LOCATION: (9)..(9)
<223> OTHER INFORMATION: Xaa can be any naturally occurring amino acid
      other than S

<400> SEQUENCE: 160

Xaa Xaa Xaa Xaa Xaa Xaa Xaa Xaa Xaa
1 5

<210> SEQ ID NO 161
<211> LENGTH: 9
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than S
<220> FEATURE:
<221> NAME/KEY: MISC_FEATURE
<222> LOCATION: (3)..(3)
<223> OTHER INFORMATION: Xaa can be any naturally occurring amino acid other than Q
<220> FEATURE:
<221> NAME/KEY: MISC_FEATURE
<222> LOCATION: (4)..(4)
<223> OTHER INFORMATION: Xaa can be any naturally occurring amino acid other than A
<220> FEATURE:
<221> NAME/KEY: MISC_FEATURE
<222> LOCATION: (5)..(5)
<223> OTHER INFORMATION: Xaa can be any naturally occurring amino acid other than G
<220> FEATURE:
<221> NAME/KEY: MISC_FEATURE
<222> LOCATION: (6)..(7)
<223> OTHER INFORMATION: Xaa can be any naturally occurring amino acid other than S
<220> FEATURE:
<221> NAME/KEY: MISC_FEATURE
<222> LOCATION: (8)..(8)
<223> OTHER INFORMATION: Xaa can be any naturally occurring amino acid other than G
<220> FEATURE:
<221> NAME/KEY: MISC_FEATURE
<222> LOCATION: (9)..(9)
<223> OTHER INFORMATION: Xaa can be any naturally occurring amino acid other than R

<400> SEQUENCE: 161

Xaa Xaa Xaa Xaa Xaa Xaa Xaa Xaa Xaa
1 5

<210> SEQ ID NO 162
<211> LENGTH: 5
<212> TYPE: PRT
<213> ORGANISM: Artificial
<220> FEATURE:
<223> OTHER INFORMATION: Targeting peptide sequence

<400> SEQUENCE: 162

Phe Val Phe Leu Pro
1 5

<210> SEQ ID NO 163
<211> LENGTH: 4
<212> TYPE: PRT
<213> ORGANISM: Artificial
<220> FEATURE:
<223> OTHER INFORMATION: Targeting peptide sequence
<220> FEATURE:

-continued

<221> NAME/KEY: MISC_FEATURE
<222> LOCATION: (1)..(1)
<223> OTHER INFORMATION: Xaa can be any basic amino acid
<220> FEATURE:
<221> NAME/KEY: MISC_FEATURE
<222> LOCATION: (2)..(3)
<223> OTHER INFORMATION: Xaa can be any neutral and/or hydrophobic amino acid
<220> FEATURE:
<221> NAME/KEY: MISC_FEATURE
<222> LOCATION: (4)..(4)
<223> OTHER INFORMATION: Xaa can be any basic amino acid

<400> SEQUENCE: 163

Xaa Xaa Xaa Xaa
1

<210> SEQ ID NO 164
<211> LENGTH: 4
<212> TYPE: PRT
<213> ORGANISM: Artificial
<220> FEATURE:
<223> OTHER INFORMATION: Targeting peptide sequence

<400> SEQUENCE: 164

Arg Gly Asn Arg
1

<210> SEQ ID NO 165
<211> LENGTH: 7
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (7)..(7)
<223> OTHER INFORMATION: Xaa can be G or S

<400> SEQUENCE: 165

Asn Ser Val Arg Asp Leu Xaa
1               5

<210> SEQ ID NO 166
<211> LENGTH: 7
<212> TYPE: PRT
<213> ORGANISM: Artificial
<220> FEATURE:
<223> OTHER INFORMATION: Targeting peptide sequence

<400> SEQUENCE: 166

Pro Arg Ser Val Thr Val Pro
1               5

<210> SEQ ID NO 167
<211> LENGTH: 7
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be S or A

<400> SEQUENCE: 167

-continued

Asn Ser Val Ser Ser Xaa Xaa
1 5

<210> SEQ ID NO 168
<211> LENGTH: 6
<212> TYPE: PRT
<213> ORGANISM: Artificial
<220> FEATURE:
<223> OTHER INFORMATION: Targeting peptide sequence

<400> SEQUENCE: 168

Asn Gly Arg Ala His Ala
1 5

<210> SEQ ID NO 169
<211> LENGTH: 7
<212> TYPE: PRT
<213> ORGANISM: Artificial
<220> FEATURE:
<223> OTHER INFORMATION: Targeting peptide sequence

<400> SEQUENCE: 169

Gln Pro Glu His Ser Ser Thr
1 5

<210> SEQ ID NO 170
<211> LENGTH: 7
<212> TYPE: PRT
<213> ORGANISM: Artificial
<220> FEATURE:
<223> OTHER INFORMATION: Targeting peptide sequence

<400> SEQUENCE: 170

Val Asn Thr Ala Asn Ser Thr
1 5

<210> SEQ ID NO 171
<211> LENGTH: 7
<212> TYPE: PRT
<213> ORGANISM: Artificial
<220> FEATURE:
<223> OTHER INFORMATION: Targeting peptide sequence

<400> SEQUENCE: 171

His Gly Pro Met Gln Lys Ser
1 5

<210> SEQ ID NO 172
<211> LENGTH: 7
<212> TYPE: PRT
<213> ORGANISM: Artificial
<220> FEATURE:
<223> OTHER INFORMATION: Targeting peptide sequence

<400> SEQUENCE: 172

Pro His Lys Pro Pro Leu Ala
1 5

<210> SEQ ID NO 173
<211> LENGTH: 7
<212> TYPE: PRT
<213> ORGANISM: Artificial
<220> FEATURE:
<223> OTHER INFORMATION: Targeting peptide sequence

<400> SEQUENCE: 173

Ile Lys Asn Asn Glu Met Trp 1 5

<210> SEQ ID NO 174
<211> LENGTH: 7
<212> TYPE: PRT
<213> ORGANISM: Artificial
<220> FEATURE:
<223> OTHER INFORMATION: Targeting peptide sequence

<400> SEQUENCE: 174

Arg Asn Leu Asp Thr Pro Met
1 5

<210> SEQ ID NO 175
<211> LENGTH: 7
<212> TYPE: PRT
<213> ORGANISM: Artificial
<220> FEATURE:
<223> OTHER INFORMATION: Targeting peptide sequence

<400> SEQUENCE: 175

Val Asp Ser His Arg Gln Ser
1 5

<210> SEQ ID NO 176
<211> LENGTH: 7
<212> TYPE: PRT
<213> ORGANISM: Artificial
<220> FEATURE:
<223> OTHER INFORMATION: Targeting peptide sequence

<400> SEQUENCE: 176

Tyr Asp Ser Lys Thr Lys Thr
1 5

<210> SEQ ID NO 177
<211> LENGTH: 7
<212> TYPE: PRT
<213> ORGANISM: Artificial
<220> FEATURE:
<223> OTHER INFORMATION: Targeting peptide sequence

<400> SEQUENCE: 177

Ser Gln Leu Pro His Gln Lys
1 5

<210> SEQ ID NO 178
<211> LENGTH: 7
<212> TYPE: PRT
<213> ORGANISM: Artificial
<220> FEATURE:
<223> OTHER INFORMATION: Targeting peptide sequence

<400> SEQUENCE: 178

Ser Thr Met Gln Gln Asn Thr
1 5

<210> SEQ ID NO 179
<211> LENGTH: 7
<212> TYPE: PRT
<213> ORGANISM: Artificial
<220> FEATURE:
<223> OTHER INFORMATION: Targeting peptide sequence

<400> SEQUENCE: 179

Thr Glu Arg Tyr Met Thr Gln
1 5

<210> SEQ ID NO 180
<211> LENGTH: 7
<212> TYPE: PRT
<213> ORGANISM: Artificial
<220> FEATURE:
<223> OTHER INFORMATION: Targeting peptide sequence

<400> SEQUENCE: 180

Gln Pro Glu His Ser Ser Thr
1 5

<210> SEQ ID NO 181
<211> LENGTH: 7
<212> TYPE: PRT
<213> ORGANISM: Artificial
<220> FEATURE:
<223> OTHER INFORMATION: Targeting peptide sequence

<400> SEQUENCE: 181

Asp Ala Ser Leu Ser Thr Ser
1 5

<210> SEQ ID NO 182
<211> LENGTH: 7
<212> TYPE: PRT
<213> ORGANISM: Artificial
<220> FEATURE:
<223> OTHER INFORMATION: Targeting peptide sequence

<400> SEQUENCE: 182

Asp Leu Pro Asn Lys Lys Thr
1 5

<210> SEQ ID NO 183
<211> LENGTH: 7
<212> TYPE: PRT
<213> ORGANISM: Artificial
<220> FEATURE:
<223> OTHER INFORMATION: Targeting peptide sequence

<400> SEQUENCE: 183

Asp Leu Thr Ala Ala Arg Leu
1 5

<210> SEQ ID NO 184
<211> LENGTH: 7
<212> TYPE: PRT
<213> ORGANISM: Artificial
<220> FEATURE:
<223> OTHER INFORMATION: Targeting peptide sequence

<400> SEQUENCE: 184

Glu Pro His Gln Phe Asn Tyr
1 5

<210> SEQ ID NO 185
<211> LENGTH: 7
<212> TYPE: PRT
<213> ORGANISM: Artificial
<220> FEATURE:
<223> OTHER INFORMATION: Targeting peptide sequence

<400> SEQUENCE: 185

Glu Pro Gln Ser Asn His Thr
1 5

<210> SEQ ID NO 186
<211> LENGTH: 7
<212> TYPE: PRT
<213> ORGANISM: Artificial
<220> FEATURE:
<223> OTHER INFORMATION: Targeting peptide sequence

<400> SEQUENCE: 186

Met Ser Ser Trp Pro Ser Gln
1 5

<210> SEQ ID NO 187
<211> LENGTH: 7
<212> TYPE: PRT
<213> ORGANISM: Artificial
<220> FEATURE:
<223> OTHER INFORMATION: Targeting peptide sequence

<400> SEQUENCE: 187

Asn Pro Lys His Asn Ala Thr
1 5

<210> SEQ ID NO 188
<211> LENGTH: 7
<212> TYPE: PRT
<213> ORGANISM: Artificial
<220> FEATURE:
<223> OTHER INFORMATION: Targeting peptide sequence

<400> SEQUENCE: 188

Pro Asp Gly Met Arg Thr Thr
1 5

<210> SEQ ID NO 189
<211> LENGTH: 7
<212> TYPE: PRT
<213> ORGANISM: Artificial
<220> FEATURE:
<223> OTHER INFORMATION: Targeting peptide sequence

<400> SEQUENCE: 189

Pro Asn Asn Asn Lys Thr Thr
1 5

<210> SEQ ID NO 190
<211> LENGTH: 7
<212> TYPE: PRT
<213> ORGANISM: Artificial
<220> FEATURE:
<223> OTHER INFORMATION: Targeting peptide sequence

<400> SEQUENCE: 190

Gln Ser Thr Thr His Asp Ser
1 5

<210> SEQ ID NO 191
<211> LENGTH: 7
<212> TYPE: PRT
<213> ORGANISM: Artificial
<220> FEATURE:
<223> OTHER INFORMATION: Targeting peptide sequence

<400> SEQUENCE: 191

Thr Gly Ser Lys Gln Lys Gln
1 5

<210> SEQ ID NO 192
<211> LENGTH: 7
<212> TYPE: PRT
<213> ORGANISM: Artificial
<220> FEATURE:
<223> OTHER INFORMATION: Targeting peptide sequence

<400> SEQUENCE: 192

Ser Leu Lys His Gln Ala Leu
1 5

<210> SEQ ID NO 193
<211> LENGTH: 7
<212> TYPE: PRT
<213> ORGANISM: Artificial
<220> FEATURE:
<223> OTHER INFORMATION: Targeting peptide sequence

<400> SEQUENCE: 193

Ser Pro Ile Asp Gly Glu Gln
1 5

<210> SEQ ID NO 194
<211> LENGTH: 8
<212> TYPE: PRT
<213> ORGANISM: Artificial
<220> FEATURE:
<223> OTHER INFORMATION: Targeting peptide sequence

<400> SEQUENCE: 194

Trp Ile Phe Pro Trp Ile Gln Leu
1 5

<210> SEQ ID NO 195
<211> LENGTH: 9
<212> TYPE: PRT
<213> ORGANISM: Artificial
<220> FEATURE:
<223> OTHER INFORMATION: Targeting peptide sequence

<400> SEQUENCE: 195

Cys Asp Cys Arg Gly Asp Cys Phe Cys
1 5

<210> SEQ ID NO 196
<211> LENGTH: 5
<212> TYPE: PRT
<213> ORGANISM: Artificial
<220> FEATURE:
<223> OTHER INFORMATION: Targeting peptide sequence

<400> SEQUENCE: 196

Cys Asn Gly Arg Cys
1 5

<210> SEQ ID NO 197
<211> LENGTH: 7
<212> TYPE: PRT
<213> ORGANISM: Artificial
<220> FEATURE:
<223> OTHER INFORMATION: Targeting peptide sequence

<400> SEQUENCE: 197

Cys Pro Arg Glu Cys Glu Ser
1 5

<210> SEQ ID NO 198

<211> LENGTH: 10
<212> TYPE: PRT
<213> ORGANISM: Artificial
<220> FEATURE:
<223> OTHER INFORMATION: Targeting peptide sequence

<400> SEQUENCE: 198

Cys Thr Thr His Trp Gly Phe Thr Leu Cys
1               5                   10

<210> SEQ ID NO 199
<211> LENGTH: 9
<212> TYPE: PRT
<213> ORGANISM: Artificial
<220> FEATURE:
<223> OTHER INFORMATION: Targeting peptide sequence

<400> SEQUENCE: 199

Cys Gly Arg Arg Ala Gly Gly Ser Cys
1               5

<210> SEQ ID NO 200
<211> LENGTH: 9
<212> TYPE: PRT
<213> ORGANISM: Artificial
<220> FEATURE:
<223> OTHER INFORMATION: Targeting peptide sequence

<400> SEQUENCE: 200

Cys Lys Gly Gly Arg Ala Lys Asp Cys
1               5

<210> SEQ ID NO 201
<211> LENGTH: 9
<212> TYPE: PRT
<213> ORGANISM: Artificial
<220> FEATURE:
<223> OTHER INFORMATION: Targeting peptide sequence

<400> SEQUENCE: 201

Cys Val Pro Glu Leu Gly His Glu Cys
1               5

<210> SEQ ID NO 202
<211> LENGTH: 9
<212> TYPE: PRT
<213> ORGANISM: Artificial
<220> FEATURE:
<223> OTHER INFORMATION: Targeting peptide sequence

<400> SEQUENCE: 202

Cys Arg Arg Glu Thr Ala Trp Ala Lys
1               5

<210> SEQ ID NO 203
<211> LENGTH: 14
<212> TYPE: PRT
<213> ORGANISM: Artificial
<220> FEATURE:
<223> OTHER INFORMATION: Targeting peptide sequence

<400> SEQUENCE: 203

Val Ser Trp Phe Ser His Arg Tyr Ser Pro Phe Ala Val Ser
1               5                   10

<210> SEQ ID NO 204
<211> LENGTH: 13

<212> TYPE: PRT
<213> ORGANISM: Artificial
<220> FEATURE:
<223> OTHER INFORMATION: Targeting peptide sequence

<400> SEQUENCE: 204

Gly Tyr Arg Asp Gly Tyr Ala Gly Pro Ile Leu Tyr Asn
1 5 10

<210> SEQ ID NO 205
<211> LENGTH: 7
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: misc_feature
<222> LOCATION: (5)..(7)
<223> OTHER INFORMATION: Xaa can be any naturally occurring amino acid

<400> SEQUENCE: 205

Xaa Xaa Xaa Tyr Xaa Xaa Xaa
1 5

<210> SEQ ID NO 206
<211> LENGTH: 4
<212> TYPE: PRT
<213> ORGANISM: Artificial
<220> FEATURE:
<223> OTHER INFORMATION: Targeting peptide sequence
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MISC_FEATURE
<222> LOCATION: (2)..(2)
<223> OTHER INFORMATION: Xaa can be E or M

<400> SEQUENCE: 206

Tyr Xaa Asn Trp
1

<210> SEQ ID NO 207
<211> LENGTH: 7
<212> TYPE: PRT
<213> ORGANISM: Artificial
<220> FEATURE:
<223> OTHER INFORMATION: Targeting peptide sequence

<400> SEQUENCE: 207

Arg Pro Leu Pro Pro Leu Pro
1 5

<210> SEQ ID NO 208
<211> LENGTH: 7
<212> TYPE: PRT
<213> ORGANISM: Artificial
<220> FEATURE:
<223> OTHER INFORMATION: Targeting peptide sequence

<400> SEQUENCE: 208

Ala Pro Pro Leu Pro Pro Arg
1               5

<210> SEQ ID NO 209
<211> LENGTH: 12
<212> TYPE: PRT
<213> ORGANISM: Artificial
<220> FEATURE:
<223> OTHER INFORMATION: Targeting peptide sequence

<400> SEQUENCE: 209

Asp Val Phe Tyr Pro Tyr Pro Tyr Ala Ser Gly Ser
1               5                   10

<210> SEQ ID NO 210
<211> LENGTH: 6
<212> TYPE: PRT
<213> ORGANISM: Artificial
<220> FEATURE:
<223> OTHER INFORMATION: Targeting peptide sequence

<400> SEQUENCE: 210

Met Tyr Trp Tyr Pro Tyr
1               5

<210> SEQ ID NO 211
<211> LENGTH: 12
<212> TYPE: PRT
<213> ORGANISM: Artificial
<220> FEATURE:
<223> OTHER INFORMATION: Targeting peptide sequence

<400> SEQUENCE: 211

Asp Ile Thr Trp Asp Gln Leu Trp Asp Leu Met Lys
1               5                   10

<210> SEQ ID NO 212
<211> LENGTH: 8
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (5)..(5)
<223> OTHER INFORMATION: Xaa can be G or L

<400> SEQUENCE: 212

Cys Trp Asp Asp Xaa Trp Leu Cys
1               5

<210> SEQ ID NO 213
<211> LENGTH: 14
<212> TYPE: PRT
<213> ORGANISM: Artificial
<220> FEATURE:
<223> OTHER INFORMATION: Targeting peptide sequence

<400> SEQUENCE: 213

Glu Trp Cys Glu Tyr Leu Gly Gly Tyr Leu Arg Cys Tyr Ala
1               5                   10

<210> SEQ ID NO 214
<211> LENGTH: 14
<212> TYPE: PRT
<213> ORGANISM: Artificial
<220> FEATURE:
<223> OTHER INFORMATION: Targeting peptide sequence

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 214

Tyr Xaa Cys Xaa Xaa Gly Pro Xaa Thr Trp Xaa Cys Xaa Pro
1               5                   10


<210> SEQ ID NO 215
<211> LENGTH: 14
<212> TYPE: PRT
<213> ORGANISM: Artificial
<220> FEATURE:
<223> OTHER INFORMATION: Targeting peptide sequence

<400> SEQUENCE: 215

Ile Glu Gly Pro Thr Leu Arg Gln Trp Leu Ala Ala Arg Ala
1               5                   10


<210> SEQ ID NO 216
<211> LENGTH: 5
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Y, W, F or H

<400> SEQUENCE: 216

Leu Trp Xaa Xaa Xaa
1               5


<210> SEQ ID NO 217
<211> LENGTH: 7
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 217

Xaa Phe Xaa Xaa Tyr Leu Trp
```

1 5

<210> SEQ ID NO 218
<211> LENGTH: 13
<212> TYPE: PRT
<213> ORGANISM: Artificial
<220> FEATURE:
<223> OTHER INFORMATION: Targeting peptide sequence

<400> SEQUENCE: 218

Ser Ser Ile Ile Ser His Phe Arg Trp Gly Leu Cys Asp
1 5 10

<210> SEQ ID NO 219
<211> LENGTH: 13
<212> TYPE: PRT
<213> ORGANISM: Artificial
<220> FEATURE:
<223> OTHER INFORMATION: Targeting peptide sequence

<400> SEQUENCE: 219

Met Ser Arg Pro Ala Cys Pro Pro Asn Asp Lys Tyr Glu
1 5 10

<210> SEQ ID NO 220
<211> LENGTH: 8
<212> TYPE: PRT
<213> ORGANISM: Artificial
<220> FEATURE:
<223> OTHER INFORMATION: Targeting peptide sequence

<400> SEQUENCE: 220

Cys Leu Arg Ser Gly Arg Gly Cys
1 5

<210> SEQ ID NO 221
<211> LENGTH: 9
<212> TYPE: PRT
<213> ORGANISM: Artificial
<220> FEATURE:
<223> OTHER INFORMATION: Targeting peptide sequence

<400> SEQUENCE: 221

Cys His Trp Met Phe Ser Pro Trp Cys
1 5

<210> SEQ ID NO 222
<211> LENGTH: 4
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 222

Trp Xaa Xaa Phe
1

<210> SEQ ID NO 223
<211> LENGTH: 8
<212> TYPE: PRT
<213> ORGANISM: Artificial
<220> FEATURE:
<223> OTHER INFORMATION: Targeting peptide sequence

<400> SEQUENCE: 223

Cys Ser Ser Arg Leu Asp Ala Cys
1 5

<210> SEQ ID NO 224
<211> LENGTH: 7
<212> TYPE: PRT
<213> ORGANISM: Artificial
<220> FEATURE:
<223> OTHER INFORMATION: Targeting peptide sequence

<400> SEQUENCE: 224

Cys Leu Pro Val Ala Ser Cys
1 5

<210> SEQ ID NO 225
<211> LENGTH: 13
<212> TYPE: PRT
<213> ORGANISM: Artificial
<220> FEATURE:
<223> OTHER INFORMATION: Targeting peptide sequence

<400> SEQUENCE: 225

Cys Gly Phe Glu Cys Val Arg Gln Cys Pro Glu Arg Cys
1 5 10

<210> SEQ ID NO 226
<211> LENGTH: 13
<212> TYPE: PRT
<213> ORGANISM: Artificial
<220> FEATURE:
<223> OTHER INFORMATION: Targeting peptide sequence

<400> SEQUENCE: 226

Cys Val Ala Leu Cys Arg Glu Ala Cys Gly Glu Gly Cys
1 5 10

<210> SEQ ID NO 227
<211> LENGTH: 9
<212> TYPE: PRT
<213> ORGANISM: Artificial
<220> FEATURE:
<223> OTHER INFORMATION: Targeting peptide sequence

<400> SEQUENCE: 227

Ser Trp Cys Glu Pro Gly Trp Cys Arg
1 5

<210> SEQ ID NO 228
<211> LENGTH: 7
<212> TYPE: PRT
<213> ORGANISM: Artificial
<220> FEATURE:
<223> OTHER INFORMATION: Targeting peptide sequence

<400> SEQUENCE: 228

Tyr Ser Gly Lys Trp Gly Trp
1 5

<210> SEQ ID NO 229
<211> LENGTH: 7
<212> TYPE: PRT
<213> ORGANISM: Artificial
<220> FEATURE:
<223> OTHER INFORMATION: Targeting peptide sequence

<400> SEQUENCE: 229

Gly Leu Ser Gly Gly Arg Ser
1 5

<210> SEQ ID NO 230
<211> LENGTH: 7
<212> TYPE: PRT
<213> ORGANISM: Artificial
<220> FEATURE:
<223> OTHER INFORMATION: Targeting peptide sequence

<400> SEQUENCE: 230

Leu Met Leu Pro Arg Ala Asp
1 5

<210> SEQ ID NO 231
<211> LENGTH: 9
<212> TYPE: PRT
<213> ORGANISM: Artificial
<220> FEATURE:
<223> OTHER INFORMATION: Targeting peptide sequence

<400> SEQUENCE: 231

Cys Ser Cys Phe Arg Asp Val Cys Cys
1 5

<210> SEQ ID NO 232
<211> LENGTH: 9
<212> TYPE: PRT
<213> ORGANISM: Artificial
<220> FEATURE:
<223> OTHER INFORMATION: Targeting peptide sequence

<400> SEQUENCE: 232

Cys Arg Asp Val Val Ser Val Ile Cys
1 5

<210> SEQ ID NO 233
<211> LENGTH: 5
<212> TYPE: PRT
<213> ORGANISM: Artificial
<220> FEATURE:
<223> OTHER INFORMATION: Targeting peptide sequence

<400> SEQUENCE: 233

Cys Asn Gly Arg Cys
1 5

<210> SEQ ID NO 234
<211> LENGTH: 6
<212> TYPE: PRT
<213> ORGANISM: Artificial
<220> FEATURE:
<223> OTHER INFORMATION: Targeting peptide sequence

<400> SEQUENCE: 234

Met Ala Arg Ser Gly Leu
1 5

<210> SEQ ID NO 235
<211> LENGTH: 6
<212> TYPE: PRT
<213> ORGANISM: Artificial
<220> FEATURE:
<223> OTHER INFORMATION: Targeting peptide sequence

<400> SEQUENCE: 235

Met Ala Arg Ala Lys Glu
1 5

<210> SEQ ID NO 236
<211> LENGTH: 6
<212> TYPE: PRT
<213> ORGANISM: Artificial
<220> FEATURE:
<223> OTHER INFORMATION: Targeting peptide sequence

<400> SEQUENCE: 236

Met Ser Arg Thr Met Ser
1 5

<210> SEQ ID NO 237
<211> LENGTH: 6
<212> TYPE: PRT
<213> ORGANISM: Artificial
<220> FEATURE:
<223> OTHER INFORMATION: Targeting peptide sequence

<400> SEQUENCE: 237

Lys Cys Cys Tyr Ser Leu
1 5

<210> SEQ ID NO 238
<211> LENGTH: 14
<212> TYPE: PRT
<213> ORGANISM: Artificial
<220> FEATURE:
<223> OTHER INFORMATION: Targeting peptide sequence

<400> SEQUENCE: 238

Met Tyr Trp Gly Asp Ser His Trp Leu Gln Tyr Trp Tyr Glu
1 5 10

<210> SEQ ID NO 239
<211> LENGTH: 7
<212> TYPE: PRT
<213> ORGANISM: Artificial
<220> FEATURE:
<223> OTHER INFORMATION: Targeting peptide sequence

<400> SEQUENCE: 239

Met Gln Leu Pro Leu Ala Thr
1 5

<210> SEQ ID NO 240
<211> LENGTH: 4
<212> TYPE: PRT
<213> ORGANISM: Artificial
<220> FEATURE:
<223> OTHER INFORMATION: Targeting peptide sequence

<400> SEQUENCE: 240

Glu Trp Leu Ser
1

<210> SEQ ID NO 241
<211> LENGTH: 4
<212> TYPE: PRT
<213> ORGANISM: Artificial
<220> FEATURE:
<223> OTHER INFORMATION: Targeting peptide sequence

<400> SEQUENCE: 241

Ser Asn Glu Trp

1

<210> SEQ ID NO 242
<211> LENGTH: 4
<212> TYPE: PRT
<213> ORGANISM: Artificial
<220> FEATURE:
<223> OTHER INFORMATION: Targeting peptide sequence

<400> SEQUENCE: 242

Thr Asn Tyr Leu
1

<210> SEQ ID NO 243
<211> LENGTH: 8
<212> TYPE: PRT
<213> ORGANISM: Artificial
<220> FEATURE:
<223> OTHER INFORMATION: Targeting peptide sequence

<400> SEQUENCE: 243

Trp Ile Phe Pro Trp Ile Gln Leu
1 5

<210> SEQ ID NO 244
<211> LENGTH: 12
<212> TYPE: PRT
<213> ORGANISM: Artificial
<220> FEATURE:
<223> OTHER INFORMATION: Targeting peptide sequence

<400> SEQUENCE: 244

Trp Asp Leu Ala Trp Met Phe Arg Leu Pro Val Gly
1 5 10

<210> SEQ ID NO 245
<211> LENGTH: 13
<212> TYPE: PRT
<213> ORGANISM: Artificial
<220> FEATURE:
<223> OTHER INFORMATION: Targeting peptide sequence

<400> SEQUENCE: 245

Cys Thr Val Ala Leu Pro Gly Gly Tyr Val Arg Val Cys
1 5 10

<210> SEQ ID NO 246
<211> LENGTH: 9
<212> TYPE: PRT
<213> ORGANISM: Artificial
<220> FEATURE:
<223> OTHER INFORMATION: Targeting peptide sequence

<400> SEQUENCE: 246

Cys Val Pro Glu Leu Gly His Glu Cys
1 5

<210> SEQ ID NO 247
<211> LENGTH: 9
<212> TYPE: PRT
<213> ORGANISM: Artificial
<220> FEATURE:
<223> OTHER INFORMATION: Targeting peptide sequence

<400> SEQUENCE: 247

Cys Gly Arg Arg Ala Gly Gly Ser Cys
1 5

<210> SEQ ID NO 248
<211> LENGTH: 13
<212> TYPE: PRT
<213> ORGANISM: Artificial
<220> FEATURE:
<223> OTHER INFORMATION: Targeting peptide sequence

<400> SEQUENCE: 248

Cys Val Ala Tyr Cys Ile Glu His His Cys Trp Thr Cys
1 5 10

<210> SEQ ID NO 249
<211> LENGTH: 12
<212> TYPE: PRT
<213> ORGANISM: Artificial
<220> FEATURE:
<223> OTHER INFORMATION: Targeting peptide sequence

<400> SEQUENCE: 249

Cys Val Phe Ala His Asn Tyr Asp Tyr Leu Val Cys
1 5 10

<210> SEQ ID NO 250
<211> LENGTH: 10
<212> TYPE: PRT
<213> ORGANISM: Artificial
<220> FEATURE:
<223> OTHER INFORMATION: Targeting peptide sequence

<400> SEQUENCE: 250

Cys Val Phe Thr Ser Asn Tyr Ala Phe Cys
1 5 10

<210> SEQ ID NO 251
<211> LENGTH: 7
<212> TYPE: PRT
<213> ORGANISM: Artificial
<220> FEATURE:
<223> OTHER INFORMATION: Targeting peptide sequence

<400> SEQUENCE: 251

Val His Ser Pro Asn Lys Lys
1 5

<210> SEQ ID NO 252
<211> LENGTH: 9
<212> TYPE: PRT
<213> ORGANISM: Artificial
<220> FEATURE:
<223> OTHER INFORMATION: Targeting peptide sequence

<400> SEQUENCE: 252

Cys Asp Cys Arg Gly Asp Cys Phe Cys
1 5

<210> SEQ ID NO 253
<211> LENGTH: 7
<212> TYPE: PRT
<213> ORGANISM: Artificial
<220> FEATURE:
<223> OTHER INFORMATION: Targeting peptide sequence

<400> SEQUENCE: 253

Cys Arg Gly Asp Gly Trp Cys
1 5

<210> SEQ ID NO 254
<211> LENGTH: 6
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 254

Xaa Arg Gly Cys Asp Xaa
1 5

<210> SEQ ID NO 255
<211> LENGTH: 4
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be S or T

<400> SEQUENCE: 255

Pro Xaa Xaa Xaa
1

<210> SEQ ID NO 256
<211> LENGTH: 10
<212> TYPE: PRT
<213> ORGANISM: Artificial
<220> FEATURE:
<223> OTHER INFORMATION: Targeting peptide sequence

<400> SEQUENCE: 256

Cys Thr Thr His Trp Gly Phe Thr Leu Cys
1 5 10

<210> SEQ ID NO 257
<211> LENGTH: 11
<212> TYPE: PRT
<213> ORGANISM: Artificial
<220> FEATURE:
<223> OTHER INFORMATION: Targeting peptide sequence

<400> SEQUENCE: 257

Ser Gly Lys Gly Pro Arg Gln Ile Thr Ala Leu
1 5 10

<210> SEQ ID NO 258
<211> LENGTH: 6
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (2)..(2)
<223> OTHER INFORMATION: Xaa can be A or Q
<220> FEATURE:
<221> NAME/KEY: MISC_FEATURE
<222> LOCATION: (3)..(3)
<223> OTHER INFORMATION: Xaa can be N or A
<220> FEATURE:
<221> NAME/KEY: MISC_FEATURE
<222> LOCATION: (4)..(4)
<223> OTHER INFORMATION: Xaa can be L or Y
<220> FEATURE:
<221> NAME/KEY: MISC_FEATURE
<222> LOCATION: (5)..(5)
<223> OTHER INFORMATION: Xaa can be T, V, M or R
<220> FEATURE:
<221> NAME/KEY: MISC_FEATURE
<222> LOCATION: (6)..(6)
<223> OTHER INFORMATION: Xaa can be R or K

<400> SEQUENCE: 258

Ala Xaa Xaa Xaa Xaa Xaa
1               5

<210> SEQ ID NO 259
<211> LENGTH: 6
<212> TYPE: PRT
<213> ORGANISM: Artificial
<220> FEATURE:
<223> OTHER INFORMATION: Targeting peptide sequence

<400> SEQUENCE: 259

Val Tyr Met Ser Pro Phe
1               5

<210> SEQ ID NO 260
<211> LENGTH: 7
<212> TYPE: PRT
<213> ORGANISM: Artificial
<220> FEATURE:
<223> OTHER INFORMATION: Targeting peptide sequence

<400> SEQUENCE: 260

Met Gln Leu Pro Leu Ala Thr
1               5

<210> SEQ ID NO 261
<211> LENGTH: 7
<212> TYPE: PRT
<213> ORGANISM: Artificial
<220> FEATURE:
<223> OTHER INFORMATION: Targeting peptide sequence

<400> SEQUENCE: 261

Ala Thr Trp Leu Pro Pro Arg
1               5

<210> SEQ ID NO 262
<211> LENGTH: 12
<212> TYPE: PRT
<213> ORGANISM: Artificial
<220> FEATURE:
<223> OTHER INFORMATION: Targeting peptide sequence

<400> SEQUENCE: 262

His Thr Met Tyr Tyr His His Tyr Gln His His Leu
1               5                   10

<210> SEQ ID NO 263
<211> LENGTH: 19
<212> TYPE: PRT
<213> ORGANISM: Artificial

<220> FEATURE:
<223> OTHER INFORMATION: Targeting peptide sequence

<400> SEQUENCE: 263

Ser Glu Val Gly Cys Arg Ala Gly Pro Leu Gln Trp Leu Cys Glu Lys
1 5 10 15

Tyr Phe Gly

<210> SEQ ID NO 264
<211> LENGTH: 18
<212> TYPE: PRT
<213> ORGANISM: Artificial
<220> FEATURE:
<223> OTHER INFORMATION: Targeting peptide sequence

<400> SEQUENCE: 264

Cys Gly Leu Leu Pro Val Gly Arg Pro Asp Arg Asn Val Trp Arg Trp
1 5 10 15

Leu Cys

<210> SEQ ID NO 265
<211> LENGTH: 15
<212> TYPE: PRT
<213> ORGANISM: Artificial
<220> FEATURE:
<223> OTHER INFORMATION: Targeting peptide sequence

<400> SEQUENCE: 265

Cys Lys Gly Gln Cys Asp Arg Phe Lys Gly Leu Pro Trp Glu Cys
1 5 10 15

<210> SEQ ID NO 266
<211> LENGTH: 5
<212> TYPE: PRT
<213> ORGANISM: Artificial
<220> FEATURE:
<223> OTHER INFORMATION: Targeting peptide sequence

<400> SEQUENCE: 266

Ser Gly Arg Ser Ala
1 5

<210> SEQ ID NO 267
<211> LENGTH: 4
<212> TYPE: PRT
<213> ORGANISM: Artificial
<220> FEATURE:
<223> OTHER INFORMATION: Targeting peptide sequence

<400> SEQUENCE: 267

Trp Gly Phe Pro
1

<210> SEQ ID NO 268
<211> LENGTH: 7
<212> TYPE: PRT
<213> ORGANISM: Artificial
<220> FEATURE:
<223> OTHER INFORMATION: Targeting peptide sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 268

Xaa Phe Xaa Xaa Tyr Leu Trp
1 5

<210> SEQ ID NO 269
<211> LENGTH: 17
<212> TYPE: PRT
<213> ORGANISM: Artificial
<220> FEATURE:
<223> OTHER INFORMATION: Targeting peptide sequence

<400> SEQUENCE: 269

Ala Glu Pro Met Pro His Ser Leu Asn Phe Ser Gln Tyr Leu Trp Tyr
1 5 10 15

Thr

<210> SEQ ID NO 270
<211> LENGTH: 6
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (4)..(4)
<223> OTHER INFORMATION: Xaa can be W or F

<400> SEQUENCE: 270

Trp Ala Tyr Xaa Ser Pro
1 5

<210> SEQ ID NO 271
<211> LENGTH: 7
<212> TYPE: PRT
<213> ORGANISM: Artificial
<220> FEATURE:
<223> OTHER INFORMATION: Targeting peptide sequence

<400> SEQUENCE: 271

Ile Glu Leu Leu Gln Ala Arg
1 5

<210> SEQ ID NO 272
<211> LENGTH: 12
<212> TYPE: PRT
<213> ORGANISM: Artificial
<220> FEATURE:
<223> OTHER INFORMATION: Targeting peptide sequence

<400> SEQUENCE: 272

Asp Ile Thr Trp Asp Gln Leu Trp Asp Leu Met Lys
1 5 10

<210> SEQ ID NO 273
<211> LENGTH: 16
<212> TYPE: PRT
<213> ORGANISM: Artificial
<220> FEATURE:
<223> OTHER INFORMATION: Targeting peptide sequence

<400> SEQUENCE: 273

Ala Tyr Thr Lys Cys Ser Arg Gln Trp Arg Thr Cys Met Thr Thr His
1 5 10 15

<210> SEQ ID NO 274

-continued

<211> LENGTH: 15
<212> TYPE: PRT
<213> ORGANISM: Artificial
<220> FEATURE:
<223> OTHER INFORMATION: Targeting peptide sequence

<400> SEQUENCE: 274

Pro Gln Asn Ser Lys Ile Pro Gly Pro Thr Phe Leu Asp Pro His
1 5 10 15

<210> SEQ ID NO 275
<211> LENGTH: 15
<212> TYPE: PRT
<213> ORGANISM: Artificial
<220> FEATURE:
<223> OTHER INFORMATION: Targeting peptide sequence

<400> SEQUENCE: 275

Ser Met Glu Pro Ala Leu Pro Asp Trp Trp Trp Lys Met Phe Lys
1 5 10 15

<210> SEQ ID NO 276
<211> LENGTH: 16
<212> TYPE: PRT
<213> ORGANISM: Artificial
<220> FEATURE:
<223> OTHER INFORMATION: Targeting peptide sequence

<400> SEQUENCE: 276

Ala Asn Thr Pro Cys Gly Pro Tyr Thr His Asp Cys Pro Val Lys Arg
1 5 10 15

<210> SEQ ID NO 277
<211> LENGTH: 12
<212> TYPE: PRT
<213> ORGANISM: Artificial
<220> FEATURE:
<223> OTHER INFORMATION: Targeting peptide sequence

<400> SEQUENCE: 277

Thr Ala Cys His Gln His Val Arg Met Val Arg Pro
1 5 10

<210> SEQ ID NO 278
<211> LENGTH: 12
<212> TYPE: PRT
<213> ORGANISM: Artificial
<220> FEATURE:
<223> OTHER INFORMATION: Targeting peptide sequence

<400> SEQUENCE: 278

Val Pro Trp Met Glu Pro Ala Tyr Gln Arg Phe Leu
1 5 10

<210> SEQ ID NO 279
<211> LENGTH: 8
<212> TYPE: PRT
<213> ORGANISM: Artificial
<220> FEATURE:
<223> OTHER INFORMATION: Targeting peptide sequence

<400> SEQUENCE: 279

Asp Pro Arg Ala Thr Pro Gly Ser
1 5

<210> SEQ ID NO 280
<211> LENGTH: 12

<212> TYPE: PRT
<213> ORGANISM: Artificial
<220> FEATURE:
<223> OTHER INFORMATION: Targeting peptide sequence

<400> SEQUENCE: 280

Phe Arg Pro Asn Arg Ala Gln Asp Tyr Asn Thr Asn
1 5 10

<210> SEQ ID NO 281
<211> LENGTH: 9
<212> TYPE: PRT
<213> ORGANISM: Artificial
<220> FEATURE:
<223> OTHER INFORMATION: Targeting peptide sequence

<400> SEQUENCE: 281

Cys Thr Lys Asn Ser Tyr Leu Met Cys
1 5

<210> SEQ ID NO 282
<211> LENGTH: 11
<212> TYPE: PRT
<213> ORGANISM: Artificial
<220> FEATURE:
<223> OTHER INFORMATION: Targeting peptide sequence
<220> FEATURE:
<221> NAME/KEY: MISC_FEATURE
<222> LOCATION: (2)..(2)
<223> OTHER INFORMATION: Xaa can be R or Q
<220> FEATURE:
<221> NAME/KEY: MISC_FEATURE
<222> LOCATION: (3)..(3)
<223> OTHER INFORMATION: Xaa can be L or R
<220> FEATURE:
<221> NAME/KEY: MISC_FEATURE
<222> LOCATION: (5)..(5)
<223> OTHER INFORMATION: Xaa can be G or N
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be A or V

<400> SEQUENCE: 282

Cys Xaa Xaa Thr Xaa Xaa Xaa Gly Xaa Gly Cys
1 5 10

<210> SEQ ID NO 283
<211> LENGTH: 9
<212> TYPE: PRT
<213> ORGANISM: Artificial
<220> FEATURE:
<223> OTHER INFORMATION: Targeting peptide sequence

<400> SEQUENCE: 283

Cys Pro Ile Glu Asp Arg Pro Met Cys
1 5

<210> SEQ ID NO 284
<211> LENGTH: 12
<212> TYPE: PRT
<213> ORGANISM: Artificial
<220> FEATURE:
<223> OTHER INFORMATION: Targeting peptide sequence

<400> SEQUENCE: 284

-continued

His Glu Trp Ser Tyr Leu Ala Pro Tyr Pro Trp Phe
1               5                   10

<210> SEQ ID NO 285
<211> LENGTH: 9
<212> TYPE: PRT
<213> ORGANISM: Artificial
<220> FEATURE:
<223> OTHER INFORMATION: Targeting peptide sequence

<400> SEQUENCE: 285

Met Cys Pro Lys His Pro Leu Gly Cys
1               5

<210> SEQ ID NO 286
<211> LENGTH: 15
<212> TYPE: PRT
<213> ORGANISM: Artificial
<220> FEATURE:
<223> OTHER INFORMATION: Targeting peptide sequence

<400> SEQUENCE: 286

Arg Met Trp Pro Ser Ser Thr Val Asn Leu Ser Ala Gly Arg Arg
1               5                   10                  15

<210> SEQ ID NO 287
<211> LENGTH: 20
<212> TYPE: PRT
<213> ORGANISM: Artificial
<220> FEATURE:
<223> OTHER INFORMATION: Targeting peptide sequence

<400> SEQUENCE: 287

Ser Ala Lys Thr Ala Val Ser Gln Arg Val Trp Leu Pro Ser His Arg
1               5                   10                  15

Gly Gly Glu Pro
            20

<210> SEQ ID NO 288
<211> LENGTH: 20
<212> TYPE: PRT
<213> ORGANISM: Artificial
<220> FEATURE:
<223> OTHER INFORMATION: Targeting peptide sequence

<400> SEQUENCE: 288

Lys Ser Arg Glu His Val Asn Asn Ser Ala Cys Pro Ser Lys Arg Ile
1               5                   10                  15

Thr Ala Ala Leu
            20

<210> SEQ ID NO 289
<211> LENGTH: 4
<212> TYPE: PRT
<213> ORGANISM: Artificial
<220> FEATURE:
<223> OTHER INFORMATION: Targeting peptide sequence

<400> SEQUENCE: 289

Glu Gly Phe Arg
1

<210> SEQ ID NO 290
<211> LENGTH: 6
<212> TYPE: PRT
<213> ORGANISM: Artificial

<220> FEATURE:
<223> OTHER INFORMATION: Targeting peptide sequence

<400> SEQUENCE: 290

Ala Gly Leu Gly Val Arg
1               5

<210> SEQ ID NO 291
<211> LENGTH: 15
<212> TYPE: PRT
<213> ORGANISM: Artificial
<220> FEATURE:
<223> OTHER INFORMATION: Targeting peptide sequence

<400> SEQUENCE: 291

Gly Thr Arg Gln Gly His Thr Met Arg Leu Gly Val Ser Asp Gly
1               5                   10                  15

<210> SEQ ID NO 292
<211> LENGTH: 15
<212> TYPE: PRT
<213> ORGANISM: Artificial
<220> FEATURE:
<223> OTHER INFORMATION: Targeting peptide sequence

<400> SEQUENCE: 292

Ile Ala Gly Leu Ala Thr Pro Gly Trp Ser His Trp Leu Ala Leu
1               5                   10                  15

<210> SEQ ID NO 293
<211> LENGTH: 7
<212> TYPE: PRT
<213> ORGANISM: Artificial
<220> FEATURE:
<223> OTHER INFORMATION: Targeting peptide sequence

<400> SEQUENCE: 293

Ser Met Ser Ile Ala Arg Leu
1               5

<210> SEQ ID NO 294
<211> LENGTH: 7
<212> TYPE: PRT
<213> ORGANISM: Artificial
<220> FEATURE:
<223> OTHER INFORMATION: Targeting peptide sequence

<400> SEQUENCE: 294

His Thr Phe Glu Pro Gly Val
1               5

<210> SEQ ID NO 295
<211> LENGTH: 15
<212> TYPE: PRT
<213> ORGANISM: Artificial
<220> FEATURE:
<223> OTHER INFORMATION: Targeting peptide sequence

<400> SEQUENCE: 295

Asn Thr Ser Leu Lys Arg Ile Ser Asn Lys Arg Ile Arg Arg Lys
1               5                   10                  15

<210> SEQ ID NO 296
<211> LENGTH: 15
<212> TYPE: PRT
<213> ORGANISM: Artificial
<220> FEATURE:

<223> OTHER INFORMATION: Targeting peptide sequence

<400> SEQUENCE: 296

Leu Arg Ile Lys Arg Lys Arg Arg Lys Arg Lys Lys Thr Arg Lys
1 5 10 15

<210> SEQ ID NO 297
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 297

Cys Asn Asp Glu Met Gln Val Gln Val Asn
1 5 10

<210> SEQ ID NO 298
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 298

Ser Pro Asp Ile Val Tyr Ala Asp Val Cys
1 5 10

<210> SEQ ID NO 299
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 299

Leu Asp Asp Cys His Asn Ile Asp Val Asn
1 5 10

<210> SEQ ID NO 300
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 300

Ser Cys Asp Cys Val Thr Asn Ser Val Ser
1 5 10

<210> SEQ ID NO 301
<211> LENGTH: 10
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 301

Thr Val Asp Ser Asn Pro Tyr Glu Val Asn
1 5 10

<210> SEQ ID NO 302

<211> LENGTH: 10
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 302

Gly Asp Asp His Pro Asn Pro Asp Val Leu
1 5 10

<210> SEQ ID NO 303
<211> LENGTH: 7
<212> TYPE: PRT
<213> ORGANISM: adeno-associated virus

<400> SEQUENCE: 303

Ser Ala Ser Thr Gly Ala Ser
1 5

<210> SEQ ID NO 304
<211> LENGTH: 10
<212> TYPE: PRT
<213> ORGANISM: adeno-associated virus

<400> SEQUENCE: 304

Val Phe Met Ile Pro Gln Tyr Gly Tyr Leu
1 5 10

<210> SEQ ID NO 305
<211> LENGTH: 9
<212> TYPE: PRT
<213> ORGANISM: adeno-associated virus

<400> SEQUENCE: 305

Asn Gln Ser Gly Ser Ala Gln Asn Lys
1 5

<210> SEQ ID NO 306
<211> LENGTH: 8
<212> TYPE: PRT
<213> ORGANISM: adeno-associated virus

<400> SEQUENCE: 306

Lys Thr Asp Asn Asn Asn Ser Asn
1 5

<210> SEQ ID NO 307
<211> LENGTH: 7
<212> TYPE: PRT
<213> ORGANISM: adeno-associated virus

<400> SEQUENCE: 307

Lys Asp Asp Glu Asp Lys Phe
1 5

<210> SEQ ID NO 308
<211> LENGTH: 6
<212> TYPE: PRT
<213> ORGANISM: adeno-associated virus

<400> SEQUENCE: 308

Ser Ala Gly Ala Ser Asn
1 5

<210> SEQ ID NO 309
<211> LENGTH: 10
<212> TYPE: PRT
<213> ORGANISM: adeno-associated virus

<400> SEQUENCE: 309

Ser Thr Asp Pro Ala Thr Gly Asp Val His
1 5 10

<210> SEQ ID NO 310
<211> LENGTH: 7
<212> TYPE: PRT
<213> ORGANISM: adeno-associated virus

<400> SEQUENCE: 310

Asp Asn Asn Gly Leu Tyr Thr
1 5

<210> SEQ ID NO 311
<211> LENGTH: 6
<212> TYPE: PRT
<213> ORGANISM: adeno-associated virus

<400> SEQUENCE: 311

Ser Gln Ser Gly Ala Ser
1 5

<210> SEQ ID NO 312
<211> LENGTH: 10
<212> TYPE: PRT
<213> ORGANISM: adeno-associated virus

<400> SEQUENCE: 312

Val Phe Met Val Pro Gln Tyr Gly Tyr Leu
1 5 10

<210> SEQ ID NO 313
<211> LENGTH: 9
<212> TYPE: PRT
<213> ORGANISM: adeno-associated virus

<400> SEQUENCE: 313

Thr Pro Ser Gly Thr Thr Thr Gln Ser
1 5

<210> SEQ ID NO 314
<211> LENGTH: 8
<212> TYPE: PRT
<213> ORGANISM: adeno-associated virus

<400> SEQUENCE: 314

Ser Ala Asp Asn Asn Asn Ser Glu
1 5

<210> SEQ ID NO 315
<211> LENGTH: 7
<212> TYPE: PRT
<213> ORGANISM: adeno-associated virus

<400> SEQUENCE: 315

Lys Asp Asp Glu Glu Lys Phe
1 5

<210> SEQ ID NO 316
<211> LENGTH: 6

<212> TYPE: PRT
<213> ORGANISM: adeno-associated virus

<400> SEQUENCE: 316

Gly Ser Glu Lys Thr Asn
1 5

<210> SEQ ID NO 317
<211> LENGTH: 10
<212> TYPE: PRT
<213> ORGANISM: adeno-associated virus

<400> SEQUENCE: 317

Asn Arg Gln Ala Ala Thr Ala Asp Val Asn
1 5 10

<210> SEQ ID NO 318
<211> LENGTH: 7
<212> TYPE: PRT
<213> ORGANISM: adeno-associated virus

<400> SEQUENCE: 318

Asp Thr Asn Gly Val Tyr Ser
1 5

<210> SEQ ID NO 319
<211> LENGTH: 6
<212> TYPE: PRT
<213> ORGANISM: adeno-associated virus

<400> SEQUENCE: 319

Ser Gln Ser Gly Ala Ser
1 5

<210> SEQ ID NO 320
<211> LENGTH: 10
<212> TYPE: PRT
<213> ORGANISM: adeno-associated virus

<400> SEQUENCE: 320

Val Phe Met Val Pro Gln Tyr Gly Tyr Leu
1 5 10

<210> SEQ ID NO 321
<211> LENGTH: 9
<212> TYPE: PRT
<213> ORGANISM: adeno-associated virus

<400> SEQUENCE: 321

Thr Thr Ser Gly Thr Thr Asn Gln Ser
1 5

<210> SEQ ID NO 322
<211> LENGTH: 8
<212> TYPE: PRT
<213> ORGANISM: adeno-associated virus

<400> SEQUENCE: 322

Ala Asn Asp Asn Asn Asn Ser Asn
1 5

<210> SEQ ID NO 323
<211> LENGTH: 7
<212> TYPE: PRT
<213> ORGANISM: adeno-associated virus

<400> SEQUENCE: 323

Lys Asp Asp Glu Glu Lys Phe
1               5

<210> SEQ ID NO 324
<211> LENGTH: 6
<212> TYPE: PRT
<213> ORGANISM: adeno-associated virus

<400> SEQUENCE: 324

Gly Thr Thr Ala Ser Asn
1               5

<210> SEQ ID NO 325
<211> LENGTH: 10
<212> TYPE: PRT
<213> ORGANISM: adeno-associated virus

<400> SEQUENCE: 325

Asn Thr Ala Pro Thr Thr Gly Thr Val Asn
1               5                   10

<210> SEQ ID NO 326
<211> LENGTH: 7
<212> TYPE: PRT
<213> ORGANISM: adeno-associated virus

<400> SEQUENCE: 326

Asp Thr Asn Gly Val Tyr Ser
1               5

<210> SEQ ID NO 327
<211> LENGTH: 8
<212> TYPE: PRT
<213> ORGANISM: adeno-associated virus

<400> SEQUENCE: 327

Arg Leu Gly Glu Ser Leu Gln Ser
1               5

<210> SEQ ID NO 328
<211> LENGTH: 10
<212> TYPE: PRT
<213> ORGANISM: adeno-associated virus

<400> SEQUENCE: 328

Val Phe Met Val Pro Gln Tyr Gly Tyr Cys
1               5                   10

<210> SEQ ID NO 329
<211> LENGTH: 9
<212> TYPE: PRT
<213> ORGANISM: adeno-associated virus

<400> SEQUENCE: 329

Gly Thr Thr Leu Asn Ala Gly Thr Ala
1               5

<210> SEQ ID NO 330
<211> LENGTH: 12
<212> TYPE: PRT
<213> ORGANISM: adeno-associated virus

<400> SEQUENCE: 330

Ala Asn Gln Asn Tyr Lys Ile Pro Ala Thr Gly Ser
1 5 10

<210> SEQ ID NO 331
<211> LENGTH: 7
<212> TYPE: PRT
<213> ORGANISM: adeno-associated virus

<400> SEQUENCE: 331

Gly Pro Ala Asp Ser Lys Phe
1 5

<210> SEQ ID NO 332
<211> LENGTH: 6
<212> TYPE: PRT
<213> ORGANISM: adeno-associated virus

<400> SEQUENCE: 332

Gln Asn Gly Asn Thr Ala
1 5

<210> SEQ ID NO 333
<211> LENGTH: 10
<212> TYPE: PRT
<213> ORGANISM: adeno-associated virus

<400> SEQUENCE: 333

Ser Asn Leu Pro Thr Val Asp Arg Leu Thr
1 5 10

<210> SEQ ID NO 334
<211> LENGTH: 7
<212> TYPE: PRT
<213> ORGANISM: adeno-associated virus

<400> SEQUENCE: 334

Asp Ala Ala Gly Lys Tyr Thr
1 5

<210> SEQ ID NO 335
<211> LENGTH: 10
<212> TYPE: PRT
<213> ORGANISM: adeno-associated virus

<400> SEQUENCE: 335

Glu Ile Lys Ser Gly Ser Val Asp Gly Ser
1 5 10

<210> SEQ ID NO 336
<211> LENGTH: 10
<212> TYPE: PRT
<213> ORGANISM: adeno-associated virus

<400> SEQUENCE: 336

Val Phe Thr Leu Pro Gln Tyr Gly Tyr Ala
1 5 10

<210> SEQ ID NO 337
<211> LENGTH: 9
<212> TYPE: PRT
<213> ORGANISM: adeno-associated virus

<400> SEQUENCE: 337

Ser Thr Asn Asn Thr Gly Gly Val Gln 1 5

<210> SEQ ID NO 338
<211> LENGTH: 7
<212> TYPE: PRT
<213> ORGANISM: adeno-associated virus

<400> SEQUENCE: 338

Ser Gly Val Asn Arg Ala Ser
1 5

<210> SEQ ID NO 339
<211> LENGTH: 7
<212> TYPE: PRT
<213> ORGANISM: adeno-associated virus

<400> SEQUENCE: 339

Leu Gln Gly Ser Asn Thr Tyr
1 5

<210> SEQ ID NO 340
<211> LENGTH: 8
<212> TYPE: PRT
<213> ORGANISM: adeno-associated virus

<400> SEQUENCE: 340

Ala Asn Pro Gly Thr Thr Ala Thr
1 5

<210> SEQ ID NO 341
<211> LENGTH: 10
<212> TYPE: PRT
<213> ORGANISM: adeno-associated virus

<400> SEQUENCE: 341

Thr Thr Ala Pro Ala Thr Gly Thr Tyr Asn
1 5 10

<210> SEQ ID NO 342
<211> LENGTH: 7
<212> TYPE: PRT
<213> ORGANISM: adeno-associated virus

<400> SEQUENCE: 342

Asp Ser Thr Gly Glu Tyr Arg
1 5

<210> SEQ ID NO 343
<211> LENGTH: 7
<212> TYPE: PRT
<213> ORGANISM: adeno-associated virus

<400> SEQUENCE: 343

Ser Ala Ser Thr Gly Ala Ser
1 5

<210> SEQ ID NO 344
<211> LENGTH: 10
<212> TYPE: PRT
<213> ORGANISM: adeno-associated virus

<400> SEQUENCE: 344

Val Phe Met Ile Pro Gln Tyr Gly Tyr Leu
1 5 10

<210> SEQ ID NO 345
<211> LENGTH: 9
<212> TYPE: PRT
<213> ORGANISM: adeno-associated virus

<400> SEQUENCE: 345

Asn Gln Ser Gly Ser Ala Gln Asn Lys
1               5

<210> SEQ ID NO 346
<211> LENGTH: 8
<212> TYPE: PRT
<213> ORGANISM: adeno-associated virus

<400> SEQUENCE: 346

Lys Thr Asp Asn Asn Asn Ser Asn
1               5

<210> SEQ ID NO 347
<211> LENGTH: 7
<212> TYPE: PRT
<213> ORGANISM: adeno-associated virus

<400> SEQUENCE: 347

Lys Asp Asp Lys Asp Lys Phe
1               5

<210> SEQ ID NO 348
<211> LENGTH: 6
<212> TYPE: PRT
<213> ORGANISM: adeno-associated virus

<400> SEQUENCE: 348

Ser Ala Gly Ala Ser Asn
1               5

<210> SEQ ID NO 349
<211> LENGTH: 10
<212> TYPE: PRT
<213> ORGANISM: adeno-associated virus

<400> SEQUENCE: 349

Ser Thr Asp Pro Ala Thr Gly Asp Val His
1               5                   10

<210> SEQ ID NO 350
<211> LENGTH: 7
<212> TYPE: PRT
<213> ORGANISM: adeno-associated virus

<400> SEQUENCE: 350

Asp Asn Asn Gly Leu Tyr Thr
1               5

<210> SEQ ID NO 351
<211> LENGTH: 7
<212> TYPE: PRT
<213> ORGANISM: adeno-associated virus

<400> SEQUENCE: 351

Ser Glu Thr Ala Gly Ser Thr
1               5

<210> SEQ ID NO 352

<211> LENGTH: 10
<212> TYPE: PRT
<213> ORGANISM: adeno-associated virus

<400> SEQUENCE: 352

Val Phe Met Ile Pro Gln Tyr Gly Tyr Leu
1 5 10

<210> SEQ ID NO 353
<211> LENGTH: 9
<212> TYPE: PRT
<213> ORGANISM: adeno-associated virus

<400> SEQUENCE: 353

Asn Pro Gly Gly Thr Ala Gly Asn Arg
1 5

<210> SEQ ID NO 354
<211> LENGTH: 8
<212> TYPE: PRT
<213> ORGANISM: adeno-associated virus

<400> SEQUENCE: 354

Leu Asp Gln Asn Asn Asn Ser Asn
1 5

<210> SEQ ID NO 355
<211> LENGTH: 7
<212> TYPE: PRT
<213> ORGANISM: adeno-associated virus

<400> SEQUENCE: 355

Lys Asp Asp Glu Asp Arg Phe
1 5

<210> SEQ ID NO 356
<211> LENGTH: 6
<212> TYPE: PRT
<213> ORGANISM: adeno-associated virus

<400> SEQUENCE: 356

Gly Ala Thr Asn Lys Thr
1 5

<210> SEQ ID NO 357
<211> LENGTH: 10
<212> TYPE: PRT
<213> ORGANISM: adeno-associated virus

<400> SEQUENCE: 357

Asn Thr Ala Ala Gln Thr Gln Val Val Asn
1 5 10

<210> SEQ ID NO 358
<211> LENGTH: 7
<212> TYPE: PRT
<213> ORGANISM: adeno-associated virus

<400> SEQUENCE: 358

Asp Ser Gln Gly Val Tyr Ser
1 5

<210> SEQ ID NO 359
<211> LENGTH: 8
<212> TYPE: PRT

<213> ORGANISM: adeno-associated virus

<400> SEQUENCE: 359

Asn Gly Thr Ser Gly Gly Ala Thr
1               5

<210> SEQ ID NO 360
<211> LENGTH: 10
<212> TYPE: PRT
<213> ORGANISM: adeno-associated virus

<400> SEQUENCE: 360

Val Phe Met Ile Pro Gln Tyr Gly Tyr Leu
1               5                   10

<210> SEQ ID NO 361
<211> LENGTH: 9
<212> TYPE: PRT
<213> ORGANISM: adeno-associated virus

<400> SEQUENCE: 361

Thr Thr Gly Gly Thr Ala Asn Thr Gln
1               5

<210> SEQ ID NO 362
<211> LENGTH: 8
<212> TYPE: PRT
<213> ORGANISM: adeno-associated virus

<400> SEQUENCE: 362

Thr Gly Gln Asn Asn Asn Ser Asn
1               5

<210> SEQ ID NO 363
<211> LENGTH: 7
<212> TYPE: PRT
<213> ORGANISM: adeno-associated virus

<400> SEQUENCE: 363

Lys Asp Asp Glu Glu Arg Phe
1               5

<210> SEQ ID NO 364
<211> LENGTH: 6
<212> TYPE: PRT
<213> ORGANISM: adeno-associated virus

<400> SEQUENCE: 364

Asn Ala Ala Arg Asp Asn
1               5

<210> SEQ ID NO 365
<211> LENGTH: 11
<212> TYPE: PRT
<213> ORGANISM: adeno-associated virus

<400> SEQUENCE: 365

Asn Thr Ala Pro Gln Ile Gly Thr Val Asn Ser
1               5                   10

<210> SEQ ID NO 366
<211> LENGTH: 7
<212> TYPE: PRT
<213> ORGANISM: adeno-associated virus

<400> SEQUENCE: 366

Asn Thr Glu Gly Val Tyr Ser
1 5

<210> SEQ ID NO 367
<211> LENGTH: 8
<212> TYPE: PRT
<213> ORGANISM: adeno-associated virus

<400> SEQUENCE: 367

Asn Ser Thr Ser Gly Gly Ser Ser
1 5

<210> SEQ ID NO 368
<211> LENGTH: 10
<212> TYPE: PRT
<213> ORGANISM: adeno-associated virus

<400> SEQUENCE: 368

Val Phe Met Ile Pro Gln Tyr Gly Tyr Leu
1 5 10

<210> SEQ ID NO 369
<211> LENGTH: 9
<212> TYPE: PRT
<213> ORGANISM: adeno-associated virus

<400> SEQUENCE: 369

Ile Asn Gly Ser Gly Gln Asn Gln Gln
1 5

<210> SEQ ID NO 370
<211> LENGTH: 8
<212> TYPE: PRT
<213> ORGANISM: adeno-associated virus

<400> SEQUENCE: 370

Val Thr Gln Asn Asn Asn Ser Glu
1 5

<210> SEQ ID NO 371
<211> LENGTH: 7
<212> TYPE: PRT
<213> ORGANISM: adeno-associated virus

<400> SEQUENCE: 371

Lys Glu Gly Glu Asp Arg Phe
1 5

<210> SEQ ID NO 372
<211> LENGTH: 6
<212> TYPE: PRT
<213> ORGANISM: adeno-associated virus

<400> SEQUENCE: 372

Gly Thr Gly Arg Asp Asn
1 5

<210> SEQ ID NO 373
<211> LENGTH: 10
<212> TYPE: PRT
<213> ORGANISM: adeno-associated virus

<400> SEQUENCE: 373

```
Gln Ala Gln Ala Gln Thr Gly Trp Val Gln
1               5                   10


<210> SEQ ID NO 374
<211> LENGTH: 7
<212> TYPE: PRT
<213> ORGANISM: adeno-associated virus

<400> SEQUENCE: 374

Asn Thr Glu Gly Val Tyr Ser
1               5


<210> SEQ ID NO 375
<211> LENGTH: 8
<212> TYPE: PRT
<213> ORGANISM: adeno-associated virus

<400> SEQUENCE: 375

Asn Gly Thr Ser Gly Gly Ser Thr
1               5


<210> SEQ ID NO 376
<211> LENGTH: 10
<212> TYPE: PRT
<213> ORGANISM: adeno-associated virus

<400> SEQUENCE: 376

Val Phe Met Val Pro Gln Tyr Gly Tyr Leu
1               5                   10


<210> SEQ ID NO 377
<211> LENGTH: 9
<212> TYPE: PRT
<213> ORGANISM: adeno-associated virus

<400> SEQUENCE: 377

Gln Thr Thr Gly Thr Gly Gly Thr Gln
1               5


<210> SEQ ID NO 378
<211> LENGTH: 8
<212> TYPE: PRT
<213> ORGANISM: adeno-associated virus

<400> SEQUENCE: 378

Thr Asn Gln Asn Asn Asn Ser Asn
1               5


<210> SEQ ID NO 379
<211> LENGTH: 7
<212> TYPE: PRT
<213> ORGANISM: adeno-associated virus

<400> SEQUENCE: 379

Lys Asp Asp Asp Asp Arg Phe
1               5


<210> SEQ ID NO 380
<211> LENGTH: 6
<212> TYPE: PRT
<213> ORGANISM: adeno-associated virus

<400> SEQUENCE: 380

Gly Ala Gly Asn Asp Gly
1               5
```

<210> SEQ ID NO 381
<211> LENGTH: 10
<212> TYPE: PRT
<213> ORGANISM: adeno-associated virus

<400> SEQUENCE: 381

Asn Thr Gln Ala Gln Thr Gly Leu Val His
1 5 10

<210> SEQ ID NO 382
<211> LENGTH: 7
<212> TYPE: PRT
<213> ORGANISM: adeno-associated virus

<400> SEQUENCE: 382

Asn Thr Glu Gly Val Tyr Ser
1 5

<210> SEQ ID NO 383
<211> LENGTH: 8
<212> TYPE: PRT
<213> ORGANISM: adeno-associated virus

<400> SEQUENCE: 383

Asn Gly Thr Ser Gly Gly Ser Thr
1 5

<210> SEQ ID NO 384
<211> LENGTH: 10
<212> TYPE: PRT
<213> ORGANISM: adeno-associated virus

<400> SEQUENCE: 384

Val Phe Met Ile Pro Gln Tyr Gly Tyr Leu
1 5 10

<210> SEQ ID NO 385
<211> LENGTH: 9
<212> TYPE: PRT
<213> ORGANISM: adeno-associated virus

<400> SEQUENCE: 385

Ser Thr Gly Gly Thr Ala Gly Thr Gln
1 5

<210> SEQ ID NO 386
<211> LENGTH: 8
<212> TYPE: PRT
<213> ORGANISM: adeno-associated virus

<400> SEQUENCE: 386

Leu Ser Gln Asn Asn Asn Ser Asn
1 5

<210> SEQ ID NO 387
<211> LENGTH: 7
<212> TYPE: PRT
<213> ORGANISM: adeno-associated virus

<400> SEQUENCE: 387

Lys Asp Asp Glu Glu Arg Phe
1 5

<210> SEQ ID NO 388
<211> LENGTH: 6
<212> TYPE: PRT
<213> ORGANISM: adeno-associated virus

<400> SEQUENCE: 388

Gly Ala Gly Lys Asp Asn
1 5

<210> SEQ ID NO 389
<211> LENGTH: 10
<212> TYPE: PRT
<213> ORGANISM: adeno-associated virus

<400> SEQUENCE: 389

Asn Ala Ala Pro Ile Val Gly Ala Val Asn
1 5 10

<210> SEQ ID NO 390
<211> LENGTH: 7
<212> TYPE: PRT
<213> ORGANISM: adeno-associated virus

<400> SEQUENCE: 390

Asn Thr Asp Gly Thr Tyr Ser
1 5

<210> SEQ ID NO 391
<211> LENGTH: 8
<212> TYPE: PRT
<213> ORGANISM: adeno-associated virus

<400> SEQUENCE: 391

Asn Gly Thr Ser Gly Gly Ser Thr
1 5

<210> SEQ ID NO 392
<211> LENGTH: 10
<212> TYPE: PRT
<213> ORGANISM: adeno-associated virus

<400> SEQUENCE: 392

Val Phe Met Ile Pro Gln Tyr Gly Tyr Leu
1 5 10

<210> SEQ ID NO 393
<211> LENGTH: 9
<212> TYPE: PRT
<213> ORGANISM: adeno-associated virus

<400> SEQUENCE: 393

Ser Thr Gly Gly Thr Gln Gly Thr Gln
1 5

<210> SEQ ID NO 394
<211> LENGTH: 8
<212> TYPE: PRT
<213> ORGANISM: adeno-associated virus

<400> SEQUENCE: 394

Leu Ser Gln Asn Asn Asn Ser Asn
1 5

<210> SEQ ID NO 395
<211> LENGTH: 7

<212> TYPE: PRT
<213> ORGANISM: adeno-associated virus

<400> SEQUENCE: 395

Lys Asp Asp Glu Glu Arg Phe
1 5

<210> SEQ ID NO 396
<211> LENGTH: 6
<212> TYPE: PRT
<213> ORGANISM: adeno-associated virus

<400> SEQUENCE: 396

Gly Ala Gly Arg Asp Asn
1 5

<210> SEQ ID NO 397
<211> LENGTH: 10
<212> TYPE: PRT
<213> ORGANISM: adeno-associated virus

<400> SEQUENCE: 397

Asn Thr Gly Pro Ile Val Gly Asn Val Asn
1 5 10

<210> SEQ ID NO 398
<211> LENGTH: 7
<212> TYPE: PRT
<213> ORGANISM: adeno-associated virus

<400> SEQUENCE: 398

Asn Thr Glu Gly Thr Tyr Ser
1 5

<210> SEQ ID NO 399
<211> LENGTH: 8
<212> TYPE: PRT
<213> ORGANISM: adeno-associated virus

<400> SEQUENCE: 399

Arg Leu Gly Thr Thr Ser Ser Ser
1 5

<210> SEQ ID NO 400
<211> LENGTH: 10
<212> TYPE: PRT
<213> ORGANISM: adeno-associated virus

<400> SEQUENCE: 400

Val Phe Met Val Pro Gln Tyr Gly Tyr Cys
1 5 10

<210> SEQ ID NO 401
<211> LENGTH: 9
<212> TYPE: PRT
<213> ORGANISM: adeno-associated virus

<400> SEQUENCE: 401

Gly Glu Thr Leu Asn Gln Gly Asn Ala
1 5

<210> SEQ ID NO 402
<211> LENGTH: 12
<212> TYPE: PRT
<213> ORGANISM: adeno-associated virus

<400> SEQUENCE: 402

Ala Ser Gln Asn Tyr Lys Ile Pro Ala Ser Gly Gly
1 5 10

<210> SEQ ID NO 403
<211> LENGTH: 7
<212> TYPE: PRT
<213> ORGANISM: adeno-associated virus

<400> SEQUENCE: 403

Gly Pro Ser Asp Gly Asp Phe
1 5

<210> SEQ ID NO 404
<211> LENGTH: 6
<212> TYPE: PRT
<213> ORGANISM: adeno-associated virus

<400> SEQUENCE: 404

Val Thr Gly Asn Thr Thr
1 5

<210> SEQ ID NO 405
<211> LENGTH: 10
<212> TYPE: PRT
<213> ORGANISM: adeno-associated virus

<400> SEQUENCE: 405

Thr Thr Ala Pro Ile Thr Gly Asn Val Thr
1 5 10

<210> SEQ ID NO 406
<211> LENGTH: 7
<212> TYPE: PRT
<213> ORGANISM: adeno-associated virus

<400> SEQUENCE: 406

Asp Thr Thr Gly Lys Tyr Thr
1 5

<210> SEQ ID NO 407
<211> LENGTH: 8
<212> TYPE: PRT
<213> ORGANISM: adeno-associated virus

<400> SEQUENCE: 407

Arg Ile Gly Thr Thr Ala Asn Ser
1 5

<210> SEQ ID NO 408
<211> LENGTH: 10
<212> TYPE: PRT
<213> ORGANISM: adeno-associated virus

<400> SEQUENCE: 408

Val Phe Met Val Pro Gln Tyr Gly Tyr Cys
1 5 10

<210> SEQ ID NO 409
<211> LENGTH: 9
<212> TYPE: PRT
<213> ORGANISM: adeno-associated virus

<400> SEQUENCE: 409

Gly Asn Ser Leu Asn Gln Gly Thr Ala
1 5

<210> SEQ ID NO 410
<211> LENGTH: 12
<212> TYPE: PRT
<213> ORGANISM: adeno-associated virus

<400> SEQUENCE: 410

Ala Asn Gln Asn Tyr Lys Ile Pro Ala Ser Gly Gly
1 5 10

<210> SEQ ID NO 411
<211> LENGTH: 7
<212> TYPE: PRT
<213> ORGANISM: adeno-associated virus

<400> SEQUENCE: 411

Gly Ala Gly Asp Ser Asp Phe
1 5

<210> SEQ ID NO 412
<211> LENGTH: 6
<212> TYPE: PRT
<213> ORGANISM: adeno-associated virus

<400> SEQUENCE: 412

Pro Ser Gly Asn Thr Thr
1 5

<210> SEQ ID NO 413
<211> LENGTH: 10
<212> TYPE: PRT
<213> ORGANISM: adeno-associated virus

<400> SEQUENCE: 413

Thr Thr Ala Pro His Ile Ala Asn Leu Asp
1 5 10

<210> SEQ ID NO 414
<211> LENGTH: 7
<212> TYPE: PRT
<213> ORGANISM: adeno-associated virus

<400> SEQUENCE: 414

Asp Asn Ala Gly Asn Tyr His
1 5

<210> SEQ ID NO 415
<211> LENGTH: 8
<212> TYPE: PRT
<213> ORGANISM: adeno-associated virus

<400> SEQUENCE: 415

Arg Leu Gly Thr Thr Ser Asn Ser
1 5

<210> SEQ ID NO 416
<211> LENGTH: 10
<212> TYPE: PRT
<213> ORGANISM: adeno-associated virus

<400> SEQUENCE: 416

Val Phe Met Val Pro Gln Tyr Gly Tyr Cys 1 5 10

<210> SEQ ID NO 417
<211> LENGTH: 9
<212> TYPE: PRT
<213> ORGANISM: adeno-associated virus

<400> SEQUENCE: 417

Gly Glu Thr Leu Asn Gln Gly Asn Ala
1 5

<210> SEQ ID NO 418
<211> LENGTH: 12
<212> TYPE: PRT
<213> ORGANISM: adeno-associated virus

<400> SEQUENCE: 418

Ala Ser Gln Asn Tyr Lys Ile Pro Ala Ser Gly Gly
1 5 10

<210> SEQ ID NO 419
<211> LENGTH: 7
<212> TYPE: PRT
<213> ORGANISM: adeno-associated virus

<400> SEQUENCE: 419

Gly Pro Ser Asp Gly Asp Phe
1 5

<210> SEQ ID NO 420
<211> LENGTH: 6
<212> TYPE: PRT
<213> ORGANISM: adeno-associated virus

<400> SEQUENCE: 420

Val Thr Gly Asn Thr Thr
1 5

<210> SEQ ID NO 421
<211> LENGTH: 10
<212> TYPE: PRT
<213> ORGANISM: adeno-associated virus

<400> SEQUENCE: 421

Thr Thr Ala Pro Ile Thr Gly Asn Val Thr
1 5 10

<210> SEQ ID NO 422
<211> LENGTH: 7
<212> TYPE: PRT
<213> ORGANISM: adeno-associated virus

<400> SEQUENCE: 422

Asp Thr Thr Gly Lys Tyr Thr
1 5

<210> SEQ ID NO 423
<211> LENGTH: 8
<212> TYPE: PRT
<213> ORGANISM: adeno-associated virus

<400> SEQUENCE: 423

Arg Leu Gly Ser Ser Asn Ala Ser
1 5

<210> SEQ ID NO 424
<211> LENGTH: 10
<212> TYPE: PRT
<213> ORGANISM: adeno-associated virus

<400> SEQUENCE: 424

Val Phe Met Val Pro Gln Tyr Gly Tyr Cys
1 5 10

<210> SEQ ID NO 425
<211> LENGTH: 9
<212> TYPE: PRT
<213> ORGANISM: adeno-associated virus

<400> SEQUENCE: 425

Gly Gly Thr Leu Asn Gln Gly Asn Ser
1 5

<210> SEQ ID NO 426
<211> LENGTH: 12
<212> TYPE: PRT
<213> ORGANISM: adeno-associated virus

<400> SEQUENCE: 426

Ala Ser Gln Asn Tyr Lys Ile Pro Gln Gly Arg Asn
1 5 10

<210> SEQ ID NO 427
<211> LENGTH: 7
<212> TYPE: PRT
<213> ORGANISM: adeno-associated virus

<400> SEQUENCE: 427

Ala Asn Asp Ala Thr Asp Phe
1 5

<210> SEQ ID NO 428
<211> LENGTH: 6
<212> TYPE: PRT
<213> ORGANISM: adeno-associated virus

<400> SEQUENCE: 428

Ile Thr Gly Asn Thr Thr
1 5

<210> SEQ ID NO 429
<211> LENGTH: 10
<212> TYPE: PRT
<213> ORGANISM: adeno-associated virus

<400> SEQUENCE: 429

Thr Thr Val Pro Thr Val Asp Asp Val Asp
1 5 10

<210> SEQ ID NO 430
<211> LENGTH: 7
<212> TYPE: PRT
<213> ORGANISM: adeno-associated virus

<400> SEQUENCE: 430

Asp Asn Ala Gly Ala Tyr Lys
1 5

<210> SEQ ID NO 431

-continued

<211> LENGTH: 8
<212> TYPE: PRT
<213> ORGANISM: adeno-associated virus

<400> SEQUENCE: 431

Arg Ile Gln Gly Pro Ser Gly Gly
1 5

<210> SEQ ID NO 432
<211> LENGTH: 10
<212> TYPE: PRT
<213> ORGANISM: adeno-associated virus

<400> SEQUENCE: 432

Ile Tyr Thr Ile Pro Gln Tyr Gly Tyr Cys
1 5 10

<210> SEQ ID NO 433
<211> LENGTH: 9
<212> TYPE: PRT
<213> ORGANISM: adeno-associated virus

<400> SEQUENCE: 433

Val Ser Gln Ala Gly Ser Ser Gly Arg
1 5

<210> SEQ ID NO 434
<211> LENGTH: 12
<212> TYPE: PRT
<213> ORGANISM: adeno-associated virus

<400> SEQUENCE: 434

Ala Ser Asn Ile Thr Lys Asn Asn Val Phe Ser Val
1 5 10

<210> SEQ ID NO 435
<211> LENGTH: 7
<212> TYPE: PRT
<213> ORGANISM: adeno-associated virus

<400> SEQUENCE: 435

Phe Ser Gly Glu Pro Asp Arg
1 5

<210> SEQ ID NO 436
<211> LENGTH: 8
<212> TYPE: PRT
<213> ORGANISM: adeno-associated virus

<400> SEQUENCE: 436

Val Tyr Asp Gln Thr Thr Ala Thr
1 5

<210> SEQ ID NO 437
<211> LENGTH: 10
<212> TYPE: PRT
<213> ORGANISM: adeno-associated virus

<400> SEQUENCE: 437

Val Thr Pro Gly Thr Arg Ala Ala Val Asn
1 5 10

<210> SEQ ID NO 438
<211> LENGTH: 7
<212> TYPE: PRT

<213> ORGANISM: adeno-associated virus

<400> SEQUENCE: 438

Ser Asp Thr Gly Ser Tyr Ser
1               5

<210> SEQ ID NO 439
<211> LENGTH: 53
<212> TYPE: DNA
<213> ORGANISM: Artificial
<220> FEATURE:
<223> OTHER INFORMATION: Radomized AAV1e common antigenic motif coding sequence

<400> SEQUENCE: 439
ctcaaatcag tccggaagtg gggggggggg ggacttgctg tttagccgtg ggt 53

<210> SEQ ID NO 440
<211> LENGTH: 55
<212> TYPE: DNA
<213> ORGANISM: Artificial
<220> FEATURE:
<223> OTHER INFORMATION: Radomized AAV1e common antigenic motif coding sequence

<400> SEQUENCE: 440
agcgcgtttc taaatggggg gggggggggg gggggggtaa ttttacctgg actgg 55

<210> SEQ ID NO 441
<211> LENGTH: 55
<212> TYPE: DNA
<213> ORGANISM: Artificial
<220> FEATURE:
<223> OTHER INFORMATION: Radomized AAV1e common antigenic motif coding sequence

<400> SEQUENCE: 441
tcaatttcca gagcagcttt atggacttat tattattatg gtgatggcta tggga 55

<210> SEQ ID NO 442
<211> LENGTH: 57
<212> TYPE: DNA
<213> ORGANISM: Artificial
<220> FEATURE:
<223> OTHER INFORMATION: Radomized AAV1e common antigenic motif coding sequence

<400> SEQUENCE: 442
aatctgttgt tgttgatttt actgtgaata atgataataa taagaatgag cctcgcc 57

<210> SEQ ID NO 443
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(3)
<223> OTHER INFORMATION: Xaa can be any naturally occurring amino acid other than D
<220> FEATURE:
<221> NAME/KEY: MISC_FEATURE
<222> LOCATION: (4)..(4)
<223> OTHER INFORMATION: Xaa can be any naturally occurring amino acid
other than E
<220> FEATURE:
<221> NAME/KEY: MISC_FEATURE
<222> LOCATION: (5)..(5)
<223> OTHER INFORMATION: Xaa can be any naturally occurring amino acid
other than D
<220> FEATURE:
<221> NAME/KEY: MISC_FEATURE
<222> LOCATION: (6)..(6)
<223> OTHER INFORMATION: Xaa can be any naturally occurring amino acid
other than K
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 443

Xaa Xaa Xaa Xaa Xaa Xaa Xaa
1 5

<210> SEQ ID NO 444
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than K
<220> FEATURE:
<221> NAME/KEY: MISC_FEATURE
<222> LOCATION: (2)..(3)
<223> OTHER INFORMATION: Xaa can be any naturally occurring amino acid
other than D
<220> FEATURE:
<221> NAME/KEY: MISC_FEATURE
<222> LOCATION: (4)..(5)
<223> OTHER INFORMATION: Xaa can be any naturally occurring amino acid
other than E
<220> FEATURE:
<221> NAME/KEY: MISC_FEATURE
<222> LOCATION: (6)..(6)
<223> OTHER INFORMATION: Xaa can be any naturally occurring amino acid
other than K
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 444

Xaa Xaa Xaa Xaa Xaa Xaa Xaa
1 5

<210> SEQ ID NO 445
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than K
<220> FEATURE:
<221> NAME/KEY: MISC_FEATURE
<222> LOCATION: (2)..(3)

<223> OTHER INFORMATION: Xaa can be any naturally occurring amino acid
other than D
<220> FEATURE:
<221> NAME/KEY: MISC_FEATURE
<222> LOCATION: (4)..(5)
<223> OTHER INFORMATION: Xaa can be any naturally occurring amino acid
other than E
<220> FEATURE:
<221> NAME/KEY: MISC_FEATURE
<222> LOCATION: (6)..(6)
<223> OTHER INFORMATION: Xaa can be any naturally occurring amino acid
other than K
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 445

Xaa Xaa Xaa Xaa Xaa Xaa Xaa
1 5

<210> SEQ ID NO 446
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEAURE
<222> LOCATION: (1)..(1)
<223> OTHER INFORMATION: Xaa can be any naturally occurring amino acid
other than G
<220> FEATURE:
<221> NAME/KEY: MISC_FEAURE
<222> LOCATION: (2)..(2)
<223> OTHER INFORMATION: Xaa can be any naturally occurring amino acid
other than P
<220> FEATURE:
<221> NAME/KEY: MISC_FEAURE
<222> LOCATION: (3)..(3)
<223> OTHER INFORMATION: Xaa can be any naturally occurring amino acid
other than A
<220> FEATURE:
<221> NAME/KEY: MISC_FEAURE
<222> LOCATION: (4)..(4)
<223> OTHER INFORMATION: Xaa can be any naturally occurring amino acid
other than D
<220> FEATURE:
<221> NAME/KEY: MISC_FEAURE
<222> LOCATION: (5)..(5)
<223> OTHER INFORMATION: Xaa can be any naturally occurring amino acid
other than S
<220> FEATURE:
<221> NAME/KEY: MISC_FEAURE
<222> LOCATION: (6)..(6)
<223> OTHER INFORMATION: Xaa can be any naturally occurring amino acid
other than K
<220> FEATURE:
<221> NAME/KEY: MISC_FEAURE
<222> LOCATION: (7)..(7)
<223> OTHER INFORMATION: Xaa can be any naturally occurring amino acid
other than F

<400> SEQUENCE: 446

Xaa Xaa Xaa Xaa Xaa Xaa Xaa
1 5

<210> SEQ ID NO 447
<211> LENGTH: 7
<212> TYPE: PRT
<213> ORGANISM: Artificial
<220> FEATURE:
<223> OTHER INFORMATION: AAV capsid protein common antigenic motif (CAM)

substitution sequence
<220> FEATURE:
<221> NAME/KEY: MISC_FEATURE
<222> LOCATION: (1)..(1)
<223> OTHER INFORMATION: Xaa can be any naturally occurring amino acid other than L
<220> FEATURE:
<221> NAME/KEY: MISC_FEATURE
<222> LOCATION: (2)..(2)
<223> OTHER INFORMATION: Xaa can be any naturally occurring amino acid other than Q
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE
<222> LOCATION: (4)..(4)
<223> OTHER INFORMATION: Xaa can be any naturally occurring amino acid other than S
<220> FEATURE:
<221> NAME/KEY: MISC_FEATURE
<222> LOCATION: (5)..(5)
<223> OTHER INFORMATION: Xaa can be any naturally occurring amino acid other than N
<220> FEATURE:
<221> NAME/KEY: MISC_FEATURE
<222> LOCATION: (6)..(6)
<223> OTHER INFORMATION: Xaa can be any naturally occurring amino acid other than T
<220> FEATURE:
<221> NAME/KEY: MISC_FEATURE
<222> LOCATION: (7)..(7)
<223> OTHER INFORMATION: Xaa can be any naturally occurring amino acid other than Y

<400> SEQUENCE: 447

Xaa Xaa Xaa Xaa Xaa Xaa Xaa
1               5

<210> SEQ ID NO 448
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(3)
<223> OTHER INFORMATION: Xaa can be any naturally occurring amino acid other than D
<220> FEATURE:
<221> NAME/KEY: MISC_FEATURE
<222> LOCATION: (4)..(4)
<223> OTHER INFORMATION: Xaa can be any naturally occurring amino acid other than K
<220> FEATURE:
<221> NAME/KEY: MISC_FEATURE
<222> LOCATION: (5)..(5)
<223> OTHER INFORMATION: Xaa can be any naturally occurring amino acid other than D
<220> FEATURE:
<221> NAME/KEY: MISC_FEATURE
<222> LOCATION: (6)..(6)
<223> OTHER INFORMATION: Xaa can be any naturally occurring amino acid other than K
<220> FEATURE:
<221> NAME/KEY: MISC_FEATURE
<222> LOCATION: (7)..(7)
<223> OTHER INFORMATION: Xaa can be any naturally occurring amino acid other than F

<400> SEQUENCE: 448

Xaa Xaa Xaa Xaa Xaa Xaa Xaa
1 5

<210> SEQ ID NO 449
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(3)
<223> OTHER INFORMATION: Xaa can be any naturally occurring amino acid other than D
<220> FEATURE:
<221> NAME/KEY: MISC_FEATURE
<222> LOCATION: (4)..(4)
<223> OTHER INFORMATION: Xaa can be any naturally occurring amino acid other than E
<220> FEATURE:
<221> NAME/KEY: MISC_FEATURE
<222> LOCATION: (5)..(5)
<223> OTHER INFORMATION: Xaa can be any naturally occurring amino acid other than D
<220> FEATURE:
<221> NAME/KEY: MISC_FEATURE
<222> LOCATION: (6)..(6)
<223> OTHER INFORMATION: Xaa can be any naturally occurring amino acid other than R
<220> FEATURE:
<221> NAME/KEY: MISC_FEATURE
<222> LOCATION: (7)..(7)
<223> OTHER INFORMATION: Xaa can be any naturally occurring amino acid other than F

<400> SEQUENCE: 449

Xaa Xaa Xaa Xaa Xaa Xaa Xaa
1 5

<210> SEQ ID NO 450
<211> LENGTH: 7
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than K
<220> FEATURE:
<221> NAME/KEY: MISC_FEATURE
<222> LOCATION: (2)..(3)
<223> OTHER INFORMATION: Xaa can be any naturally occurring amino acid other than D
<220> FEATURE:
<221> NAME/KEY: MISC_FEATURE
<222> LOCATION: (4)..(5)
<223> OTHER INFORMATION: Xaa can be any naturally occurring amino acid other than E
<220> FEATURE:
<221> NAME/KEY: MISC_FEATURE
<222> LOCATION: (6)..(6)
<223> OTHER INFORMATION: Xaa can be any naturally occurring amino acid other than R
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 450

Xaa Xaa Xaa Xaa Xaa Xaa Xaa
1 5

<210> SEQ ID NO 451
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than K
<220> FEATURE:
<221> NAME/KEY: MISC_FEATURE
<222> LOCATION: (2)..(2)
<223> OTHER INFORMATION: Xaa can be any naturally occurring amino acid
other than E
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than E
<220> FEATURE:
<221> NAME/KEY: MISC_FEATURE
<222> LOCATION: (5)..(5)
<223> OTHER INFORMATION: Xaa can be any naturally occurring amino acid
other than D
<220> FEATURE:
<221> NAME/KEY: MISC_FEATURE
<222> LOCATION: (6)..(6)
<223> OTHER INFORMATION: Xaa can be any naturally occurring amino acid
other than R
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 451

Xaa Xaa Xaa Xaa Xaa Xaa Xaa
1 5

<210> SEQ ID NO 452
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than K
<220> FEATURE:
<221> NAME/KEY: MISC_FEATURE
<222> LOCATION: (2)..(5)
<223> OTHER INFORMATION: Xaa can be any naturally occurring amino acid
other than E
<220> FEATURE:

```
<221> NAME/KEY: MISC_FEATURE
<222> LOCATION: (6)..(6)
<223> OTHER INFORMATION: Xaa can be any naturally occurring amino acid
      other than R
<220> FEATURE:
<221> NAME/KEY: MISC_FEATURE
<222> LOCATION: (7)..(7)
<223> OTHER INFORMATION: Xaa can be any naturally occurring amino acid
      other than F

<400> SEQUENCE: 452

Xaa Xaa Xaa Xaa Xaa Xaa Xaa
1               5


<210> SEQ ID NO 453
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than K
<220> FEATURE:
<221> NAME/KEY: MISC_FEATURE
<222> LOCATION: (2)..(3)
<223> OTHER INFORMATION: Xaa can be any naturally occurring amino acid
      other than D
<220> FEATURE:
<221> NAME/KEY: MISC_FEATURE
<222> LOCATION: (4)..(5)
<223> OTHER INFORMATION: Xaa can be any naturally occurring amino acid
      other than E
<220> FEATURE:
<221> NAME/KEY: MISC_FEATURE
<222> LOCATION: (6)..(6)
<223> OTHER INFORMATION: Xaa can be any naturally occurring amino acid
      other than R
<220> FEATURE:
<221> NAME/KEY: MISC_FEATURE
<222> LOCATION: (7)..(7)
<223> OTHER INFORMATION: Xaa can be any naturally occurring amino acid
      other than F

<400> SEQUENCE: 453

Xaa Xaa Xaa Xaa Xaa Xaa Xaa
1               5


<210> SEQ ID NO 454
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than K
<220> FEATURE:
<221> NAME/KEY: MISC_FEATURE
<222> LOCATION: (2)..(3)
<223> OTHER INFORMATION: Xaa can be any naturally occurring amino acid
      other than D
<220> FEATURE:
<221> NAME/KEY: MISC_FEATURE
<222> LOCATION: (4)..(5)
<223> OTHER INFORMATION: Xaa can be any naturally occurring amino acid
      other than E
<220> FEATURE:
<221> NAME/KEY: MISC_FEATURE
```

<222> LOCATION: (6)..(6)
<223> OTHER INFORMATION: Xaa can be any naturally occurring amino acid
      other than R
<220> FEATURE:
<221> NAME/KEY: MISC_FEATURE
<222> LOCATION: (7)..(7)
<223> OTHER INFORMATION: Xaa can be any naturally occurring amino acid
      other than F

<400> SEQUENCE: 454

Xaa Xaa Xaa Xaa Xaa Xaa Xaa
1               5

<210> SEQ ID NO 455
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than G
<220> FEATURE:
<221> NAME/KEY: MISC_FEATURE
<222> LOCATION: (2)..(2)
<223> OTHER INFORMATION: Xaa can be any naturally occurring amino acid
      other than P
<220> FEATURE:
<221> NAME/KEY: MISC_FEATURE
<222> LOCATION: (3)..(3)
<223> OTHER INFORMATION: Xaa can be any naturally occurring amino acid
      other than S
<220> FEATURE:
<221> NAME/KEY: MISC_FEATURE
<222> LOCATION: (4)..(4)
<223> OTHER INFORMATION: Xaa can be any naturally occurring amino acid
      other than D
<220> FEATURE:
<221> NAME/KEY: MISC_FEATURE
<222> LOCATION: (5)..(5)
<223> OTHER INFORMATION: Xaa can be any naturally occurring amino acid
      other than G
<220> FEATURE:
<221> NAME/KEY: MISC_FEATURE
<222> LOCATION: (6)..(6)
<223> OTHER INFORMATION: Xaa can be any naturally occurring amino acid
      other than D
<220> FEATURE:
<221> NAME/KEY: MISC_FEATURE
<222> LOCATION: (7)..(7)
<223> OTHER INFORMATION: Xaa can be any naturally occurring amino acid
      other than F

<400> SEQUENCE: 455

Xaa Xaa Xaa Xaa Xaa Xaa Xaa
1               5

<210> SEQ ID NO 456
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than G
<220> FEATURE:
<221> NAME/KEY: MISC_FEATURE
<222> LOCATION: (2)..(2)

<223> OTHER INFORMATION: Xaa can be any naturally occurring amino acid
other than A
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than D
<220> FEATURE:
<221> NAME/KEY: MISC_FEATURE
<222> LOCATION: (5)..(5)
<223> OTHER INFORMATION: Xaa can be any naturally occurring amino acid
other than S
<220> FEATURE:
<221> NAME/KEY: MISC_FEATURE
<222> LOCATION: (6)..(6)
<223> OTHER INFORMATION: Xaa can be any naturally occurring amino acid
other than D
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 456

Xaa Xaa Xaa Xaa Xaa Xaa Xaa
1               5

<210> SEQ ID NO 457
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(2)
<223> OTHER INFORMATION: Xaa can be any naturally occurring amino acid
other than P
<220> FEATURE:
<221> NAME/KEY: MISC_FEATURE
<222> LOCATION: (3)..(3)
<223> OTHER INFORMATION: Xaa can be any naturally occurring amino acid
other than S
<220> FEATURE:
<221> NAME/KEY: MISC_FEATURE
<222> LOCATION: (4)..(4)
<223> OTHER INFORMATION: Xaa can be any naturally occurring amino acid
other than D
<220> FEATURE:
<221> NAME/KEY: MISC_FEATURE
<222> LOCATION: (5)..(5)
<223> OTHER INFORMATION: Xaa can be any naturally occurring amino acid
other than G
<220> FEATURE:
<221> NAME/KEY: MISC_FEATURE
<222> LOCATION: (6)..(6)
<223> OTHER INFORMATION: Xaa can be any naturally occurring amino acid
other than D
<220> FEATURE:
<221> NAME/KEY: MISC_FEATURE
<222> LOCATION: (7)..(7)
<223> OTHER INFORMATION: Xaa can be any naturally occurring amino acid
other than F

<400> SEQUENCE: 457

```
Xaa Xaa Xaa Xaa Xaa Xaa Xaa
1               5


<210> SEQ ID NO 458
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than A
<220> FEATURE:
<221> NAME/KEY: MISC_FEATURE
<222> LOCATION: (2)..(2)
<223> OTHER INFORMATION: Xaa can be any naturally occurring amino acid
      other than N
<220> FEATURE:
<221> NAME/KEY: MISC_FEATURE
<222> LOCATION: (3)..(3)
<223> OTHER INFORMATION: Xaa can be any naturally occurring amino acid
      other than D
<220> FEATURE:
<221> NAME/KEY: MISC_FEATURE
<222> LOCATION: (4)..(4)
<223> OTHER INFORMATION: Xaa can be any naturally occurring amino acid
      other than A
<220> FEATURE:
<221> NAME/KEY: MISC_FEATURE
<222> LOCATION: (5)..(5)
<223> OTHER INFORMATION: Xaa can be any naturally occurring amino acid
      other than T
<220> FEATURE:
<221> NAME/KEY: MISC_FEATURE
<222> LOCATION: (6)..(6)
<223> OTHER INFORMATION: Xaa can be any naturally occurring amino acid
      other than D
<220> FEATURE:
<221> NAME/KEY: MISC_FEATURE
<222> LOCATION: (7)..(7)
<223> OTHER INFORMATION: Xaa can be any naturally occurring amino acid
      other than F

<400> SEQUENCE: 458

Xaa Xaa Xaa Xaa Xaa Xaa Xaa
1               5


<210> SEQ ID NO 459
<211> LENGTH: 7
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than F
<220> FEATURE:
<221> NAME/KEY: MISC_FEATURE
<222> LOCATION: (2)..(2)
<223> OTHER INFORMATION: Xaa can be any naturally occurring amino acid
      other than S
<220> FEATURE:
<221> NAME/KEY: MISC_FEATURE
<222> LOCATION: (3)..(3)
<223> OTHER INFORMATION: Xaa can be any naturally occurring amino acid
      other than G
<220> FEATURE:
<221> NAME/KEY: MISC_FEATURE
<222> LOCATION: (4)..(4)
<223> OTHER INFORMATION: Xaa can be any naturally occurring amino acid
```

other than E
<220> FEATURE:
<221> NAME/KEY: MISC_FEATURE
<222> LOCATION: (5)..(5)
<223> OTHER INFORMATION: Xaa can be any naturally occurring amino acid
other than P
<220> FEATURE:
<221> NAME/KEY: MISC_FEATURE
<222> LOCATION: (6)..(6)
<223> OTHER INFORMATION: Xaa can be any naturally occurring amino acid
other than D
<220> FEATURE:
<221> NAME/KEY: MISC_FEATURE
<222> LOCATION: (7)..(7)
<223> OTHER INFORMATION: Xaa can be any naturally occurring amino acid
other than R

<400> SEQUENCE: 459

Xaa Xaa Xaa Xaa Xaa Xaa Xaa
1 5

<210> SEQ ID NO 460
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than S
<220> FEATURE:
<221> NAME/KEY: MISC_FEATURE
<222> LOCATION: (2)..(2)
<223> OTHER INFORMATION: Xaa can be any naturally occurring amino acid
other than A
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than A
<220> FEATURE:
<221> NAME/KEY: MISC_FEATURE
<222> LOCATION: (5)..(5)
<223> OTHER INFORMATION: Xaa can be any naturally occurring amino acid
other than S
<220> FEATURE:
<221> NAME/KEY: MISC_FEATURE
<222> LOCATION: (6)..(6)
<223> OTHER INFORMATION: Xaa can be any naturally occurring amino acid
other than N

<400> SEQUENCE: 460

Xaa Xaa Xaa Xaa Xaa Xaa
1 5

<210> SEQ ID NO 461
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than G <220> FEATURE:
<221> NAME/KEY: MISC_FEATURE
<222> LOCATION: (2)..(2)
<223> OTHER INFORMATION: Xaa can be any naturally occurring amino acid other than S
<220> FEATURE:
<221> NAME/KEY: MISC_FEATURE
<222> LOCATION: (3)..(3)
<223> OTHER INFORMATION: Xaa can be any naturally occurring amino acid other than E
<220> FEATURE:
<221> NAME/KEY: MISC_FEATURE
<222> LOCATION: (4)..(4)
<223> OTHER INFORMATION: Xaa can be any naturally occurring amino acid other than K
<220> FEATURE:
<221> NAME/KEY: MISC_FEATURE
<222> LOCATION: (5)..(5)
<223> OTHER INFORMATION: Xaa can be any naturally occurring amino acid other than T
<220> FEATURE:
<221> NAME/KEY: MISC_FEATURE
<222> LOCATION: (6)..(6)
<223> OTHER INFORMATION: Xaa can be any naturally occurring amino acid other than N

<400> SEQUENCE: 461

Xaa Xaa Xaa Xaa Xaa Xaa
1               5

<210> SEQ ID NO 462
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than G
<220> FEATURE:
<221> NAME/KEY: MISC_FEATURE
<222> LOCATION: (2)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than A
<220> FEATURE:
<221> NAME/KEY: MISC_FEATURE
<222> LOCATION: (5)..(5)
<223> OTHER INFORMATION: Xaa can be any naturally occurring amino acid other than S
<220> FEATURE:
<221> NAME/KEY: MISC_FEATURE
<222> LOCATION: (6)..(6)
<223> OTHER INFORMATION: Xaa can be any naturally occurring amino acid other than N

<400> SEQUENCE: 462

Xaa Xaa Xaa Xaa Xaa Xaa
1               5

<210> SEQ ID NO 463
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:

<221> NAME/KEY: MISC_FEATURE
<222> LOCATION: (1)..(1)
<223> OTHER INFORMATION: Xaa can be any naturally occurring amino acid
other than Q
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than N
<220> FEATURE:
<221> NAME/KEY: MISC_FEATURE
<222> LOCATION: (5)..(5)
<223> OTHER INFORMATION: Xaa can be any naturally occurring amino acid
other than T
<220> FEATURE:
<221> NAME/KEY: MISC_FEATURE
<222> LOCATION: (6)..(6)
<223> OTHER INFORMATION: Xaa can be any naturally occurring amino acid
other than A

<400> SEQUENCE: 463

Xaa Xaa Xaa Xaa Xaa Xaa
1               5

<210> SEQ ID NO 464
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than A
<220> FEATURE:
<221> NAME/KEY: MISC_FEATURE
<222> LOCATION: (2)..(2)
<223> OTHER INFORMATION: Xaa can be any naturally occurring amino acid
other than N
<220> FEATURE:
<221> NAME/KEY: MISC_FEATURE
<222> LOCATION: (3)..(3)
<223> OTHER INFORMATION: Xaa can be any naturally occurring amino acid
other than P
<220> FEATURE:
<221> NAME/KEY: MISC_FEATURE
<222> LOCATION: (4)..(4)
<223> OTHER INFORMATION: Xaa can be any naturally occurring amino acid
other than G
<220> FEATURE:
<221> NAME/KEY: MISC_FEATURE
<222> LOCATION: (5)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid
other than A
<220> FEATURE:
<221> NAME/KEY: MISC_FEATURE
<222> LOCATION: (8)..(8)
<223> OTHER INFORMATION: Xaa can be any naturally occurring amino acid
other than T

<400> SEQUENCE: 464

Xaa Xaa Xaa Xaa Xaa Xaa Xaa Xaa
1 5

<210> SEQ ID NO 465
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than S
<220> FEATURE:
<221> NAME/KEY: MISC_FEATURE
<222> LOCATION: (2)..(2)
<223> OTHER INFORMATION: Xaa can be any naturally occurring amino acid other than A
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE
<222> LOCATION: (4)..(4)
<223> OTHER INFORMATION: Xaa can be any naturally occurring amino acid other than A
<220> FEATURE:
<221> NAME/KEY: MISC_FEATURE
<222> LOCATION: (5)..(5)
<223> OTHER INFORMATION: Xaa can be any naturally occurring amino acid other than S
<220> FEATURE:
<221> NAME/KEY: MISC_FEATURE
<222> LOCATION: (6)..(6)
<223> OTHER INFORMATION: Xaa can be any naturally occurring amino acid other than N

<400> SEQUENCE: 465

Xaa Xaa Xaa Xaa Xaa Xaa
1 5

<210> SEQ ID NO 466
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than G
<220> FEATURE:
<221> NAME/KEY: MISC_FEATURE
<222> LOCATION: (2)..(2)
<223> OTHER INFORMATION: Xaa can be any naturally occurring amino acid other than A
<220> FEATURE:
<221> NAME/KEY: MISC_FEATURE
<222> LOCATION: (3)..(3)
<223> OTHER INFORMATION: Xaa can be any naturally occurring amino acid other than T
<220> FEATURE:
<221> NAME/KEY: MISC_FEATURE
<222> LOCATION: (4)..(4)
<223> OTHER INFORMATION: Xaa can be any naturally occurring amino acid other than N
<220> FEATURE:
<221> NAME/KEY: MISC_FEATURE
<222> LOCATION: (5)..(5)
<223> OTHER INFORMATION: Xaa can be any naturally occurring amino acid
other than K
<220> FEATURE:
<221> NAME/KEY: MISC_FEATURE
<222> LOCATION: (6)..(6)
<223> OTHER INFORMATION: Xaa can be any naturally occurring amino acid
other than T

<400> SEQUENCE: 466

Xaa Xaa Xaa Xaa Xaa Xaa
1 5

<210> SEQ ID NO 467
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than N
<220> FEATURE:
<221> NAME/KEY: MISC_FEATURE
<222> LOCATION: (2)..(3)
<223> OTHER INFORMATION: Xaa can be any naturally occurring amino acid
other than A
<220> FEATURE:
<221> NAME/KEY: MISC_FEATURE
<222> LOCATION: (4)..(4)
<223> OTHER INFORMATION: Xaa can be any naturally occurring amino acid
other than R
<220> FEATURE:
<221> NAME/KEY: MISC_FEATURE
<222> LOCATION: (5)..(5)
<223> OTHER INFORMATION: Xaa can be any naturally occurring amino acid
other than D
<220> FEATURE:
<221> NAME/KEY: MISC_FEATURE
<222> LOCATION: (6)..(6)
<223> OTHER INFORMATION: Xaa can be any naturally occurring amino acid
other than N

<400> SEQUENCE: 467

Xaa Xaa Xaa Xaa Xaa Xaa
1 5

<210> SEQ ID NO 468
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)

<223> OTHER INFORMATION: Xaa can be any naturally occurring amino acid
      other than R
<220> FEATURE:
<221> NAME/KEY: MISC_FEATURE
<222> LOCATION: (5)..(5)
<223> OTHER INFORMATION: Xaa can be any naturally occurring amino acid
      other than D
<220> FEATURE:
<221> NAME/KEY: MISC_FEATURE
<222> LOCATION: (6)..(6)
<223> OTHER INFORMATION: Xaa can be any naturally occurring amino acid
      other than N

<400> SEQUENCE: 468

Xaa Xaa Xaa Xaa Xaa Xaa
1               5

<210> SEQ ID NO 469
<211> LENGTH: 6
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than G
<220> FEATURE:
<221> NAME/KEY: MISC_FEATURE
<222> LOCATION: (2)..(2)
<223> OTHER INFORMATION: Xaa can be any naturally occurring amino acid
      other than A
<220> FEATURE:
<221> NAME/KEY: MISC_FEATURE
<222> LOCATION: (3)..(3)
<223> OTHER INFORMATION: Xaa can be any naturally occurring amino acid
      other than G
<220> FEATURE:
<221> NAME/KEY: MISC_FEATURE
<222> LOCATION: (4)..(4)
<223> OTHER INFORMATION: Xaa can be any naturally occurring amino acid
      other than N
<220> FEATURE:
<221> NAME/KEY: MISC_FEATURE
<222> LOCATION: (5)..(5)
<223> OTHER INFORMATION: Xaa can be any naturally occurring amino acid
      other than D
<220> FEATURE:
<221> NAME/KEY: MISC_FEATURE
<222> LOCATION: (6)..(6)
<223> OTHER INFORMATION: Xaa can be any naturally occurring amino acid
      other than G

<400> SEQUENCE: 469

Xaa Xaa Xaa Xaa Xaa Xaa
1               5

<210> SEQ ID NO 470
<211> LENGTH: 6
<212> TYPE: PRT
<213> ORGANISM: Artificial
<220> FEATURE:
<223> OTHER INFORMATION: AAV capsid protein common antigenic motif (CAM)
      substitution sequence
<220> FEATURE:
<221> NAME/KEY: MISC_FEATURE
<222> LOCATION: (1)..(1)
<223> OTHER INFORMATION: Xaa can be any naturally occurring amino acid
      other than G
<220> FEATURE:
<221> NAME/KEY: MISC_FEATURE
<222> LOCATION: (2)..(2)
<223> OTHER INFORMATION: Xaa can be any naturally occurring amino acid other than A
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than K
<220> FEATURE:
<221> NAME/KEY: MISC_FEATURE
<222> LOCATION: (5)..(5)
<223> OTHER INFORMATION: Xaa can be any naturally occurring amino acid
other than D
<220> FEATURE:
<221> NAME/KEY: MISC_FEATURE
<222> LOCATION: (6)..(6)
<223> OTHER INFORMATION: Xaa can be any naturally occurring amino acid
other than N

<400> SEQUENCE: 470

Xaa Xaa Xaa Xaa Xaa Xaa
1 5

<210> SEQ ID NO 471
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than G
<220> FEATURE:
<221> NAME/KEY: MISC_FEATURE
<222> LOCATION: (2)..(2)
<223> OTHER INFORMATION: Xaa can be any naturally occurring amino acid
other than A
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than R
<220> FEATURE:
<221> NAME/KEY: MISC_FEATURE
<222> LOCATION: (5)..(5)
<223> OTHER INFORMATION: Xaa can be any naturally occurring amino acid
other than D
<220> FEATURE:
<221> NAME/KEY: MISC_FEATURE
<222> LOCATION: (6)..(6)
<223> OTHER INFORMATION: Xaa can be any naturally occurring amino acid
other than N

<400> SEQUENCE: 471

Xaa Xaa Xaa Xaa Xaa Xaa
1 5

<210> SEQ ID NO 472
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence <220> FEATURE:
<221> NAME/KEY: MISC_FEATURE
<222> LOCATION: (1)..(1)
<223> OTHER INFORMATION: Xaa can be any naturally occurring amino acid other than V
<220> FEATURE:
<221> NAME/KEY: MISC_FEATURE
<222> LOCATION: (2)..(2)
<223> OTHER INFORMATION: Xaa can be any naturally occurring amino acid other than T
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE
<222> LOCATION: (4)..(4)
<223> OTHER INFORMATION: Xaa can be any naturally occurring amino acid other than N
<220> FEATURE:
<221> NAME/KEY: MISC_FEATURE
<222> LOCATION: (5)..(6)
<223> OTHER INFORMATION: Xaa can be any naturally occurring amino acid other than T

<400> SEQUENCE: 472

Xaa Xaa Xaa Xaa Xaa Xaa
1               5

<210> SEQ ID NO 473
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:
<221> NAME/KEY: MISC_FEATURE
<222> LOCATION: (1)..(1)
<223> OTHER INFORMATION: Xaa can be any naturally occurring amino acid other than P
<220> FEATURE:
<221> NAME/KEY: MISC_FEATURE
<222> LOCATION: (2)..(2)
<223> OTHER INFORMATION: Xaa can be any naturally occurring amino acid other than S
<220> FEATURE:
<221> NAME/KEY: MISC_FEATURE
<222> LOCATION: (3)..(3)
<223> OTHER INFORMATION: Xaa can be any naturally occurring amino acid other than G
<220> FEATURE:
<221> NAME/KEY: MISC_FEATURE
<222> LOCATION: (4)..(4)
<223> OTHER INFORMATION: Xaa can be any naturally occurring amino acid other than N
<220> FEATURE:
<221> NAME/KEY: MISC_FEATURE
<222> LOCATION: (5)..(6)
<223> OTHER INFORMATION: Xaa can be any naturally occurring amino acid other than T

<400> SEQUENCE: 473

Xaa Xaa Xaa Xaa Xaa Xaa
1               5

<210> SEQ ID NO 474
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence
<220> FEATURE:

<221> NAME/KEY: MISC_FEATURE
<222> LOCATION: (1)..(1)
<223> OTHER INFORMATION: Xaa can be any naturally occurring amino acid
other than V
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than N
<220> FEATURE:
<221> NAME/KEY: MISC_FEATURE
<222> LOCATION: (5)..(6)
<223> OTHER INFORMATION: Xaa can be any naturally occurring amino acid
other than T

<400> SEQUENCE: 474

Xaa Xaa Xaa Xaa Xaa Xaa
1               5

<210> SEQ ID NO 475
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than I
<220> FEATURE:
<221> NAME/KEY: MISC_FEATURE
<222> LOCATION: (2)..(2)
<223> OTHER INFORMATION: Xaa can be any naturally occurring amino acid
other than T
<220> FEATURE:
<221> NAME/KEY: MISC_FEATURE
<222> LOCATION: (3)..(3)
<223> OTHER INFORMATION: Xaa can be any naturally occurring amino acid
other than G
<220> FEATURE:
<221> NAME/KEY: MISC_FEATURE
<222> LOCATION: (4)..(4)
<223> OTHER INFORMATION: Xaa can be any naturally occurring amino acid
other than N
<220> FEATURE:
<221> NAME/KEY: MISC_FEATURE
<222> LOCATION: (5)..(6)
<223> OTHER INFORMATION: Xaa can be any naturally occurring amino acid
other than T

<400> SEQUENCE: 475

Xaa Xaa Xaa Xaa Xaa Xaa
1               5

<210> SEQ ID NO 476
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence
<220> FEATURE:
<221> NAME/KEY: MISC_FEATURE
<222> LOCATION: (1)..(1)
<223> OTHER INFORMATION: Xaa can be any naturally occurring amino acid
other than V
<220> FEATURE:
<221> NAME/KEY: MISC_FEATURE
<222> LOCATION: (2)..(2)
<223> OTHER INFORMATION: Xaa can be any naturally occurring amino acid
other than Y
<220> FEATURE:
<221> NAME/KEY: MISC_FEATURE
<222> LOCATION: (3)..(3)
<223> OTHER INFORMATION: Xaa can be any naturally occurring amino acid
other than D
<220> FEATURE:
<221> NAME/KEY: MISC_FEATURE
<222> LOCATION: (4)..(4)
<223> OTHER INFORMATION: Xaa can be any naturally occurring amino acid
other than Q
<220> FEATURE:
<221> NAME/KEY: MISC_FEATURE
<222> LOCATION: (5)..(6)
<223> OTHER INFORMATION: Xaa can be any naturally occurring amino acid
other than T
<220> FEATURE:
<221> NAME/KEY: MISC_FEATURE
<222> LOCATION: (7)..(7)
<223> OTHER INFORMATION: Xaa can be any naturally occurring amino acid
other than A
<220> FEATURE:
<221> NAME/KEY: MISC_FEATURE
<222> LOCATION: (8)..(8)
<223> OTHER INFORMATION: Xaa can be any naturally occurring amino acid
other than T

<400> SEQUENCE: 476

Xaa Xaa Xaa Xaa Xaa Xaa Xaa Xaa
1 5

<210> SEQ ID NO 477
<211> LENGTH: 25
<212> TYPE: DNA
<213> ORGANISM: Artificial
<220> FEATURE:
<223> OTHER INFORMATION: qPCR primer sequence

<400> SEQUENCE: 477
aacatgctac gcagagaggg agtgg 25

<210> SEQ ID NO 478
<211> LENGTH: 29
<212> TYPE: DNA
<213> ORGANISM: Artificial
<220> FEATURE:
<223> OTHER INFORMATION: qPCR primer sequence

<400> SEQUENCE: 478
catgagacaa ggaaccccta gtgatggag 29

<210> SEQ ID NO 479
<211> LENGTH: 54
<212> TYPE: DNA
<213> ORGANISM: Artificial
<220> FEATURE:
<223> OTHER INFORMATION: AAV CAM library amplification primer sequence
<220> FEATURE:
<221> NAME/KEY: misc_feature
<222> LOCATION: (25)..(29)
<223> OTHER INFORMATION: n is a, c, g, or t

<400> SEQUENCE: 479
ccctacacga cgctcttccg atctnnnnnc agaactcaaa atcagtccgg aagt 54

<210> SEQ ID NO 480
<211> LENGTH: 58
<212> TYPE: DNA
<213> ORGANISM: Artificial
<220> FEATURE:
<223> OTHER INFORMATION: AAV CAM library amplification primer sequence
<220> FEATURE:
<221> NAME/KEY: misc_feature
<222> LOCATION: (33)..(37)
<223> OTHER INFORMATION: n is a, c, g, or t

<400> SEQUENCE: 480
gactggagtt cagacgtgtg ctcttccgat ctnnnnngcc aggtaatgct cccatagc 58

<210> SEQ ID NO 481
<211> LENGTH: 22
<212> TYPE: DNA
<213> ORGANISM: Artificial
<220> FEATURE:
<223> OTHER INFORMATION: qPCR primer sequence

<400> SEQUENCE: 481
ccttcgcttc aaaaaatgga ac 22

<210> SEQ ID NO 482
<211> LENGTH: 24
<212> TYPE: DNA
<213> ORGANISM: Artificial
<220> FEATURE:
<223> OTHER INFORMATION: qPCR primer sequence

<400> SEQUENCE: 482
aaaagcactc tgattgacaa atac 24

<210> SEQ ID NO 483
<211> LENGTH: 4
<212> TYPE: PRT
<213> ORGANISM: adeno-associated virus

<400> SEQUENCE: 483

Ala Gln Asn Lys
1

<210> SEQ ID NO 484
<211> LENGTH: 7
<212> TYPE: PRT
<213> ORGANISM: adeno-associated virus

<400> SEQUENCE: 484

Lys Thr Asp Asn Asn Asn Ser
1 5

<210> SEQ ID NO 485
<211> LENGTH: 8
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 485

Thr Pro Gly Gly Asn Ala Thr Arg
1 5

<210> SEQ ID NO 486
<211> LENGTH: 9

<212> TYPE: PRT
<213> ORGANISM: Artificial
<220> FEATURE:
<223> OTHER INFORMATION: AAV capsid protein common antigenic motif (CAM)
substitution

<400> SEQUENCE: 486

Thr Ala Asp His Asp Thr Lys Gly Val
1 5

<210> SEQ ID NO 487
<211> LENGTH: 10
<212> TYPE: PRT
<213> ORGANISM: Artificial
<220> FEATURE:
<223> OTHER INFORMATION: AAV capsid protein common antigenic motif (CAM)
substitution

<400> SEQUENCE: 487

Asp Leu Asp Pro Lys Ala Thr Glu Val Glu
1 5 10

<210> SEQ ID NO 488
<211> LENGTH: 6
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 488

Ser Asn Gly Arg Gly Val
1 5

<210> SEQ ID NO 489
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 489

Val Asn Thr Ser Leu Val Gly
1 5

<210> SEQ ID NO 490
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 490

Ile Arg Gly Ala Gly Ala Val
1 5

<210> SEQ ID NO 491
<211> LENGTH: 7
<212> TYPE: PRT
<213> ORGANISM: Artificial
<220> FEATURE:
<223> OTHER INFORMATION: AAV capsid protein common antigenic motif (CAM)
substitution sequence

<400> SEQUENCE: 491

Tyr Pro Gly Gly Asn Tyr Lys 1 5

<210> SEQ ID NO 492
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 492

Lys Gln Lys Asn Val Asn
1 5

<210> SEQ ID NO 493
<211> LENGTH: 6
<212> TYPE: PRT
<213> ORGANISM: Artificial
<220> FEATURE:
<223> OTHER INFORMATION: AAV capsid protein common antigenic motif (CAM) substitution sequence

<400> SEQUENCE: 493

Arg Met Ser Ser Ile Lys
1 5

<210> SEQ ID NO 494
<211> LENGTH: 221
<212> TYPE: DNA
<213> ORGANISM: Artificial
<220> FEATURE:
<223> OTHER INFORMATION: AAV1e

<400> SEQUENCE: 494
ctcaaatcag tccggaagtg gggggggggg ggacttgctg tttagccgtg ggtagcgcgt 60
ttctaaatgg gggggggggg gggggggggg taattttacc tggactggtc aatttccaga 120
gcagctttat ggactttatt attattatgg tgatggctat gggaaatctg ttgttgttga 180
ttttactgtg aataatgata ataataagaa tgagcctcgc c 221

<210> SEQ ID NO 495
<211> LENGTH: 4
<212> TYPE: PRT
<213> ORGANISM: Artificial
<220> FEATURE:
<223> OTHER INFORMATION: Evolved library amino acid sequence

<400> SEQUENCE: 495

Thr Gly Pro Arg
1

<210> SEQ ID NO 496
<211> LENGTH: 4
<212> TYPE: PRT
<213> ORGANISM: Artificial
<220> FEATURE:
<223> OTHER INFORMATION: Evolved library amino acid sequence

<400> SEQUENCE: 496

Ser Arg Gly Thr
1

<210> SEQ ID NO 497
<211> LENGTH: 4
<212> TYPE: PRT
<213> ORGANISM: Artificial

<220> FEATURE:
<223> OTHER INFORMATION: Evolved library amino acid sequence

<400> SEQUENCE: 497

Gln Gly Phe Arg
1

<210> SEQ ID NO 498
<211> LENGTH: 4
<212> TYPE: PRT
<213> ORGANISM: Artificial
<220> FEATURE:
<223> OTHER INFORMATION: Evolved library amino acid sequence

<400> SEQUENCE: 498

Arg Pro Gly Gly
1

<210> SEQ ID NO 499
<211> LENGTH: 4
<212> TYPE: PRT
<213> ORGANISM: Artificial
<220> FEATURE:
<223> OTHER INFORMATION: Evolved library amino acid sequence

<400> SEQUENCE: 499

Leu Ala Ser Arg
1

<210> SEQ ID NO 500
<211> LENGTH: 4
<212> TYPE: PRT
<213> ORGANISM: Artificial
<220> FEATURE:
<223> OTHER INFORMATION: Evolved library amino acid sequence

<400> SEQUENCE: 500

Leu Arg Asp Arg
1

<210> SEQ ID NO 501
<211> LENGTH: 8
<212> TYPE: PRT
<213> ORGANISM: Artificial
<220> FEATURE:
<223> OTHER INFORMATION: Evolved library amino acid sequence

<400> SEQUENCE: 501

Lys Pro Gly Gly Asn Ala Thr Arg
1               5

<210> SEQ ID NO 502
<211> LENGTH: 8
<212> TYPE: PRT
<213> ORGANISM: Artificial
<220> FEATURE:
<223> OTHER INFORMATION: Evolved library amino acid sequence

<400> SEQUENCE: 502

Thr Lys Thr Asp Asn Asn Asn Ser
1               5

<210> SEQ ID NO 503
<211> LENGTH: 8
<212> TYPE: PRT
<213> ORGANISM: Artificial
<220> FEATURE:

<223> OTHER INFORMATION: Evolved library amino acid sequence

<400> SEQUENCE: 503

Thr Ser Gly Gly Asn Ala Thr Arg
1               5

<210> SEQ ID NO 504
<211> LENGTH: 7
<212> TYPE: PRT
<213> ORGANISM: Artificial
<220> FEATURE:
<223> OTHER INFORMATION: Evolved library amino acid sequence

<400> SEQUENCE: 504

Thr Pro Gly Val Met Arg Arg
1               5

<210> SEQ ID NO 505
<211> LENGTH: 8
<212> TYPE: PRT
<213> ORGANISM: Artificial
<220> FEATURE:
<223> OTHER INFORMATION: Evolved library amino acid sequence

<400> SEQUENCE: 505

Thr Pro Gly Gly Asn Ala Pro Arg
1               5

<210> SEQ ID NO 506
<211> LENGTH: 8
<212> TYPE: PRT
<213> ORGANISM: Artificial
<220> FEATURE:
<223> OTHER INFORMATION: Evolved library amino acid sequence

<400> SEQUENCE: 506

Thr Thr Gly Gly Asn Ala Thr Arg
1               5

<210> SEQ ID NO 507
<211> LENGTH: 8
<212> TYPE: PRT
<213> ORGANISM: Artificial
<220> FEATURE:
<223> OTHER INFORMATION: Evolved library amino acid sequence

<400> SEQUENCE: 507

Thr Pro Gly Gly Asn Ala Lys Arg
1               5

<210> SEQ ID NO 508
<211> LENGTH: 8
<212> TYPE: PRT
<213> ORGANISM: Artificial
<220> FEATURE:
<223> OTHER INFORMATION: Evolved library amino acid sequence

<400> SEQUENCE: 508

Met Pro Gly Gly Asn Ala Thr Arg
1               5

<210> SEQ ID NO 509
<211> LENGTH: 8
<212> TYPE: PRT
<213> ORGANISM: Artificial
<220> FEATURE:
<223> OTHER INFORMATION: Evolved library amino acid sequence

<400> SEQUENCE: 509

Thr Pro Arg Gly Asn Ala Thr Arg
1 5

<210> SEQ ID NO 510
<211> LENGTH: 10
<212> TYPE: PRT
<213> ORGANISM: Artificial
<220> FEATURE:
<223> OTHER INFORMATION: Evolved library amino acid sequence

<400> SEQUENCE: 510

Thr Lys Asp Pro Ser Asn Ser Pro Val Tyr
1 5 10

<210> SEQ ID NO 511
<211> LENGTH: 10
<212> TYPE: PRT
<213> ORGANISM: Artificial
<220> FEATURE:
<223> OTHER INFORMATION: Evolved library amino acid sequence

<400> SEQUENCE: 511

Ser Lys Asp Thr Asn Ser Val Asn Val Phe
1 5 10

<210> SEQ ID NO 512
<211> LENGTH: 10
<212> TYPE: PRT
<213> ORGANISM: Artificial
<220> FEATURE:
<223> OTHER INFORMATION: Evolved library amino acid sequence

<400> SEQUENCE: 512

Thr Lys Asp Pro Glu Gln Tyr Ala Val Gln
1 5 10

<210> SEQ ID NO 513
<211> LENGTH: 10
<212> TYPE: PRT
<213> ORGANISM: Artificial
<220> FEATURE:
<223> OTHER INFORMATION: Evolved library amino acid sequence

<400> SEQUENCE: 513

Thr Lys Asp Val Lys Met Asp Asn Val Phe
1 5 10

<210> SEQ ID NO 514
<211> LENGTH: 10
<212> TYPE: PRT
<213> ORGANISM: Artificial
<220> FEATURE:
<223> OTHER INFORMATION: Evolved library amino acid sequence

<400> SEQUENCE: 514

Thr Ala Asp His Asp Thr Lys Glu Val Leu
1 5 10

<210> SEQ ID NO 515
<211> LENGTH: 10
<212> TYPE: PRT
<213> ORGANISM: Artificial
<220> FEATURE:
<223> OTHER INFORMATION: Evolved library amino acid sequence

<400> SEQUENCE: 515

Ser Val Asp Pro Asp Ser Lys His Val Leu
1               5                   10

<210> SEQ ID NO 516
<211> LENGTH: 10
<212> TYPE: PRT
<213> ORGANISM: Artificial
<220> FEATURE:
<223> OTHER INFORMATION: Evolved library amino acid sequence

<400> SEQUENCE: 516

Asp Thr Asp Ala Arg Asn Gln Ala Val Phe
1               5                   10

<210> SEQ ID NO 517
<211> LENGTH: 10
<212> TYPE: PRT
<213> ORGANISM: Artificial
<220> FEATURE:
<223> OTHER INFORMATION: Evolved library amino acid sequence

<400> SEQUENCE: 517

Ser Thr Gly Pro Ala Thr Gly Asp Val His
1               5                   10

<210> SEQ ID NO 518
<211> LENGTH: 10
<212> TYPE: PRT
<213> ORGANISM: Artificial
<220> FEATURE:
<223> OTHER INFORMATION: Evolved library amino acid sequence

<400> SEQUENCE: 518

Asp Ser Asp Ser Pro Thr Asn Asn Val Val
1               5                   10

<210> SEQ ID NO 519
<211> LENGTH: 10
<212> TYPE: PRT
<213> ORGANISM: Artificial
<220> FEATURE:
<223> OTHER INFORMATION: Evolved library amino acid sequence

<400> SEQUENCE: 519

Glu Leu Asp Gly Gln Ile Gly Asn Val Cys
1               5                   10

<210> SEQ ID NO 520
<211> LENGTH: 10
<212> TYPE: PRT
<213> ORGANISM: Artificial
<220> FEATURE:
<223> OTHER INFORMATION: Evolved library amino acid sequence

<400> SEQUENCE: 520

Gly Val Asp Val Val Asn Gln Pro Val Val
1               5                   10

<210> SEQ ID NO 521
<211> LENGTH: 10
<212> TYPE: PRT
<213> ORGANISM: Artificial
<220> FEATURE:
<223> OTHER INFORMATION: Evolved library amino acid sequence

<400> SEQUENCE: 521

Ser Ala Asp Pro Ala Thr Gly Asp Val His
1 5 10

<210> SEQ ID NO 522
<211> LENGTH: 10
<212> TYPE: PRT
<213> ORGANISM: Artificial
<220> FEATURE:
<223> OTHER INFORMATION: Evolved library amino acid sequence

<400> SEQUENCE: 522

Ala Pro Asp Gly Gly Gly Arg Asp Val Val
1 5 10

<210> SEQ ID NO 523
<211> LENGTH: 10
<212> TYPE: PRT
<213> ORGANISM: Artificial
<220> FEATURE:
<223> OTHER INFORMATION: Evolved library amino acid sequence

<400> SEQUENCE: 523

Asp Val Asp Ala Arg Ile Gln Asp Val Phe
1 5 10

<210> SEQ ID NO 524
<211> LENGTH: 8
<212> TYPE: PRT
<213> ORGANISM: Artificial
<220> FEATURE:
<223> OTHER INFORMATION: amino acid sequence for lead variant

<400> SEQUENCE: 524

Thr Pro Gly Gly Asn Ala Thr Arg
1 5

<210> SEQ ID NO 525
<211> LENGTH: 9
<212> TYPE: PRT
<213> ORGANISM: Artificial
<220> FEATURE:
<223> OTHER INFORMATION: amino acid sequence for lead variant

<400> SEQUENCE: 525

Thr Ala Asp His Asp Thr Lys Gly Val
1 5

<210> SEQ ID NO 526
<211> LENGTH: 10
<212> TYPE: PRT
<213> ORGANISM: Artificial
<220> FEATURE:
<223> OTHER INFORMATION: amino acid sequence for lead variant

<400> SEQUENCE: 526

Asp Leu Asp Pro Lys Ala Thr Glu Val Glu
1 5 10

<210> SEQ ID NO 527
<211> LENGTH: 4
<212> TYPE: PRT
<213> ORGANISM: Artificial
<220> FEATURE:

-continued

```
<223> OTHER INFORMATION: amino acid sequence for lead variant

<400> SEQUENCE: 527

Ser Glu Arg Arg
1
```

UNITED STATES PATENT AND TRADEMARK OFFICE
CERTIFICATE OF CORRECTION

PATENT NO. : 10,745,447 B2
APPLICATION NO. : 15/763706
DATED : August 18, 2020
INVENTOR(S) : Asokan et al.

Page 1 of 2

It is certified that error appears in the above-identified patent and that said Letters Patent is hereby corrected as shown below:

In the Specification

Column 11, Line 8: Please correct "n-islet" to read -- β-islet --

Column 16, Line 56: Please correct "AAV1" to read -- AAV11 --

Column 17, Line 57: Please correct "$X^1$" to read -- $X^8$ --

Column 18, Line 5: Please correct "X" to read -- $X^4$ --

Column 18, Line 24: Please correct "$X^1$" to read -- $X^{10}$ --

Column 20, Line 51: Please correct "X" to read -- $X^3$ --

Column 20, Line 60: Please correct "-$X^5$-6-$X^7$-" to read -- -$X^5$- $X^6$- $X^7$- --

Column 23, Line 66: Please correct "X" to read -- $X^3$ --

Column 30, Line 51: Please correct "X" to read -- $X^4$ --

Column 31, Line 1: Please correct "$X^5$" to read -- $X^8$ --

Column 40, Line 48: Please correct "451" to read -- 451I --

Column 45, Line 43: Please correct "n3-barrel" to read -- β-barrel --

Column 47, Line 46: Please correct "(N/AX)(IY)(TN/V/M/RXR/K)" to read -- (N/A)(L/Y)(T/V/M/R)(R/K) --

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,745,447 B2

Column 55, Line 48: Please correct "(SW)" to read -- (SIV) --

Column 79, Line 65: Please correct "101±g/ml" to read -- 10μg/ml --

Column 81, Line 44: Please correct "DHIOB" to read -- DH10B --

Column 82, Lines 10-11: Please correct "Neagaacta ggaagt-3'" to read -- Ncagaactcagtccggaagt-3' --

Column 83, Lines 42-43: Please correct "'5'-CCTTCGCITAAAAAATGGAAC-3'"
to read -- 5'-CCTTCGCTTCAAAAAATGGAAC-3' --

Column 84, Line 13: Please correct "vg/l" to read -- vg/μl --